US009580708B2

(12) United States Patent
Uhlmann et al.

(10) Patent No.: US 9,580,708 B2
(45) Date of Patent: Feb. 28, 2017

(54) MULTIMERIC OLIGONUCLEOTIDES COMPOUNDS

(75) Inventors: Eugen Uhlmann, Glashutten (DE); Markus Weber, Langenfeld (DE); Romesh Subramanian, Framingham, MA (US); Thomas Dino Rockel, Dusseldorf (DE); Arthur M. Krieg, Cambridge, MA (US)

(73) Assignee: RaNA Therapeutics, Inc., Cambridge, MA (US)

( * ) Notice: Subject to any disclaimer, the term of this patent is extended or adjusted under 35 U.S.C. 154(b) by 0 days.

(21) Appl. No.: 14/344,523

(22) PCT Filed: Sep. 14, 2012

(86) PCT No.: PCT/US2012/055535
§ 371 (c)(1),
(2), (4) Date: Apr. 3, 2015

(87) PCT Pub. No.: WO2013/040429
PCT Pub. Date: Mar. 21, 2013

(65) Prior Publication Data
US 2015/0299695 A1    Oct. 22, 2015

Related U.S. Application Data

(60) Provisional application No. 61/534,561, filed on Sep. 14, 2011.

(51) Int. Cl.
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/3231* (2013.01); *C12N 2310/341* (2013.01); *C12N 2310/346* (2013.01); *C12N 2310/51* (2013.01); *C12N 2310/52* (2013.01)

(58) Field of Classification Search
CPC ............ C12N 15/113; C12N 2310/315; C12N 2310/51
See application file for complete search history.

(56) References Cited

U.S. PATENT DOCUMENTS

| | | | |
|---|---|---|---|
| 4,725,677 A | 2/1988 | Köster et al. | |
| 5,491,133 A | 2/1996 | Walder et al. | |
| 5,576,208 A | 11/1996 | Monia et al. | |
| 5,623,065 A | 4/1997 | Cook et al. | |
| 5,652,355 A | 7/1997 | Metelev et al. | |
| 5,661,134 A | 8/1997 | Cook et al. | |
| 5,734,039 A | 3/1998 | Calabretta et al. | |
| 5,912,332 A | 6/1999 | Agrawal et al. | |
| 5,914,396 A | 6/1999 | Cook et al. | |
| 5,919,619 A | 7/1999 | Tullis | |
| 5,965,722 A | 10/1999 | Ecker et al. | |
| 6,015,710 A | 1/2000 | Shay et al. | |
| 6,046,307 A | 4/2000 | Shay et al. | |
| 6,107,094 A | 8/2000 | Crooke | |
| 6,143,881 A | 11/2000 | Metelev et al. | |
| 6,146,829 A | 11/2000 | Cook et al. | |
| 6,197,944 B1 | 3/2001 | Walder et al. | |
| 6,210,892 B1 | 4/2001 | Bennett et al. | |
| 6,294,650 B1 | 9/2001 | Shay et al. | |
| 6,326,199 B1 | 12/2001 | Cook et al. | |
| 6,346,614 B1 | 2/2002 | Metelev et al. | |
| 6,359,124 B1 | 3/2002 | Ecker et al. | |
| 6,395,492 B1 | 5/2002 | Manoharan et al. | |
| 6,451,991 B1 | 9/2002 | Martin et al. | |
| 6,531,584 B1 | 3/2003 | Cook et al. | |
| 6,608,035 B1 | 8/2003 | Agrawal et al. | |
| 6,677,445 B1 | 1/2004 | Innis et al. | |
| 6,727,355 B2 | 4/2004 | Matsuo et al. | |
| 6,753,423 B1 | 6/2004 | Cook et al. | |
| 6,831,166 B2 | 12/2004 | Manoharan et al. | |
| 6,919,439 B2 | 7/2005 | Manoharan et al. | |
| 7,015,315 B1 | 3/2006 | Cook et al. | |
| 7,041,816 B2 | 5/2006 | Ravikumar et al. | |
| 7,045,609 B2 | 5/2006 | Metelev et al. | |
| 7,687,617 B2 | 3/2010 | Thrue et al. | |
| 7,879,992 B2 | 2/2011 | Vickers et al. | |
| 7,888,012 B2 | 2/2011 | Iversen et al. | |

(Continued)

FOREIGN PATENT DOCUMENTS

CA    2805791 A1    1/2012
EP    1 044 987 A2   10/2000
(Continued)

OTHER PUBLICATIONS

International Search Report and Written Opinion for PCT/US2012/055535 mailed Feb. 26, 2013.
Davidson et al., Singles engage the RNA interference pathway. Cell. Aug. 31, 2012;150(5):873-5. doi: 10.1016/j.cell.2012.08.008.
Frieden et al., Expanding the design horizon of antisense oligonucleotides with alpha-L-LNA. Nucleic Acids Res. Nov. 1, 2003;31(21):6365-72.
Johansson et al., Target-specific arrest of mRNA translation by antisense 2'-O-alkyloligoribonucleotides. Nucleic Acids Res. Nov. 11, 1994;22(22):4591-8.
Kukis et al., Cleavable linkers to enhance selectivity of antibody-targeted therapy of cancer. Cancer Biother Radiopharm. Dec. 2001;16(6):457-67. Review.
Lima et al., Single-stranded siRNAs activate RNAi in animals. Cell. Aug. 31, 2012;150(5):883-94. doi: 10.1016/j.cell.2012.08.014.
Morris et al., Small interfering RNA-induced transcriptional gene silencing in human cells. Science. Aug. 27, 2004;305(5688):1289-92. Epub Aug. 5, 2004.

(Continued)

*Primary Examiner* — J. E. Angell
(74) *Attorney, Agent, or Firm* — Wolf, Greenfield & Sacks, P.C.

(57) ABSTRACT

The disclosure provides multimeric oligonucleotide compounds, comprising two or more target-specific oligonucleotides (e.g., antisense oligonucleotides (ASOs)), each being resistant to cleavage, and linked together by a cleavable linker. In particular, two or more linked target-specific oligonucleotides, each to a different target, allows concomitant inhibition of multiple genes' expression levels, while exhibiting favorable pharmacokinetic and pharmacodynamic properties. Methods of making and uses of the described compounds are also provided.

25 Claims, 45 Drawing Sheets

(56) References Cited

U.S. PATENT DOCUMENTS

| | | | |
|---|---|---|---|
| 8,129,515 B2 | 3/2012 | Esau et al. |
| 8,153,602 B1 | 4/2012 | Bennett et al. |
| 8,288,356 B2 | 10/2012 | Obad et al. |
| 8,314,226 B2 | 11/2012 | Tabatadze et al. |
| 8,361,980 B2 | 1/2013 | Kauppinen et al. |
| 8,404,659 B2 | 3/2013 | Kauppinen et al. |
| 8,415,313 B2 | 4/2013 | Mourich et al. |
| 8,846,639 B2 | 9/2014 | Swayze et al. |
| 2002/0160379 A1 | 10/2002 | Cook et al. |
| 2003/0219402 A1 | 11/2003 | Rutter |
| 2003/0228690 A1 | 12/2003 | Baker et al. |
| 2004/0038274 A1 | 2/2004 | Cook et al. |
| 2004/0248840 A1 | 12/2004 | Hansen et al. |
| 2005/0026160 A1 | 2/2005 | Allerson et al. |
| 2005/0054836 A1 | 3/2005 | Krainer et al. |
| 2005/0130924 A1 | 6/2005 | Monia et al. |
| 2005/0203042 A1 | 9/2005 | Frieden et al. |
| 2005/0233455 A1 | 10/2005 | Damha et al. |
| 2005/0261218 A1 | 11/2005 | Esau et al. |
| 2006/0128646 A1 | 6/2006 | Christensen et al. |
| 2006/0270624 A1 | 11/2006 | Cook et al. |
| 2007/0032446 A1 | 2/2007 | Cook et al. |
| 2007/0269815 A1 | 11/2007 | Rivory et al. |
| 2008/0015162 A1 | 1/2008 | Bhanot et al. |
| 2008/0293655 A1 | 11/2008 | Aygun et al. |
| 2009/0092988 A1 | 4/2009 | Schwartz et al. |
| 2009/0143326 A1 | 6/2009 | Obad et al. |
| 2009/0221685 A1 | 9/2009 | Esau et al. |
| 2010/0112042 A1 | 5/2010 | Polisky et al. |
| 2010/0197762 A1 | 8/2010 | Swayze et al. |
| 2010/0210712 A1 | 8/2010 | Hansen et al. |
| 2010/0249214 A1 | 9/2010 | Brown |
| 2011/0077286 A1 | 3/2011 | Damha et al. |
| 2011/0172292 A1 | 7/2011 | Hansen et al. |
| 2011/0251261 A1 | 10/2011 | Burnett et al. |
| 2011/0263687 A1 | 10/2011 | Mattick et al. |
| 2011/0287009 A1 | 11/2011 | Scheer et al. |
| 2012/0083596 A1 | 4/2012 | Elmen et al. |
| 2012/0288869 A1 | 11/2012 | Schwartz et al. |
| 2012/0289581 A1* | 11/2012 | Chang ............ C12Q 1/6886 514/44 A |
| 2012/0322851 A1 | 12/2012 | Hardee et al. |
| 2013/0079505 A1 | 3/2013 | Moeller et al. |
| 2013/0164846 A1 | 6/2013 | Saetrom |
| 2013/0245099 A1 | 9/2013 | Collard et al. |
| 2015/0073124 A1 | 3/2015 | Ohgi et al. |
| 2015/0152410 A1 | 6/2015 | Krieg et al. |
| 2015/0159160 A1 | 6/2015 | Krieg et al. |
| 2015/0159161 A1 | 6/2015 | Krieg et al. |
| 2015/0191722 A1 | 7/2015 | Krieg et al. |
| 2015/0218560 A1 | 8/2015 | Krieg et al. |
| 2015/0225717 A1 | 8/2015 | Lee et al. |
| 2015/0247141 A1 | 9/2015 | Uhlmann et al. |
| 2015/0315585 A1 | 11/2015 | Uhlmann et al. |
| 2015/0315586 A1 | 11/2015 | Uhlmann et al. |
| 2015/0315587 A1 | 11/2015 | Uhlmann et al. |
| 2015/0315588 A1 | 11/2015 | Uhlmann et al. |

FOREIGN PATENT DOCUMENTS

| | | |
|---|---|---|
| EP | 1 695 979 A2 | 8/2006 |
| JP | 2002-540813 A | 12/2002 |
| JP | 2010-536787 A | 12/2010 |
| WO | WO 89/05358 A1 | 6/1989 |
| WO | WO 93/13121 A1 | 7/1993 |
| WO | WO 94/02499 A1 | 2/1994 |
| WO | WO 94/17093 A1 | 8/1994 |
| WO | WO 2004/092356 A2 | 10/2004 |
| WO | WO 2005/042018 A2 | 5/2005 |
| WO | WO 2005/061710 A1 | 7/2005 |
| WO | WO 2005/094370 A2 | 10/2005 |
| WO | WO 2007/076328 A2 | 7/2007 |
| WO | WO 2007/091269 A2 | 8/2007 |
| WO | WO 2007/131237 A2 | 11/2007 |
| WO | WO 2007/133812 A2 | 11/2007 |
| WO | WO 2008/029619 A1 | 3/2008 |
| WO | WO 2008/109105 A2 | 9/2008 |
| WO | WO 2008/113832 A2 | 9/2008 |
| WO | WO 2009/023819 A2 | 2/2009 |
| WO | WO 2009/043353 A2 | 4/2009 |
| WO | WO 2009/090182 A1 | 7/2009 |
| WO | WO 2009/124341 A1 | 10/2009 |
| WO | WO 2010/000665 A1 | 1/2010 |
| WO | WO 2010/083615 A1 | 7/2010 |
| WO | WO 2010/090452 A2 | 8/2010 |
| WO | WO 2010/120969 A1 | 10/2010 |
| WO | WO 2011/009624 A1 | 1/2011 |
| WO | WO 2011/031520 A1 | 3/2011 |
| WO | WO 2011/048125 A1 | 4/2011 |
| WO | WO 2011/117353 A1 | 9/2011 |
| WO | WO 2011/159836 A2 | 12/2011 |
| WO | WO 2013/040429 A1 | 3/2013 |
| WO | WO 2014/043544 A1 | 3/2014 |
| WO | WO 2014/076195 A1 | 5/2014 |

OTHER PUBLICATIONS

Vickers et al., Fully modified 2' MOE oligonucleotides redirect polyadenylation. Nucleic Acids Res. Mar. 15, 2001;29(6):1293-9.

Yu et al., Single-stranded RNAs use RNAi to potently and allele-selectively inhibit mutant huntingtin expression. Cell. Aug. 31, 2012;150(5):895-908. doi: 10.1016/j.cell.2012.08.002.

Third Party Observation for Application No. EP 12 830 969.7 dated Jul. 1, 2016.

Third Party Observation for Application No. EP 12 830 969.7 dated Feb. 2, 2016.

Response as Filed for Application No. EP 12 830 969.7 dated Mar. 9, 2016.

Submission. EBI Accession No. EMBL:GC092872. Palma et al. Aug. 31, 2008.

Buck et al., Design strategies and performance of custom DNA sequencing primers. Biotechniques. Sep. 1999;27(3):528-36.

Crooke, Antisense drug technology. Principles, strategies, and applications. 2nd edition. CRC Press. 2007. 170, 198-203.

Jepsen et al., Locked nucleic acid: a potent nucleic acid analog in therapeutics and biotechnology. Oligonucleotides. 2004;14(2):130-46. Review.

Kharma et al., Automated design of hammerhead ribozymes and validation by targeting the PABPN1 gene transcript. Nucleic Acids Res. Nov. 2, 2015. pii: gkv1111.

Latorra et al., Design considerations and effects of LNA in PCR primers. Mol Cell Probes. Oct. 2003;17(5):253-9.

Lyngstadaas. Synthetic hammerhead ribozymes as tools in gene expression. Crit Rev Oral Biol Med. 2001;12(6):469-78.

Macrae et al., Structural basis for double-stranded RNA processing by Dicer. Science. Jan. 13, 2006;311(5758):195-8.

Petersen et al., LNA: a versatile tool for therapeutics and genomics. TRENDS Biotech. Feb. 2003;21(2):74-81. Review.

Smicun et al., Enhanced intracellular availability and survival of hammerhead ribozymes increases target ablation in a cellular model of osteogenesis imperfecta. Gene Ther. Nov. 2003;10(24):2005-12.

Yang et al., High fidelity PCR with an off/on switch mediated by proofreading polymerases combining with phosphorothioate-modified primer. Biochem Biophys Res Commun. Mar. 4, 2005;328(1):265-72. Erratum in: Biochem Biophys Res Commun. Jun. 3, 2005;331(2):682. Zhang, Jia [removed]; Li, Kai [removed].

Rubenstein et al., Synthesis of branched antisense oligonucleotides having multiple specificities. Treatment of hormone insensitive prostate cancer. Med Hypotheses. 2006;67(6):1375-80. Epub Jul. 25, 2006.

Seyhan et al., RNA interference from multimeric shRNAs generated by rolling circle transcription. Oligonucleotides. 2006 Winter;16(4):353-63.

Subramanian et al., Enhancing antisense efficacy with multimers and multi-targeting oligonucleotides (MTOs) using cleavable linkers. Nucleic Acids Res. Oct. 30, 2015;43(19):9123-32. doi: 10.1093/nar/gkv992. Epub Oct. 7, 2015.

(56) References Cited

OTHER PUBLICATIONS

European Search Report mailed Mar. 16, 2015 for Application No. EP 12830969.7.
International Preliminary Report on Patentability for PCT/US2012/055535 mailed Mar. 27, 2014.
Anderson et al., Bispecific short hairpin siRNA constructs targeted to CD4, CXCR4, and CCR5 confer HIV-1 resistance. Oligonucleotides. 2003;13(5):303-12.
Krützfeldt et al., Silencing of microRNAs in vivo with 'antagomirs'. Nature. Dec. 1, 2005;438(7068):685-9. Epub Oct. 30, 2005.
ørom et al., LNA-modified oligonucleotides mediate specific inhibition of microRNA function. Gene. May 10, 2006;372:137-41. Epub Feb. 24, 2006.
Submission. EBI Accession No. ADH50651. Baker et al. Mar. 25, 2004.
Chaltin et al., Delivery of antisense oligonucleotides using cholesterol-modified sense dendrimers and cationic lipids. Bioconjug Chem. Jul.-Aug. 2005;16(4):827-36.
Hernandez et al., Degradation of nuclease-stabilized RNA oligonucleotides in Mycoplasma-contaminated cell culture media. Nucleic Acid Ther. Feb. 2012;22(1):58-68. doi: 10.1089/nat.2011.0316. Epub Jan. 9, 2012.
Kierzek et al., The influence of locked nucleic acid residues on the thermodynamic properties of 2'-O-methyl RNA/RNA heteroduplexes. Nucleic Acids Res. Sep. 9, 2005;33(16):5082-93. Print 2005.
Lennox et al., Improved Performance of Anti-miRNA Oligonucleotides Using a Novel Non-Nucleotide Modifier. Mol Ther Nucleic Acids. Aug. 27, 2013;2:e117. doi: 10.1038/mtna.2013.46.
Loh et al., A trans-acting riboswitch controls expression of the virulence regulator PrfA in Listeria monocytogenes. Cell. Nov. 13, 2009;139(4):770-9. doi: 10.1016/j.cell.2009.08.046.
Lu et al., A single anti-microRNA antisense oligodeoxyribonucleotide (AMO) targeting multiple microRNAs offers an improved approach for microRNA interference. Nucleic Acids Res. Feb. 2009;37(3):e24. doi: 10.1093/nar/gkn1053. Epub Jan. 9, 2009.
Nishida et al., Synthesis, RNA selective hybridization and high nuclease resistance of an oligonucleotide containing novel bridged nucleic acid with cyclic urea structure. Chem Commun (Camb). Aug. 7, 2010;46(29):5283-5. doi: 10.1039/c0cc00154f. Epub Jun. 22, 2010.
Peterson et al., Cathepsin substrates as cleavable peptide linkers in bioconjugates, selected from a fluorescence quench combinatorial library. Bioconjug Chem. Sep.-Oct. 1998;9(5):618-26.
Rozen et al., Primer3 on the WWW for general users and for biologist programmers. Methods Mol Biol. 2000;132:365-86.
Rubenstein et al., Increased prostate-specific membrane antigen expression in LNCaP cells following treatment with bispecific antisense oligonucleotides directed against bcl-2 and EGFR. Med Oncol. Dec. 2010;27(4):1212-8. doi: 10.1007/s12032-009-9361-2. Epub Nov. 24, 2009.

* cited by examiner

SEQUENCE LISTING

```
<160> NUMBER OF SEQ ID NOS: 138

<210> SEQ ID NO 1
<211> LENGTH: 14
<212> TYPE: DNA
<213> ORGANISM: Artificial Sequence
<220> FEATURE:
<223> OTHER INFORMATION: 3LNA-8DNA-3LNA gapmer (monomeric), fully
      phosphorothioated, ApoC3
<220> FEATURE:
<221> NAME/KEY: misc_feature
<222> LOCATION: (1)..(2)
<223> OTHER INFORMATION: LNA [2',4']-locked adenosine
<220> FEATURE:
<221> NAME/KEY: misc_feature
<222> LOCATION: (3)..(3)
<223> OTHER INFORMATION: LNA [2',3']-locked guanosine
<220> FEATURE:
<221> NAME/KEY: misc_feature
<222> LOCATION: (12)..(12)
<223> OTHER INFORMATION: LNA [2',4']-locked adenosine
<220> FEATURE:
<221> NAME/KEY: misc_feature
<222> LOCATION: (13)..(14)
<223> OTHER INFORMATION: LNA [2',3']-locked guanosine

<400> SEQUENCE: 1
nnncaaccta cnnn                                                       14

<210> SEQ ID NO 2
<211> LENGTH: 31
<212> TYPE: DNA
<213> ORGANISM: Artificial Sequence
<220> FEATURE:
<223> OTHER INFORMATION: linear homodimer from SEQ ID NO:1 with 3 nt
      phosphodiester linker, ApoC3
<220> FEATURE:
<221> NAME/KEY: misc_feature
<222> LOCATION: (1)..(2)
<223> OTHER INFORMATION: LNA [2',4']-locked adenosine
<220> FEATURE:
<221> NAME/KEY: misc_feature
<222> LOCATION: (3)..(3)
<223> OTHER INFORMATION: LNA [2',3']-locked guanosine
<220> FEATURE:
<221> NAME/KEY: misc_feature
<222> LOCATION: (12)..(12)
<223> OTHER INFORMATION: LNA [2',4']-locked adenosine
<220> FEATURE:
<221> NAME/KEY: misc_feature
<222> LOCATION: (13)..(14)
<223> OTHER INFORMATION: LNA [2',3']-locked guanosine
<220> FEATURE:
<221> NAME/KEY: misc_feature
<222> LOCATION: (18)..(19)
<223> OTHER INFORMATION: LNA [2',4']-locked adenosine
<220> FEATURE:
<221> NAME/KEY: misc_feature
<222> LOCATION: (20)..(20)
<223> OTHER INFORMATION: LNA [2',3']-locked guanosine
<220> FEATURE:
<221> NAME/KEY: misc_feature
<222> LOCATION: (29)..(29)
<223> OTHER INFORMATION: LNA [2',4']-locked adenosine
<220> FEATURE:
<221> NAME/KEY: misc_feature
<222> LOCATION: (30)..(31)
<223> OTHER INFORMATION: LNA [2',3']-locked guanosine

<400> SEQUENCE: 2
```
nnncaaccta cnnntttnnn caacctacnn n          31

<210> SEQ ID NO 3
<211> LENGTH: 29
<212> TYPE: DNA
<213> ORGANISM: Artificial Sequence
<220> FEATURE:
<223> OTHER INFORMATION: linear homodimer from SEQ ID NO:1
      with disulfide linker, ApoC3
<220> FEATURE:
<221> NAME/KEY: misc_feature
<222> LOCATION: (1)..(2)
<223> OTHER INFORMATION: LNA [2',4']-locked adenosine
<220> FEATURE:
<221> NAME/KEY: misc_feature
<222> LOCATION: (3)..(3)
<223> OTHER INFORMATION: LNA [2',3']-locked guanosine
<220> FEATURE:
<221> NAME/KEY: misc_feature
<222> LOCATION: (12)..(12)
<223> OTHER INFORMATION: LNA [2',4']-locked adenosine
<220> FEATURE:
<221> NAME/KEY: misc_feature
<222> LOCATION: (13)..(14)
<223> OTHER INFORMATION: LNA [2',3']-locked guanosine
<220> FEATURE:
<221> NAME/KEY: misc_feature
<222> LOCATION: (15)..(15)
<223> OTHER INFORMATION: triethylenglycol disulfide linker
<220> FEATURE:
<221> NAME/KEY: misc_feature
<222> LOCATION: (16)..(17)
<223> OTHER INFORMATION: LNA [2',4']-locked adenosine
<220> FEATURE:
<221> NAME/KEY: misc_feature
<222> LOCATION: (18)..(18)
<223> OTHER INFORMATION: LNA [2',3']-locked guanosine
<220> FEATURE:
<221> NAME/KEY: misc_feature
<222> LOCATION: (27)..(27)
<223> OTHER INFORMATION: LNA [2',4']-locked adenosine
<220> FEATURE:
<221> NAME/KEY: misc_feature
<222> LOCATION: (28)..(29)
<223> OTHER INFORMATION: LNA [2',3']-locked guanosine

<400> SEQUENCE: 3
nnncaaccta cnnnnnnnca acctacnnn             29

<210> SEQ ID NO 4
<211> LENGTH: 19
<212> TYPE: DNA
<213> ORGANISM: Artificial Sequence
<220> FEATURE:
<223> OTHER INFORMATION: 3'3'-branched homodimer from SEQ ID NO:1
      with 2x4 nt phosphodiester linker, ApoC3
<220> FEATURE:
<221> NAME/KEY: misc_feature
<222> LOCATION: (1)..(2)
<223> OTHER INFORMATION: LNA [2',4']- locked adenosine
<220> FEATURE:
<221> NAME/KEY: misc_feature
<222> LOCATION: (3)..(3)
<223> OTHER INFORMATION: LNA [2',3']- locked guanosine
<220> FEATURE:
<221> NAME/KEY: misc_feature
<222> LOCATION: (12)..(12)
<223> OTHER INFORMATION: LNA [2',4']- locked adenosine
<220> FEATURE:
<221> NAME/KEY: misc_feature
<222> LOCATION: (13)..(14)
<223> OTHER INFORMATION: LNA [2',3']- locked guanosine
<220> FEATURE:
<221> NAME/KEY: misc_feature
<222> LOCATION: (19)..(19)

-continued

```
<223> OTHER INFORMATION: doubler triethylenglycol linker

<400> SEQUENCE: 4
nnncaaccta cnnnttttn                                                  19

<210> SEQ ID NO 5
<211> LENGTH: 17
<212> TYPE: DNA
<213> ORGANISM: Artificial Sequence
<220> FEATURE:
<223> OTHER INFORMATION: 3'3'-branched homodimer from SEQ ID NO:1
      with disulfide linker, ApoC3
<220> FEATURE:
<221> NAME/KEY: misc_feature
<222> LOCATION: (1)..(2)
<223> OTHER INFORMATION: LNA [2',4']-locked adenosine
<220> FEATURE:
<221> NAME/KEY: misc_feature
<222> LOCATION: (3)..(3)
<223> OTHER INFORMATION: LNA [2',3']-locked guanosine
<220> FEATURE:
<221> NAME/KEY: misc_feature
<222> LOCATION: (12)..(12)
<223> OTHER INFORMATION: LNA [2',4']-locked adenosine
<220> FEATURE:
<221> NAME/KEY: misc_feature
<222> LOCATION: (13)..(14)
<223> OTHER INFORMATION: LNA [2',3']-locked guanosine
<220> FEATURE:
<221> NAME/KEY: misc_feature
<222> LOCATION: (15)..(15)
<223> OTHER INFORMATION: triethylenglycol linker
<220> FEATURE:
<221> NAME/KEY: misc_feature
<222> LOCATION: (16)..(16)
<223> OTHER INFORMATION: disulfide linker
<220> FEATURE:
<221> NAME/KEY: misc_feature
<222> LOCATION: (17)..(17)
<223> OTHER INFORMATION: doubler triethylenglycol linker

<400> SEQUENCE: 5
nnncaaccta cnnnnnn                                                    17

<210> SEQ ID NO 6
<211> LENGTH: 31
<212> TYPE: DNA
<213> ORGANISM: Artificial Sequence
<220> FEATURE:
<223> OTHER INFORMATION: mouse ortholog of SEQ ID NO:2, ApoC3
<220> FEATURE:
<221> NAME/KEY: misc_feature
<222> LOCATION: (1)..(2)
<223> OTHER INFORMATION: LNA [2',4']-locked adenosine
<220> FEATURE:
<221> NAME/KEY: misc_feature
<222> LOCATION: (3)..(3)
<223> OTHER INFORMATION: LNA [2',3']-locked guanosine
<220> FEATURE:
<221> NAME/KEY: misc_feature
<222> LOCATION: (12)..(12)
<223> OTHER INFORMATION: LNA [2',4']-locked adenosine
<220> FEATURE:
<221> NAME/KEY: misc_feature
<222> LOCATION: (13)..(14)
<223> OTHER INFORMATION: LNA [2',3']-locked guanosine
<220> FEATURE:
<221> NAME/KEY: misc_feature
<222> LOCATION: (18)..(19)
<223> OTHER INFORMATION: LNA [2',4']-locked adenosine
<220> FEATURE:
<221> NAME/KEY: misc_feature
<222> LOCATION: (20)..(20)
<223> OTHER INFORMATION: LNA [2',3']-locked guanosine
<220> FEATURE:
```

```
<221> NAME/KEY: misc_feature
<222> LOCATION: (29)..(29)
<223> OTHER INFORMATION: LNA [2',4']-locked adenosine
<220> FEATURE:
<221> NAME/KEY: misc_feature
<222> LOCATION: (30)..(31)
<223> OTHER INFORMATION: LNA [2',3']-locked guanosine

<400> SEQUENCE: 6
nnncaacctt cnnntttnnn caaccttcnn n                              31

<210> SEQ ID NO 7
<211> LENGTH: 30
<212> TYPE: DNA
<213> ORGANISM: Artificial Sequence
<220> FEATURE:
<223> OTHER INFORMATION: linear heterodimer with 3 nt
      phosphodiester-linker, ApoB/ApoC3 (mouse)
<220> FEATURE:
<221> NAME/KEY: misc_feature
<222> LOCATION: (1)..(2)
<223> OTHER INFORMATION: LNA [2',4']-locked adenosine
<220> FEATURE:
<221> NAME/KEY: misc_feature
<222> LOCATION: (3)..(3)
<223> OTHER INFORMATION: LNA [2',3']-locked guanosine
<220> FEATURE:
<221> NAME/KEY: misc_feature
<222> LOCATION: (12)..(12)
<223> OTHER INFORMATION: LNA [2',4']-locked adenosine
<220> FEATURE:
<221> NAME/KEY: misc_feature
<222> LOCATION: (13)..(14)
<223> OTHER INFORMATION: LNA [2',3']-locked guanosine
<220> FEATURE:
<221> NAME/KEY: misc_feature
<222> LOCATION: (18)..(18)
<223> OTHER INFORMATION: LNA [2',3']-locked guanosine
<220> FEATURE:
<221> NAME/KEY: misc_feature
<222> LOCATION: (19)..(19)
<223> OTHER INFORMATION: LNA [2',4']-locked 5-methyl-cytidine
<220> FEATURE:
<221> NAME/KEY: misc_feature
<222> LOCATION: (28)..(28)
<223> OTHER INFORMATION: LNA [2',4']-locked "ribo"-thymidine
<220> FEATURE:
<221> NAME/KEY: misc_feature
<222> LOCATION: (29)..(29)
<223> OTHER INFORMATION: LNA [2',4']-locked 5-methyl-cytidine
<220> FEATURE:
<221> NAME/KEY: misc_feature
<222> LOCATION: (30)..(30)
<223> OTHER INFORMATION: LNA [2',4']-locked adenosine

<400> SEQUENCE: 7
nnncaacctt cnnntttnna ttggtatnnn                                30

<210> SEQ ID NO 8
<211> LENGTH: 29
<212> TYPE: DNA
<213> ORGANISM: Artificial Sequence
<220> FEATURE:
<223> OTHER INFORMATION: linear heterodimer with 3 nt
      phosphodiester-linker, ApoB/ApoC3
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
```

```
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (17)..(17)
<223> OTHER INFORMATION: LNA [2',4']-locked "ribo"-thymidine
<220> FEATURE:
<221> NAME/KEY: misc_feature
<222> LOCATION: (18)..(19)
<223> OTHER INFORMATION: LNA [2',4']-locked 5-methyl-cytidine
<220> FEATURE:
<221> NAME/KEY: misc_feature
<222> LOCATION: (27)..(27)
<223> OTHER INFORMATION: LNA [2',4']-locked 5-methyl-cytidine
<220> FEATURE:
<221> NAME/KEY: misc_feature
<222> LOCATION: (28)..(28)
<223> OTHER INFORMATION: LNA [2',4']-locked "ribo"-thymidine
<220> FEATURE:
<221> NAME/KEY: misc_feature
<222> LOCATION: (29)..(29)
<223> OTHER INFORMATION: LNA [2',3']-locked guanosine

<400> SEQUENCE: 8
nnattggtat nnntttnnnt cggcctnnn                                      29

<210> SEQ ID NO 9
<211> LENGTH: 14
<212> TYPE: DNA
<213> ORGANISM: Artificial Sequence
<220> FEATURE:
<223> OTHER INFORMATION: 3LNA-8DNA-3LNA gapmer (monomeric),
      fully phosphorothioated, ApoB
<220> FEATURE:
<221> NAME/KEY: misc_feature
<222> LOCATION: (1)..(2)
<223> OTHER INFORMATION: LNA [2',4']-locked 5-methyl-cytidine
<220> FEATURE:
<221> NAME/KEY: misc_feature
<222> LOCATION: (3)..(3)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked "ribo"-thymidine
<220> FEATURE:
<221> NAME/KEY: misc_feature
<222> LOCATION: (14)..(14)
<223> OTHER INFORMATION: LNA [2',3']-locked guanosine

<400> SEQUENCE: 9
nnncttcggc cnnn                                                      14

<210> SEQ ID NO 10
<211> LENGTH: 13
<212> TYPE: DNA
<213> ORGANISM: Artificial Sequence
<220> FEATURE:
<223> OTHER INFORMATION: 3LNA-7DNA-3LNA gapmer (monomeric),
      fully phosphorothioated, ApoC3
<220> FEATURE:
<221> NAME/KEY: misc_feature
<222> LOCATION: (1)..(1)
```

```
<223> OTHER INFORMATION: LNA [2',4']-locked "ribo"-thymidine
<220> FEATURE:
<221> NAME/KEY: misc_feature
<222> LOCATION: (2)..(3)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked 5-methyl-cytidine
<220> FEATURE:
<221> NAME/KEY: misc_feature
<222> LOCATION: (12)..(12)
<223> OTHER INFORMATION: LNA [2',4']-locked "ribo"-thymidine
<220> FEATURE:
<221> NAME/KEY: misc_feature
<222> LOCATION: (13)..(13)
<223> OTHER INFORMATION: LNA [2',3']-locked guanosine

<400> SEQUENCE: 10
nnntcggcct nnn                                                        13

<210> SEQ ID NO 11
<211> LENGTH: 12
<212> TYPE: DNA
<213> ORGANISM: Artificial Sequence
<220> FEATURE:
<223> OTHER INFORMATION: 3LNA-7DNA-2LNA gapmer (monomeric),
      fully phosphorothioated, ApoB
<220> FEATURE:
<221> NAME/KEY: misc_feature
<222> LOCATION: (1)..(1)
<223> OTHER INFORMATION: LNA [2',4']-locked "ribo"-thymidine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (3)..(3)
<223> OTHER INFORMATION: LNA [2',4']-locked "ribo"-thymidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',3']-locked guanosine

<400> SEQUENCE: 11
nnntcggccc nn                                                         12

<210> SEQ ID NO 12
<211> LENGTH: 12
<212> TYPE: DNA
<213> ORGANISM: Artificial Sequence
<220> FEATURE:
<223> OTHER INFORMATION: 5-methyl-dC (Z) analog of SEQ ID NO:11, ApoB
<220> FEATURE:
<221> NAME/KEY: misc_feature
<222> LOCATION: (1)..(1)
<223> OTHER INFORMATION: LNA [2',4']-locked "ribo"-thymidine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (3)..(3)
<223> OTHER INFORMATION: LNA [2',4']-locked "ribo"-thymidine
<220> FEATURE:
<221> NAME/KEY: misc_feature
<222> LOCATION: (5)..(5)
<223> OTHER INFORMATION: 5-methyl-2'-deoxy-cytidine
<220> FEATURE:
```

```
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',3']-locked guanosine

<400> SEQUENCE: 12
nnntnggccc nn                                                          12

<210> SEQ ID NO 13
<211> LENGTH: 13
<212> TYPE: DNA
<213> ORGANISM: Artificial Sequence
<220> FEATURE:
<223> OTHER INFORMATION: 2LNA-8DNA-3LNA gapmer (monomeric),
      fully phosphorothioated, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine

<400> SEQUENCE: 13
nnattggtat nnn                                                         13

<210> SEQ ID NO 14
<211> LENGTH: 14
<212> TYPE: DNA
<213> ORGANISM: Artificial Sequence
<220> FEATURE:
<223> OTHER INFORMATION: mouse ortholog of SEQ ID NO:1, ApoC3
<220> FEATURE:
<221> NAME/KEY: misc_feature
<222> LOCATION: (1)..(2)
<223> OTHER INFORMATION: LNA [2',4']-locked adenosine
<220> FEATURE:
<221> NAME/KEY: misc_feature
<222> LOCATION: (3)..(3)
<223> OTHER INFORMATION: LNA [2',3']-locked guanosine
<220> FEATURE:
<221> NAME/KEY: misc_feature
<222> LOCATION: (12)..(12)
<223> OTHER INFORMATION: LNA [2',4']-locked adenosine
<220> FEATURE:
<221> NAME/KEY: misc_feature
<222> LOCATION: (13)..(14)
<223> OTHER INFORMATION: LNA [2',3']-locked guanosine

<400> SEQUENCE: 14
nnncaacctt cnnn                                                        14

<210> SEQ ID NO 15
<211> LENGTH: 32
<212> TYPE: DNA
<213> ORGANISM: Artificial Sequence
<220> FEATURE:
```

<223> OTHER INFORMATION: linear homodimer from SEQ ID NO:30 with
      4 nt phosphodiester DNA linker, ApoC3
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked "ribo"-thymidine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked 5-methyl-cytidine
<220> FEATURE:
<221> NAME/KEY: misc_feature
<222> LOCATION: (32)..(32)
<223> OTHER INFORMATION: LNA [2',4']-locked "ribo"-thymidine

<400> SEQUENCE: 15
nnactgagaa tannttttnn actgagaata nn                                        32

<210> SEQ ID NO 16
<211> LENGTH: 32
<212> TYPE: DNA
<213> ORGANISM: Artificial Sequence
<220> FEATURE:
<223> OTHER INFORMATION: linear homodimer from SEQ ID NO:30 with
      4 nt phosphorothioate DNA linker, ApoC3
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked "ribo"-thymidine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked 5-methyl-cytidine
<220> FEATURE:
<221> NAME/KEY: misc_feature
<222> LOCATION: (32)..(32)
<223> OTHER INFORMATION: LNA [2',4']-locked "ribo"-thymidine -continued

<400> SEQUENCE: 16
nnactgagaa tannttttnn actgagaata nn                                32

<210> SEQ ID NO 17
<211> LENGTH: 19
<212> TYPE: DNA
<213> ORGANISM: Artificial Sequence
<220> FEATURE:
<223> OTHER INFORMATION: 3'3'-branched homodimer from SEQ ID NO:30,
      2x4 nt phosphodiester DNA linker, ApoC3
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked "ribo"-thymidine
<220> FEATURE:
<221> NAME/KEY: misc_feature
<222> LOCATION: (19)..(19)
<223> OTHER INFORMATION: doubler triethylenglycol linker

<400> SEQUENCE: 17
nnactgagaa tannttttn                                               19

<210> SEQ ID NO 18
<211> LENGTH: 30
<212> TYPE: DNA
<213> ORGANISM: Artificial Sequence
<220> FEATURE:
<223> OTHER INFORMATION: linear homodimer from SEQ ID NO:13 with
      phosphodiester DNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (18)..(18)
<223> OTHER INFORMATION: LNA [2',3']-locked guanosine
<220> FEATURE:
<221> NAME/KEY: misc_feature
<222> LOCATION: (19)..(19)
<223> OTHER INFORMATION: LNA [2',4']-locked 5-methyl-cytidine
<220> FEATURE:
<221> NAME/KEY: misc_feature
<222> LOCATION: (28)..(28)
<223> OTHER INFORMATION: LNA [2',4']-locked "ribo"-thymidine
<220> FEATURE:

```
<221> NAME/KEY: misc_feature
<222> LOCATION: (29)..(29)
<223> OTHER INFORMATION: LNA [2',4']-locked 5-methyl-cytidine
<220> FEATURE:
<221> NAME/KEY: misc_feature
<222> LOCATION: (30)..(30)
<223> OTHER INFORMATION: LNA [2',4']-locked adenosine

<400> SEQUENCE: 18
nnattggtat nnnttttnna ttggtatnnn                                               30

<210> SEQ ID NO 19
<211> LENGTH: 30
<212> TYPE: DNA
<213> ORGANISM: Artificial Sequence
<220> FEATURE:
<223> OTHER INFORMATION: linear homodimer from SEQ ID NO:13 with
      phosphorothioate DNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (18)..(18)
<223> OTHER INFORMATION: LNA [2',3']-locked guanosine
<220> FEATURE:
<221> NAME/KEY: misc_feature
<222> LOCATION: (19)..(19)
<223> OTHER INFORMATION: LNA [2',4']-locked 5-methyl-cytidine
<220> FEATURE:
<221> NAME/KEY: misc_feature
<222> LOCATION: (28)..(28)
<223> OTHER INFORMATION: LNA [2',4']-locked "ribo"-thymidine
<220> FEATURE:
<221> NAME/KEY: misc_feature
<222> LOCATION: (29)..(29)
<223> OTHER INFORMATION: LNA [2',4']-locked 5-methyl-cytidine
<220> FEATURE:
<221> NAME/KEY: misc_feature
<222> LOCATION: (30)..(30)
<223> OTHER INFORMATION: LNA [2',4']-locked adenosine

<400> SEQUENCE: 19
nnattggtat nnnttttnna ttggtatnnn                                               30

<210> SEQ ID NO 20
<211> LENGTH: 18
<212> TYPE: DNA
<213> ORGANISM: Artificial Sequence
<220> FEATURE:
<223> OTHER INFORMATION: 3'3'-branched homodimer from SEQ ID NO:13,
      phosphodiester DNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
```

```
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (18)..(18)
<223> OTHER INFORMATION: doubler triethylenglycol linker

<400> SEQUENCE: 20
nnattggtat nnnttttn                                                   18

<210> SEQ ID NO 21
<211> LENGTH: 31
<212> TYPE: DNA
<213> ORGANISM: Artificial Sequence
<220> FEATURE:
<223> OTHER INFORMATION: linear heterodimer with phosphodiester
      DNA linker, ApoC3/ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked "ribo"-thymidine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (29)..(29)
<223> OTHER INFORMATION: LNA [2',4']-locked "ribo"-thymidine
<220> FEATURE:
<221> NAME/KEY: misc_feature
<222> LOCATION: (30)..(30)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked adenosine

<400> SEQUENCE: 21
nnactgagaa tannttttnn attggtatnn n                                    31

<210> SEQ ID NO 22
<211> LENGTH: 31
<212> TYPE: DNA
<213> ORGANISM: Artificial Sequence
<220> FEATURE:
<223> OTHER INFORMATION: linear heterodimer with phosphodiester
```

```
        DNA linker, ApoB/ApoC3
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (18)..(18)
<223> OTHER INFORMATION: LNA [2',3']-locked guanosine
<220> FEATURE:
<221> NAME/KEY: misc_feature
<222> LOCATION: (19)..(19)
<223> OTHER INFORMATION: LNA [2',4']-locked 5-methyl-cytidine
<220> FEATURE:
<221> NAME/KEY: misc_feature
<222> LOCATION: (30)..(30)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked "ribo"-thymidine

<400> SEQUENCE: 22
nnattggtat nnnttttnna ctgagaatan n                              31

<210> SEQ ID NO 23
<211> LENGTH: 30
<212> TYPE: DNA
<213> ORGANISM: Artificial Sequence
<220> FEATURE:
<223> OTHER INFORMATION: linear heterodimer with phosphodiester DNA
      linker, HIF-1alpha/survivin
<220> FEATURE:
<221> NAME/KEY: misc_feature
<222> LOCATION: (1)..(2)
<223> OTHER INFORMATION: LNA [2',3']-locked guanosine
<220> FEATURE:
<221> NAME/KEY: misc_feature
<222> LOCATION: (11)..(11)
<223> OTHER INFORMATION: LNA [2',4']-locked 5-methyl-cytidine
<220> FEATURE:
<221> NAME/KEY: misc_feature
<222> LOCATION: (12)..(12)
<223> OTHER INFORMATION: LNA [2',4']-locked "ribo"-thymidine
<220> FEATURE:
<221> NAME/KEY: misc_feature
<222> LOCATION: (13)..(13)
<223> OTHER INFORMATION: LNA [2',3']-locked guanosine
<220> FEATURE:
<221> NAME/KEY: misc_feature
<222> LOCATION: (18)..(18)
<223> OTHER INFORMATION: LNA [2',4']-locked 5-methyl-cytidine
<220> FEATURE:
<221> NAME/KEY: misc_feature
<222> LOCATION: (19)..(19)
<223> OTHER INFORMATION: LNA [2',4']-locked adenosine
<220> FEATURE:
<221> NAME/KEY: misc_feature
<222> LOCATION: (28)..(28)
<223> OTHER INFORMATION: LNA [2',4']-locked 5-methyl-cytidine
<220> FEATURE:
```

<221> NAME/KEY: misc_feature
<222> LOCATION: (29)..(29)
<223> OTHER INFORMATION: LNA [2',4']-locked adenosine
<220> FEATURE:
<221> NAME/KEY: misc_feature
<222> LOCATION: (30)..(30)
<223> OTHER INFORMATION: LNA [2',3']-locked guanosine

<400> SEQUENCE: 23
nncaagcatc nnnttttnna tccatggnnn                                    30

<210> SEQ ID NO 24
<211> LENGTH: 31
<212> TYPE: DNA
<213> ORGANISM: Artificial Sequence
<220> FEATURE:
<223> OTHER INFORMATION: linear heterodimer with phosphodiester DNA
      linker, HIF-1alpha/B2M
<220> FEATURE:
<221> NAME/KEY: misc_feature
<222> LOCATION: (1)..(2)
<223> OTHER INFORMATION: LNA [2',3']-locked guanosine
<220> FEATURE:
<221> NAME/KEY: misc_feature
<222> LOCATION: (11)..(11)
<223> OTHER INFORMATION: LNA [2',4']-locked 5-methyl-cytidine
<220> FEATURE:
<221> NAME/KEY: misc_feature
<222> LOCATION: (12)..(12)
<223> OTHER INFORMATION: LNA [2',4']-locked "ribo"-thymidine
<220> FEATURE:
<221> NAME/KEY: misc_feature
<222> LOCATION: (13)..(13)
<223> OTHER INFORMATION: LNA [2',3']-locked guanosine
<220> FEATURE:
<221> NAME/KEY: misc_feature
<222> LOCATION: (18)..(18)
<223> OTHER INFORMATION: LNA [2',3']-locked guanosine
<220> FEATURE:
<221> NAME/KEY: misc_feature
<222> LOCATION: (19)..(19)
<223> OTHER INFORMATION: LNA [2',4']-locked 5-methyl-cytidine
<220> FEATURE:
<221> NAME/KEY: misc_feature
<222> LOCATION: (20)..(20)
<223> OTHER INFORMATION: LNA [2',3']-locked guanosine
<220> FEATURE:
<221> NAME/KEY: misc_feature
<222> LOCATION: (29)..(30)
<223> OTHER INFORMATION: LNA [2',4']-locked "ribo"-thymidine
<220> FEATURE:
<221> NAME/KEY: misc_feature
<222> LOCATION: (31)..(31)
<223> OTHER INFORMATION: LNA [2',3']-locked guanosine

<400> SEQUENCE: 24
nncaagcatc nnnttttnnn tgcataaann n                                   31

<210> SEQ ID NO 25
<211> LENGTH: 30
<212> TYPE: DNA
<213> ORGANISM: Artificial Sequence
<220> FEATURE:
<223> OTHER INFORMATION: linear heterodimer with phosphodiester DNA
      linker, HIF-1alpha/ApoB
<220> FEATURE:
<221> NAME/KEY: misc_feature
<222> LOCATION: (1)..(2)
<223> OTHER INFORMATION: LNA [2',3']-locked guanosine
<220> FEATURE:
<221> NAME/KEY: misc_feature
<222> LOCATION: (11)..(11)
<223> OTHER INFORMATION: LNA [2',4']-locked 5-methyl-cytidine
<220> FEATURE:
<221> NAME/KEY: misc_feature
<222> LOCATION: (12)..(12)
<223> OTHER INFORMATION: LNA [2',4']-locked "ribo"-thymidine
<220> FEATURE:
<221> NAME/KEY: misc_feature
<222> LOCATION: (13)..(13)
<223> OTHER INFORMATION: LNA [2',3']-locked guanosine
<220> FEATURE:
<221> NAME/KEY: misc_feature
<222> LOCATION: (18)..(18)
<223> OTHER INFORMATION: LNA [2',3']-locked guanosine
<220> FEATURE:
<221> NAME/KEY: misc_feature
<222> LOCATION: (19)..(19)
<223> OTHER INFORMATION: LNA [2',4']-locked 5-methyl-cytidine
<220> FEATURE:
<221> NAME/KEY: misc_feature
<222> LOCATION: (28)..(28)
<223> OTHER INFORMATION: LNA [2',4']-locked "ribo"-thymidine
<220> FEATURE:
<221> NAME/KEY: misc_feature
<222> LOCATION: (29)..(29)
<223> OTHER INFORMATION: LNA [2',4']-locked 5-methyl-cytidine
<220> FEATURE:
<221> NAME/KEY: misc_feature
<222> LOCATION: (30)..(30)
<223> OTHER INFORMATION: LNA [2',4']-locked adenosine

<400> SEQUENCE: 25
nncaagcatc nnnttttnna ttggtatnnn                                    30

<210> SEQ ID NO 26
<211> LENGTH: 48
<212> TYPE: DNA
<213> ORGANISM: Artificial Sequence
<220> FEATURE:
<223> OTHER INFORMATION: linear heterotrimer with two phosphodiesterDNA
      linkers, ApoB/ApoC3/HIF-1alpha
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (18)..(18)
<223> OTHER INFORMATION: LNA [2',3']-locked guanosine
<220> FEATURE:
<221> NAME/KEY: misc_feature
<222> LOCATION: (19)..(19)
<223> OTHER INFORMATION: LNA [2',4']-locked 5-methyl-cytidine
<220> FEATURE:
<221> NAME/KEY: misc_feature
<222> LOCATION: (30)..(30)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked "ribo"-thymidine
<220> FEATURE:
<221> NAME/KEY: misc_feature
<222> LOCATION: (36)..(37)
<223> OTHER INFORMATION: LNA [2',3']-locked guanosine

```
<220> FEATURE:
<221> NAME/KEY: misc_feature
<222> LOCATION: (46)..(46)
<223> OTHER INFORMATION: LNA [2',4']-locked 5-methyl-cytidine
<220> FEATURE:
<221> NAME/KEY: misc_feature
<222> LOCATION: (47)..(47)
<223> OTHER INFORMATION: LNA [2',4']-locked "ribo"-thymidine
<220> FEATURE:
<221> NAME/KEY: misc_feature
<222> LOCATION: (48)..(48)
<223> OTHER INFORMATION: LNA [2',3']-locked guanosine

<400> SEQUENCE: 26
nnattggtat nnnttttnna ctgagaatan nttttnncaa gcatcnnn                        48

<210> SEQ ID NO 27
<211> LENGTH: 13
<212> TYPE: DNA
<213> ORGANISM: Artificial Sequence
<220> FEATURE:
<223> OTHER INFORMATION: 2LNA-8DNA-3LNA gapmer (monomeric), fully
      phosphorothioated, HIF-1alpha
<220> FEATURE:
<221> NAME/KEY: misc_feature
<222> LOCATION: (1)..(2)
<223> OTHER INFORMATION: LNA [2',3']-locked guanosine
<220> FEATURE:
<221> NAME/KEY: misc_feature
<222> LOCATION: (11)..(11)
<223> OTHER INFORMATION: LNA [2',4']-locked 5-methyl-cytidine
<220> FEATURE:
<221> NAME/KEY: misc_feature
<222> LOCATION: (12)..(12)
<223> OTHER INFORMATION: LNA [2',4']-locked "ribo"-thymidine
<220> FEATURE:
<221> NAME/KEY: misc_feature
<222> LOCATION: (13)..(13)
<223> OTHER INFORMATION: LNA [2',3']-locked guanosine

<400> SEQUENCE: 27
nncaagcatc nnn                                                              13

<210> SEQ ID NO 28
<211> LENGTH: 13
<212> TYPE: DNA
<213> ORGANISM: Artificial Sequence
<220> FEATURE:
<223> OTHER INFORMATION: 2LNA-8DNA-3LNA gapmer (monomeric), fully
      phosphorothioated, Survivin
<220> FEATURE:
<221> NAME/KEY: misc_feature
<222> LOCATION: (1)..(1)
<223> OTHER INFORMATION: LNA [2',4']-locked 5-methyl-cytidine
<220> FEATURE:
<221> NAME/KEY: misc_feature
<222> LOCATION: (2)..(2)
<223> OTHER INFORMATION: LNA [2',4']-locked adenosine
<220> FEATURE:
<221> NAME/KEY: misc_feature
<222> LOCATION: (11)..(11)
<223> OTHER INFORMATION: LNA [2',4']-locked 5-methyl-cytidine
<220> FEATURE:
<221> NAME/KEY: misc_feature
<222> LOCATION: (12)..(12)
<223> OTHER INFORMATION: LNA [2',4']-locked adenosine
<220> FEATURE:
<221> NAME/KEY: misc_feature
<222> LOCATION: (13)..(13)
<223> OTHER INFORMATION: LNA [2',3']-locked guanosine

<400> SEQUENCE: 28
nnatccatgg nnn                                                              13
```

```
<210> SEQ ID NO 29
<211> LENGTH: 14
<212> TYPE: DNA
<213> ORGANISM: Artificial Sequence
<220> FEATURE:
<223> OTHER INFORMATION: 3LNA-8DNA-3LNA gapmer (monomeric),
      fully phosphorothioated, B2M
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (3)..(3)
<223> OTHER INFORMATION: LNA [2',3']-locked guanosine
<220> FEATURE:
<221> NAME/KEY: misc_feature
<222> LOCATION: (12)..(13)
<223> OTHER INFORMATION: LNA [2',4']-locked "ribo"-thymidine
<220> FEATURE:
<221> NAME/KEY: misc_feature
<222> LOCATION: (14)..(14)
<223> OTHER INFORMATION: LNA [2',3']-locked guanosine

<400> SEQUENCE: 29
nnntgcataa annn                                                        14

<210> SEQ ID NO 30
<211> LENGTH: 14
<212> TYPE: DNA
<213> ORGANISM: Artificial Sequence
<220> FEATURE:
<223> OTHER INFORMATION: 2LNA-10DNA-2LNA gapmer (monomeric),
      fully phosphorothioated, ApoC3
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked "ribo"-thymidine

<400> SEQUENCE: 30
nnactgagaa tann                                                        14

<210> SEQ ID NO 31
<211> LENGTH: 13
<212> TYPE: DNA
<213> ORGANISM: Artificial Sequence
<220> FEATURE:
<223> OTHER INFORMATION: 2LNA-8DNA-3LNA gapmer (monomeric), fully
      phosphorothioated, ApoB negative control (mismatched)
<220> FEATURE:
<221> NAME/KEY: misc_feature
<222> LOCATION: (1)..(1)
<223> OTHER INFORMATION: LNA [2',4']-locked 5-methyl-cytidine
<220> FEATURE:
<221> NAME/KEY: misc_feature
<222> LOCATION: (2)..(2)
<223> OTHER INFORMATION: LNA [2',3']-locked guanosine
<220> FEATURE:
```

```
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked adenosine
<220> FEATURE:
<221> NAME/KEY: misc_feature
<222> LOCATION: (13)..(13)
<223> OTHER INFORMATION: LNA [2',3']-locked guanosine

<400> SEQUENCE: 31
nntctatgta nnn                                                          13

<210> SEQ ID NO 32
<211> LENGTH: 14
<212> TYPE: DNA
<213> ORGANISM: Artificial Sequence
<220> FEATURE:
<223> OTHER INFORMATION: 2me-9DNA-2me gapmer with 2 G-clamps, fully
      phosphorothioated (monomeric), ApoC3
<220> FEATURE:
<221> NAME/KEY: misc_feature
<222> LOCATION: (1)..(2)
<223> OTHER INFORMATION: 2'-O-methyl-uridine
<220> FEATURE:
<221> NAME/KEY: misc_feature
<222> LOCATION: (3)..(3)
<223> OTHER INFORMATION: G-clamp deoxyphenoxazine
<220> FEATURE:
<221> NAME/KEY: misc_feature
<222> LOCATION: (12)..(12)
<223> OTHER INFORMATION: 2'-O-methyl-guanosine
<220> FEATURE:
<221> NAME/KEY: misc_feature
<222> LOCATION: (13)..(13)
<223> OTHER INFORMATION: 2'-O-methyl-adenosine
<220> FEATURE:
<221> NAME/KEY: misc_feature
<222> LOCATION: (14)..(14)
<223> OTHER INFORMATION: G-clamp deoxyphenoxazine

<400> SEQUENCE: 32
nnnagtgtga tnnn                                                         14

<210> SEQ ID NO 33
<211> LENGTH: 31
<212> TYPE: DNA
<213> ORGANISM: Artificial Sequence
<220> FEATURE:
<223> OTHER INFORMATION: linear heterodimer with phosphodiester DNA
      linker, ApoC3/ApoB
<220> FEATURE:
<221> NAME/KEY: misc_feature
<222> LOCATION: (1)..(2)
<223> OTHER INFORMATION: LNA [2',4']-locked 5-methyl-cytidine
<220> FEATURE:
<221> NAME/KEY: misc_feature
<222> LOCATION: (3)..(3)
<223> OTHER INFORMATION: 2'-O-methyl-adenosine
<220> FEATURE:
<221> NAME/KEY: misc_feature
<222> LOCATION: (12)..(12)
<223> OTHER INFORMATION: 2'-O-methyl-uridine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked adenosine
<220> FEATURE:
<221> NAME/KEY: misc_feature
```

```
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (29)..(29)
<223> OTHER INFORMATION: LNA [2',4']-locked "ribo"-thymidine
<220> FEATURE:
<221> NAME/KEY: misc_feature
<222> LOCATION: (30)..(30)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked adenosine

<400> SEQUENCE: 33
nnngtagtct tnnnttttnn attggtatnn n                              31

<210> SEQ ID NO 34
<211> LENGTH: 31
<212> TYPE: DNA
<213> ORGANISM: Artificial Sequence
<220> FEATURE:
<223> OTHER INFORMATION: linear heterodimer with phosphodiester DNA
      linker, ApoC3/ApoB
<220> FEATURE:
<221> NAME/KEY: misc_feature
<222> LOCATION: (1)..(2)
<223> OTHER INFORMATION: LNA [2',4']-locked 5-methyl-cytidine
<220> FEATURE:
<221> NAME/KEY: misc_feature
<222> LOCATION: (3)..(3)
<223> OTHER INFORMATION: 2'-O-methyl-adenosine
<220> FEATURE:
<221> NAME/KEY: misc_feature
<222> LOCATION: (12)..(12)
<223> OTHER INFORMATION: 2'-O-methyl-uridine
<220> FEATURE:
<221> NAME/KEY: misc_feature
<222> LOCATION: (13)..(13)
<223> OTHER INFORMATION: 2'-O-methyl-cytidine
<220> FEATURE:
<221> NAME/KEY: misc_feature
<222> LOCATION: (14)..(14)
<223> OTHER INFORMATION: 2'-O-methyl-adenosine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (29)..(29)
<223> OTHER INFORMATION: LNA [2',4']-locked "ribo"-thymidine
<220> FEATURE:
<221> NAME/KEY: misc_feature
<222> LOCATION: (30)..(30)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked adenosine

<400> SEQUENCE: 34
nnngtagtct tnnnttttnn attggtatnn n                              31

<210> SEQ ID NO 35
<211> LENGTH: 31
```

```
<212> TYPE: DNA
<213> ORGANISM: Artificial Sequence
<220> FEATURE:
<223> OTHER INFORMATION: linear heterodimer with phosphodiester DNA
      linker, ApoC3/ApoB
<220> FEATURE:
<221> NAME/KEY: misc_feature
<222> LOCATION: (1)..(2)
<223> OTHER INFORMATION: LNA [2',4']-locked 5-methyl-cytidine
<220> FEATURE:
<221> NAME/KEY: misc_feature
<222> LOCATION: (3)..(3)
<223> OTHER INFORMATION: 2'-fluoro-ribo-adenosine
<220> FEATURE:
<221> NAME/KEY: misc_feature
<222> LOCATION: (12)..(12)
<223> OTHER INFORMATION: 2'-fluoro-ribo-uridine
<220> FEATURE:
<221> NAME/KEY: misc_feature
<222> LOCATION: (13)..(13)
<223> OTHER INFORMATION: 2'-fluoro-ribo-cytidine
<220> FEATURE:
<221> NAME/KEY: misc_feature
<222> LOCATION: (14)..(14)
<223> OTHER INFORMATION: 2'-fluoro-ribo-adenosine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (29)..(29)
<223> OTHER INFORMATION: LNA [2',4']-locked "ribo"-thymidine
<220> FEATURE:
<221> NAME/KEY: misc_feature
<222> LOCATION: (30)..(30)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked adenosine

<400> SEQUENCE: 35
nnngtagtct tnnnttttnn attggtatnn n                                   31

<210> SEQ ID NO 36
<211> LENGTH: 31
<212> TYPE: DNA
<213> ORGANISM: Artificial Sequence
<220> FEATURE:
<223> OTHER INFORMATION: linear heterodimer with phosphodiester DNA
      linker, ApoC3/ApoB
<220> FEATURE:
<221> NAME/KEY: misc_feature
<222> LOCATION: (2)..(2)
<223> OTHER INFORMATION: LNA [2',3']-locked guanosine
<220> FEATURE:
<221> NAME/KEY: misc_feature
<222> LOCATION: (3)..(4)
<223> OTHER INFORMATION: LNA [2',4']-locked adenosine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (29)..(29)
<223> OTHER INFORMATION: LNA [2',4']-locked "ribo"-thymidine
<220> FEATURE:
```

```
<221> NAME/KEY: misc_feature
<222> LOCATION: (30)..(30)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked adenosine

<400> SEQUENCE: 36
gnnnctgaag ccatttttnn attggtatnn n                             31

<210> SEQ ID NO 37
<211> LENGTH: 31
<212> TYPE: DNA
<213> ORGANISM: Artificial Sequence
<220> FEATURE:
<223> OTHER INFORMATION: linear heterodimer with phosphodiester DNA
      linker, ApoC3/ApoB
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked "ribo"-thymidine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (29)..(29)
<223> OTHER INFORMATION: LNA [2',4']-locked "ribo"-thymidine
<220> FEATURE:
<221> NAME/KEY: misc_feature
<222> LOCATION: (30)..(30)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked adenosine

<400> SEQUENCE: 37
gnactgagaa tannttttnn attggtatnn n                             31

<210> SEQ ID NO 38
<211> LENGTH: 32
<212> TYPE: DNA
<213> ORGANISM: Artificial Sequence
<220> FEATURE:
<223> OTHER INFORMATION: linear heterodimer with phosphodiester DNA
      linker, ApoC3/ApoB
<220> FEATURE:
<221> NAME/KEY: misc_feature
<222> LOCATION: (1)..(2)
<223> OTHER INFORMATION: 2'-O-methyl-uridine
<220> FEATURE:
<221> NAME/KEY: misc_feature
<222> LOCATION: (3)..(3)
<223> OTHER INFORMATION: G-clamp deoxyphenoxazine
<220> FEATURE:
<221> NAME/KEY: misc_feature
<222> LOCATION: (12)..(12)
<223> OTHER INFORMATION: 2'-O-methyl-guanosine
<220> FEATURE:
<221> NAME/KEY: misc_feature
```

```
<222> LOCATION: (13)..(13)
<223> OTHER INFORMATION: 2'-O-methyl-adenosine
<220> FEATURE:
<221> NAME/KEY: misc_feature
<222> LOCATION: (14)..(14)
<223> OTHER INFORMATION: G-clamp deoxyphenoxazine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked 5-methyl-cytidine
<220> FEATURE:
<221> NAME/KEY: misc_feature
<222> LOCATION: (32)..(32)
<223> OTHER INFORMATION: LNA [2',4']-locked "ribo"-thymidine

<400> SEQUENCE: 38
nnnagtgtga tnnnttttnn actgagaata nn                                32

<210> SEQ ID NO 39
<211> LENGTH: 31
<212> TYPE: DNA
<213> ORGANISM: Artificial Sequence
<220> FEATURE:
<223> OTHER INFORMATION: linear heterodimer with phosphodiester DNA
      linker, ApoC3/ApoB
<220> FEATURE:
<221> NAME/KEY: misc_feature
<222> LOCATION: (1)..(2)
<223> OTHER INFORMATION: LNA [2',4']-locked adenosine
<220> FEATURE:
<221> NAME/KEY: misc_feature
<222> LOCATION: (3)..(3)
<223> OTHER INFORMATION: LNA [2',3']-locked guanosine
<220> FEATURE:
<221> NAME/KEY: misc_feature
<222> LOCATION: (12)..(12)
<223> OTHER INFORMATION: LNA [2',4']-locked adenosine
<220> FEATURE:
<221> NAME/KEY: misc_feature
<222> LOCATION: (13)..(14)
<223> OTHER INFORMATION: LNA [2',3']-locked guanosine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (29)..(29)
<223> OTHER INFORMATION: LNA [2',4']-locked "ribo"-thymidine
<220> FEATURE:
<221> NAME/KEY: misc_feature
<222> LOCATION: (30)..(30)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked adenosine

<400> SEQUENCE: 39
nnncaaccta cnnnttttnn attggtatnn n                                 31

<210> SEQ ID NO 40
<211> LENGTH: 19
```

```
<212> TYPE: DNA
<213> ORGANISM: Artificial Sequence
<220> FEATURE:
<223> OTHER INFORMATION: 3'3'-branched homodimer, phosphodiester DNA
      linker, ApoC3
<220> FEATURE:
<221> NAME/KEY: misc_feature
<222> LOCATION: (1)..(2)
<223> OTHER INFORMATION: LNA [2',3']-locked guanosine
<220> FEATURE:
<221> NAME/KEY: misc_feature
<222> LOCATION: (3)..(4)
<223> OTHER INFORMATION: LNA [2',4']-locked adenosine
<220> FEATURE:
<221> NAME/KEY: misc_feature
<222> LOCATION: (19)..(19)
<223> OTHER INFORMATION: doubler triethylenglycol linker

<400> SEQUENCE: 40
nnnnctgaag ccatttttn                                                 19

<210> SEQ ID NO 41
<211> LENGTH: 32
<212> TYPE: DNA
<213> ORGANISM: Artificial Sequence
<220> FEATURE:
<223> OTHER INFORMATION: linear homodimer with 5-propynyl-dC with
      phosphodiester DNA linker, ApoC3
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (4)..(4)
<223> OTHER INFORMATION: 5-propynyl-2'-deoxycytidine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked "ribo"-thymidine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (22)..(22)
<223> OTHER INFORMATION: 5-propynyl-2'-deoxycytidine
<220> FEATURE:
<221> NAME/KEY: misc_feature
<222> LOCATION: (31)..(31)
<223> OTHER INFORMATION: LNA [2',4']-locked 5-methyl-cytidine
<220> FEATURE:
<221> NAME/KEY: misc_feature
<222> LOCATION: (32)..(32)
<223> OTHER INFORMATION: LNA [2',4']-locked "ribo"-thymidine

<400> SEQUENCE: 41
nnantgagaa tannttttnn antgagaata nn                                  32

<210> SEQ ID NO 42
<211> LENGTH: 32
<212> TYPE: DNA
```

<213> ORGANISM: Artificial Sequence
<220> FEATURE:
<223> OTHER INFORMATION: linear homodimer with phosphodiester
      DNA linker, ApoC3
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (4)..(4)
<223> OTHER INFORMATION: 5-propynyl-2'-deoxycytidine
<220> FEATURE:
<221> NAME/KEY: misc_feature
<222> LOCATION: (5)..(5)
<223> OTHER INFORMATION: 5-propynyl-2'-deoxythymidine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked "ribo"-thymidine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (22)..(22)
<223> OTHER INFORMATION: 5-propynyl-2'-deoxycytidine
<220> FEATURE:
<221> NAME/KEY: misc_feature
<222> LOCATION: (23)..(23)
<223> OTHER INFORMATION: 5-propynyl-2'-deoxythymidine
<220> FEATURE:
<221> NAME/KEY: misc_feature
<222> LOCATION: (31)..(31)
<223> OTHER INFORMATION: LNA [2',4']-locked 5-methyl-cytidine
<220> FEATURE:
<221> NAME/KEY: misc_feature
<222> LOCATION: (32)..(32)
<223> OTHER INFORMATION: LNA [2',4']-locked "ribo"-thymidine

<400> SEQUENCE: 42
nnanngagaa tanntttttnn anngagaata nn                                 32

<210> SEQ ID NO 43
<211> LENGTH: 32
<212> TYPE: DNA
<213> ORGANISM: Artificial Sequence
<220> FEATURE:
<223> OTHER INFORMATION: linear homodimer with phosphodiester
      DNA linker, ApoC3
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (4)..(4)
<223> OTHER INFORMATION: 5-propynyl-2'-deoxycytidine
<220> FEATURE:
<221> NAME/KEY: misc_feature

```
<222> LOCATION: (5)..(5)
<223> OTHER INFORMATION: 5-propynyl-2'-deoxythymidine
<220> FEATURE:
<221> NAME/KEY: misc_feature
<222> LOCATION: (11)..(11)
<223> OTHER INFORMATION: 5-propynyl-2'-deoxythymidine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked "ribo"-thymidine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (22)..(22)
<223> OTHER INFORMATION: 5-propynyl-2'-deoxycytidine
<220> FEATURE:
<221> NAME/KEY: misc_feature
<222> LOCATION: (23)..(23)
<223> OTHER INFORMATION: 5-propynyl-2'-deoxythymidine
<220> FEATURE:
<221> NAME/KEY: misc_feature
<222> LOCATION: (29)..(29)
<223> OTHER INFORMATION: 5-propynyl-2'-deoxythymidine
<220> FEATURE:
<221> NAME/KEY: misc_feature
<222> LOCATION: (31)..(31)
<223> OTHER INFORMATION: LNA [2',4']-locked 5-methyl-cytidine
<220> FEATURE:
<221> NAME/KEY: misc_feature
<222> LOCATION: (32)..(32)
<223> OTHER INFORMATION: LNA [2',4']-locked "ribo"-thymidine

<400> SEQUENCE: 43
nnanngagaa nanntttttnn anngagaana nn                                 32

<210> SEQ ID NO 44
<211> LENGTH: 28
<212> TYPE: DNA
<213> ORGANISM: Artificial Sequence
<220> FEATURE:
<223> OTHER INFORMATION: linear homodimer with phosphodiester bonds in
      DNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (16)..(16)
<223> OTHER INFORMATION: LNA [2',3']-locked guanosine
```

```
<220> FEATURE:
<221> NAME/KEY: misc_feature
<222> LOCATION: (17)..(17)
<223> OTHER INFORMATION: LNA [2',4']-locked 5-methyl-cytidine
<220> FEATURE:
<221> NAME/KEY: misc_feature
<222> LOCATION: (26)..(26)
<223> OTHER INFORMATION: LNA [2',4']-locked "ribo"-thymidine
<220> FEATURE:
<221> NAME/KEY: misc_feature
<222> LOCATION: (27)..(27)
<223> OTHER INFORMATION: LNA [2',4']-locked 5-methyl-cytidine
<220> FEATURE:
<221> NAME/KEY: misc_feature
<222> LOCATION: (28)..(28)
<223> OTHER INFORMATION: LNA [2',4']-locked adenosine

<400> SEQUENCE: 44
nnattggtat nnnttnnatt ggtatnnn                                          28

<210> SEQ ID NO 45
<211> LENGTH: 29
<212> TYPE: DNA
<213> ORGANISM: Artificial Sequence
<220> FEATURE:
<223> OTHER INFORMATION: linear homodimer with phosphodiester bonds in
      DNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (17)..(17)
<223> OTHER INFORMATION: LNA [2',3']-locked guanosine
<220> FEATURE:
<221> NAME/KEY: misc_feature
<222> LOCATION: (18)..(18)
<223> OTHER INFORMATION: LNA [2',4']-locked 5-methyl-cytidine
<220> FEATURE:
<221> NAME/KEY: misc_feature
<222> LOCATION: (27)..(27)
<223> OTHER INFORMATION: LNA [2',4']-locked "ribo"-thymidine
<220> FEATURE:
<221> NAME/KEY: misc_feature
<222> LOCATION: (28)..(28)
<223> OTHER INFORMATION: LNA [2',4']-locked 5-methyl-cytidine
<220> FEATURE:
<221> NAME/KEY: misc_feature
<222> LOCATION: (29)..(29)
<223> OTHER INFORMATION: LNA [2',4']-locked adenosine

<400> SEQUENCE: 45
nnattggtat nnntttnnat tggtatnnn                                         29

<210> SEQ ID NO 46
<211> LENGTH: 30
<212> TYPE: DNA
<213> ORGANISM: Artificial Sequence
```

```
<220> FEATURE:
<223> OTHER INFORMATION: linear homodimer with phosphodiester linkages
      in DNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (18)..(18)
<223> OTHER INFORMATION: LNA [2',3']-locked guanosine
<220> FEATURE:
<221> NAME/KEY: misc_feature
<222> LOCATION: (19)..(19)
<223> OTHER INFORMATION: LNA [2',4']-locked 5-methyl-cytidine
<220> FEATURE:
<221> NAME/KEY: misc_feature
<222> LOCATION: (28)..(28)
<223> OTHER INFORMATION: LNA [2',4']-locked "ribo"-thymidine
<220> FEATURE:
<221> NAME/KEY: misc_feature
<222> LOCATION: (29)..(29)
<223> OTHER INFORMATION: LNA [2',4']-locked 5-methyl-cytidine
<220> FEATURE:
<221> NAME/KEY: misc_feature
<222> LOCATION: (30)..(30)
<223> OTHER INFORMATION: LNA [2',4']-locked adenosine

<400> SEQUENCE: 46
nnattggtat nnnttttnna ttggtatnnn                                     30

<210> SEQ ID NO 47
<211> LENGTH: 31
<212> TYPE: DNA
<213> ORGANISM: Artificial Sequence
<220> FEATURE:
<223> OTHER INFORMATION: linear homodimer with phosphodiester bonds in
      DNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (19)..(19)
```

<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (29)..(29)
<223> OTHER INFORMATION: LNA [2',4']-locked "ribo"-thymidine
<220> FEATURE:
<221> NAME/KEY: misc_feature
<222> LOCATION: (30)..(30)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked adenosine

<400> SEQUENCE: 47
nnattggtat nnntttttnn attggtatnn n                                31

<210> SEQ ID NO 48
<211> LENGTH: 32
<212> TYPE: DNA
<213> ORGANISM: Artificial Sequence
<220> FEATURE:
<223> OTHER INFORMATION: linear homodimer with 7 phosphodiester linkages
      in DNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (20)..(20)
<223> OTHER INFORMATION: LNA [2',3']-locked guanosine
<220> FEATURE:
<221> NAME/KEY: misc_feature
<222> LOCATION: (21)..(21)
<223> OTHER INFORMATION: LNA [2',4']-locked 5-methyl-cytidine
<220> FEATURE:
<221> NAME/KEY: misc_feature
<222> LOCATION: (30)..(30)
<223> OTHER INFORMATION: LNA [2',4']-locked "ribo"-thymidine
<220> FEATURE:
<221> NAME/KEY: misc_feature
<222> LOCATION: (31)..(31)
<223> OTHER INFORMATION: LNA [2',4']-locked 5-methyl-cytidine
<220> FEATURE:
<221> NAME/KEY: misc_feature
<222> LOCATION: (32)..(32)
<223> OTHER INFORMATION: LNA [2',4']-locked adenosine

<400> SEQUENCE: 48
nnattggtat nnntttttn nattggtatn nn                                32

<210> SEQ ID NO 49
<211> LENGTH: 33
<212> TYPE: DNA

```
<213> ORGANISM: Artificial Sequence
<220> FEATURE:
<223> OTHER INFORMATION: linear homodimer with 8 phosphodiester bonds in
      DNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (21)..(21)
<223> OTHER INFORMATION: LNA [2',3']-locked guanosine
<220> FEATURE:
<221> NAME/KEY: misc_feature
<222> LOCATION: (22)..(22)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked "ribo"-thymidine
<220> FEATURE:
<221> NAME/KEY: misc_feature
<222> LOCATION: (32)..(32)
<223> OTHER INFORMATION: LNA [2',4']-locked 5-methyl-cytidine
<220> FEATURE:
<221> NAME/KEY: misc_feature
<222> LOCATION: (33)..(33)
<223> OTHER INFORMATION: LNA [2',4']-locked adenosine

<400> SEQUENCE: 49
nnattggtat nnntttttttt nnattggtat nnn                                33

<210> SEQ ID NO 50
<211> LENGTH: 33
<212> TYPE: DNA
<213> ORGANISM: Artificial Sequence
<220> FEATURE:
<223> OTHER INFORMATION: linear homodimer with phosphorothioate bonds in
      DNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
```

```
<222> LOCATION: (21)..(21)
<223> OTHER INFORMATION: LNA [2',3']-locked guanosine
<220> FEATURE:
<221> NAME/KEY: misc_feature
<222> LOCATION: (22)..(22)
<223> OTHER INFORMATION: LNA [2',4']-locked 5-methyl-cytidine
<220> FEATURE:
<221> NAME/KEY: misc_feature
<222> LOCATION: (31)..(31)
<223> OTHER INFORMATION: LNA [2',4']-locked "ribo"-thymidine
<220> FEATURE:
<221> NAME/KEY: misc_feature
<222> LOCATION: (32)..(32)
<223> OTHER INFORMATION: LNA [2',4']-locked 5-methyl-cytidine
<220> FEATURE:
<221> NAME/KEY: misc_feature
<222> LOCATION: (33)..(33)
<223> OTHER INFORMATION: LNA [2',4']-locked adenosine

<400> SEQUENCE: 50
nnattggtat nnntttttt nnattggtat nnn                              33

<210> SEQ ID NO 51
<211> LENGTH: 27
<212> TYPE: DNA
<213> ORGANISM: Artificial Sequence
<220> FEATURE:
<223> OTHER INFORMATION: linear homodimer with phosphorothioate bonds
      in RNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (15)..(15)
<223> OTHER INFORMATION: LNA [2',3']-locked guanosine
<220> FEATURE:
<221> NAME/KEY: misc_feature
<222> LOCATION: (16)..(16)
<223> OTHER INFORMATION: LNA [2',4']-locked 5-methyl-cytidine
<220> FEATURE:
<221> NAME/KEY: misc_feature
<222> LOCATION: (25)..(25)
<223> OTHER INFORMATION: LNA [2',4']-locked "ribo"-thymidine
<220> FEATURE:
<221> NAME/KEY: misc_feature
<222> LOCATION: (26)..(26)
<223> OTHER INFORMATION: LNA [2',4']-locked 5-methyl-cytidine
<220> FEATURE:
<221> NAME/KEY: misc_feature
<222> LOCATION: (27)..(27)
<223> OTHER INFORMATION: LNA [2',4']-locked adenosine

<400> SEQUENCE: 51
nnattggtat nnnunnattg gtatnnn                                    27

<210> SEQ ID NO 52
<211> LENGTH: 28
```

```
<212> TYPE: DNA
<213> ORGANISM: Artificial Sequence
<220> FEATURE:
<223> OTHER INFORMATION: linear homodimer with phosphorothioate bonds
      in RNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (16)..(16)
<223> OTHER INFORMATION: LNA [2',3']-locked guanosine
<220> FEATURE:
<221> NAME/KEY: misc_feature
<222> LOCATION: (17)..(17)
<223> OTHER INFORMATION: LNA [2',4']-locked 5-methyl-cytidine
<220> FEATURE:
<221> NAME/KEY: misc_feature
<222> LOCATION: (26)..(26)
<223> OTHER INFORMATION: LNA [2',4']-locked "ribo"-thymidine
<220> FEATURE:
<221> NAME/KEY: misc_feature
<222> LOCATION: (27)..(27)
<223> OTHER INFORMATION: LNA [2',4']-locked 5-methyl-cytidine
<220> FEATURE:
<221> NAME/KEY: misc_feature
<222> LOCATION: (28)..(28)
<223> OTHER INFORMATION: LNA [2',4']-locked adenosine

<400> SEQUENCE: 52
nnattggtat nnnuunnatt ggtatnnn                                          28

<210> SEQ ID NO 53
<211> LENGTH: 29
<212> TYPE: DNA
<213> ORGANISM: Artificial Sequence
<220> FEATURE:
<223> OTHER INFORMATION: linear homodimer with phosphorothioate
      bonds in RNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
```

```
<221> NAME/KEY: misc_feature
<222> LOCATION: (17)..(17)
<223> OTHER INFORMATION: LNA [2',3']-locked guanosine
<220> FEATURE:
<221> NAME/KEY: misc_feature
<222> LOCATION: (18)..(18)
<223> OTHER INFORMATION: LNA [2',4']-locked 5-methyl-cytidine
<220> FEATURE:
<221> NAME/KEY: misc_feature
<222> LOCATION: (27)..(27)
<223> OTHER INFORMATION: LNA [2',4']-locked "ribo"-thymidine
<220> FEATURE:
<221> NAME/KEY: misc_feature
<222> LOCATION: (28)..(28)
<223> OTHER INFORMATION: LNA [2',4']-locked 5-methyl-cytidine
<220> FEATURE:
<221> NAME/KEY: misc_feature
<222> LOCATION: (29)..(29)
<223> OTHER INFORMATION: LNA [2',4']-locked adenosine

<400> SEQUENCE: 53
nnattggtat nnnuuunnat tggtatnnn                              29

<210> SEQ ID NO 54
<211> LENGTH: 30
<212> TYPE: DNA
<213> ORGANISM: Artificial Sequence
<220> FEATURE:
<223> OTHER INFORMATION: linear homodimer with phosphorothioate
      linkages in RNA linker, ApoB
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (11)..(11)
<223> OTHER INFORMATION: LNA [2',4']-locked "ribo"-thymidine
<220> FEATURE:
<221> NAME/KEY: misc_feature
<222> LOCATION: (12)..(12)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (18)..(18)
<223> OTHER INFORMATION: LNA [2',3']-locked guanosine
<220> FEATURE:
<221> NAME/KEY: misc_feature
<222> LOCATION: (19)..(19)
<223> OTHER INFORMATION: LNA [2',4']-locked 5-methyl-cytidine
<220> FEATURE:
<221> NAME/KEY: misc_feature
<222> LOCATION: (28)..(28)
<223> OTHER INFORMATION: LNA [2',4']-locked "ribo"-thymidine
<220> FEATURE:
<221> NAME/KEY: misc_feature
<222> LOCATION: (29)..(29)
<223> OTHER INFORMATION: LNA [2',4']-locked 5-methyl-cytidine
<220> FEATURE:
<221> NAME/KEY: misc_feature
<222> LOCATION: (30)..(30)
<223> OTHER INFORMATION: LNA [2',4']-locked adenosine

<400> SEQUENCE: 54
nnattggtat nnnuuuunna ttggtatnnn                             30

<210> SEQ ID NO 55
```

```
<211> LENGTH: 14
<212> TYPE: DNA
<213> ORGANISM: Artificial Sequence
<220> FEATURE:
<223> OTHER INFORMATION: 2LNA-1me-8DNA-1me-2LNA gapmer (monomeric),
      fully phosphorothioated, ApoC3
<220> FEATURE:
<221> NAME/KEY: misc_feature
<222> LOCATION: (1)..(2)
<223> OTHER INFORMATION: LNA [2',4']-locked 5-methyl-cytidine
<220> FEATURE:
<221> NAME/KEY: misc_feature
<222> LOCATION: (3)..(3)
<223> OTHER INFORMATION: 2'-O-methyl-adenosine
<220> FEATURE:
<221> NAME/KEY: misc_feature
<222> LOCATION: (12)..(12)
<223> OTHER INFORMATION: 2'-O-methyl-uridine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked adenosine

<400> SEQUENCE: 55
nnngtagtct tnnn                                                       14

<210> SEQ ID NO 56
<211> LENGTH: 14
<212> TYPE: DNA
<213> ORGANISM: Artificial Sequence
<220> FEATURE:
<223> OTHER INFORMATION: 2LNA-1me-8DNA-3me gapmer (monomeric),
      fully phosphorothioated, ApoC3
<220> FEATURE:
<221> NAME/KEY: misc_feature
<222> LOCATION: (1)..(2)
<223> OTHER INFORMATION: LNA [2',4']-locked 5-methyl-cytidine
<220> FEATURE:
<221> NAME/KEY: misc_feature
<222> LOCATION: (3)..(3)
<223> OTHER INFORMATION: 2'-O-methyl-adenosine
<220> FEATURE:
<221> NAME/KEY: misc_feature
<222> LOCATION: (12)..(12)
<223> OTHER INFORMATION: 2'-O-methyl-uridine
<220> FEATURE:
<221> NAME/KEY: misc_feature
<222> LOCATION: (13)..(13)
<223> OTHER INFORMATION: 2'-O-methyl-cytidine
<220> FEATURE:
<221> NAME/KEY: misc_feature
<222> LOCATION: (14)..(14)
<223> OTHER INFORMATION: 2'-O-methyl-adenosine

<400> SEQUENCE: 56
nnngtagtct tnnn                                                       14

<210> SEQ ID NO 57
<211> LENGTH: 14
<212> TYPE: DNA
<213> ORGANISM: Artificial Sequence
<220> FEATURE:
<223> OTHER INFORMATION: 2LNA-1fluoro-8DNA-3fluoro gapmer (monomeric),
      fully phosphorothioated, ApoC3
<220> FEATURE:
<221> NAME/KEY: misc_feature
<222> LOCATION: (1)..(2)
<223> OTHER INFORMATION: LNA [2',4']-locked 5-methyl-cytidine
<220> FEATURE:
<221> NAME/KEY: misc_feature
<222> LOCATION: (3)..(3)
```

-continued

```
<223> OTHER INFORMATION: 2'-fluoro-ribo-adenosine
<220> FEATURE:
<221> NAME/KEY: misc_feature
<222> LOCATION: (12)..(12)
<223> OTHER INFORMATION: 2'-fluoro-ribo-uridine
<220> FEATURE:
<221> NAME/KEY: misc_feature
<222> LOCATION: (13)..(13)
<223> OTHER INFORMATION: 2'-fluoro-ribo-cytidine
<220> FEATURE:
<221> NAME/KEY: misc_feature
<222> LOCATION: (14)..(14)
<223> OTHER INFORMATION: 2'-fluoro-ribo-adenosine

<400> SEQUENCE: 57
nnngtagtct tnnn                                                     14

<210> SEQ ID NO 58
<211> LENGTH: 14
<212> TYPE: DNA
<213> ORGANISM: Artificial Sequence
<220> FEATURE:
<223> OTHER INFORMATION: 4LNA-10DNA antisense (monomeric), fully
      phosphorothioated, ApoC3
<220> FEATURE:
<221> NAME/KEY: misc_feature
<222> LOCATION: (1)..(2)
<223> OTHER INFORMATION: LNA [2',3']-locked guanosine
<220> FEATURE:
<221> NAME/KEY: misc_feature
<222> LOCATION: (3)..(4)
<223> OTHER INFORMATION: LNA [2',4']-locked adenosine

<400> SEQUENCE: 58
nnnnctgaag ccat                                                     14

<210> SEQ ID NO 59
<211> LENGTH: 31
<212> TYPE: DNA
<213> ORGANISM: Artificial Sequence
<220> FEATURE:
<223> OTHER INFORMATION: fully phosphothioated, ApoC3/ApoB ASO
      heterodimer
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked "ribo"-thymidine
<220> FEATURE:
<221> NAME/KEY: misc_feature
<222> LOCATION: (19)..(19)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked 5-methyl-cytidine
<220> FEATURE:
<221> NAME/KEY: misc_feature
<222> LOCATION: (29)..(29)
<223> OTHER INFORMATION: LNA [2',4']-locked "ribo"-thymidine
<220> FEATURE:
<221> NAME/KEY: misc_feature
<222> LOCATION: (30)..(30)
<223> OTHER INFORMATION: LNA [2',4']-locked 5-methyl-cytidine
```

```
<220> FEATURE:
<221> NAME/KEY: misc_feature
<222> LOCATION: (31)..(31)
<223> OTHER INFORMATION: LNA [2',4']-locked adenosine

<400> SEQUENCE: 59
nnactgagaa tanntttnn attggtatnn n                                           31

<210> SEQ ID NO 60
<211> LENGTH: 28
<212> TYPE: DNA
<213> ORGANISM: Artificial Sequence
<220> FEATURE:
<223> OTHER INFORMATION: ApoC3/ApoB ASO heterodimer linked with PEG-6
<220> FEATURE:
<221> NAME/KEY: misc_feature
<222> LOCATION: (1)..(1)
<223> OTHER INFORMATION: LNA [2',3']-locked guanosine
<220> FEATURE:
<221> NAME/KEY: misc_feature
<222> LOCATION: (2)..(2)
<223> OTHER INFORMATION: LNA [2',4']-locked 5-methyl-cytidine
<220> FEATURE:
<221> NAME/KEY: misc_feature
<222> LOCATION: (13)..(13)
<223> OTHER INFORMATION: LNA [2',4']-locked 5-methyl-cytidine
<220> FEATURE:
<221> NAME/KEY: misc_feature
<222> LOCATION: (14)..(14)
<223> OTHER INFORMATION: LNA [2',4']-locked "ribo"-thymidine
<220> FEATURE:
<221> NAME/KEY: misc_feature
<222> LOCATION: (15)..(15)
<223> OTHER INFORMATION: HEG (---O(CH2)2-O[(CH2)2-O]4-(CH2)2-O----)
<220> FEATURE:
<221> NAME/KEY: misc_feature
<222> LOCATION: (16)..(16)
<223> OTHER INFORMATION: LNA [2',3']-locked guanosine
<220> FEATURE:
<221> NAME/KEY: misc_feature
<222> LOCATION: (17)..(17)
<223> OTHER INFORMATION: LNA [2',4']-locked 5-methyl-cytidine
<220> FEATURE:
<221> NAME/KEY: misc_feature
<222> LOCATION: (26)..(26)
<223> OTHER INFORMATION: LNA [2',4']-locked "ribo"-thymidine
<220> FEATURE:
<221> NAME/KEY: misc_feature
<222> LOCATION: (27)..(27)
<223> OTHER INFORMATION: LNA [2',4']-locked 5-methyl-cytidine
<220> FEATURE:
<221> NAME/KEY: misc_feature
<222> LOCATION: (28)..(28)
<223> OTHER INFORMATION: LNA [2',4']-locked adenosine

<400> SEQUENCE: 60
nnactgagaa tannnnnatt ggtatnnn                                              28

<210> SEQ ID NO 61
<211> LENGTH: 31
<212> TYPE: DNA
<213> ORGANISM: Artificial Sequence
<220> FEATURE:
<223> OTHER INFORMATION: Unmodified version of SEQ ID NO: 2

<400> SEQUENCE: 61
aagcaaccta caggtttaag caacctacag g                                          31

<210> SEQ ID NO 62
<211> LENGTH: 29
<212> TYPE: DNA
<213> ORGANISM: Artificial Sequence
<220> FEATURE:
```

```
<223> OTHER INFORMATION: Unmodified version of SEQ ID NO: 3
<220> FEATURE:
<221> NAME/KEY: misc_feature
<222> LOCATION: (15)..(15)
<223> OTHER INFORMATION: Triethyenglycol disulfide linker

<400> SEQUENCE: 62
aagcaaccta caggnaagca acctacagg                                           29

<210> SEQ ID NO 63
<211> LENGTH: 19
<212> TYPE: DNA
<213> ORGANISM: Artificial Sequence
<220> FEATURE:
<223> OTHER INFORMATION: Unmodified version of SEQ ID NO: 4
<220> FEATURE:
<221> NAME/KEY: misc_feature
<222> LOCATION: (19)..(19)
<223> OTHER INFORMATION: Triethylenglycol disulfide linker

<400> SEQUENCE: 63
aagcaaccta caggttttn                                                      19

<210> SEQ ID NO 64
<211> LENGTH: 16
<212> TYPE: DNA
<213> ORGANISM: Artificial Sequence
<220> FEATURE:
<223> OTHER INFORMATION: Unmodified version of SEQ ID NO: 5
<220> FEATURE:
<221> NAME/KEY: misc_feature
<222> LOCATION: (15)..(15)
<223> OTHER INFORMATION: Triethyleneglycol disulfide linker
<220> FEATURE:
<221> NAME/KEY: misc_feature
<222> LOCATION: (16)..(16)
<223> OTHER INFORMATION: Doubler triethyleneglycol linker

<400> SEQUENCE: 64
aagcaaccta caggnn                                                         16

<210> SEQ ID NO 65
<211> LENGTH: 31
<212> TYPE: DNA
<213> ORGANISM: Artificial Sequence
<220> FEATURE:
<223> OTHER INFORMATION: Unmodified version of SEQ ID NO: 6

<400> SEQUENCE: 65
aagcaacctt caggtttaag caaccttcag g                                        31

<210> SEQ ID NO 66
<211> LENGTH: 30
<212> TYPE: DNA
<213> ORGANISM: Artificial Sequence
<220> FEATURE:
<223> OTHER INFORMATION: Unmodified version of SEQ ID NO: 7
<220> FEATURE:
<221> NAME/KEY: misc_feature
<222> LOCATION: (19)..(19)
<223> OTHER INFORMATION: 5-methyl-cytosine
<220> FEATURE:
<221> NAME/KEY: misc_feature
<222> LOCATION: (29)..(29)
<223> OTHER INFORMATION: 5-methyl-cytosine

<400> SEQUENCE: 66
aagcaacctt caggtttgna ttggtattna                                          30
```

-continued

```
<210> SEQ ID NO 67
<211> LENGTH: 29
<212> TYPE: DNA
<213> ORGANISM: Artificial Sequence
<220> FEATURE:
<223> OTHER INFORMATION: Unmodified version of SEQ ID NO: 8
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (18)..(19)
<223> OTHER INFORMATION: 5-methyl-cytosine
<220> FEATURE:
<221> NAME/KEY: misc_feature
<222> LOCATION: (27)..(27)
<223> OTHER INFORMATION: 5-methyl-cytosine

<400> SEQUENCE: 67
gnattggtat tnattttnnt cggcctntg                                         29

<210> SEQ ID NO 68
<211> LENGTH: 14
<212> TYPE: DNA
<213> ORGANISM: Artificial Sequence
<220> FEATURE:
<223> OTHER INFORMATION: Unmodified version of SEQ ID NO: 9
<220> FEATURE:
<221> NAME/KEY: misc_feature
<222> LOCATION: (1)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine

<400> SEQUENCE: 68
nntcttcggc cntg                                                         14

<210> SEQ ID NO 69
<211> LENGTH: 13
<212> TYPE: DNA
<213> ORGANISM: Artificial Sequence
<220> FEATURE:
<223> OTHER INFORMATION: Unmodified version of SEQ ID NO: 10
<220> FEATURE:
<221> NAME/KEY: misc_feature
<222> LOCATION: (2)..(3)
<223> OTHER INFORMATION: 5-methyl-cytosine
<220> FEATURE:
<221> NAME/KEY: misc_feature
<222> LOCATION: (11)..(11)
<223> OTHER INFORMATION: 5-methyl-cytosine

<400> SEQUENCE: 69
tnntcggcct ntg                                                          13

<210> SEQ ID NO 70
<211> LENGTH: 12
<212> TYPE: DNA
<213> ORGANISM: Artificial Sequence
<220> FEATURE:
<223> OTHER INFORMATION: Unmodified version of SEQ ID NO: 11
<220> FEATURE:
<221> NAME/KEY: misc_feature
<222> LOCATION: (2)..(2)
<223> OTHER INFORMATION: 5-methyl-cytosine
```

```
<400> SEQUENCE: 70
tnttcggccc tg                                                            12

<210> SEQ ID NO 71
<211> LENGTH: 12
<212> TYPE: DNA
<213> ORGANISM: Artificial Sequence
<220> FEATURE:
<223> OTHER INFORMATION: Unmodified version of SEQ ID NO: 12
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (5)..(5)
<223> OTHER INFORMATION: 5-methyl-cytosine

<400> SEQUENCE: 71
tnttnggccc tg                                                            12

<210> SEQ ID NO 72
<211> LENGTH: 13
<212> TYPE: DNA
<213> ORGANISM: Artificial Sequence
<220> FEATURE:
<223> OTHER INFORMATION: Unmodified version of SEQ ID NO: 13
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine

<400> SEQUENCE: 72
gnattggtat tna                                                           13

<210> SEQ ID NO 73
<211> LENGTH: 14
<212> TYPE: DNA
<213> ORGANISM: Artificial Sequence
<220> FEATURE:
<223> OTHER INFORMATION: Unmodified version of SEQ ID NO: 14

<400> SEQUENCE: 73
aagcaacctt cagg                                                          14

<210> SEQ ID NO 74
<211> LENGTH: 32
<212> TYPE: DNA
<213> ORGANISM: Artificial Sequence
<220> FEATURE:
<223> OTHER INFORMATION: Unmodified version of SEQ ID NO: 15
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (13)..(13)
<223> OTHER INFORMATION: 5-methyl-cytosine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (31)..(31)
<223> OTHER INFORMATION: 5-methyl-cytosine
```

-continued

<400> SEQUENCE: 74
gnactgagaa tantttttgn actgagaata nt                                    32

<210> SEQ ID NO 75
<211> LENGTH: 32
<212> TYPE: DNA
<213> ORGANISM: Artificial Sequence
<220> FEATURE:
<223> OTHER INFORMATION: Unmodified version of SEQ ID NO: 16
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (13)..(13)
<223> OTHER INFORMATION: 5-methyl-cytosine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (31)..(31)
<223> OTHER INFORMATION: 5-methyl-cytosine

<400> SEQUENCE: 75
gnactgagaa tantttttgn actgagaata nt                                    32

<210> SEQ ID NO 76
<211> LENGTH: 19
<212> TYPE: DNA
<213> ORGANISM: Artificial Sequence
<220> FEATURE:
<223> OTHER INFORMATION: Unmodified version of SEQ ID NO: 17
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (13)..(13)
<223> OTHER INFORMATION: 5-methyl-cytosine
<220> FEATURE:
<221> NAME/KEY: misc_feature
<222> LOCATION: (19)..(19)
<223> OTHER INFORMATION: Doubler triethylenglycol linker

<400> SEQUENCE: 76
gnactgagaa tanttttttn                                                  19

<210> SEQ ID NO 77
<211> LENGTH: 30
<212> TYPE: DNA
<213> ORGANISM: Artificial Sequence
<220> FEATURE:
<223> OTHER INFORMATION: Unmodified version of SEQ ID NO: 18
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (19)..(19)
<223> OTHER INFORMATION: 5-methyl-cytosine
<220> FEATURE:
<221> NAME/KEY: misc_feature
<222> LOCATION: (29)..(29)

<223> OTHER INFORMATION: 5-methyl-cytosine

<400> SEQUENCE: 77
gnattggtat tnattttgna ttggtattna                                    30

<210> SEQ ID NO 78
<211> LENGTH: 30
<212> TYPE: DNA
<213> ORGANISM: Artificial Sequence
<220> FEATURE:
<223> OTHER INFORMATION: Unmodified version of SEQ ID NO: 19
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (19)..(19)
<223> OTHER INFORMATION: 5-methyl-cytosine
<220> FEATURE:
<221> NAME/KEY: misc_feature
<222> LOCATION: (29)..(29)
<223> OTHER INFORMATION: 5-methyl-cytosine

<400> SEQUENCE: 78
gnattggtat tnattttgna ttggtattna                                    30

<210> SEQ ID NO 79
<211> LENGTH: 18
<212> TYPE: DNA
<213> ORGANISM: Artificial Sequence
<220> FEATURE:
<223> OTHER INFORMATION: Unmodified version of SEQ ID NO: 20
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (18)..(18)
<223> OTHER INFORMATION: Doubler triethylenglycol linker

<400> SEQUENCE: 79
gnattggtat tnattttn                                                 18

<210> SEQ ID NO 80
<211> LENGTH: 31
<212> TYPE: DNA
<213> ORGANISM: Artificial Sequence
<220> FEATURE:
<223> OTHER INFORMATION: Unmodified version of SEQ ID NO: 21
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (13)..(13)
<223> OTHER INFORMATION: 5-methyl-cytosine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature

```
<222> LOCATION: (30)..(30)
<223> OTHER INFORMATION: 5-methyl-cytosine

<400> SEQUENCE: 80
gnactgagaa tantttttgn attggtattn a                                    31

<210> SEQ ID NO 81
<211> LENGTH: 31
<212> TYPE: DNA
<213> ORGANISM: Artificial Sequence
<220> FEATURE:
<223> OTHER INFORMATION: Unmodified version of SEQ ID NO: 22
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (19)..(19)
<223> OTHER INFORMATION: 5-methyl-cytosine
<220> FEATURE:
<221> NAME/KEY: misc_feature
<222> LOCATION: (30)..(30)
<223> OTHER INFORMATION: 5-methyl-cytosine

<400> SEQUENCE: 81
gnattggtat tnattttgna ctgagaatan t                                    31

<210> SEQ ID NO 82
<211> LENGTH: 30
<212> TYPE: DNA
<213> ORGANISM: Artificial Sequence
<220> FEATURE:
<223> OTHER INFORMATION: Unmodified version of SEQ ID NO: 23
<220> FEATURE:
<221> NAME/KEY: misc_feature
<222> LOCATION: (11)..(11)
<223> OTHER INFORMATION: 5-methyl-cytosine
<220> FEATURE:
<221> NAME/KEY: misc_feature
<222> LOCATION: (18)..(18)
<223> OTHER INFORMATION: 5-methyl-cytosine
<220> FEATURE:
<221> NAME/KEY: misc_feature
<222> LOCATION: (28)..(28)
<223> OTHER INFORMATION: 5-methyl-cytosine

<400> SEQUENCE: 82
ggcaagcatc ntgttttnaa tccatggnag                                      30

<210> SEQ ID NO 83
<211> LENGTH: 31
<212> TYPE: DNA
<213> ORGANISM: Artificial Sequence
<220> FEATURE:
<223> OTHER INFORMATION: Unmodified version of SEQ ID NO: 24
<220> FEATURE:
<221> NAME/KEY: misc_feature
<222> LOCATION: (11)..(11)
<223> OTHER INFORMATION: 5-methyl-cytosine
<220> FEATURE:
<221> NAME/KEY: misc_feature
<222> LOCATION: (19)..(19)
<223> OTHER INFORMATION: 5-methyl-cytosine

<400> SEQUENCE: 83
ggcaagcatc ntgttttgng tgcataaatt g                                    31
```

```
<210> SEQ ID NO 84
<211> LENGTH: 30
<212> TYPE: DNA
<213> ORGANISM: Artificial Sequence
<220> FEATURE:
<223> OTHER INFORMATION: Unmodified version of SEQ ID NO: 25
<220> FEATURE:
<221> NAME/KEY: misc_feature
<222> LOCATION: (11)..(11)
<223> OTHER INFORMATION: 5-methyl-cytosine
<220> FEATURE:
<221> NAME/KEY: misc_feature
<222> LOCATION: (19)..(19)
<223> OTHER INFORMATION: 5-methyl-cytosine
<220> FEATURE:
<221> NAME/KEY: misc_feature
<222> LOCATION: (29)..(29)
<223> OTHER INFORMATION: 5-methyl-cytosine

<400> SEQUENCE: 84
ggcaagcatc ntgttttgna ttggtattna                                  30

<210> SEQ ID NO 85
<211> LENGTH: 48
<212> TYPE: DNA
<213> ORGANISM: Artificial Sequence
<220> FEATURE:
<223> OTHER INFORMATION: Unmodified version of SEQ ID NO: 26
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (19)..(19)
<223> OTHER INFORMATION: 5-methyl-cytosine
<220> FEATURE:
<221> NAME/KEY: misc_feature
<222> LOCATION: (30)..(30)
<223> OTHER INFORMATION: 5-methyl-cytosine
<220> FEATURE:
<221> NAME/KEY: misc_feature
<222> LOCATION: (46)..(46)
<223> OTHER INFORMATION: 5-methyl-cytosine

<400> SEQUENCE: 85
gnattggtat tnattttgna ctgagaatan tttttggcaa gcatcntg              48

<210> SEQ ID NO 86
<211> LENGTH: 13
<212> TYPE: DNA
<213> ORGANISM: Artificial Sequence
<220> FEATURE:
<223> OTHER INFORMATION: Unmodified version of SEQ ID NO: 27
<220> FEATURE:
<221> NAME/KEY: misc_feature
<222> LOCATION: (11)..(11)
<223> OTHER INFORMATION: 5-methyl-cytosine

<400> SEQUENCE: 86
ggcaagcatc ntg                                                    13

<210> SEQ ID NO 87
<211> LENGTH: 13
<212> TYPE: DNA
<213> ORGANISM: Artificial Sequence
<220> FEATURE:
<223> OTHER INFORMATION: Unmodified version of SEQ ID NO: 28
```

```
<220> FEATURE:
<221> NAME/KEY: misc_feature
<222> LOCATION: (1)..(1)
<223> OTHER INFORMATION: 5-methyl-cytosine
<220> FEATURE:
<221> NAME/KEY: misc_feature
<222> LOCATION: (11)..(11)
<223> OTHER INFORMATION: 5-methyl-cytosine

<400> SEQUENCE: 87
naatccatgg nag                                                        13

<210> SEQ ID NO 88
<211> LENGTH: 14
<212> TYPE: DNA
<213> ORGANISM: Artificial Sequence
<220> FEATURE:
<223> OTHER INFORMATION: Unmodified version of SEQ ID NO: 29
<220> FEATURE:
<221> NAME/KEY: misc_feature
<222> LOCATION: (2)..(2)
<223> OTHER INFORMATION: 5-methyl-cytosine

<400> SEQUENCE: 88
gngtgcataa attg                                                       14

<210> SEQ ID NO 89
<211> LENGTH: 14
<212> TYPE: DNA
<213> ORGANISM: Artificial Sequence
<220> FEATURE:
<223> OTHER INFORMATION: Unmodified version of SEQ ID NO: 30
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (13)..(13)
<223> OTHER INFORMATION: 5-methyl-cytosine

<400> SEQUENCE: 89
gnactgagaa tant                                                       14

<210> SEQ ID NO 90
<211> LENGTH: 13
<212> TYPE: DNA
<213> ORGANISM: Artificial Sequence
<220> FEATURE:
<223> OTHER INFORMATION: Unmodified version of SEQ ID NO: 31
<220> FEATURE:
<221> NAME/KEY: misc_feature
<222> LOCATION: (1)..(1)
<223> OTHER INFORMATION: 5-methyl-cytosine

<400> SEQUENCE: 90
ngtctatgta tag                                                        13

<210> SEQ ID NO 91
<211> LENGTH: 14
<212> TYPE: DNA
<213> ORGANISM: Artificial Sequence
<220> FEATURE:
<223> OTHER INFORMATION: Unmodified version of SEQ ID NO: 32
<220> FEATURE:
<221> NAME/KEY: misc_feature
<222> LOCATION: (3)..(3)
<223> OTHER INFORMATION: G-clamp deoxyphenoxazine
<220> FEATURE:
<221> NAME/KEY: misc_feature
<222> LOCATION: (14)..(14)
```

<223> OTHER INFORMATION: G-clamp deoxyphenoxazine

<400> SEQUENCE: 91
uunagtgtga tgan                                                           14

<210> SEQ ID NO 92
<211> LENGTH: 31
<212> TYPE: DNA
<213> ORGANISM: Artificial Sequence
<220> FEATURE:
<223> OTHER INFORMATION: Unmodified version of SEQ ID NO: 33
<220> FEATURE:
<221> NAME/KEY: misc_feature
<222> LOCATION: (1)..(2)
<223> OTHER INFORMATION: 5-methyl-cytosine
<220> FEATURE:
<221> NAME/KEY: misc_feature
<222> LOCATION: (13)..(13)
<223> OTHER INFORMATION: 5-methyl-cytosine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (30)..(30)
<223> OTHER INFORMATION: 5-methyl-cytosine

<400> SEQUENCE: 92
nnagtagtct tunattttgn attggtattn a                                        31

<210> SEQ ID NO 93
<211> LENGTH: 31
<212> TYPE: DNA
<213> ORGANISM: Artificial Sequence
<220> FEATURE:
<223> OTHER INFORMATION: Unmodified version of SEQ ID NO: 34
<220> FEATURE:
<221> NAME/KEY: misc_feature
<222> LOCATION: (1)..(2)
<223> OTHER INFORMATION: 5-methyl-cytosine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (30)..(30)
<223> OTHER INFORMATION: 5-methyl-cytosine

<400> SEQUENCE: 93
nnagtagtct tucattttgn attggtattn a                                        31

<210> SEQ ID NO 94
<211> LENGTH: 31
<212> TYPE: DNA
<213> ORGANISM: Artificial Sequence
<220> FEATURE:
<223> OTHER INFORMATION: Unmodified version of SEQ ID NO: 35
<220> FEATURE:
<221> NAME/KEY: misc_feature
<222> LOCATION: (1)..(2)
<223> OTHER INFORMATION: 5-methyl-cytosine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (30)..(30)
<223> OTHER INFORMATION: 5-methyl-cytosine

<400> SEQUENCE: 94
nnagtagtct tucattttgn attggtattn a                                    31

<210> SEQ ID NO 95
<211> LENGTH: 31
<212> TYPE: DNA
<213> ORGANISM: Artificial Sequence
<220> FEATURE:
<223> OTHER INFORMATION: Unmodified version of SEQ ID NO: 36
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (30)..(30)
<223> OTHER INFORMATION: 5-methyl-cytosine

<400> SEQUENCE: 95
ggaactgaag ccattttgn attggtattn a                                     31

<210> SEQ ID NO 96
<211> LENGTH: 31
<212> TYPE: DNA
<213> ORGANISM: Artificial Sequence
<220> FEATURE:
<223> OTHER INFORMATION: Unmodified version of SEQ ID NO: 37
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (13)..(13)
<223> OTHER INFORMATION: 5-methyl-cytosine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (30)..(30)
<223> OTHER INFORMATION: 5-methyl-cytosine

<400> SEQUENCE: 96
gnactgagaa tantttttgn attggtattn a                                    31

<210> SEQ ID NO 97
<211> LENGTH: 32
<212> TYPE: DNA
<213> ORGANISM: Artificial Sequence
<220> FEATURE:
<223> OTHER INFORMATION: Unmodified version of SEQ ID NO: 38
<220> FEATURE:
<221> NAME/KEY: misc_feature
<222> LOCATION: (3)..(3)
<223> OTHER INFORMATION: G-clamp deoxyphenoxazine
<220> FEATURE:
<221> NAME/KEY: misc_feature
<222> LOCATION: (14)..(14)
<223> OTHER INFORMATION: G-clamp deoxyphenoxazine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (31)..(31)
<223> OTHER INFORMATION: 5-methyl-cytosine

<400> SEQUENCE: 97
uunagtgtga tgantttgn actgagaata nt                                    32

<210> SEQ ID NO 98
<211> LENGTH: 31
<212> TYPE: DNA
<213> ORGANISM: Artificial Sequence
<220> FEATURE:
<223> OTHER INFORMATION: Unmodified version of SEQ ID NO: 39
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (30)..(30)
<223> OTHER INFORMATION: 5-methyl-cytosine

<400> SEQUENCE: 98
aagcaaccta caggttttgn attggtattn a                                     31

<210> SEQ ID NO 99
<211> LENGTH: 19
<212> TYPE: DNA
<213> ORGANISM: Artificial Sequence
<220> FEATURE:
<223> OTHER INFORMATION: Unmodified version of SEQ ID NO: 40
<220> FEATURE:
<221> NAME/KEY: misc_feature
<222> LOCATION: (19)..(19)
<223> OTHER INFORMATION: Doubler triethylenglycol linker

<400> SEQUENCE: 99
ggaactgaag ccattttn                                                    19

<210> SEQ ID NO 100
<211> LENGTH: 32
<212> TYPE: DNA
<213> ORGANISM: Artificial Sequence
<220> FEATURE:
<223> OTHER INFORMATION: Unmodified version of SEQ ID NO: 41
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (4)..(4)
<223> OTHER INFORMATION: 5-propynyl-cytidine
<220> FEATURE:
<221> NAME/KEY: misc_feature
<222> LOCATION: (13)..(13)
<223> OTHER INFORMATION: 5-methyl-cytosine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (22)..(22)
<223> OTHER INFORMATION: 5-propynyl-cytidine
<220> FEATURE:
<221> NAME/KEY: misc_feature
<222> LOCATION: (31)..(31)
<223> OTHER INFORMATION: 5-methyl-cytosine

<400> SEQUENCE: 100
gnantgagaa tantttttgn antgagaata nt                                    32

<210> SEQ ID NO 101
<211> LENGTH: 32
<212> TYPE: DNA
<213> ORGANISM: Artificial Sequence
<220> FEATURE:
<223> OTHER INFORMATION: Unmodified version of SEQ ID NO: 42

-continued

```
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (4)..(4)
<223> OTHER INFORMATION: 5-propynyl-cytidine
<220> FEATURE:
<221> NAME/KEY: misc_feature
<222> LOCATION: (5)..(5)
<223> OTHER INFORMATION: 5-propynyl-uridine
<220> FEATURE:
<221> NAME/KEY: misc_feature
<222> LOCATION: (13)..(13)
<223> OTHER INFORMATION: 5-methyl-cytosine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (22)..(22)
<223> OTHER INFORMATION: 5-propynyl-cytidine
<220> FEATURE:
<221> NAME/KEY: misc_feature
<222> LOCATION: (23)..(23)
<223> OTHER INFORMATION: 5-propynyl-uridine
<220> FEATURE:
<221> NAME/KEY: misc_feature
<222> LOCATION: (31)..(31)
<223> OTHER INFORMATION: 5-methyl-cytosine

<400> SEQUENCE: 101
gnanngagaa tantttttgn anngagaata nt                                   32

<210> SEQ ID NO 102
<211> LENGTH: 32
<212> TYPE: DNA
<213> ORGANISM: Artificial Sequence
<220> FEATURE:
<223> OTHER INFORMATION: Unmodified version of SEQ ID NO: 43
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (4)..(4)
<223> OTHER INFORMATION: 5-propynyl-cytidine
<220> FEATURE:
<221> NAME/KEY: misc_feature
<222> LOCATION: (5)..(5)
<223> OTHER INFORMATION: 5-propynyl-uridine
<220> FEATURE:
<221> NAME/KEY: misc_feature
<222> LOCATION: (11)..(11)
<223> OTHER INFORMATION: 5-propynyl-uridine
<220> FEATURE:
<221> NAME/KEY: misc_feature
<222> LOCATION: (13)..(13)
<223> OTHER INFORMATION: 5-methyl-cytosine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (22)..(22)
<223> OTHER INFORMATION: 5-propynyl-cytidine
<220> FEATURE:
<221> NAME/KEY: misc_feature
<222> LOCATION: (23)..(23)
<223> OTHER INFORMATION: 5-propynyl-uridine
<220> FEATURE:
<221> NAME/KEY: misc_feature
<222> LOCATION: (29)..(29)
```

<223> OTHER INFORMATION: 5-propynyl-uridine
<220> FEATURE:
<221> NAME/KEY: misc_feature
<222> LOCATION: (31)..(31)
<223> OTHER INFORMATION: 5-methyl-cytosine

<400> SEQUENCE: 102
gnanngagaa nantttttgn anngagaana nt                                    32

<210> SEQ ID NO 103
<211> LENGTH: 28
<212> TYPE: DNA
<213> ORGANISM: Artificial Sequence
<220> FEATURE:
<223> OTHER INFORMATION: Unmodified version of SEQ ID NO: 44
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (17)..(17)
<223> OTHER INFORMATION: 5-methyl-cytosine
<220> FEATURE:
<221> NAME/KEY: misc_feature
<222> LOCATION: (27)..(27)
<223> OTHER INFORMATION: 5-methyl-cytosine

<400> SEQUENCE: 103
gnattggtat tnattgnatt ggtattna                                         28

<210> SEQ ID NO 104
<211> LENGTH: 29
<212> TYPE: DNA
<213> ORGANISM: Artificial Sequence
<220> FEATURE:
<223> OTHER INFORMATION: Unmodified version of SEQ ID NO: 45
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (18)..(18)
<223> OTHER INFORMATION: 5-methyl-cytosine
<220> FEATURE:
<221> NAME/KEY: misc_feature
<222> LOCATION: (28)..(28)
<223> OTHER INFORMATION: 5-methyl-cytosine

<400> SEQUENCE: 104
gnattggtat tnatttgnat tggtattna                                        29

<210> SEQ ID NO 105
<211> LENGTH: 30
<212> TYPE: DNA
<213> ORGANISM: Artificial Sequence
<220> FEATURE:
<223> OTHER INFORMATION: Unmodified version of SEQ ID NO: 46
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature

```
<222> LOCATION: (12)..(12)
<223> OTHER INFORMATION: 5-methyl-cytosine
<220> FEATURE:
<221> NAME/KEY: misc_feature
<222> LOCATION: (19)..(19)
<223> OTHER INFORMATION: 5-methyl-cytosine
<220> FEATURE:
<221> NAME/KEY: misc_feature
<222> LOCATION: (29)..(29)
<223> OTHER INFORMATION: 5-methyl-cytosine

<400> SEQUENCE: 105
gnattggtat tnattttgna ttggtattna                                    30

<210> SEQ ID NO 106
<211> LENGTH: 31
<212> TYPE: DNA
<213> ORGANISM: Artificial Sequence
<220> FEATURE:
<223> OTHER INFORMATION: Unmodified version of SEQ ID NO: 47
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (20)..(20)
<223> OTHER INFORMATION: 5-methyl-cytosine
<220> FEATURE:
<221> NAME/KEY: misc_feature
<222> LOCATION: (30)..(30)
<223> OTHER INFORMATION: 5-methyl-cytosine

<400> SEQUENCE: 106
gnattggtat tnattttgn attggtattn a                                   31

<210> SEQ ID NO 107
<211> LENGTH: 32
<212> TYPE: DNA
<213> ORGANISM: Artificial Sequence
<220> FEATURE:
<223> OTHER INFORMATION: Unmodified version of SEQ ID NO: 48
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (21)..(21)
<223> OTHER INFORMATION: 5-methyl-cytosine
<220> FEATURE:
<221> NAME/KEY: misc_feature
<222> LOCATION: (31)..(31)
<223> OTHER INFORMATION: 5-methyl-cytosine

<400> SEQUENCE: 107
gnattggtat tnattttttg nattggtatt na                                 32

<210> SEQ ID NO 108
<211> LENGTH: 33
<212> TYPE: DNA
<213> ORGANISM: Artificial Sequence
<220> FEATURE:
<223> OTHER INFORMATION: Unmodified version of SEQ ID NO: 49
<220> FEATURE:
```

```
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (22)..(22)
<223> OTHER INFORMATION: 5-methyl-cytosine
<220> FEATURE:
<221> NAME/KEY: misc_feature
<222> LOCATION: (32)..(32)
<223> OTHER INFORMATION: 5-methyl-cytosine

<400> SEQUENCE: 108
gnattggtat tnatttttt gnattggtat tna                              33

<210> SEQ ID NO 109
<211> LENGTH: 33
<212> TYPE: DNA
<213> ORGANISM: Artificial Sequence
<220> FEATURE:
<223> OTHER INFORMATION: Unmodified version of SEQ ID NO: 50
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (22)..(22)
<223> OTHER INFORMATION: 5-methyl-cytosine
<220> FEATURE:
<221> NAME/KEY: misc_feature
<222> LOCATION: (32)..(32)
<223> OTHER INFORMATION: 5-methyl-cytosine

<400> SEQUENCE: 109
gnattggtat tnatttttt gnattggtat tna                              33

<210> SEQ ID NO 110
<211> LENGTH: 27
<212> TYPE: DNA
<213> ORGANISM: Artificial Sequence
<220> FEATURE:
<223> OTHER INFORMATION: Unmodified version of SEQ ID NO: 51
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (16)..(16)
<223> OTHER INFORMATION: 5-methyl-cytosine
<220> FEATURE:
<221> NAME/KEY: misc_feature
<222> LOCATION: (26)..(26)
<223> OTHER INFORMATION: 5-methyl-cytosine

<400> SEQUENCE: 110
gnattggtat tnaugnattg gtattna                                    27

<210> SEQ ID NO 111
<211> LENGTH: 28
```

```
<212> TYPE: DNA
<213> ORGANISM: Artificial Sequence
<220> FEATURE:
<223> OTHER INFORMATION: Unmodified version of SEQ ID NO: 52
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (17)..(17)
<223> OTHER INFORMATION: 5-methyl-cytosine
<220> FEATURE:
<221> NAME/KEY: misc_feature
<222> LOCATION: (27)..(27)
<223> OTHER INFORMATION: 5-methyl-cytosine

<400> SEQUENCE: 111
gnattggtat tnauugnatt ggtattna                                  28

<210> SEQ ID NO 112
<211> LENGTH: 29
<212> TYPE: DNA
<213> ORGANISM: Artificial Sequence
<220> FEATURE:
<223> OTHER INFORMATION: Unmodified version of SEQ ID NO: 53
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (18)..(18)
<223> OTHER INFORMATION: 5-methyl-cytosine
<220> FEATURE:
<221> NAME/KEY: misc_feature
<222> LOCATION: (28)..(28)
<223> OTHER INFORMATION: 5-methyl-cytosine

<400> SEQUENCE: 112
gnattggtat tnauuugnat tggtattna                                 29

<210> SEQ ID NO 113
<211> LENGTH: 30
<212> TYPE: DNA
<213> ORGANISM: Artificial Sequence
<220> FEATURE:
<223> OTHER INFORMATION: Unmodified version of SEQ ID NO: 54
<220> FEATURE:
<221> NAME/KEY: misc_feature
<222> LOCATION: (2)..(2)
<223> OTHER INFORMATION: 5-methyl-cytosine
<220> FEATURE:
<221> NAME/KEY: misc_feature
<222> LOCATION: (12)..(12)
<223> OTHER INFORMATION: 5-methyl-cytosine
<220> FEATURE:
<221> NAME/KEY: misc_feature
<222> LOCATION: (19)..(19)
<223> OTHER INFORMATION: 5-methyl-cytosine
<220> FEATURE:
<221> NAME/KEY: misc_feature
<222> LOCATION: (29)..(29)
<223> OTHER INFORMATION: 5-methyl-cytosine

<400> SEQUENCE: 113
```

-continued

```
gnattggtat tnauuuugna ttggtattna                              30
```

<210> SEQ ID NO 114
<211> LENGTH: 14
<212> TYPE: DNA
<213> ORGANISM: Artificial Sequence
<220> FEATURE:
<223> OTHER INFORMATION: Unmodified version of SEQ ID NO: 55
<220> FEATURE:
<221> NAME/KEY: misc_feature
<222> LOCATION: (1)..(2)
<223> OTHER INFORMATION: 5-methyl-cytosine
<220> FEATURE:
<221> NAME/KEY: misc_feature
<222> LOCATION: (13)..(13)
<223> OTHER INFORMATION: 5-methyl-cytosine

<400> SEQUENCE: 114

```
nnagtagtct tuna                                               14
```

<210> SEQ ID NO 115
<211> LENGTH: 14
<212> TYPE: DNA
<213> ORGANISM: Artificial Sequence
<220> FEATURE:
<223> OTHER INFORMATION: Unmodified version of SEQ ID NO: 56
<220> FEATURE:
<221> NAME/KEY: misc_feature
<222> LOCATION: (1)..(2)
<223> OTHER INFORMATION: 5-methyl-cytosine

<400> SEQUENCE: 115

```
nnagtagtct tuca                                               14
```

<210> SEQ ID NO 116
<211> LENGTH: 14
<212> TYPE: DNA
<213> ORGANISM: Artificial Sequence
<220> FEATURE:
<223> OTHER INFORMATION: Unmodified version of SEQ ID NO: 57
<220> FEATURE:
<221> NAME/KEY: misc_feature
<222> LOCATION: (1)..(2)
<223> OTHER INFORMATION: 5-methyl-cytosine

<400> SEQUENCE: 116

```
nnagtagtct tuca                                               14
```

<210> SEQ ID NO 117
<211> LENGTH: 14
<212> TYPE: DNA
<213> ORGANISM: Artificial Sequence
<220> FEATURE:
<223> OTHER INFORMATION: Unmodified version of SEQ ID NO: 58

<400> SEQUENCE: 117

```
ggaactgaag ccat                                               14
```

<210> SEQ ID NO 118
<211> LENGTH: 14
<212> TYPE: DNA
<213> ORGANISM: Artificial Sequence
<220> FEATURE:
<223> OTHER INFORMATION: Unmodified version of SEQ ID NO: 1

<400> SEQUENCE: 118

```
aagcaaccta cagg                                               14
```

```
<210> SEQ ID NO 119
<211> LENGTH: 14
<212> TYPE: DNA
<213> ORGANISM: Artificial Sequence
<220> FEATURE:
<223> OTHER INFORMATION: negative control ASO
<220> FEATURE:
<221> NAME/KEY: misc_feature
<222> LOCATION: (1)..(1)
<223> OTHER INFORMATION: LNA [2',4']-locked "ribo"-thymidine
<220> FEATURE:
<221> NAME/KEY: misc_feature
<222> LOCATION: (2)..(3)
<223> OTHER INFORMATION: LNA [2',4']-locked adenosine
<220> FEATURE:
<221> NAME/KEY: misc_feature
<222> LOCATION: (5)..(5)
<223> OTHER INFORMATION: 5-methyl-2'-deoxy-cytidine
<220> FEATURE:
<221> NAME/KEY: misc_feature
<222> LOCATION: (8)..(8)
<223> OTHER INFORMATION: 5-methyl-2'-deoxy-cytidine
<220> FEATURE:
<221> NAME/KEY: misc_feature
<222> LOCATION: (12)..(12)
<223> OTHER INFORMATION: LNA [2',4']-locked adenosine
<220> FEATURE:
<221> NAME/KEY: misc_feature
<222> LOCATION: (13)..(14)
<223> OTHER INFORMATION: LNA [2',4']-locked 5-methyl-cytidine

<400> SEQUENCE: 119
nnntngtnga tnnn                                                     14

<210> SEQ ID NO 120
<211> LENGTH: 11
<212> TYPE: DNA
<213> ORGANISM: Artificial Sequence
<220> FEATURE:
<223> OTHER INFORMATION: (C12-amino)(Spacer-18)(Spacer-18)-8mer LNA
<220> FEATURE:
<221> NAME/KEY: misc_feature
<222> LOCATION: (1)..(1)
<223> OTHER INFORMATION: C12-amino
<220> FEATURE:
<221> NAME/KEY: misc_feature
<222> LOCATION: (2)..(3)
<223> OTHER INFORMATION: Spacer-18 (hexaethyleneglycole phosphate,
      PEG-282)
<220> FEATURE:
<221> NAME/KEY: misc_feature
<222> LOCATION: (4)..(4)
<223> OTHER INFORMATION: LNA [2',3']-locked guanosine
<220> FEATURE:
<221> NAME/KEY: misc_feature
<222> LOCATION: (5)..(5)
<223> OTHER INFORMATION: LNA [2',4']-locked cytidine
<220> FEATURE:
<221> NAME/KEY: misc_feature
<222> LOCATION: (6)..(10)
<223> OTHER INFORMATION: LNA [2',4']-locked adenosine
<220> FEATURE:
<221> NAME/KEY: misc_feature
<222> LOCATION: (11)..(11)
<223> OTHER INFORMATION: LNA [2',3']-locked guanosine

<400> SEQUENCE: 120
nnnnnnnnnn n                                                        11

<210> SEQ ID NO 121
<211> LENGTH: 10
<212> TYPE: DNA
<213> ORGANISM: Artificial Sequence
<220> FEATURE:
<223> OTHER INFORMATION: apoB probe
```

```
<220> FEATURE:
<221> NAME/KEY: misc_feature
<222> LOCATION: (1)..(1)
<223> OTHER INFORMATION: LNA [2',4']-locked-cytidine
<220> FEATURE:
<221> NAME/KEY: misc_feature
<222> LOCATION: (2)..(3)
<223> OTHER INFORMATION: LNA [2',4']-locked adenosine
<220> FEATURE:
<221> NAME/KEY: misc_feature
<222> LOCATION: (4)..(4)
<223> OTHER INFORMATION: LNA [2',4']-locked "ribo"-thymidine
<220> FEATURE:
<221> NAME/KEY: misc_feature
<222> LOCATION: (5)..(5)
<223> OTHER INFORMATION: LNA [2',3']-locked guanosine
<220> FEATURE:
<221> NAME/KEY: misc_feature
<222> LOCATION: (6)..(6)
<223> OTHER INFORMATION: LNA [2',4']-locked-cytidine
<220> FEATURE:
<221> NAME/KEY: misc_feature
<222> LOCATION: (7)..(8)
<223> OTHER INFORMATION: Spacer-18 (hexaethyleneglycole phosphate,
      PEG-282)
<220> FEATURE:
<221> NAME/KEY: misc_feature
<222> LOCATION: (9)..(9)
<223> OTHER INFORMATION: 2'-deoxythmidine-biotin
<220> FEATURE:
<221> NAME/KEY: misc_feature
<222> LOCATION: (10)..(10)
<223> OTHER INFORMATION: biotin triethylenglycol

<400> SEQUENCE: 121 nnnnnnnnnn                                                          10

<210> SEQ ID NO 122
<211> LENGTH: 11
<212> TYPE: DNA
<213> ORGANISM: Artificial Sequence
<220> FEATURE:
<223> OTHER INFORMATION: dimer probe
<220> FEATURE:
<221> NAME/KEY: misc_feature
<222> LOCATION: (1)..(1)
<223> OTHER INFORMATION: LNA [2',4']-locked "ribo"-thymidine
<220> FEATURE:
<221> NAME/KEY: misc_feature
<222> LOCATION: (2)..(2)
<223> OTHER INFORMATION: LNA [2',4']-locked cytidine
<220> FEATURE:
<221> NAME/KEY: misc_feature
<222> LOCATION: (3)..(3)
<223> OTHER INFORMATION: LNA [2',4']-locked adenosine
<220> FEATURE:
<221> NAME/KEY: misc_feature
<222> LOCATION: (4)..(4)
<223> OTHER INFORMATION: LNA [2',3']-locked guanosine
<220> FEATURE:
<221> NAME/KEY: misc_feature
<222> LOCATION: (5)..(5)
<223> OTHER INFORMATION: LNA [2',4']-locked "ribo"-thymidine
<220> FEATURE:
<221> NAME/KEY: misc_feature
<222> LOCATION: (6)..(6)
<223> OTHER INFORMATION: LNA [2',3']-locked guanosine
<220> FEATURE:
<221> NAME/KEY: misc_feature
<222> LOCATION: (7)..(7)
<223> OTHER INFORMATION: LNA [2',4']-locked cytidine
<220> FEATURE:
<221> NAME/KEY: misc_feature
<222> LOCATION: (8)..(9)
<223> OTHER INFORMATION: Spacer-18 (hexaethyleneglycole phosphate,
      PEG-282)
<220> FEATURE:
```

```
<221> NAME/KEY: misc_feature
<222> LOCATION: (10)..(10)
<223> OTHER INFORMATION: 2'-deoxythmidine biotin
<220> FEATURE:
<221> NAME/KEY: misc_feature
<222> LOCATION: (11)..(11)
<223> OTHER INFORMATION: biotin triethylenglycol

<400> SEQUENCE: 122
nnnnnnnnnn n                                                                11

<210> SEQ ID NO 123
<211> LENGTH: 10
<212> TYPE: DNA
<213> ORGANISM: Artificial Sequence
<220> FEATURE:
<223> OTHER INFORMATION: (C12-amino)(Spacer-18)(Spacer-18)-7mer LNA
<220> FEATURE:
<221> NAME/KEY: misc_feature
<222> LOCATION: (1)..(1)
<223> OTHER INFORMATION: C12-amino
<220> FEATURE:
<221> NAME/KEY: misc_feature
<222> LOCATION: (2)..(3)
<223> OTHER INFORMATION: Spacer-18 (hexaethyleneglycole phosphate,
      PEG-282)
<220> FEATURE:
<221> NAME/KEY: misc_feature
<222> LOCATION: (4)..(4)
<223> OTHER INFORMATION: LNA [2',4']-locked "ribo"-thymidine
<220> FEATURE:
<221> NAME/KEY: misc_feature
<222> LOCATION: (5)..(5)
<223> OTHER INFORMATION: LNA [2',3']-locked guanosine
<220> FEATURE:
<221> NAME/KEY: misc_feature
<222> LOCATION: (6)..(7)
<223> OTHER INFORMATION: LNA [2',4']-locked adenosine
<220> FEATURE:
<221> NAME/KEY: misc_feature
<222> LOCATION: (8)..(8)
<223> OTHER INFORMATION: LNA [2',4']-locked "ribo"-thymidine
<220> FEATURE:
<221> NAME/KEY: misc_feature
<222> LOCATION: (9)..(9)
<223> OTHER INFORMATION: LNA [2',4']-locked adenosine
<220> FEATURE:
<221> NAME/KEY: misc_feature
<222> LOCATION: (10)..(10)
<223> OTHER INFORMATION: LNA [2',4']-locked cytidine

<400> SEQUENCE: 123 nnnnnnnnnn                                                                   10

<210> SEQ ID NO 124
<211> LENGTH: 10
<212> TYPE: DNA
<213> ORGANISM: Artificial Sequence
<220> FEATURE:
<223> OTHER INFORMATION: apoB probe, capture
<220> FEATURE:
<221> NAME/KEY: misc_feature
<222> LOCATION: (1)..(1)
<223> OTHER INFORMATION: C12-amino
<220> FEATURE:
<221> NAME/KEY: misc_feature
<222> LOCATION: (2)..(3)
<223> OTHER INFORMATION: Spacer-18 (hexaethyleneglycole phosphate,
      PEG-282)
<220> FEATURE:
<221> NAME/KEY: misc_feature
<222> LOCATION: (4)..(4)
<223> OTHER INFORMATION: LNA [2',4']-locked "ribo"-thymidine
<220> FEATURE:
<221> NAME/KEY: misc_feature
```

```
<222> LOCATION: (5)..(5)
<223> OTHER INFORMATION: LNA [2',3']-locked guanosine
<220> FEATURE:
<221> NAME/KEY: misc_feature
<222> LOCATION: (6)..(7)
<223> OTHER INFORMATION: LNA [2',4']-locked adenosine
<220> FEATURE:
<221> NAME/KEY: misc_feature
<222> LOCATION: (8)..(8)
<223> OTHER INFORMATION: LNA [2',4']-locked "ribo"-thymidine
<220> FEATURE:
<221> NAME/KEY: misc_feature
<222> LOCATION: (9)..(9)
<223> OTHER INFORMATION: LNA [2',4']-locked adenosine
<220> FEATURE:
<221> NAME/KEY: misc_feature
<222> LOCATION: (10)..(10)
<223> OTHER INFORMATION: LNA [2',4']-locked cytidine

<400> SEQUENCE: 124 nnnnnnnnnn                                                            10

<210> SEQ ID NO 125
<211> LENGTH: 4
<212> TYPE: PRT
<213> ORGANISM: Artificial Sequence
<220> FEATURE:
<223> OTHER INFORMATION: peptide linker

<400> SEQUENCE: 125

Ala Leu Ala Leu
1

<210> SEQ ID NO 126
<211> LENGTH: 9
<212> TYPE: PRT
<213> ORGANISM: Artificial Sequence
<220> FEATURE:
<223> OTHER INFORMATION: peptide linker

<400> SEQUENCE: 126

Ala Pro Ile Ser Phe Phe Glu Leu Gly
1               5

<210> SEQ ID NO 127
<211> LENGTH: 11
<212> TYPE: PRT
<213> ORGANISM: Artificial Sequence
<220> FEATURE:
<223> OTHER INFORMATION: peptide linker

<400> SEQUENCE: 127

Gly Arg Trp His Thr Val Gly Leu Arg Trp Glu
1               5                   10

<210> SEQ ID NO 128
<211> LENGTH: 15
<212> TYPE: DNA
<213> ORGANISM: Artificial Sequence
<220> FEATURE:
<223> OTHER INFORMATION: 122 gap-mono
<220> FEATURE:
<221> NAME/KEY: misc_feature
<222> LOCATION: (1)..(1)
<223> OTHER INFORMATION: LNA [2',4']-locked-cytidine
<220> FEATURE:
<221> NAME/KEY: misc_feature
<222> LOCATION: (2)..(2)
<223> OTHER INFORMATION: LNA [2',4']-locked adenosine
<220> FEATURE:
<221> NAME/KEY: misc_feature
```

```
<222> LOCATION: (3)..(3)
<223> OTHER INFORMATION: LNA [2',4']-locked "ribo"-thymidine
<220> FEATURE:
<221> NAME/KEY: misc_feature
<222> LOCATION: (13)..(14)
<223> OTHER INFORMATION: LNA [2',4']-locked-cytidine
<220> FEATURE:
<221> NAME/KEY: misc_feature
<222> LOCATION: (15)..(15)
<223> OTHER INFORMATION: LNA [2',4']-locked adenosine

<400> SEQUENCE: 128
nnntgtcaca ctnnn                                                     15

<210> SEQ ID NO 129
<211> LENGTH: 34
<212> TYPE: DNA
<213> ORGANISM: Artificial Sequence
<220> FEATURE:
<223> OTHER INFORMATION: 122gap-dimer
<220> FEATURE:
<221> NAME/KEY: misc_feature
<222> LOCATION: (1)..(1)
<223> OTHER INFORMATION: LNA [2',4']-locked-cytidine
<220> FEATURE:
<221> NAME/KEY: misc_feature
<222> LOCATION: (2)..(2)
<223> OTHER INFORMATION: LNA [2',4']-locked adenosine
<220> FEATURE:
<221> NAME/KEY: misc_feature
<222> LOCATION: (3)..(3)
<223> OTHER INFORMATION: LNA [2',4']-locked "ribo"thymidine
<220> FEATURE:
<221> NAME/KEY: misc_feature
<222> LOCATION: (13)..(14)
<223> OTHER INFORMATION: LNA [2',4']-locked-cytidine
<220> FEATURE:
<221> NAME/KEY: misc_feature
<222> LOCATION: (15)..(15)
<223> OTHER INFORMATION: LNA [2',4']-locked adenosine
<220> FEATURE:
<221> NAME/KEY: misc_feature
<222> LOCATION: (20)..(20)
<223> OTHER INFORMATION: LNA [2',4']-locked-cytidine
<220> FEATURE:
<221> NAME/KEY: misc_feature
<222> LOCATION: (21)..(21)
<223> OTHER INFORMATION: LNA [2',4']-locked adenosine
<220> FEATURE:
<221> NAME/KEY: misc_feature
<222> LOCATION: (22)..(22)
<223> OTHER INFORMATION: LNA [2',4']-locked "ribo"thymidine
<220> FEATURE:
<221> NAME/KEY: misc_feature
<222> LOCATION: (32)..(33)
<223> OTHER INFORMATION: LNA [2',4']-locked-cytidine
<220> FEATURE:
<221> NAME/KEY: misc_feature
<222> LOCATION: (34)..(34)
<223> OTHER INFORMATION: LNA [2',4']-locked adenosine

<400> SEQUENCE: 129
nnntgtcaca ctnnnttttn nntgtcacac tnnn                                34

<210> SEQ ID NO 130
<211> LENGTH: 15
<212> TYPE: DNA
<213> ORGANISM: Artificial Sequence
<220> FEATURE:
<223> OTHER INFORMATION: 122gap-control-mono
<220> FEATURE:
<221> NAME/KEY: misc_feature
<222> LOCATION: (1)..(1)
<223> OTHER INFORMATION: LNA [2',4']-locked "ribo"-thymidine
<220> FEATURE:
```

```
<221> NAME/KEY: misc_feature
<222> LOCATION: (2)..(2)
<223> OTHER INFORMATION: LNA [2',3']-locked guanosine
<220> FEATURE:
<221> NAME/KEY: misc_feature
<222> LOCATION: (3)..(3)
<223> OTHER INFORMATION: LNA [2',4']-locked adenosine
<220> FEATURE:
<221> NAME/KEY: misc_feature
<222> LOCATION: (13)..(13)
<223> OTHER INFORMATION: LNA [2',4']-locked-cytidine
<220> FEATURE:
<221> NAME/KEY: misc_feature
<222> LOCATION: (14)..(15)
<223> OTHER INFORMATION: LNA [2',4']-locked "ribo"-thymidine

<400> SEQUENCE: 130
nnnaggttcc tcnnn                                                    15

<210> SEQ ID NO 131
<211> LENGTH: 34
<212> TYPE: DNA
<213> ORGANISM: Artificial Sequence
<220> FEATURE:
<223> OTHER INFORMATION: 122gap-control-dimer
<220> FEATURE:
<221> NAME/KEY: misc_feature
<222> LOCATION: (1)..(1)
<223> OTHER INFORMATION: LNA [2',4']-locked "ribo"-thymidine
<220> FEATURE:
<221> NAME/KEY: misc_feature
<222> LOCATION: (2)..(2)
<223> OTHER INFORMATION: LNA [2',3']-locked guanosine
<220> FEATURE:
<221> NAME/KEY: misc_feature
<222> LOCATION: (3)..(3)
<223> OTHER INFORMATION: LNA [2',4']-locked adenosine
<220> FEATURE:
<221> NAME/KEY: misc_feature
<222> LOCATION: (13)..(13)
<223> OTHER INFORMATION: LNA [2',4']-locked cytidine
<220> FEATURE:
<221> NAME/KEY: misc_feature
<222> LOCATION: (14)..(15)
<223> OTHER INFORMATION: LNA [2',4']-locked "ribo"-thymidine
<220> FEATURE:
<221> NAME/KEY: misc_feature
<222> LOCATION: (20)..(20)
<223> OTHER INFORMATION: LNA [2',4']-locked "ribo"-thymidine
<220> FEATURE:
<221> NAME/KEY: misc_feature
<222> LOCATION: (21)..(21)
<223> OTHER INFORMATION: LNA [2',3']-locked guanosine
<220> FEATURE:
<221> NAME/KEY: misc_feature
<222> LOCATION: (22)..(22)
<223> OTHER INFORMATION: LNA [2',4']-locked adenosine
<220> FEATURE:
<221> NAME/KEY: misc_feature
<222> LOCATION: (32)..(32)
<223> OTHER INFORMATION: LNA [2',4']-locked cytidine
<220> FEATURE:
<221> NAME/KEY: misc_feature
<222> LOCATION: (33)..(34)
<223> OTHER INFORMATION: LNA [2',4']-locked "ribo"-thymidine

<400> SEQUENCE: 131
nnnaggttcc tcnnnttttn nnaggttcct cnnn                               34

<210> SEQ ID NO 132
<211> LENGTH: 15
<212> TYPE: DNA
<213> ORGANISM: Artificial Sequence
<220> FEATURE:
<223> OTHER INFORMATION: Malat1-gap-mono
```

<220> FEATURE:
<221> NAME/KEY: misc_feature
<222> LOCATION: (1)..(1)
<223> OTHER INFORMATION: LNA [2',4']-locked cytidine
<220> FEATURE:
<221> NAME/KEY: misc_feature
<222> LOCATION: (2)..(2)
<223> OTHER INFORMATION: LNA [2',4']-locked "ribo"thymidine
<220> FEATURE:
<221> NAME/KEY: misc_feature
<222> LOCATION: (3)..(3)
<223> OTHER INFORMATION: LNA [2',4']-locked adenosine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (14)..(14)
<223> OTHER INFORMATION: LNA [2',4']-locked "ribo"thymidine
<220> FEATURE:
<221> NAME/KEY: misc_feature
<222> LOCATION: (15)..(15)
<223> OTHER INFORMATION: LNA [2',3']-locked guanosine

<400> SEQUENCE: 132
nnngttcact gannn                                                      15

<210> SEQ ID NO 133
<211> LENGTH: 34
<212> TYPE: DNA
<213> ORGANISM: Artificial Sequence
<220> FEATURE:
<223> OTHER INFORMATION: Malat1-gap-dimer
<220> FEATURE:
<221> NAME/KEY: misc_feature
<222> LOCATION: (1)..(1)
<223> OTHER INFORMATION: LNA [2',4']-locked cytidine
<220> FEATURE:
<221> NAME/KEY: misc_feature
<222> LOCATION: (2)..(2)
<223> OTHER INFORMATION: LNA [2',4']-locked "ribo"thymidine
<220> FEATURE:
<221> NAME/KEY: misc_feature
<222> LOCATION: (3)..(3)
<223> OTHER INFORMATION: LNA [2',4']-locked adenosine
<220> FEATURE:
<221> NAME/KEY: misc_feature
<222> LOCATION: (13)..(13)
<223> OTHER INFORMATION: LNA [2',4']-locked adenosine
<220> FEATURE:
<221> NAME/KEY: misc_feature
<222> LOCATION: (14)..(14)
<223> OTHER INFORMATION: LNA [2',4']-locked "ribo"thymidine
<220> FEATURE:
<221> NAME/KEY: misc_feature
<222> LOCATION: (15)..(15)
<223> OTHER INFORMATION: LNA [2',3']-locked guanosine
<220> FEATURE:
<221> NAME/KEY: misc_feature
<222> LOCATION: (20)..(20)
<223> OTHER INFORMATION: LNA [2',4']-locked cytidine
<220> FEATURE:
<221> NAME/KEY: misc_feature
<222> LOCATION: (21)..(21)
<223> OTHER INFORMATION: LNA [2',4']-locked "ribo"thymidine
<220> FEATURE:
<221> NAME/KEY: misc_feature
<222> LOCATION: (22)..(22)
<223> OTHER INFORMATION: LNA [2',4']-locked adenosine
<220> FEATURE:
<221> NAME/KEY: misc_feature
<222> LOCATION: (32)..(32)
<223> OTHER INFORMATION: LNA [2',4']-locked adenosine
<220> FEATURE:
<221> NAME/KEY: misc_feature
<222> LOCATION: (33)..(33)

```
<223> OTHER INFORMATION: LNA [2',4']-locked "ribo"thymidine
<220> FEATURE:
<221> NAME/KEY: misc_feature
<222> LOCATION: (34)..(34)
<223> OTHER INFORMATION: LNA [2',3']-locked guanosine

<400> SEQUENCE: 133
nnngttcact gannntttn nngttcactg annn                                 34

<210> SEQ ID NO 134
<211> LENGTH: 15
<212> TYPE: DNA
<213> ORGANISM: Artificial Sequence
<220> FEATURE:
<223> OTHER INFORMATION: Malat1-gap-control-mono
<220> FEATURE:
<221> NAME/KEY: misc_feature
<222> LOCATION: (1)..(2)
<223> OTHER INFORMATION: LNA [2',4']-locked "ribo"thymidine
<220> FEATURE:
<221> NAME/KEY: misc_feature
<222> LOCATION: (3)..(3)
<223> OTHER INFORMATION: LNA [2',4']-locked cytidine
<220> FEATURE:
<221> NAME/KEY: misc_feature
<222> LOCATION: (13)..(13)
<223> OTHER INFORMATION: LNA [2',4']-locked "ribo"thymidine
<220> FEATURE:
<221> NAME/KEY: misc_feature
<222> LOCATION: (14)..(15)
<223> OTHER INFORMATION: LNA [2',4']-locked cytidine

<400> SEQUENCE: 134
nnncctgaag gtnnn                                                     15

<210> SEQ ID NO 135
<211> LENGTH: 34
<212> TYPE: DNA
<213> ORGANISM: Artificial Sequence
<220> FEATURE:
<223> OTHER INFORMATION: Malat1-gap-control-dimer
<220> FEATURE:
<221> NAME/KEY: misc_feature
<222> LOCATION: (1)..(2)
<223> OTHER INFORMATION: LNA [2',4']-locked "ribo"thymidine
<220> FEATURE:
<221> NAME/KEY: misc_feature
<222> LOCATION: (3)..(3)
<223> OTHER INFORMATION: LNA [2',4']-locked cytidine
<220> FEATURE:
<221> NAME/KEY: misc_feature
<222> LOCATION: (13)..(13)
<223> OTHER INFORMATION: LNA [2',4']-locked "ribo"thymidine
<220> FEATURE:
<221> NAME/KEY: misc_feature
<222> LOCATION: (14)..(15)
<223> OTHER INFORMATION: LNA [2',4']-locked cytidine
<220> FEATURE:
<221> NAME/KEY: misc_feature
<222> LOCATION: (20)..(21)
<223> OTHER INFORMATION: LNA [2',4']-locked "ribo"thymidine
<220> FEATURE:
<221> NAME/KEY: misc_feature
<222> LOCATION: (22)..(22)
<223> OTHER INFORMATION: LNA [2',4']-locked cytidine
<220> FEATURE:
<221> NAME/KEY: misc_feature
<222> LOCATION: (32)..(32)
<223> OTHER INFORMATION: LNA [2',4']-locked "ribo"thymidine
<220> FEATURE:
<221> NAME/KEY: misc_feature
<222> LOCATION: (33)..(34)
<223> OTHER INFORMATION: LNA [2',4']-locked cytidine

<400> SEQUENCE: 135
```

```
nnncctgaag gtnnnttttn nncctgaagg tnnn                                34

<210> SEQ ID NO 136
<211> LENGTH: 7
<212> TYPE: PRT
<213> ORGANISM: Artificial Sequence
<220> FEATURE:
<223> OTHER INFORMATION: Linker
<220> FEATURE:
<221> NAME/KEY: MISC_FEATURE
<222> LOCATION: (1)..(1)
<223> OTHER INFORMATION: maleimidocaproyl

<400> SEQUENCE: 136

Xaa Arg Arg Ala Leu Ala Leu
1               5

<210> SEQ ID NO 137
<211> LENGTH: 11
<212> TYPE: PRT
<213> ORGANISM: Artificial Sequence
<220> FEATURE:
<223> OTHER INFORMATION: Linker

<400> SEQUENCE: 137

Gly Arg Trp Pro Pro Met Gly Leu Pro Trp Glu
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Linker

<400> SEQUENCE: 138

Gly Arg Trp His Pro Met Gly Ala Pro Trp Glu
1               5                   10
```

MULTIMERIC OLIGONUCLEOTIDES COMPOUNDS

RELATED APPLICATION

This application is a national stage filing under 35 U.S.C. §371 of international PCT patent application, PCT/US2012/055535, filed Sep. 14, 2012, entitled "Multimeric Oligonucleotides Compounds," which claims priority under 35 U.S.C. §119 (e) to U.S. provisional patent application, U.S.S.N. 61/534,561, filed Sep. 14, 2011, entitled "Multimeric Antisense Oligonucleotides," the entire contents of each of which are incorporated herein by reference.

FIELD OF THE INVENTION

This invention relates to oligonucleotide reagents, oligonucleotide therapeutics, and methods of making and using thereof.

BACKGROUND OF THE INVENTION

The development of oligonucleotides into clinical medicines and their use as basic research tools is an ongoing endeavor. For example, the use of antisense oligonucleotides for gene silencing was described as early as 1978. Since this time other oligonucleotide based approaches have emerged for regulating gene expression, including RNA interference, microRNAs, and, recently, targeted inhibition or inactivation of long non-coding RNAs.

Although natural phosphodiester-backbone oligonucleotides are taken up by cells efficiently, they are highly susceptible to nuclease degradation in plasma, which limits their effectiveness as therapeutics in some cases. In some instances, therefore, it is advantageous to limit or control the extent to which oligonucleotides are degraded by nucleases. In this regard, a number of modified nucleotides (e.g., LNAs) and backbone modifications (e.g., phosphorothioates, methylphosphonates) have been reported that improve stability in some instances. Nonetheless, it remains as current objective in oligonucleotide based research and development to obtain oligonucleotides having favorable pharmacokinetic and pharmacodynamic properties.

SUMMARY OF THE INVENTION

According to some aspects of the invention, multimeric oligonucleotide compounds are provided that are useful for regulating gene expression and function. Some aspects of the invention are based on the discovery that relatively high levels of a monomeric oligonucleotides can be achieved in a target tissue or cell when monomeric units are connected by a cleavable linker (e.g., an endonuclease-sensitive linker) and administered as a multimer. In some embodiments, the properties of a linker are selected to modulate the pharmacokinetic and pharmacodynamic properties of the multimeric oligonucleotide compounds. For example, in some embodiments, linker properties can be tuned to control the extent to which monomeric units are released in a particular tissue-type or cell-type to be targeted.

In some embodiments, an advantage of using multimers is that it allows simultaneous knockdown of multiple targets, while exploiting the pharmacokinetic and/or pharmacodynamic advantages of the administered oligonucleotide. In some embodiments, a sequence-specific concomitant knockdown of two or more targets may be achieved with a heteromultimer containing targeting oligonucleotides directed against several target gene combinations.

In some embodiments, multimeric oligonucleotides compounds provided herein comprise two or more targeting oligonucleotides linked together by a cleavable linker. In some embodiments, each targeting oligonucleotide has a region complementary to a target region of a genomic target sequence. In some embodiments, the targeting oligonucleotides hybridize to a target nucleic acid encoded by a genomic target sequence and inhibit the function and/or effect degradation of the target nucleic acid. The target nucleic acid may be, for example, a long non-coding RNA (lncRNA), microRNA, or mRNA.

In some embodiments, the targeting oligonucleotide is an antisense oligonucleotide (ASO), siRNA (e.g., a single stranded siRNA), miRNA sponge, or anti-microRNA antisense oligonucleotide (AMO). In some embodiments, the targeting oligonucleotide binds specifically to a target nucleic acid in a cell and brings about degradation of the target nucleic acid. In some embodiments, the degradation is mediated by RNAse H. In some embodiments, the degradation is mediated by an RNAi pathway. In some embodiments, the targeting oligonucleotide binds specifically to its target nucleic acid in a cell and inhibits the function of the target nucleic acid. For example, in some embodiments, the targeting oligonucleotide binds to a target lncRNA and inhibits interaction of the lncRNA with one or more interacting proteins (e.g., a subunit of Polycomb Repressor Complex 2 (PRC2)).

According to some aspects of the invention, compounds are provided that comprise the general formula: X-L-$[X-L]_i$-X, in which i is an integer from 0 to 9, the value of which indicates the number of units of $[X-L]_i$ present in the compound, in which each X is independently a targeting oligonucleotide having a region of complementarity comprising at least 7 contiguous nucleotides complementary to a target region of a genomic target sequence, and each L is a linker that links at least two Xs and that is more susceptible to cleavage in a mammalian extract than each X. In some embodiments, when i=0, and the general formula is 5'X3'-L-5'X3' and when the target regions complementary to the first X and second X do not overlap in the genomic target sequence, the 5'-end of the target region complementary to the first X and the 3'-end of the target region complementary to the second X are not within a distance of 0 to 4 nucleotides in the genomic target sequence. In some embodiments, the 5'-end of the target region complementary to the first X and the 3'-end of the target region complementary to the second X are not within a distance of 0 to 1, 0 to 2, 0 to 3, 0 to 4, 0 to 5, 0 to 6, 0 to 7, 0 to 8, 0 to 9, 0 to 10, 0 to 15, 0 to 20, 0 to 25 or more nucleotides in the genomic target sequence. In some embodiments, the targeting oligonucleotides are 8 to 15, 10 to 16, 10 to 20, 10 to 25, 15 to 30, 8 to 50, 10 to 100 or more nucleotides in length. In some embodiments, the targeting oligonucleotides are 8, 10, 11, 12, 13, 14, 15, 16, 17, 18, 19, 20, 21, 22, 23, 24, 25, 30, 40, 50, 60, 70, 80, 90, 100 or more nucleotides in length.

In some embodiments, at least one L does not comprise an oligonucleotide having a self-complementary nucleotide sequence. In some embodiments, all Ls do not comprise an oligonucleotide having a self-complementary nucleotide sequence. In some embodiments, at least one L does not comprise an oligonucleotide having a nucleotide sequence that is complementary to a region of the genomic target sequence that is contiguous with the target regions complementary to two immediately flanking Xs of the at least one L. In some embodiments, the compound does not comprise a ribozyme. In some embodiments, all Ls do not comprise an oligonucleotide having a nucleotide sequence that is complementary to a region of the genomic target sequence that is contiguous with the target regions complementary to two immediately flanking Xs.

In some embodiments, i is an integer from 0 to 3, 1 to 3, 1 to 5, 1 to 9, 1 to 15, 1 to 20. In some embodiments, i is 1, 2, 3, 4, 5, 6, 7, 8, 9, 10, 15, 20 or more. In some embodiments, the at least one L linker comprises an oligonucleotide that is more susceptible to cleavage by an endonuclease in the mammalian extract than the targeting oligonucleotides. In certain embodiments, at least one L is a linker having a nucleotide sequence comprising from 1 to 10 thymidines or uridines. In some embodiments, at least one L is a linker having a nucleotide sequence comprising deoxyribonucleotides linked through phosphodiester internucleotide linkages. In certain embodiments, at least one L is a linker having a nucleotide sequence comprising from 1 to 10 thymidines linked through phosphodiester internucleotide linkages. In some embodiments, at least one L is a linker having a nucleotide sequence comprising from 1 to 10 uridines linked through phosphorothioate internucleotide linkages. In certain embodiments, at least one L is a linker having the formula:

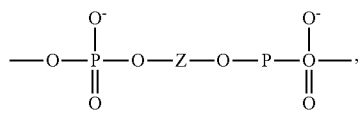

in which Z is an oligonucleotide. In some embodiments, Z has a nucleotide sequence comprising from 1 to 10 thymidines or uridines. In certain embodiments, at least one L does not comprise an oligonucleotide having a self-complementary nucleotide sequence and does not comprise an oligonucleotide having a nucleotide sequence that is complementary to a region of the genomic target sequence that is contiguous with two flanking target regions. In some embodiments, at least one L is a linker that does not comprise an oligonucleotide having an abasic site.

In certain embodiments, for at least one L, the linker comprises a polypeptide that is more susceptible to cleavage by an endopeptidase in the mammalian extract than the targeting oligonucleotides. In some embodiments, the endopeptidase is trypsin, chymotrypsin, elastase, thermolysin, pepsin, or endopeptidase V8. In some embodiments, the endopeptidase is cathepsin B, cathepsin D, cathepsin L, cathepsin C, papain, cathepsin S or endosomal acidic insulinase. In certain embodiments, at least one L is a linker comprising a peptide having an amino acid sequence selected from: ALAL (SEQ ID NO: 125), APISFFELG (SEQ ID NO: 126), FL, GFN, R/KXX, GRWHTVGLRWE (SEQ ID NO: 127), YL, GF, and FF, in which X is any amino acid.

In some embodiments, at least one L is a linker comprising the formula $—(CH_2)_nS—S(CH_2)_m—$, wherein n and m are independently integers from 0 to 10. In certain embodiments, at least one L the linker comprises a low pH-labile bond. In some embodiments, the low pH-labile bond comprises an amine, an imine, an ester, a benzoic imine, an amino ester, a diortho ester, a polyphosphoester, a polyphosphazene, an acetal, a vinyl ether, a hydrazone, an azidomethyl-methylmaleic anhydride, a thiopropionate, a masked endosomolytic agent or a citraconyl group.

In some embodiments, at least one L is a branched linker. In certain embodiments, the branched linker comprises a phosphoramidite linkage. In certain embodiments, the compound is a non-symmetrical branched trimer. In certain embodiments, the compound is a symmetrical branched trimer. In some embodiments, at least one L is a linker that is at least 2-fold more sensitive to cleavage in the presence of a mammalian extract than the targeting oligonucleotides.

In some embodiments, the compound may have the following general formula:

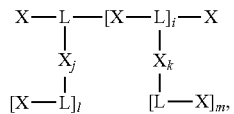

in which i is 0, 1, 2, 3, 4, 5, 6, 7, 8, 9, 10 or more, in which j and k are independently 0 or 1, the value of which indicates, respectively, the number of $X_j$ and $X_k$ present, and in which l and m are independently 0, 1, 2, 3, 4, 5, 6, 7, 8, 9, 10 or more, the value of which indicates, respectively, the number of units of $[X-L]_l$ and $[L-X]_m$ present in the compound. In some embodiments, at least one of $[X-L]_l$ and $[L-X]_m$ are present.

In some embodiments, the compound has the following general formula: X-L-[X-L]-X. In some embodiments, the compound has the following general formula:

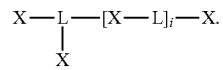

In some embodiments, the compound has the following general formula:

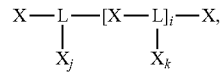

in which j and k are independently 0 or 1, the value of which indicates, respectively, the number of $X_j$ and $X_k$ present in the compound, and at least one of $X_j$ and $X_k$ are present in the compound.

According to some aspects of the invention, compounds are provided that comprise at least two targeting oligonucleotides linked through a linker that is at least 2-fold more sensitive to enzymatic cleavage in the presence of a mammalian extract than the at least two targeting oligonucleotides, wherein each targeting oligonucleotide has a region of complementarity comprising at least 7 contiguous nucleotides complementary to a target region of a genomic target sequence. In some embodiments, the targeting oligonucleotides are 8 to 15, 10 to 16, 12 to 16, 10 to 20, 10 to 25, 15 to 30, 8 to 50, 10 to 100 or more nucleotides in length. In some embodiments, the targeting oligonucleotides are 8, 10, 11, 12, 13, 14, 15, 16, 17, 18, 19, 20, 21, 22, 23, 24, 25, 30, 40, 50, 60, 70, 80, 90, 100 or more nucleotides in length.

In some embodiments, the linker is at least 5-fold, at least 6-fold, at least 7-fold, at least 8-fold, at least 9-fold, at least 10-fold or more sensitive to enzymatic cleavage in the presence of a mammalian extract than the two targeting oligonucleotides. In some embodiments, the linker is an oligonucleotide. In some embodiments, the oligonucleotide has a sequence that is not complementary to the genomic target sequence at a position immediately adjacent to the target region. In certain embodiments, the mammalian extract is an extract from kidney, liver, intestinal or tumor tissue. In some embodiments, the mammalian extract is a cell extract. In some embodiments, the mammalian extract is an endosomal extract.

In certain embodiments, at least one targeting oligonucleotide comprises at least one ribonucleotide, at least one deoxyribonucleotide, or at least one bridged nucleotide. In some embodiments, the bridged nucleotide is a LNA nucleotide, a cEt nucleotide or a ENA modified nucleotide. In some embodiments, at least one targeting oligonucleotide comprises at least one a 2'-fluoro-deoxyribonucleotide. In some embodiments, at least one targeting oligonucleotide comprises deoxyribonucleotides flanked by at least one bridged nucleotide on each of the 5' and 3' ends of the deoxyribonucleotides. In some embodiments, at least one targeting oligonucleotide comprises phosphorothioate internucleotide linkages between at least two nucleotides. In certain embodiments, at least one targeting oligonucleotide comprises a 2' O-methyl. In some embodiments, at least one targeting oligonucleotide comprises a G-clamp, 5-propynyl, or 5-octadienyl-pyrimidine. In certain embodiments, at least one targeting oligonucleotide is a gapmer comprising RNase H recruiting nucleotides. In some embodiments, at least one targeting oligonucleotide is a single stranded siRNA.

In certain embodiments, the compound is linked to a functional moiety (e.g., a lipophilic moiety or targeting moiety that binds to a cell surface receptor). In some embodiments, the functional moiety is linked to a targeting oligonucleotide. In some embodiments, the functional moiety is linked to a linker.

In certain embodiments, at least two targeting oligonucleotides are in the same 5' to 3' orientation relative to the linker. In some embodiments, at least two targeting oligonucleotides are in opposite 5' to 3' orientations relative to the linker. In certain embodiments, at least one targeting oligonucleotide is linked to the linker through a terminal nucleotide. In certain embodiments, at least one targeting oligonucleotide is linked to the linker through an internal nucleotide. In some embodiments, at least one targeting oligonucleotide is a single-stranded oligonucleotide.

In certain embodiments, the target region complementary to at least one targeting oligonucleotide is present in the sense strand of a gene. In some embodiments, the gene is an non-coding RNA gene. In certain embodiments, the non-coding RNA gene is a long non-coding RNA gene. In some embodiments, the non-coding RNA gene is an miRNA gene. In some embodiments, the gene is a protein coding gene. In certain embodiments, the genomic target sequence of at least one targeting oligonucleotide is the sequence of a PRC-2 associated region. In certain embodiments, at least two target regions are present in the sense strand of different genes. In certain embodiments, at least two target regions are present in the sense strand of the same gene. In some embodiments, at least two target regions are different. In some embodiments, at least two target regions are identical. In certain embodiments, the product of the gene mediates gene expression through an epigenetic mechanism.

According to some aspects of the invention, compositions are provided that comprise any of the compounds disclosed herein and a carrier. In some embodiments, the compositions comprise a buffered solution. In some embodiments, the compound is conjugated to the carrier. According to some aspects of the invention, pharmaceutical compositions are provided that comprise any of the compounds disclosed herein and a pharmaceutically acceptable carrier. In some embodiments, kits are provided that comprise a container housing any of the compounds or compositions disclosed herein.

According to some aspects of the invention, methods of increasing expression of a target gene in a cell are provided. In some embodiments, the methods comprise: contacting the cell with any of the compounds disclosed herein, and maintaining the cell under conditions in which the compound enters into the cell. In some embodiments of the methods, the genomic target sequence of at least one targeting oligonucleotide of the compound is present in the sense strand of an lncRNA gene, the product of which is an lncRNA that inhibits expression of the target gene. In some embodiments, presence of the compound in the cell results in a level of expression of the target gene that is at least 50% greater, at least 60% greater, at least 70% greater, at least 80%, or at least 90% greater than a level of expression of the target gene in a control cell that does not contain the compound.

According to some aspects of the invention, methods of increasing levels of a target gene in a subject are provided. In some embodiments, the methods comprise administering any of the compounds disclosed herein to the subject. In some embodiments, the genomic target sequence of at least one targeting oligonucleotide of the compound is present in the sense strand of an lncRNA gene, the product of which inhibits expression of the target gene.

According to some aspects of the invention, methods of treating a condition associated with altered levels of expression of a target gene in a subject are provided. In some embodiments, the condition is associated with decreased or increased levels of expression of the target gene compared to a control subject who does not have the condition. In some embodiments, the methods comprise administering the compound to the subject. In some embodiments, the genomic target sequence of at least one targeting oligonucleotide of the compound is present in the sense strand of an lncRNA gene, the product of which inhibits expression of the target gene. Accordingly, in some embodiments, the at least one targeting oligonucleotide hybridizes to the lncRNA and inhibits its function or brings about its degradation.

According to some aspects of the invention, methods of modulating activity of a target gene in a cell are provided. In some embodiments, the methods comprise contacting the cell with any of the compounds disclosed herein, and maintaining the cell under conditions in which the compound enters into the cell. In some embodiments, presence of the compound in the cell results in reduced expression or activity of the target gene in the cell. According to some aspects of the invention, methods of modulating levels of a target gene in a subject are provided. In some embodiments, the methods comprise administering any of the compounds disclosed herein to the subject. In some embodiments the genomic target sequence of at least one targeting oligonucleotide is present in the sense strand of the target gene. In some embodiments, the target gene is a protein coding gene or non-coding gene.

In some embodiments, multimeric oligonucleotide compounds are provided that comprise two or more targeting oligonucleotides (e.g., ASOs), each having a nuclease-resistant modified backbone, wherein the targeting oligonucleotides are linked to each other by one or more degradable linkers. In some embodiments, the backbone contains internucleoside linkages. In some embodiments, the individual linked targeting oligonucleotides, contained in a compound, may be directed to the same target, or to multiple targets.

The multimeric compounds can be homodimers, homotrimers, etc., heterodimers, heterotrimers, etc. They can be linear, branched, or circular.

In some embodiments, the invention is based, in part, on the discovery that multimeric oligonucleotide compounds (e.g., a 14-mer ASO linked to another 14-mer ASO) show significantly higher levels of the corresponding monomeric oligonucleotide compounds in the liver when the monomer units are connected by a rapidly degradable linker (e.g., a nuclease-sensitive linker or a disulfide linker), as opposed to a linker that is nuclease-resistant and, therefore, slowly degradable. Unexpectedly, the detected liver levels of the dimer-derived monomeric units were five to ten times higher than that of the corresponding monomers administered in the monomeric form. The increased delivery to the liver was also associated with a more effective target mRNA knockdown after 14 days of dosing in mice. The invention is therefore, in part, based on the realization that the type and properties of the linker can thus be used to modulate the pharmacokinetic and pharmacodynamic properties of the dimer antisense molecules. In some embodiments, rapidly degradable linkers are referred as "cleavable" (such as, e.g., a nuclease-sensitive, phosphodiester, linkage or a linker comprising a disulfide bond), while more stable linkages, such as, e.g., nuclease-resistant phosphorothioates, as referred to as "noncleavable."

In illustrative embodiments, the compounds are directed to one or more hepatic targets ASOs are directed to hepatic targets, including but not limited to ApoC3 and ApoB.

In some embodiments, targeting oligonucleotides (e.g., ASOs) contain 12 to 16 nucleotide bases, wherein one or more targeting oligonucleotides are gapmers. Targeting oligonucleotides (e.g., ASOs), including gapmers, can comprise a 2' modification in the sugar residues (e.g., locked-nucleic acid (LNA) modification), 2'-O-methyl and 2'-fluoro modification, and/or a nucleotide modification such as G-clamp, 5-propynyl, and 5-octadienyl-pyrimidine.

The invention further provides pharmaceutical compositions, comprising compounds of the invention along with pharmaceutically acceptable excipients. In certain embodiments, the pharmaceutical composition is characterized by one or more of the following properties when administered in vivo:
(a) increased concentration in the liver and reduced clearance by kidneys as compared to respective monomeric targeting oligonucleotides (e.g., ASOs);
(b) longer duration of target knockdown as compared to respective monomeric targeting oligonucleotides (e.g., ASOs); and
(c) lower effective concentrations as compared to respective monomeric targeting oligonucleotides (e.g., ASOs) and/or the same multimeric oligonucleotide compound, wherein the cleavable linker is substituted with a noncleavable linker.

The invention further provides methods of inhibiting mRNA levels of one or more targets, comprising administering to a cell or a subject the compound of the invention in an amount effective to inhibit the expression of the target(s). In some embodiments, the methods provide a therapeutically effective knockdown of the target(s) persists for two weeks or longer following the administration. The method can be used with targets that are associated with a metabolic disease, cancer, cardiovascular disease, and other conditions.

The foregoing and following descriptions are illustrative and explanatory only and are not restrictive of the invention, as claimed in this text, the multimeric targeting oligonucleotides (e.g., ASOs) may be referred to by the respective target names only, e.g., "ApoC3-ApoC3 dimer" stands as a short hand for "ApoC3-ApoC3 ASO dimer."

BRIEF DESCRIPTION OF THE FIGURES

FIG. 2 demonstrates in vitro stability of dimers in plasmas and their degradation in liver homogenates, as determined by liquid chromatography-mass spectrometry (LC-MS).

FIG. 5A demonstrates an associated increased reduction of the liver ApoC3 mRNA levels in human ApoC3 transgenic mice following treatment with the endonuclease-sensitive, phosphodiester-linked, homodimers (SEQ ID NO:4 and SEQ ID NO:2). Homodimers SEQ ID NO:4 and 2 exhibited an increased reduction of liver ApoC3 mRNA levels compared to the monomer (SEQ ID NO:1) after 14 days.

FIGS. 5B and 5C show ApoC3 protein knockdown 7 days (FIG. 5B) and 14 days (FIG. 5C) after a single 10 mg/kg dose of the SEQ ID NO:1 monomer and dimeric LNA gapmers SEQ ID NO:2—SEQ ID NO:5 in human ApoC3 transgenic mice. The figures demonstrate increased duration in the reduction of serum ApoC3 protein levels in human ApoC3 transgenic mice following treatment with the endonuclease-sensitive phosphodiester-linked homodimers, SEQ ID NO:1, SEQ ID NO:4 and SEQ ID NO:2. Homodimers SEQ ID NO:4 and SEQ ID NO:2 exhibited a reduction of serum ApoC3 levels similar to monomer SEQ ID NO:1 after 7 days, but in contrast to the monomer, the reduction in the reduction in target gene expression in cells treated with the cleavable dimers (SEQ ID NO:2 or 4) was sustained and, as a result, increased compared to SEQ ID NO:1 after 14 days.

Figure 1A:
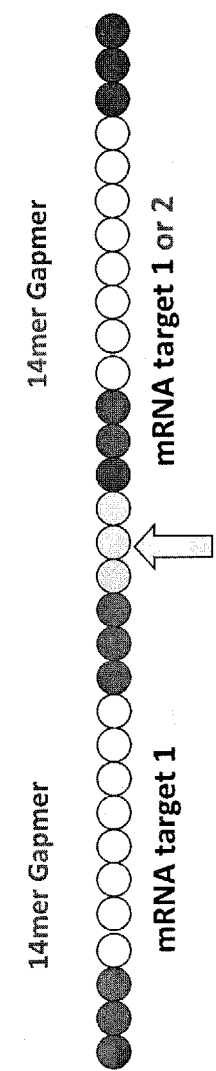
FIG. 1A shows a schematic representation of an exemplary construct, in which two 14-mer gapmers (e.g., 3LNA-8DNA-3LNA as illustrated) are connected via a linker (represented light shaded circles).

Unless otherwise stated, the numbers in the figures with hash signs (such as #1, #50, etc.) correspond to the respective SEQ ID NOs as per Table 1.

DETAILED DESCRIPTION OF THE INVENTION

Multimeric oligonucleotide compounds are provided that are useful for regulating gene expression and/or function. In general, the multimeric oligonucleotides compounds provided herein comprise two or more targeting oligonucleotides linked together by a cleavable linker. The multimeric oligonucleotides are useful for regulating the expression or function of a wide range of target nucleic acids including, for example, a long non-coding RNA (lncRNA), microRNA, or mRNA. In some embodiments, the targeting oligonucleotide of the multimer is an antisense oligonucleotide (ASO), siRNA (e.g., a single stranded siRNA), miRNA sponge, or anti-microRNA antisense oligonucleotide (AMO). However, other types of targeting oligonucleotides may be used.

A. General Structure of Multimeric Oligonucleotides

Multimeric oligonucleotide compounds are provided that comprise the general formula: X-L-[X-L]$_i$-X, in which i is an integer, the value of which indicates the number of units of [X-L]$_i$ present in the compound, and in which each X is a targeting oligonucleotide and each L is a linker that links at least two Xs and that is more susceptible to cleavage in a mammalian extract than each X. In some embodiments, i is 0, 1, 2, 3, 4, 5, 6, 7, 8, 9, 10 or more, As used herein, the term "mammalian extract" refers to a sample extracted from a mammalian tissue, cell or subcellular compartment (e.g., an endosome). Generally, a mammalian extract comprises one or more biomolecules (e.g., enzymes) from the tissue, cell or subcellular compartment. In some embodiments, a mammalian extract comprises one or more of a nuclease, peptidase, protease, phosphatase, oxidase, and reductase. The mammalian extract may be an extract from any tissue, including, for example, kidney, liver, intestinal or tumor tissue. The mammalian extract may be a cell extract or an extract from a subcellular component, such as a nuclear extract, or an endosomal extract.

As used herein, the term "cleavage" refers to the breaking of one or more chemical bonds in a relatively large molecule in a manner that produces two or more relatively small molecules. Cleavage in the mammalian extract may be mediated by a nuclease, peptidase, protease, phosphatase, oxidase, or reductase, for example. In some embodiments, the term "cleavable," as used herein, refers to rapidly degradable linkers, such as, e.g., phosphodiester and disulfides, while the term "noncleavable" refer to more stable linkages, such as, e.g., nuclease-resistant phosphorothioates (e.g., a racemic mixture of Sp and Rp diastereoisomers, as used in the Examples below, or a backbone enriched in Sp form). The properties of cleavable and noncleavable linkers are described in further detail herein.

In one example, the compound has the following general formula:

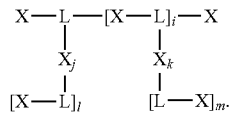

In this formula, i is an integer indicating the number of units of [X-L]$_i$ present in the compound; j and k are independently 0 or 1, the value of which indicates, respectively, the number of $X_j$ and $X_k$ present in the compound; and l and m are integers the value of which indicate, respectively, the number of units of [X-L]$_l$ and [L-X]$_m$ present in the compound. In some embodiments, i is 0, 1, 2, 3, 4, 5, 6, 7, 8, 9, 10, 15, 20 or more. In certain embodiments, l and m are independently 0, 1, 2, 3, 4, 5, 6, 7, 8, 9, 10, 15, 20 or more. In certain embodiments, at least one of [X-L]$_l$ and [L-X]$_m$ are present in the compound. In some embodiments, i, j, k, l, and m are 0. In some embodiments, i is 1, and j, k, l, and m are 0.

In one example, the compound may have the following general formula: X-L-[X-L]$_i$-X, in which i is 0, 1, 2, 3, 4, 5, 6, 7, 8, 9, 10 or more.

In another example, the compound may have the following general formula:

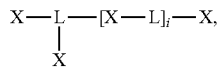

in which i is 0, 1, 2, 3, 4, 5, 6, 7, 8, 9, 10 or more.

In another example, the compound may have the following general formula:

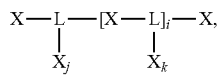

in which j and k are independently 0 or 1, the value of which indicates, respectively, the number of X$_j$ and X$_k$ present, and at least one of X$_j$ and X$_k$ are present in the compound.

Typically, the targeting oligonucleotide has a region of complementarity comprising at least 4, at least 5, at least 6, at least 7, at least 8, at least 9, at least 10, at least 15, or at least 20 contiguous nucleotides complementary to a target region of a genomic target sequence. The targeting oligonucleotide may have a region of complementarity comprising 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, or 50 contiguous nucleotides complementary to a target region of a genomic target sequence. It should be appreciated that, in some embodiments, the region of complementary may have one or more mismatches compared with the nucleotide sequence of the target region provided that the targeting oligonucleotide is still capable of hybridizing with the target region. In some embodiments, the region of complementary has no mismatches compared with the nucleotide sequence of the target region. It should also be appreciated that a targeting oligonucleotide may hybridize with a target region through Watson-Crick base pairing, Hoogsteen base pairing, reverse-Hoogsteen binding, or other binding mechanism. In some embodiments, the targeting oligonucleotide is an aptamer, e.g., an aptamer that binds to an intracellular or nuclear protein.

In some multimeric oligonucleotides, for two Xs, a first X and a second X, that are separated by a single L, the 5'-end of the target region complementary to the first X and the 3'-end of the target region complementary to the second X are not within a distance of 0 to 1, 0 to 2, 0 to 3, 0 to 4, 0 to 5, 0 to 10, 0 to 15, 0 to 20, 0 to 25, 0 to 50, nucleotides in the genomic target sequence when the target regions complementary to the first X and second X do not overlap in the genomic target sequence. In some instances the different X's have complementarity to the same target and in other instances to different target. When the X's have complementarity to the same target the nucleic acid sequence of the X's may be identical with one another or overlapping or completely distinct.

In some embodiments, multimeric oligonucleotide compounds comprises ASOs. The invention provides in some embodiments multimeric oligonucleotide compounds, comprising two or more target-specific antisense oligonucleotides (ASOs), each ASO having a nuclease-resistant modified backbone, in which the targeting oligonucleotides are linked to each other by one or more degradable linkers. The term "monomeric" or "monomer," in the context of targeting oligonucleotides (e.g., ASOs), refers to an targeting oligonucleotide that (i) is directed to a single site or a single contiguous stretch of nucleotides on a target and (ii) is not covalently linked to the another targeting oligonucleotide directed to the same or another site on the same or another target. Multimeric oligonucleotide compounds are not monomeric because they contain targeting oligonucleotides (e.g., ASOs) that are covalently linked to each other.

The number of targeting oligonucleotides (e.g., ASOs) in a multimeric oligonucleotide compound of the invention may be two or more, three or more, four or more, etc. For example, a multimeric oligonucleotide compound may contain 2, 3, 4, 5, 6, 7, 8, 9, 10, or more individual Targeting oligonucleotides (e.g., ASOs) directed to one or more targets. The individual Targeting oligonucleotides (e.g., ASOs) can be specific to the same or different targets. For example, as illustrated in FIG. 1A, in some embodiments, the targeting oligonucleotide is a dimer comprising two targeting oligonucleotides specific to the same target, or a dimer comprising two targeting oligonucleotides specific to two different targets, or alternatively, a trimer comprising three targeting oligonucleotides specific to the same target, or a trimer comprising three targeting oligonucleotides specific three different targets, etc. In some cases, the individual targeting oligonucleotides can be specific to the same target, yet directed to distinct target sites on the target, such as two sites on the target sequence that are separated by at least 10, 20, 50, 100, 300 or more nucleotides. In some embodiments, the target sites can be directly adjacent to each other and not separated by any intervening sequences.

Figure 1B:
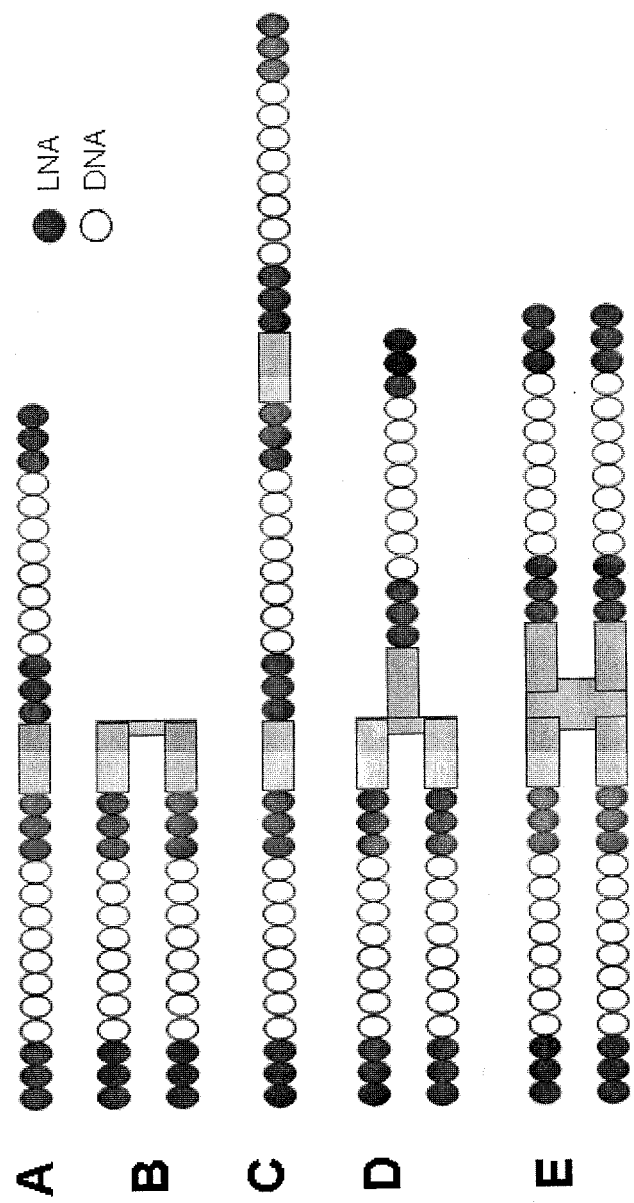
FIG. 1B shows examples of various configurations of dimers and multimers (homopolymers or heteropolymers).

As shown in FIG. 1B, the multimers can be linear or branched or a combination thereof. For example, two ASO may be connected head-to-tail (5'-to-3'-linear) (type A) or as in type B, tail-to-tail (3'-to-3'-branched); the ASOs could also be connected head-to-head (5'-to-5'-branched). Similarly, three or more antisense molecules can be connected (examples C, D, E in FIG. 1B). In an alternative embodiment, the multimer can be in the form of a circular nucleic acid.

B. Targeting Oligonucleotides

In some embodiments, multimeric oligonucleotides provided herein comprise two or more targeting oligonucleotides linked together by a cleavable linker. In some embodiments, each targeting oligonucleotide has a region complementary to a target region of a genomic target sequence. In some embodiments, the targeting oligonucleotide is an antisense oligonucleotide (ASO), siRNA (e.g., a single stranded siRNA), miRNA sponge, or anti-microRNA antisense oligonucleotide (AMO). In some embodiments, the targeting oligonucleotide binds specifically to a target RNA in a cell and brings about degradation of the RNA. In some embodiments, the degradation is mediated by RNAse H. In some embodiments, the degradation is mediated by an RNAi pathway. It should be appreciated that unless otherwise apparent from context "a targeting oligonucleotide" or "the targeting oligonucleotide" as referred to herein, generally means at least one of the targeting oligonucleotides present in a multimeric compound. Similarly, it should be appreciated that unless otherwise apparent from context "a linker" or "the linker," as referred to herein, generally means at least one of the linkers present in a multimeric compound.

As used herein, the term "genomic target sequence" refers to a nucleotide sequence of clinical, therapeutic or research interest in a genome (e.g., a mammalian genome, e.g., a human or mouse genome). Typically, a genomic target sequence is a sequence of a genome that comprises a gene coding or regulatory region, or that is present within a gene coding or regulatory region. In some embodiments, a genomic target sequence is a sequence that encodes at least a portion of a gene. The gene may be an non-coding RNA gene or a protein coding gene. The non-coding RNA gene may be a long non-coding RNA gene or an miRNA gene, for example. The product of the gene may be an RNA or protein that mediates gene expression through an epigenetic mechanism. In other embodiments, a genomic target sequence is a sequence positioned in a regulatory region of one or more genes, such as a promoter, enhancer, silencer region, locus control region and other functional region of a genome.

In some embodiments, the genomic target sequence is present in the sense strand of a gene. The sense strand or coding strand is the segment of double stranded DNA running from 5'-3' that is complementary to the antisense strand or template strand of a gene. The sense strand is the strand of DNA that has the same sequence as the RNA transcribed from the gene (e.g., mRNA, lncRNA, or miRNA), which takes the antisense strand as its template during transcription.

The "target region" of a genomic target sequence is a sequence of nucleotides that constitutes a hybridization site of a targeting oligonucleotide. The actual target oligonucleotide may hybridize with the genomic target itself (e.g., a promoter element) or an nucleic acid encoded by the genomic target sequence or containing the genomic target sequence (e.g., an lncRNA, miRNA, or mRNA). In some embodiments, the target region encodes a site on a transcribed RNA, and hybridization of a targeting oligonucleotide to the site results in inactivation or degradation of the transcribed RNA. Accordingly, in some embodiments, the targeting oligonucleotides hybridize to a transcribed RNA encoded by a genomic target sequence and inhibit the function and/or effect degradation of the transcribed RNA. The RNA may be, for example, a long non-coding RNA (lncRNA), microRNA, or mRNA.

It should be appreciated that multimeric oligonucleotides compounds provided herein may comprise two or more targeting oligonucleotides that are each complementary to the same or different genomic target sequences, and thus that may regulate the same or different genes. In some embodiments, the genomic target sequences is present in the sense strand of different genes. In some embodiments, the genomic target sequences is present in the sense strand of the same gene.

In some embodiments, the genomic target sequence of at least one targeting oligonucleotide is or comprises the sequence of a PRC-2 associated region. As used herein, the term "PRC2-associated region" refers to a region of a nucleic acid that comprises or encodes a sequence of nucleotides that interact directly or indirectly with a component of PRC2. A PRC2-associated region may be present in a RNA (e.g., a long non-coding RNA (lncRNA)) that interacts with a PRC2. A PRC2-associated region may be present in a DNA that encodes an RNA that interacts with PRC2.

In some embodiments, a PRC2-associated region is a region of an RNA that crosslinks to a component of PRC2 in response to in situ ultraviolet irradiation of a cell that expresses the RNA, or a region of genomic DNA that encodes that RNA region. In some embodiments, a PRC2-associated region is a region of an RNA that immunoprecipitates with an antibody that targets a component of PRC2, or a region of genomic DNA that encodes that RNA region. In some embodiments, a PRC2-associated region is a region of an RNA that immunoprecipitates with an antibody that binds specifically to SUZ12, EED, EZH2 or RBBP4 (which as noted above are components of PRC2), or a region of genomic DNA that encodes that RNA region.

In some embodiments, a PRC2-associated region is a region of an RNA that is protected from nucleases (e.g., RNases) in an RNA-immunoprecipitation assay that employs an antibody that targets a component of PRC2, or a region of genomic DNA that encodes that protected RNA region. In some embodiments, a PRC2-associated region is a region of an RNA that is protected from nucleases (e.g., RNases) in an RNA-immunoprecipitation assay that employs an antibody that targets SUZ12, EED, EZH2 or RBBP4, or a region of genomic DNA that encodes that protected RNA region.

In some embodiments, a PRC2-associated region is a region of an RNA within which occur a relatively high frequency of sequence reads in a sequencing reaction of products of an RNA-immunoprecipitation assay that employs an antibody that targets a component of PRC2, or a region of genomic DNA that encodes that RNA region. In some embodiments, a PRC2-associated region is a region of an RNA within which occur a relatively high frequency of sequence reads in a sequencing reaction of products of an RNA-immunoprecipitation assay that employs an antibody that binds specifically to SUZ12, EED, EZH2 or RBBP4, or a region of genomic DNA that encodes that protected RNA region. In such embodiments, the PRC2-associated region may be referred to as a "peak."

In some embodiments, a PRC2-associated region comprises a sequence of 40 to 60 nucleotides that interact with PRC2 complex. In some embodiments, a PRC2-associated region comprises a sequence of 40 to 60 nucleotides that encode an RNA that interacts with PRC2. In some embodiments, a PRC2-associated region comprises a sequence of up to 5 kb in length that comprises a sequence (e.g., of 40 to 60 nucleotides) that interacts with PRC2. In some embodiments, a PRC2-associated region comprises a sequence of up to 5 kb in length within which an RNA is encoded that has a sequence (e.g., of 40 to 60 nucleotides) that is known to interact with PRC2. In some embodiments, a PRC2-associated region comprises a sequence of about 4 kb in length that comprise a sequence (e.g., of 40 to 60 nucleotides) that interacts with PRC2. In some embodiments, a PRC2-associated region comprises a sequence of about 4 kb in length within which an RNA is encoded that includes a sequence (e.g., of 40 to 60 nucleotides) that is known to interact with PRC2.

In some embodiments, a PRC2-associated region has a sequence as set forth in SEQ ID NOS: 632,564, 1 to 916,209, or 916,626 to 934,931 of International Patent Appl. Pub. No.: WO/2012/087983, or SEQ ID NOS: 1 to 193,049 of International Patent Appl. Pub. No.: WO/2012/065143, each of which is entitled, POLYCOMB-ASSOCIATED NON-CODING RNAS, and the contents of each of which are incorporated by reference herein in their entireties.

In some embodiments, the targeting oligonucleotides interfere with the binding of and function of PRC2 by preventing recruitment of PRC2 to a specific chromosomal locus through lncRNAs. For example, in some embodiments, administration of multimeric oligonucleotide compounds comprising targeting oligonucleotides designed to specifically bind a PRC2-associated region of a lncRNA can stably displace not only the lncRNA, but also the PRC2 that binds to the lncRNA, from binding chromatin. Further, lncRNA can recruit PRC2 in a cis fashion, repressing gene expression at or near the specific chromosomal locus from which the lncRNA was transcribed. Thus, in some embodiments, the compounds disclosed herein may be used to inhibit cis mediated gene repression by lncRNAs.

In some embodiments, targeting oligonucleotides may comprise at least one ribonucleotide, at least one deoxyribonucleotide, and/or at least one bridged nucleotide. In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotide comprises a nucleotide analog disclosed in one of the following U.S. patent or Patent Application Publications: U.S. Pat. Nos. 7,399,845, 7,741,457, 8,022,193, 7,569,686, 7,335,765,7,314,923,7, 335,765, and 7,816,333, US 20110009471, the entire contents of each of which are incorporated herein by reference for all purposes. The targeting oligonucleotide may have one or more 2' O-methyl nucleotides. The oligonucleotide may consist entirely of 2' O-methyl nucleotides.

The targeting oligonucleotide may contain one or more nucleotide analogues. For example, the targeting oligonucleotide may have at least one nucleotide analogue that results in an increase in $T_m$ of the oligonucleotide in a range of 1° C., 2° C., 3° C., 4° C., or 5° C. compared with an oligonucleotide that does not have the at least one nucleotide analogue. The targeting oligonucleotide may have a plurality of nucleotide analogues that results in a total increase in $T_m$ of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the nucleotide analogue.

In some embodiments, the targeting oligonucleotide may be of up to 50 nucleotides in length or up to 100 nucleotides in length, in which 2 to 10, 2 to 15, 2 to 16, 2 to 17, 2 to 18, 2 to 19, 2 to 20, 2 to 25, 2 to 30, 2 to 40, 2 to 45, 2 to 75, 2 to 95, or more nucleotides of the oligonucleotide are nucleotide analogues. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are nucleotide analogues. The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are nucleotide analogues. Optionally, the oligonucleotides may have every nucleotide except 1, 2, 3, 4, 5, 6, 7, 8, 9, or 10 nucleotides modified.

The targeting oligonucleotide may consist entirely of bridged nucleotides (e.g., LNA nucleotides, cEt nucleotides, ENA nucleotides). The oligonucleotide may comprise alternating deoxyribonucleotides and 2'-fluoro-deoxyribonucleotides. The oligonucleotide may comprise alternating deoxyribonucleotides and 2'-O-methyl nucleotides. The oligonucleotide may comprise alternating deoxyribonucleotides and ENA nucleotide analogues. The oligonucleotide may comprise alternating deoxyribonucleotides and LNA nucleotides. The oligonucleotide may comprise alternating LNA nucleotides and 2'-O-methyl nucleotides. The oligonucleotide may have a 5' nucleotide that is a bridged nucleotide (e.g., a LNA nucleotide, cEt nucleotide, ENA nucleotide). The oligonucleotide may have a 5' nucleotide that is a deoxyribonucleotide.

The targeting oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. The 3' position of the oligonucleotide may have a 3' hydroxyl group. The 3' position of the oligonucleotide may have a 3' thiophosphate.

The targeting oligonucleotide may be conjugated with a label. For example, the oligonucleotide may be conjugated with a biotin moiety, cholesterol, Vitamin A, folate, sigma receptor ligands, aptamers, peptides, such as CPP, hydrophobic molecules, such as lipids, ASGPR or dynamic polyconjugates and variants thereof at its 5' or 3' end.

The targeting oligonucleotide may comprise one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the targeting oligonucleotides are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric targeting oligonucleotides of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the targeting oligonucleotide comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than a native oligodeoxynucleotide; these modified oligos survive intact for a longer time than unmodified oligonucleotides, in some experimental or therapeutics contexts. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone, $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids.

Examples of LNAs are described in WO/2008/043753 and include compounds of the following general formula.

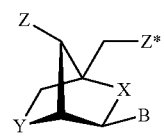

in which X and Y are independently selected among the groups —O—, —S—, —N(H)—, N(R)—, —$CH_2$— or —CH— (if part of a double bond), —$CH_2$—O—, —$CH_2$—S—, —$CH_2$—N(H)—, —$CH_2$—N(R)—, —$CH_2$—$CH_2$— or —$CH_2$—CH— (if part of a double bond), —CH=CH—, where R is selected from hydrogen and $C_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the oligonucleotides described herein comprises at least one LNA unit according any of the formulas

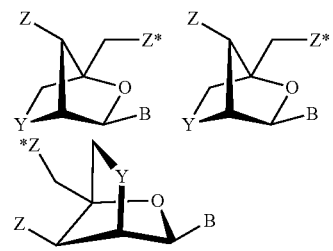

in which Y is —O—, —S—, —NH—, or N(R$^H$); Z and Z* are independently selected among an internucleoside linkage, a terminal group or a protecting group; B constitutes a natural or non-natural nucleotide base moiety, and RH is selected from hydrogen and C$_{1-4}$-alkyl.

Preferably, the Locked Nucleic Acid (LNA) used in the oligonucleotides described herein comprises at least one nucleotide comprises a Locked Nucleic Acid (LNA) unit according any of the formulas shown in Scheme 2 of PCT/DK2006/000512.

Preferably, the LNA used in the oligomer of the invention comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, where R$^H$ is selected from hydrogen and C$_{1-4}$-alkyl.

Specifically preferred LNA units are shown in scheme 2:

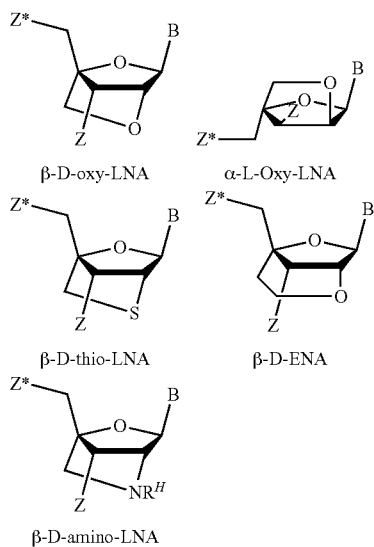

Scheme 2

β-D-oxy-LNA    α-L-Oxy-LNA

β-D-thio-LNA    β-D-ENA

β-D-amino-LNA

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail herein.

One or more substituted sugar moieties can also be included, e.g., one of the following at the 2' position: OH, SH, SCH$_3$, F, OCN, OCH$_3$OCH$_3$, OCH$_3$O(CH$_2$)nCH$_3$, O(CH$_2$)nNH$_2$ or O(CH$_2$)nCH$_3$ where n is from 1 to about 10; Ci to C10 lower alkyl, alkoxyalkoxy, substituted lower alkyl, alkaryl or aralkyl; Cl; Br; CN; CF$_3$; OCF$_3$; O-, S-, or N-alkyl; O-, S-, or N-alkenyl; SOCH$_3$; SO$_2$CH$_3$; ONO$_2$; NO$_2$; N$_3$; NH2; heterocycloalkyl; heterocycloalkaryl; amino alkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy[2'-O—CH$_2$CH$_2$OCH$_3$, also known as 2'-O-(2-methoxyethyl)] (Martin et al, Helv. Chim. Acta, 1995, 78, 486). Other preferred modifications include 2'-methoxy(2'-O—CH$_3$), 2'-propoxy(2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Targeting oligonucleotides can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2° C. (Sanghvi, in Crooke, and Lebleu, eds., Antisense Research and Applications, CRC Press, Boca Raton, 1993, pp. 276-278) and may be used as base substitutions. It should be appreciated that one or more modified bases may be present in a region of complementarity of a targeting oligonucleotide.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990, those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the targeting oligonucleotides are chemically linked to one or more moieties or conjugates that enhance the activity, cellular distribution, or cellular uptake of the oligonucleotide. For example, one or more targeting oligonucleotides, of the same or different types, can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxy-cholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, targeting oligonucleotide modification include modification of the 5' or 3' end of the oligonucleotide. In some embodiments, the 3' end of the oligonucleotide comprises a hydroxyl group or a thiophosphate. It should be appreciated that additional molecules (e.g. a biotin moiety or a fluorophor) can be conjugated to the 5' or 3' end of the targeting oligonucleotide. In some embodiments, the targeting oligonucleotide comprises a biotin moiety conjugated to the 5' nucleotide.

In some embodiments, the targeting oligonucleotide comprises locked nucleic acids (LNA), ENA modified nucleotides, 2'-O-methyl nucleotides, or 2'-fluoro-deoxyribonucleotides. In some embodiments, the targeting oligonucleotide comprises alternating deoxyribonucleotides and 2'-fluoro-deoxyribonucleotides. In some embodiments, the targeting oligonucleotide comprises alternating deoxyribonucleotides and 2'-O-methyl nucleotides. In some embodiments, the targeting oligonucleotide comprises alternating deoxyribonucleotides and ENA modified nucleotides. In some embodiments, the targeting oligonucleotide comprises alternating deoxyribonucleotides and locked nucleic acid nucleotides. In some embodiments, the targeting oligonucleotide comprises alternating locked nucleic acid nucleotides and 2'-O-methyl nucleotides.

In some embodiments, the 5' nucleotide of the oligonucleotide is a deoxyribonucleotide. In some embodiments, the 5' nucleotide of the oligonucleotide is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, the targeting oligonucleotide comprises phosphorothioate internucleotide linkages. In some embodiments, the targeting oligonucleotide comprises phosphorothioate internucleotide linkages between at least two nucleotides. In some embodiments, the targeting oligonucleotide comprises phosphorothioate internucleotide linkages between all nucleotides.

It should be appreciated that the targeting oligonucleotide can have any combination of modifications as described herein.

It should also be appreciated that oligonucleotide based linkers may also include any of the modifications disclosed herein.

C. Antisense-Based Targeting Oligonucleotides

In illustrative embodiments, the targeting oligonucleotides are targeting oligonucleotides that contain locked nucleic acid 3-8-3 gapmers which have a phosphorothioate backbone. However, in general, the chemistry of the oligonucleotide is not limited to LNA (2'-O,4'-C-methylene-bridged nucleic acids described, e.g., in PCT patent application WO 98/39352), LNA gapmers, or the phosphorothioate backbone, and can be expected to work with any chemistry for which the target knock-down using a monomeric ASO is effective. Such chemistries include, for instance, 2'-O,4'-C-ethylene-bridged nucleic acids (ENA; European patent No. EP 1152009), hexitol nucleic acids (HNA; WO 93/25565 and WO 97/30064), fluoro-HNA, 2'-deoxy-2'-fluoro-13-D-arabino nucleic acids (FANA; EP 1088066), 2'-modified analogs such as 2'-O-methyl(2'-OMe) and 2'-O-(2-methoxyethyl) (MOE) modified nucleic acids, CeNA (EP 1210347 and EP 1244667) as well as phosphate-modified analogs such as phosphoroamidate, morpholinos, base-modified analogs, such as G-clamps (WO 99/24452) and 5-alkynyl-pyrimidines. Examples of LNA other gapmers are described in PCT patent applications published as WO 01/25248, WO 01/48190, WO 2003/085110, WO 2004/046160, WO 2008/113832, WO 2005/023825 and WO 2007/14651; examples of FANA/DNA/FANA gapmers are described in EP 1315807; examples of 2'-OMe/FANA/2'-OMe gapmers are described in U.S. Pat. No. 6,673,611.

The backbone may be stabilized by other modifications, for example, methylphosphonate or other chemistries. The antisense oligonucleotides of this invention can work via an RNase H mechanism, but can also work by steric blocking only, which also includes transcriptional gene silencing and transcriptional gene activation (see, e.g., Hawkins et al., 2009, Nucl. Acids Res., 37(9):2984-2995 and Schwartz et al., 2008, Nature Struct. Mol. Biol., 15:842-848). The dimer/multimer approach can also be combined with any modification which increases the delivery into cells, including lipophilic modifications, conjugates to cell surface receptors or ligands (e.g., folate), aptamers, etc. For example, to exploit the RNAse H mechanism, DNA:mRNA or gapmer:RNA duplexes need to be formed to permit RNAse to bind to the substrate. However, in the case of steric blocking, RNA:RNA, RNA:2'-O-methyl-RNA, RNA:PNA or RNA:LNA duplexes (without a DNA gap) may be used. Thus, the ASO chemistry may be adjusted based on the intended use. Any chemistry suitable for the antisense oligonucleotides should be applicable to the dimer/multimer approach of the invention (for the state-of-the-art chemistries, see, e.g., Bennett and Swaize, 2009, Ann. Rev. Pharmacol. Toxicol., 50:259-293; Yokota at al., 2010, Arch. Neurol., 66:32-38; Aboul-Fadl, 2005, Curr. Med. Chem., 12:2193-2214; Kurreck, 2003, Eur. J. Biochem., 270:1628-1644).

In some illustrative embodiments, the targeting oligonucleotides are 14-nucleotide long, but could be generally longer or shorter. For example, the targeting oligonucleotide could be 8-50-nucleotide long, or 10-40, 10-25, 8-20, 10-25, 12-25, 12-20, 12-16, 12-15, 12-14, 12-13, 13-16, 13-15, or 13-14 nucleotides long. In some embodiments, targeting oligonucleotides are so-called tiny LNAs, containing as few as 8 or fewer nucleotides (see, e.g., Obad et al. (2011) Nature Genetics, 43:371).

Further, in some embodiments, a targeting oligonucleotide (e.g., ASO) comprises at least 7 contiguous nucleotides complementary to the target sequence. In further embodiments, targeting oligonucleotide (e.g., ASO) comprises at least 8, 9, 10, 11, 12, 13, 14, 15, 16, 17, 18, 19, 20, 21, 22, 23, 24, 25, 30, 35, or 40 contiguous nucleotides complementary to a target sequence. Due to specificities and isoform variations, ASO may additionally comprise 1, 2, 3 or more non-complementary nucleotides, either within the contiguous sequences or flanking them. In some embodiments, at least one or all of the targeting oligonucleotides are gapmers. In other embodiments, the targeting oligonucleotides (e.g., ASOs) are X—N—Y gapmers, wherein at X or Y contains 0, 1, 2, 3, 4, 5 or more modified nucleotides, e.g., LNA, ENA, FANA, G-clamp, and N is 3, 4, 5, 6, 7, 8, 9, or 10 deoxynucleotides with non-modified sugars. For example, ASO can be a 3-8-3, 2-10-2, 3-9-2, 2-9-3, 2-8-2, 3-7-2, 2-7-3 gapmer or another type of gapmer or mixmer.

D. Linkers

The term "linker" generally refers to a chemical moiety that is capable of covalently linking two or more targeting oligonucleotides, in which at least one bond comprised within the linker is capable of being cleaved (e.g., in a biological context, such as in a mammalian extract, such as an endosomal extract), such that at least two targeting oligonucleotides are no longer covalently linked to one another after bond cleavage. It will be appreciated that a provided linker may include a region that is non-cleavable, as long as the linker also comprises at least one bond that is cleavable.

In some embodiments, the linker comprises a polypeptide that is more susceptible to cleavage by an endopeptidase in the mammalian extract than the targeting oligonucleotides. The endopeptidase may be a trypsin, chymotrypsin, elastase, thermolysin, pepsin, or endopeptidase V8. The endopeptidase may be a cathepsin B, cathepsin D, cathepsin L, cathepsin C, papain, cathepsin S or endosomal acidic insulinase. For example, the linker comprise a peptide having an amino acid sequence selected from: ALAL (SEQ ID NO:

125), APISFFELG (SEQ ID NO: 126), FL, GFN, R/KXX, GRWHTVGLRWE (SEQ ID NO: 127), YL, GF, and FF, in which X is any amino acid.

In some embodiments, the linker comprises the formula $-(CH_2)_n S-S(CH_2)_m-$, wherein n and m are independently integers from 0 to 10.

For example, the linker of a multimeric oligonucleotide may comprise an oligonucleotide that is more susceptible to cleavage by an endonuclease in the mammalian extract than the targeting oligonucleotides. The linker may have a nucleotide sequence comprising from 1 to 10 thymidines or uridines. The linker may have a nucleotide sequence comprising deoxyribonucleotides linked through phosphodiester internucleotide linkages. The linker may have a nucleotide sequence comprising from 1 to 10 thymidines linked through phosphodiester internucleotide linkages. The linker may have a nucleotide sequence comprising from 1 to 10 uridines linked through phosphorothioate internucleotide linkages. The linker may have the formula:

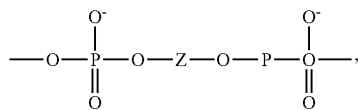

in which Z is an oligonucleotide. Z may have a nucleotide sequence comprising from 1 to 10 thymidines or uridines.

In some embodiments, the linker does not comprise an oligonucleotide having a self-complementary nucleotide sequence. In some embodiments, the linker does not comprise an oligonucleotide having a nucleotide sequence that is complementary to a region of the genomic target sequence that is contiguous with two flanking target regions. In some embodiments, the linker does not comprise an oligonucleotide having a self-complementary nucleotide sequence and does not comprise an oligonucleotide having a nucleotide sequence that is complementary to a region of the genomic target sequence that is contiguous with two flanking target regions of the particular linker. In some embodiments, the at least one L is a linker that does not comprise an oligonucleotide having an abasic site.

In other embodiments, multimeric oligonucleotide compounds are provided that comprise at least two targeting oligonucleotides each of which is linked to one or two other targeting oligonucleotides through a linker. In some embodiments, at least one linker is 2-fold, 3-fold, 4-fold, 5-fold, 10-fold or more sensitive to enzymatic cleavage in the presence of a mammalian extract than at least two targeting oligonucleotides. It should be appreciated that different linkers can be designed to be cleaved at different rates and/or by different enzymes in compounds comprising two or more linkers. Similarly different linkers can be designed to be sensitive to cleavage in different tissues, cells or subcellular compartments in compounds comprising two or more linkers. This can advantageously permit compounds to have targeting oligonucleotides that are released from compounds at different rates, by different enzymes, or in different tissues, cells or subcellular compartments thereby controlling release of the monomeric oligonucleotides to a desired in vivo location or at a desired time following administration.

In some embodiments, the invention also provides ASO multimers comprising targeting oligonucleotides having nuclease-resistant backbone (e.g., phosphorothioate), wherein the targeting oligonucleotides are linked to each other by one or more cleavable linkers.

In certain embodiments, linkers are stable in plasma, blood or serum which are richer in exonucleases, and less stable in the intracellular environments which are relatively rich in endonucleases. The intracellular stability of linkers can be assessed in vitro or in vivo as described in the Examples. In some embodiments, a linker is considered "non-cleavable" if the linker's half-life is at least 24, or 28, 32, 36, 48, 72, 96 hours or longer under the conditions described here, such as in liver homogenates. Conversely, in some embodiments, a linker is considered "cleavable" if the half-life of the linker is at most 10, or 8, 6, 5 hours or shorter.

In some embodiments, the linker is a nuclease-cleavable oligonucleotide linker. In some embodiments, the nuclease-cleavable linker contains one or more phosphodiester bonds in the oligonucleotide backbone. For example, the linker may contain a single phosphodiester bridge or 2, 3, 4, 5, 6, 7 or more phosphodiester linkages, for example as a string of 1-10 deoxynucleotides, e.g., dT, or ribonucleotides, e.g., rU, in the case of RNA linkers. In the case of dT or other DNA nucleotides dN in the linker, in certain embodiments the cleavable linker contains one or more phosphodiester linkages. In other embodiments, in the case of rU or other RNA nucleotides rN, the cleavable linker may consist of phosphorothioate linkages only. In contrast to phosphorothioate-linked deoxynucleotides, which are only cleaved slowly by nucleases (thus termed "noncleavable"), phosphorothioate-linked rU undergoes relatively rapid cleavage by ribonucleases and therefore is considered cleavable herein. It is also possible to combine dN and rN into the linker region, which are connected by phosphodiester or phosphorothioate linkages. In other embodiments, the linker can also contain chemically modified nucleotides, which are still cleavable by nucleases, such as, e.g., 2'-O-modified analogs. In particular, 2'-O-methyl or 2'-fluoro nucleotides can be combined with each other or with dN or rN nucleotides. Generally, in the case of nucleotide linkers, the linker is a part of the multimer that is usually not complementary to a target, although it could be. This is because the linker is generally cleaved prior to targeting oligonucleotides action on the target, and therefore, the linker identity with respect to a target is inconsequential. Accordingly, in some embodiments, a linker is an (oligo)nucleotide linker that is not complementary to any of the targets against which the targeting oligonucleotides are designed.

In some embodiments, the cleavable linker is oligonucleotide linker that contains a continuous stretch of deliberately introduced Rp phosphorothioate stereoisomers (e.g., 4, 5, 6, 7 or longer stretches). The Rp stereoisoform, unlike Sp isoform, is known to be susceptible to nuclease cleavage (Krieg et al., 2003, Oligonucleotides, 13:491-499). Such a linker would not include a racemic mix of PS linkages oligonucleotides since the mixed linkages are relatively stable and are not likely to contain long stretches of the Rp stereoisomers, and therefore, considered "non-cleavable" herein. Thus, in some embodiments, a linker comprises a stretch of 4, 5, 6, 7 or more phosphorothioated nucleotides, wherein the stretch does not contain a substantial amount or any of the Sp stereoisoform. The amount could be considered substantial if it exceeds 10% on per-mole basis.

In some embodiments, the linker is a non-nucleotide linker, for example, a single phosphodiester bridge. Another example of such cleavable linkers is a chemical group comprising a disulfide bond, for example, $-(CH_2)_n S-S(CH_2)_m-$, wherein n and m are integers from 0 to 10. In illustrative embodiments, n=m=6. Additional example of non-nucleotide linkers are described below.

The cleavable linkers may be present in other linear or branched multimers. For example in some branched embodiments, the cleavable linker comprises a "doubler," "trebler," or another branching chemical group with multiple "arms" that link phosphodiester linked nucleotides, as for example, illustrated in FIGS. 1C and 1D and Formulas IV, V, and VIII. In some linear embodiments, cleavable linkers can be incorporated as shown in Formulas I and II.

The linker can be designed so as to undergo a chemical or enzymatic cleavage reaction. Chemical reactions involve, for example, cleavage in acidic environment (e.g., endosomes), reductive cleavage (e.g., cytosolic cleavage) or oxidative cleavage (e.g., in liver microsomes). The cleavage reaction can also be initiated by a rearrangement reaction. Enzymatic reactions can include reactions mediated by nucleases, peptidases, proteases, phosphatases, oxidases, reductases, etc. For example, a linker can be pH-sensitive, cathepsin-sensitive, or predominantly cleaved in endosomes and/or cytosol.

In some embodiments, the linker comprises a peptide. In certain embodiments, the linker comprises a peptide which includes a sequence that is cleavable by an endopeptidase. In addition to the cleavable peptide sequence, the linker may comprise additional amino acid residues and/or non-peptide chemical moieties, such as an alkyl chain. In certain embodiments, the linker comprises Ala-Leu-Ala-Leu (SEQ ID NO.: 125), which is a substrate for cathepsin B. See, for example, the maleimidocaproyl-Arg-Arg-Ala-Leu-Ala-Leu (SEQ ID NO.: 136) linkers described in Schmid et al, Bioconjugate Chem 2007, 18, 702-716. In certain embodiments, a cathepsin B-cleavable linker is cleaved in tumor cells. In certain embodiments, the linker comprises Ala-Pro-Ile-Ser-Phe-Phe-Glu-Leu-Gly (SEQ ID NO.: 126), which is a substrate for cathepsins D, L, and B (see, for example, Fischer et al, Chembiochem 2006, 7, 1428-1434). In certain embodiments, a cathepsin-cleavable linker is cleaved in HeLA cells. In some embodiments, the linker comprises Phe-Lys, which is a substrate for cathepsin B. For example, in certain embodiments, the linker comprises Phe-Lys-p-aminobenzoic acid (PABA). See, e.g., the maleimidocaproyl-Phe-Lys-PABA linker described in Walker et al, Bioorg. Med. Chem. Lett. 2002, 12, 217-219. In certain embodiments, the linker comprises Gly-Phe-2-naphthylamide, which is a substrate for cathepsin C (see, for example, Berg et al. Biochem. J. 1994, 300, 229-235). In certain embodiments, a cathepsin C-cleavable linker is cleaved in hepatocytes, in some embodiments, the linker comprises a cathepsin S cleavage site. For example, in some embodiments, the linker comprises Gly-Arg-Trp-His-Thr-Val-Gly-Leu-Arg-Trp-Glu (SEQ ID NO.: 127), Gly-Arg-Trp-Pro-Pro-Met-Gly-Leu-Pro-Trp-Glu (SEQ ID NO.: 137), or Gly-Arg-Trp-His-Pro-Met-Gly-Ala-Pro-Trp-Glu (SEQ ID NO.: 138), for example, as described in Lutzner et al, J. Biol. Chem. 2008, 283, 36185-36194. In certain embodiments, a cathepsin S-cleavable linker is cleaved in antigen presenting cells. In some embodiments, the linker comprises a papain cleavage site. Papain typically cleaves a peptide having the sequence —R/K—X—X (see Chapman et al, Annu. Rev. Physiol 1997, 59, 63-88). In certain embodiments, a papain-cleavable linker is cleaved in endosomes. In some embodiments, the linker comprises an endosomal acidic insulinase cleavage site. For example, in some embodiments, the linker comprises Tyr-Leu, Gly-Phe, or Phe-Phe (see, e.g., Authier et al, FEBS Lett. 1996, 389, 55-60). In certain embodiments, an endosomal acidic insulinase-cleavable linker is cleaved in hepatic cells.

In some embodiments, the linker is pH sensitive. In certain embodiments, the linker comprises a low pH-labile bond. As used herein, a low-pH labile bond is a bond that is selectively broken under acidic conditions (pH<7). Such bonds may also be termed endosomally labile bonds, because cell endosomes and lysosomes have a pH less than 7. For example, in certain embodiments, the linker comprises an amine, an imine, an ester, a benzoic imine, an amino ester, a diortho ester, a polyphosphoester, a polyphosphazene, an acetal, a vinyl ether, a hydrazone, an azidomethyl-methylmaleic anhydride, a thiopropionate, a masked endosomolytic agent or a citraconyl group.

In certain embodiments, the linker comprises a low pH-labile bond selected from the following: ketals that are labile in acidic environments (e.g., pH less than 7, greater than about 4) to form a diol and a ketone; acetals that are labile in acidic environments (e.g., pH less than 7, greater than about 4) to form a diol and an aldehyde; imines or minimums that are labile in acidic environments (e.g., pH less than 7, greater than about 4) to form an amine and an aldehyde or a ketone; silicon-oxygen-carbon linkages that are labile under acidic condition; silicon-nitrogen (silazane) linkages; silicon-carbon linkages (e.g., acylsilanes, vinylsilanes, and allylsilanes); maleamates (amide bonds synthesized from maleic anhydride derivatives and amines); ortho esters; hydrazones; activated carboxylic acid derivatives (e.g., esters, amides) designed to undergo acid catalyzed hydrolysis); or vinyl ethers. Further examples may be found in International Patent Appln. Pub. No. WO 2008/022309, entitled POLYCONJUGATES FOR IN VIVO DELIVERY OF POLYNUCLEOTIDES, the contents of which are incorporated herein by reference.

Organosilanes (e.g., silyl ethers, silyl enol ethers) are used as oxygen protecting groups in organic synthesis. Silicon-oxygen-carbon linkages are susceptible to hydrolysis under acidic conditions to form silanols and an alcohol (or enol). The substitution on both the silicon atom and the alcohol carbon can affect the rate of hydrolysis due to steric and electronic effects. This allows for the possibility of tuning the rate of hydrolysis of the silicon-oxygen-carbon linkage by changing the substitution on either the organosilane, the alcohol, or both the organosilane and alcohol. In addition, charged or reactive groups, such as amines or carboxylate, may be attached to the silicon atom, which confers the labile compound with charge and/or reactivity.

Hydrolysis of a silazane leads to the formation of a silanol and an amine. Silazanes are inherently more susceptible to hydrolysis than is the silicon-oxygen-carbon linkage, however, the rate of hydrolysis is increased under acidic conditions. The substitution on both the silicon atom and the amine can affect the rate of hydrolysis due to steric and electronic effects. This allows for the possibility of tuning the rate of hydrolysis of the silazane by changing the substitution on either the silicon or the amine.

Another example of a pH labile bond is an acid labile enol ether bond. The rate at which this labile bond is cleaved depends on the structures of the carbonyl compound formed and the alcohol released. For example analogs of ethyl isopropenyl ether, which may be synthesized from β-haloethers, generally have shorter half lives than analogs of ethyl cyclohexenyl ether, which may be synthesized from phenol ethers Reaction of an anhydride with an amine forms an amide and an acid. Typically, the reverse reaction (formation of an anhydride and amine) is very slow and energetically unfavorable. However, if the anhydride is a cyclic anhydride, reaction with an amine yields a molecule in which the amide and the acid are in the same molecule, an amide acid. The presence of both reactive groups (the amide and the carboxylic acid) in the same molecule accelerates the reverse reaction. In certain embodiments, the linker comprises maleamic acid. Cleavage of the amide acid to form an amine and an anhydride is pH-dependent, and is greatly accelerated at acidic pH. This pH-dependent reactivity can be exploited to form reversible pH-sensitive bonds and linkers. Cis-aconitic acid has been used as such a pH-sensitive linker molecule. The γ-carboxylate is first coupled to a molecule. In a second step, either the α or β carboxylate is coupled to a second molecule to form a pH-sensitive coupling of the two molecules.

In some embodiments, the linker comprises a benzoic imine as a low-pH labile bond. See, for example, the conjugates described in Zhu et al, Langmuir 2012, 28, 11988-96; Ding et al, Bioconjug. Chem. 2009, 20, 1163-70.

In some embodiments, the linker comprises a low pH-labile hydrazone bond. Such acid-labile bonds have been extensively used in the field of conjugates, e.g., antibody-drug conjugates. See, for example, Zhou et al, Biomacromolecules 2011, 12, 1460-7; Yuan et al, Acta Biomater. 2008, 4, 1024-37; Zhang et al, Acta Biomater. 2007, 6, 838-50; Yang et al, J. Pharmacol. Exp. Ther. 2007, 321, 462-8; Reddy et al, Cancer Chemother. Pharmacol. 2006, 58, 229-36; Doronina et al, Nature Biotechnol. 2003, 21, 778-84. In some embodiments, the linker comprises a low pH-labile vinyl ether. See, for example, Shin et al, J. Control. Release 2003, 91, 187-200. In some embodiments, the linker comprises a low pH-labile phosphoamine bond. In some embodiments, the linker comprises a low pH-labile traceless click linker. For example, in certain embodiments, the linker comprises azidomethyl-methylmaleic anhydride (see Maier et al, J. Am. Chem. Soc. 2012 134, 10169-73. In some embodiments, the linker comprises a low pH-labile 4-hydrazinosulfonyl benzoic acid linker. See, for example, Kaminskas et al, Mol. Pharm. 2012 9, 422-32; Kaminskas et al, J. Control. Release 2011, 152, 241-8. In some embodiments, the linker comprises a low pH-labile para-phenylpropionic acid linker (see, e.g., Indira Chandran et al, Cancer Lett. 2012 316, 151-6). In some embodiments, the linker comprises a low pH-labile β-thiopropionate linker (see, e.g., Dan et al, Langmuir 2011, 27, 612-7). In some embodiments, the linker comprises a low pH-labile ester (see, for example, Zhu et al, Bioconjug. Chem. 2010, 21, 2119-27). In some embodiments, the linker comprises a low pH-labile ketal (see, e.g., Abraham et al, J. Biomater. Sci. Polym. Ed. 2011, 22, 1001-22) or acetal (see, e.g., Liu et al, J. Am. Chem. Soc. 2010, 132, 1500). In some embodiments, the linker comprises a low pH-labile 4-(4'-acetylphenoxy)butanoic acid linker (see, e.g., DiJoseph et al, Blood 2004, 103, 1807-14). In some embodiments, the linker comprises a low pH-labile cis-aconityl linker (see, e.g., Haas et al, J. Drug Target 2002, 10, 81-9; Ahmad et al, Anticancer Res. 1990, 10, 837-43; Dillman et al, Cancer Res. 1988, 48, 6097-102). In some embodiments, the linker comprises a low pH-labile diortho ester (see, e.g., Guo et al, Bioconjug. Chem. 2001, 12, 291-300).

In some embodiments, the linker comprises a masked endosomolytic agent. Endosomolytic polymers are polymers that, in response to a change in pH, are able to cause disruption or lysis of an endosome or provide for escape of a normally membrane-impermeable compound, such as a polynucleotide or protein, from a cellular internal membrane-enclosed vesicle, such as an endosome or lysosome. A subset of endosomolytic compounds is fusogenic compounds, including fusogenic peptides. Fusogenic peptides can facilitate endosomal release of agents such as oligomeric compounds to the cytoplasm. See, for example, US Patent Application Publication Nos. 20040198687, 20080281041, 20080152661, and 20090023890, which are incorporated herein by reference.

The linker can also be designed to undergo an organ/tissue-specific cleavage. For example, for certain targets, which are expressed in multiple tissues, only the knock-down in liver may be desirable, as knock-down in other organs may lead to undesired side effects. Thus, linkers susceptible to liver-specific enzymes, such as pyrrolase (TPO) and glucose-6-phosphatase (G-6-Pase), can be engineered, so as to limit the antisense effect to the liver mainly. Alternatively, linkers not susceptible to liver enzymes but susceptible to kidney-specific enzymes, such as gamma-glutamyltranspeptidase, can be engineered, so that the antisense effect is limited to the kidneys mainly. Analogously, intestine-specific peptidases cleaving Phe-Ala and Leu-Ala could be considered for orally administered multimeric targeting oligonucleotides. Similarly, by placing an enzyme recognition site into the linker, which is recognized by an enzyme over-expressed in tumors, such as plasmin (e.g., PHEA-D-Val-Leu-Lys recognition site), tumor-specific knock-down should be feasible. By selecting the right enzyme recognition site in the linker, specific cleavage and knock-down should be achievable in many organs. In addition, the linker can also contain a targeting signal, such as N-acetyl galactosamine for liver targeting, or folate, vitamin A or RGD-peptide in the case of tumor or activated macrophage targeting. Accordingly, in some embodiments, the cleavable linker is organ- or tissue-specific, for example, liver-specific, kidney-specific, intestine-specific, etc.

The targeting oligonucleotides can be linked through any part of the individual targeting oligonucleotide, e.g., via the phosphate, the sugar (e.g., ribose, deoxyribose), or the nucleobase. In certain embodiments, when linking two oligonucleotides together, the linker can be attached e.g. to the 5'-end of the first oligonucleotide and the 3'-end of the second nucleotide, to the 5'-end of the first oligonucleotide and the 5'end of the second nucleotide, to the 3'-end of the first oligonucleotide and the 3'-end of the second nucleotide. In other embodiments, when linking two oligonucleotides together, the linker can attach internal residues of each oligonucleotides, e.g., via a modified nucleobase. One of ordinary skill in the art will understand that many such permutations are available for multimers.

The linkers described herein can also be used to attach other moieties to an oligonucleotide. Such moieties include lipophilic moieties, targeting moieties (e.g., a ligand of a cell surface receptor), and tags (e.g., a fluorescent moiety for imaging or an affinity tag such as biotin).

In certain embodiments, the linker is attached to an oligonucleotide via click chemistry (for a review of using click chemistry with DNA, see El-Sagheer et al, Chem. Soc. Rev. 2010, 39, 1388-1405). The term "click chemistry" is used to describe any facile reaction that occurs in high yields, under mild conditions, and in the presence of diverse functional groups, but it is most commonly used to refer to a [3+2] azide-alkyne cycloaddition reaction. Such reactions are generally catalyzed by $Cu^I$ and proceed in the presence of functional groups typically encountered in biological molecules. In some embodiments, an unnatural base is introduced into the oligonucleotide, wherein the base is modified to comprise an alkyne or azide. See below for exemplary base modifications:

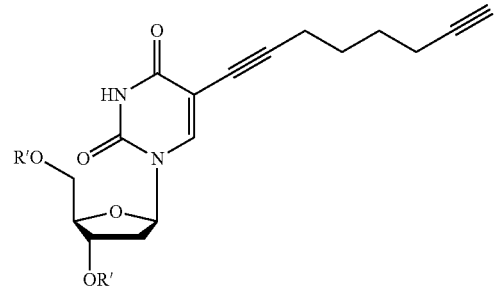

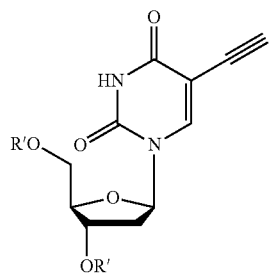

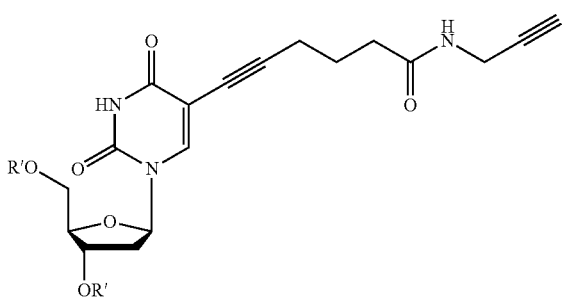

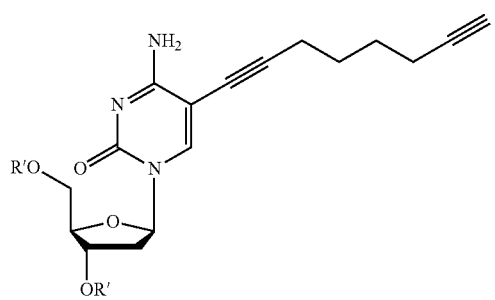

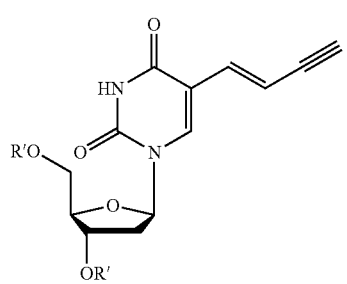

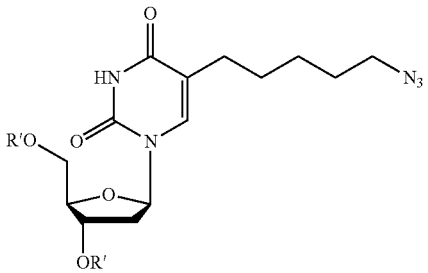

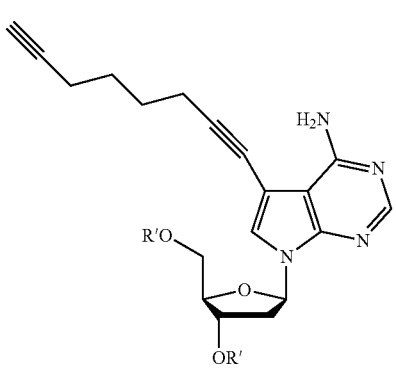

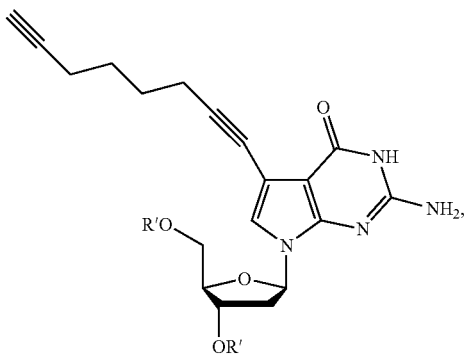

wherein R' is, for example, hydrogen, a suitable protecting group or coupling moiety (e.g., 4,4'-dimethoxytrityl (DMT), or a phosphoramidite group), a triphosphate, or R' denotes the point of connection to the rest of an oligonucleotide.

In some embodiments, an oligonucleotide is modified such that the ribose moiety comprises an alkyne or azide for coupling the linker. For example:

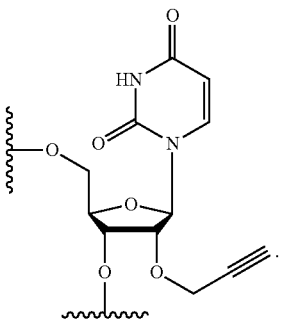

In some embodiments, an oligonucleotide is modified on the 5' or 3' end with an alkyne or azide for coupling the linker via click chemistry. For example, the nucleosides shown below can be used to synthesize such oligonucleotides:

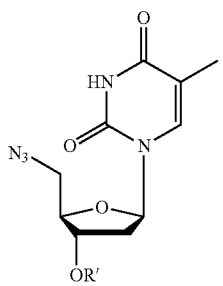

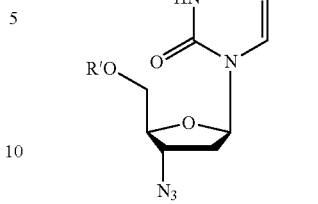
-continued

Exemplary reagents which allow linking targeting oligonucleotides through a nucleobase include protected amino functionality at the base that can then be coupled to other suitable functional groups. In certain embodiments, Fmoc Amino-Modifier C6 dT (Glen Research catalog number 10-1536-xx) is used as a starting material:

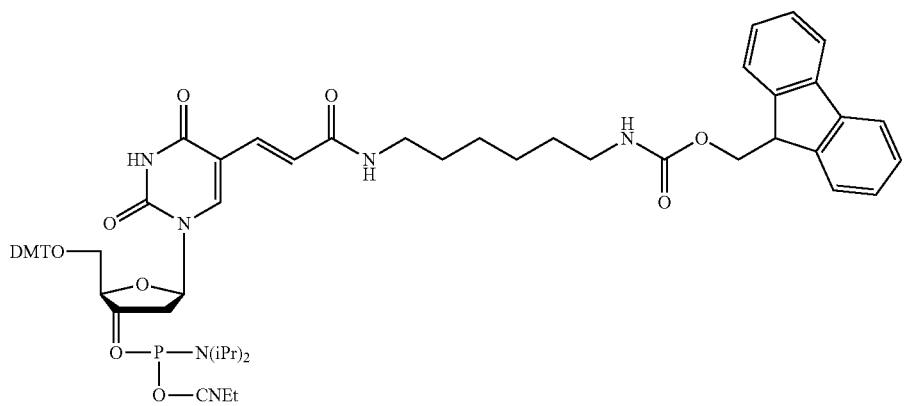

Fmoc Amino-Modifier C6 dT

-continued

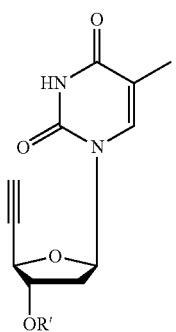

Other exemplary reagents which allow linking targeting oligonucleotides through a nucleobase include protected thiol functionality at the base that can then be coupled to other suitable functional groups or used to form a disulfide bond. In certain embodiments, S-Bz-Thiol-Modifier C6 dT (Glen Research catalog number 10-1039-xx) is used as a starting material:

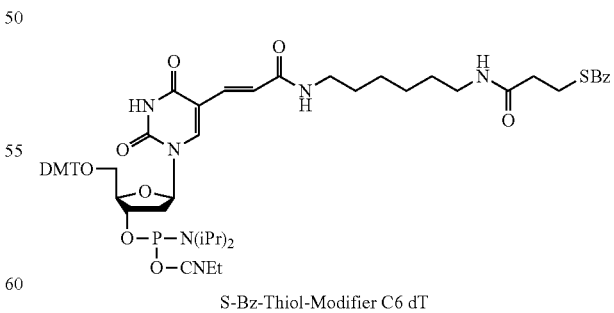

S-Bz-Thiol-Modifier C6 dT

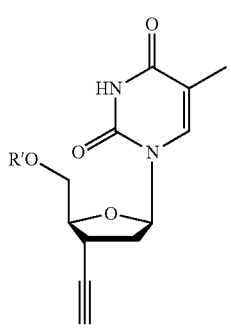

In other embodiments, Amino-Modifier Serinol Phosphoramidite (Glen Research catalog number 10-1997-xx) or 3'-Amino-Modifier Serinol CPG (Glen Research catalog number 20-2997-xx) is used to introduce amino-functionalized linkers that can then be coupled with other suitable functional groups:

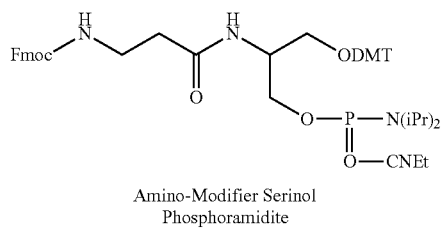

Amino-Modifier Serinol Phosphoramidite

-continued

5'-Maleimide-Modifier Phosphoramidite

In some embodiments, Cholesteryl-TEG Phosphoramidite (Glen Research catalog number 10-1975-xx) or α-Tocopherol-TEG Phosphoramidite (Glen Research catalog number 10-1977-xx) is used in phosphoramidite synthesis to add a lipophilic moiety to an targeting oligonucleotide:

Cholesteryl-TEG Phosphoramidite

α-Tocopherol-TEG Phosphoramidite

-continued

3'-Amino-Modifier Serinol CPG

In other embodiments, Thiol-Modifier C6 S—S(Glen Research catalog number 10-1936-xx), 3'-Thiol-Modifier C3 S—S CPG (Glen Research catalog number 20-2933-xx), or 5'-Maleimide-Modifier Phosphoramidite (Glen Research catalog number 10-1938-xx) is used to introduce a linker:

Thiol-Modifier C6 S—S

3'-Thiol-Modifier C3 S—S CPG

In some embodiments, one or more of the following starting materials are used in oligonucleotide synthesis to introduce an alkyne into an targeting oligonucleotide that can be reacted via click chemistry with an azide to attach another targeting oligonucleotide or another moiety such as a lipophilic group or targeting group:

37
-continued
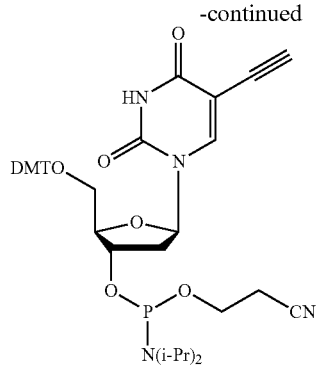
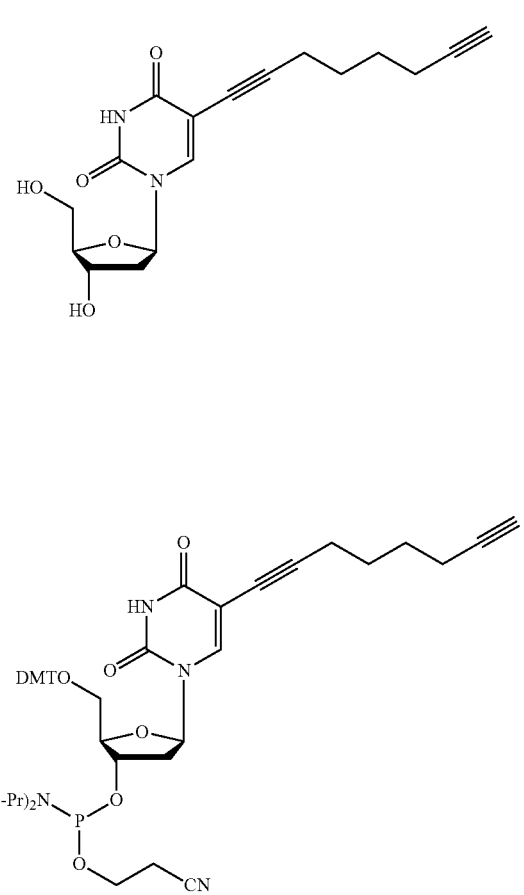
38
-continued
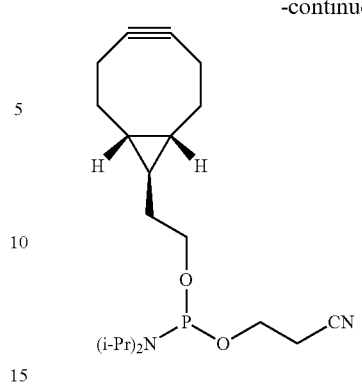
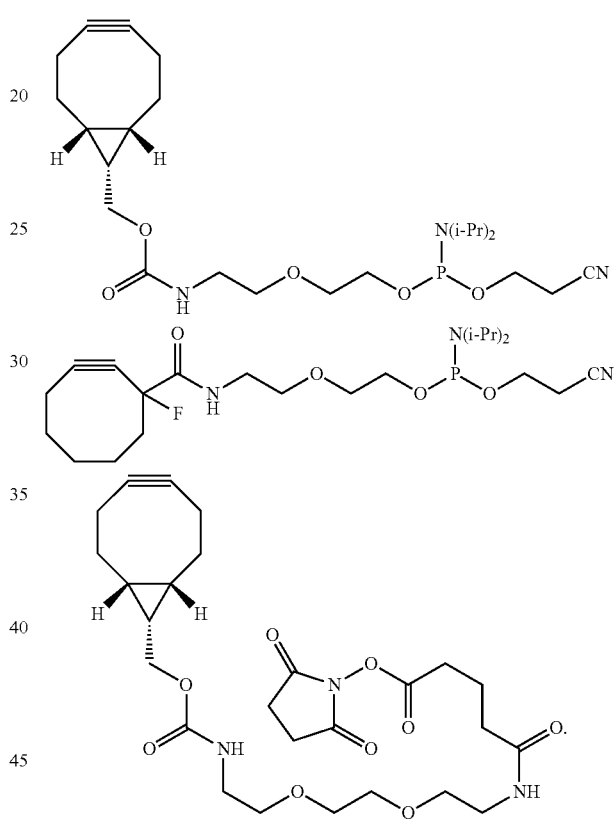
In some embodiments, one or more of the following starting materials are used to attach a lipophilic group or targeting group via click chemistry to an targeting oligonucleotide functionalized with an alkyne, such as the ones described above:
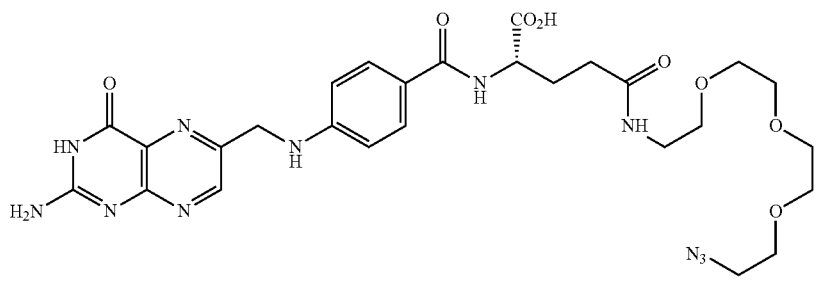

-continued

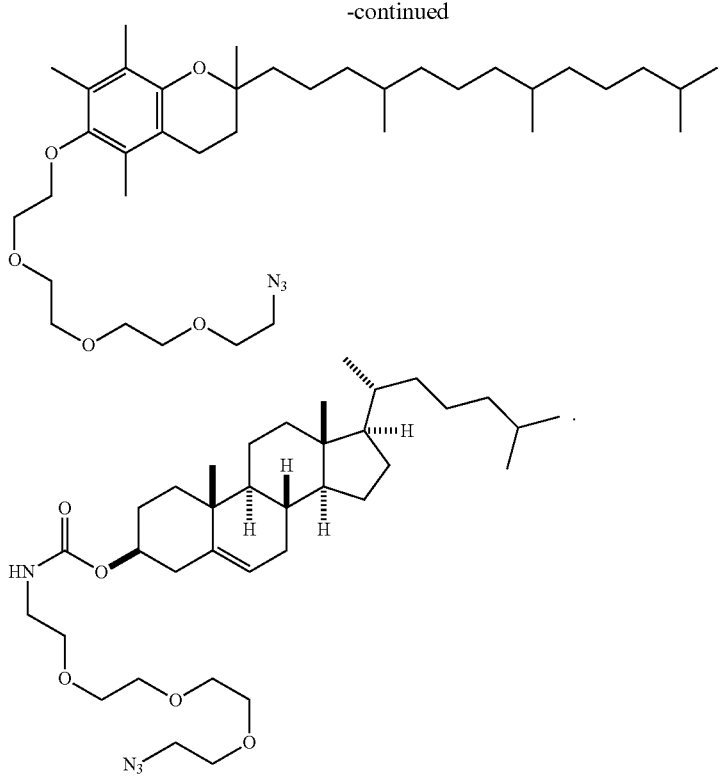

E. Targets and Uses

The disclosure provides a method of inhibiting target expression levels of one or more targets, comprising administering to a cell or a subject the compounds of the invention in an amount effective to inhibit the expression of the target(s). In certain embodiments, the target is an mRNA. In other embodiments, the target could be a microRNA, as described above. In such cases, the individual targeting oligonucleotides may be referred to as "antagomiRs." In other embodiments, the target can be a non-coding RNA naturally expressed in the cells.

The subjects treated according to the methods of the invention can be animals, including humans, primates, and rodents. Cells can be present in vitro, or treated ex vivo. In some cases, ex vivo treated cells are re-administered to the subject.

The invention also encompasses dual and multiple target antisense inhibitors, in particular those to treat liver diseases, metabolic diseases, cardiovascular diseases, inflammatory diseases, neurological diseases, viral, bacterial, parasitic, or prion infections and cancer. In particular, it includes the use of dimeric antisense inhibitors to inhibit liver targets (also referred to as "hepatic targets"), such as ApoB and ApoC3 dual inhibition. Since knock-down of ApoB has been reported to lead to undesired lipid deposition in the liver, the simultaneous knock-down of ApoC3 can decrease this side effect.

In cancer, the simultaneous knock-down of two targets can lead to synergistic anti-tumor effects. In particular, combination of targets with different mechanisms of action and signaling pathways should be of interest, e.g., a combination of cytostatic mechanism with anti-metastatic mechanism.

By selecting appropriate sequences against various cancer or tumor related targets, the present invention is also suitable for cancer treatment. Thus, it is possible to use multimeric oligonucleotides compounds of the invention that comprise targeting oligonucleotides which are directed 1) against targets responsible for the differentiation, development, or growth of cancers, such as: oncoproteins or transcription factors, e.g., c-myc, N-myc, c-myb, c-fos, c-fos/jun, PCNA, p120, EJ-ras, c-Ha-ras, N-ras, rrg, bcl-2, bcl-x, bcl-w, cdc-2, c-raf-1, c-mos, c-src, c-abl, c-ets; 2) against cellular receptors, such as EGF receptor, Her-2, c-erbA, VEGF receptor (KDR-1), retinoid receptors; 3) against protein kinases, c-fms, Tie-2, c-raf-1 kinase, PKC-alpha, protein kinase A (R1 alpha); 4) against growth or angiogenic factors, such as bFGF, VEGF, EGF, HB-EGF, PDGF and TGF-$\beta$; 5) against cytokines, such as IL-10, against cell cycle proteins, such as cyclin-E; 6) against tumor proteins, such as MAT-8; or 7) against inhibitors of tumor suppressor genes such as MDM-2. Also of use are antisense or directed against 8) components of spindle formation, such as eg5 and PLK1, or 9) against targets to suppress metastasis, such as CXCR4. Of use are antisense sequences directed against 10) factors which suppress apoptosis, such as survivin, stat3 and hdm2, or which suppress the expression of multiple drug resistance genes, such as MDR1 (P-glycoprotein).

The dimer/multimer can also degrade or antagonize microRNA (miRNA) which are single-stranded RNA molecules of about 21-23 nucleotides in length regulating gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to down-regulate gene expression. It appears that many miRNA sequences discovered in the human genome contribute to the development of cancer. Some miRNAs are significantly deregulated in cancer. Further, miRNA which is over-expressed (e.g., TGF-β2 receptor, RB1 and PLAG1) leading to tumor growth can be down-regulated using antisense approaches as described before. An miRNA expression signature of human solid tumors defining cancer gene targets was reported, for example, by Volinia et al., PNAS, 2006, 103, 2257-61.

Further provided are pharmaceutical compositions, comprising a compound of the invention and one or more pharmaceutically acceptable excipients. Methods of formulating and administering oligonucleotides to a cell or a subject are known in the art (see, e.g., Hardee, Gregory E.; Tillman, Lloyd G.; Geary, Richard S. Routes and Formulations For Delivery of Antisense Oligonucleotides. Antisense Drug Technology (2nd Edition) 2008, 217-236. Publisher: CRC Press LLC, Boca Raton, Fla.; Zhao et al., 2009, Expert Opin. Drug Deliv., 6:673-686; Juliano et al., 2008, Nucleic Acids Res., 36:4158-4171; Augner, 2006, J. Biomed. Biotechnol. 1-15; Wilson et al., 2005, Advances Genetics, 54:21-41; Hassane et al., 2010, Cell. Mol. Life Sci., 67:715-726; and Nakagawa et al., 2010, J. Am. Chem. Soc., 132: 8848-8849.

In some embodiments, the compounds of the invention possess favorable pharmacokinetic and/or pharmacodynamic properties. For example, in some case, a therapeutically effective knockdown of the target(s) persists for two weeks or longer following the administration. In some embodiments, the compositions of the invention are characterized by one or more of the following properties when administered in vivo:

(d) increased concentration in the liver (or other tissues) and reduced clearance by kidneys as compared to respective monomeric targeting oligonucleotides;

(e) longer duration of target knockdown as compared to respective monomeric targeting oligonucleotides; and (f) lower effective concentrations as compared to respective monomeric targeting oligonucleotides and/or the same multimeric oligonucleotide compound, wherein the cleavable linker is substituted with a noncleavable linker.

F. Routes of Delivery

A composition that includes a multimeric oligonucleotide compound can be delivered to a subject by a variety of routes. Exemplary routes include: intravenous, intradermal, topical, rectal, parenteral, anal, intravaginal, intranasal, pulmonary, ocular. The term "therapeutically effective amount" is the amount of multimeric oligonucleotide compound present in the composition that is needed to provide the desired level of target gene modulation (e.g., inhibition or activation) in the subject to be treated to give the anticipated physiological response. The term "physiologically effective amount" is that amount delivered to a subject to give the desired palliative or curative effect. The term "pharmaceutically acceptable carrier" means that the carrier can be administered to a subject with no significant adverse toxicological effects to the subject.

The multimeric oligonucleotide compound molecules of the invention can be incorporated into pharmaceutical compositions suitable for administration. Such compositions typically include one or more species of multimeric oligonucleotide compounds and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the multimeric oligonucleotide compound in aerosol form. The vascular endothelial cells could be targeted by coating a balloon catheter with the multimeric oligonucleotide compound and mechanically introducing the oligonucleotide.

Topical administration refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy. In addition, iontophoresis (transfer of ionic solutes through biological membranes under the influence of an electric field), phonophoresis or sonophoresis (use of ultrasound to enhance the absorption of various therapeutic agents across biological membranes, notably the skin and the cornea), and optimization of vehicle characteristics relative to dose position and retention at the site of administration may be useful methods for enhancing the transport of topically applied compositions across skin and mucosal sites.

Both the oral and nasal membranes offer advantages over other routes of administration. For example, oligonucleotides administered through these membranes may have a rapid onset of action, provide therapeutic plasma levels, avoid first pass effect of hepatic metabolism, and avoid exposure of the oligonucleotides to the hostile gastrointestinal (GI) environment. Additional advantages include easy access to the membrane sites so that the oligonucleotide can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many agents. Further, the sublingual mucosa is convenient, acceptable and easily accessible.

A pharmaceutical composition of multimeric oligonucleotide compound may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Compositions for oral administration include powders or granules, suspensions or solutions in water, syrups, slurries, emulsions, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Parenteral administration includes intravenous drip, subcutaneous, intraperitoneal or intramuscular injection, intrathecal or intraventricular administration. In some embodiments, parental administration involves administration directly to the site of disease (e.g. injection into a tumor).

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

Any of the multimeric oligonucleotide compounds described herein can be administered to ocular tissue. For example, the compositions can be applied to the surface of the eye or nearby tissue, e.g., the inside of the eyelid. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The multimeric oligonucleotide compound can also be administered to the interior of the eye, and can be introduced by a needle or other delivery device which can introduce it to a selected area or structure.

Pulmonary delivery compositions can be delivered by inhalation by the patient of a dispersion so that the composition, preferably multimeric oligonucleotide compounds, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver agents that may be readily formulated as dry powders. A multimeric oligonucleotide compound may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 μm in diameter preferably with a relatively uniform spheroidal shape distribution. More preferably the diameter is less than about 7.5 μm and most preferably less than about 5.0 μm. Usually the particle size distribution is between about 0.1 μm and about 5 μm in diameter, particularly about 0.3 μm to about 5 μm.

The term "dry" means that the composition has a moisture content below about 10% by weight (% w) water, usually below about 5% w and preferably less it than about 3% w. A dry composition can be such that the particles are readily dispersible in an inhalation device to form an aerosol.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Suitable pH adjusters or buffers include organic salts prepared from organic acids and bases, such as sodium citrate, sodium ascorbate, and the like; sodium citrate is preferred. Pulmonary administration of a micellar multimeric oligonucleotide compound formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to a multimeric oligonucleotide compound, e.g., a device can release insulin.

In one embodiment, unit doses or measured doses of a composition that includes multimeric oligonucleotide compound are dispensed by an implanted device. The device can include a sensor that monitors a parameter within a subject. For example, the device can include pump, e.g., and, optionally, associated electronics.

Tissue, e.g., cells or organs can be treated with a multimeric oligonucleotide compound, ex vivo and then administered or implanted in a subject. The tissue can be autologous, allogeneic, or xenogeneic tissue. E.g., tissue can be treated to reduce graft v. host disease. In other embodiments, the tissue is allogeneic and the tissue is treated to treat a disorder characterized by unwanted gene expression in that tissue. E.g., tissue, e.g., hematopoietic cells, e.g., bone marrow hematopoietic cells, can be treated to inhibit unwanted cell proliferation. Introduction of treated tissue, whether autologous or transplant, can be combined with other therapies. In some implementations, the multimeric oligonucleotide compound treated cells are insulated from other cells, e.g., by a semi-permeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains a multimeric oligonucleotide compound. Exemplary devices include condoms, diaphragms, IUD (implantable uterine devices, sponges, vaginal sheaths, and birth control devices.

G. Dosage

In one aspect, the invention features a method of administering a multimeric oligonucleotide compound to a subject (e.g., a human subject). In one embodiment, the unit dose is between about 10 mg and 25 mg per kg of bodyweight. In one embodiment, the unit dose is between about 1 mg and 100 mg per kg of bodyweight. In one embodiment, the unit dose is between about 0.1 mg and 500 mg per kg of bodyweight. In some embodiments, the unit dose is more than 0.001, 0.005, 0.01, 0.05, 0.1, 0.5, 1, 2, 5, 10, 25, 50 or 100 mg per kg of bodyweight.

The defined amount can be an amount effective to treat or prevent a disease or disorder, e.g., a disease or disorder associated with a particular target gene. The unit dose, for example, can be administered by injection (e.g., intravenous or intramuscular), an inhaled dose, or a topical application.

In some embodiments, the unit dose is administered daily. In some embodiments, less frequently than once a day, e.g., less than every 2, 4, 8 or 30 days. In another embodiment, the unit dose is not administered with a frequency (e.g., not a regular frequency). For example, the unit dose may be administered a single time. In some embodiments, the unit dose is administered more than once a day, e.g., once an hour, two hours, four hours, eight hours, twelve hours, etc.

In one embodiment, a subject is administered an initial dose and one or more maintenance doses of a multimeric oligonucleotide compound. The maintenance dose or doses are generally lower than the initial dose, e.g., one-half less of the initial dose. A maintenance regimen can include treating the subject with a dose or doses ranging from 0.0001 to 100 mg/kg of body weight per day, e.g., 100, 10, 1, 0.1, 0.01, 0.001, or 0.0001 mg per kg of bodyweight per day. The maintenance doses may be administered no more than once every 1, 5, 10, or 30 days. Further, the treatment regimen may last for a period of time which will vary depending upon the nature of the particular disease, its severity and the overall condition of the patient. In some embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the oligonucleotide may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Following successful treatment, it may be desirable to have the patient undergo maintenance therapy to prevent the recurrence of the disease state, wherein the compound of the invention is administered in maintenance doses, ranging from 0.0001 mg to 100 mg per kg of body weight.

The concentration of the multimeric oligonucleotide compound is an amount sufficient to be effective in treating or preventing a disorder or to regulate a physiological condition in humans. The concentration or amount of multimeric oligonucleotide compound administered will depend on the parameters determined for the agent and the method of administration, e.g. nasal, buccal, pulmonary. For example, nasal formulations may tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a multimeric oligonucleotide compound can include a single treatment or, preferably, can include a series of treatments. It will also be appreciated that the effective dosage of a multimeric oligonucleotide compound used for treatment may increase or decrease over the course of a particular treatment. For example, the subject can be monitored after administering a multimeric oligonucleotide compound. Based on information from the monitoring, an additional amount of the multimeric oligonucleotide compound can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of target gene expression levels in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human target gene. In another embodiment, the composition for testing includes a multimeric oligonucleotide compound that is complementary, at least in an internal region, to a sequence that is conserved between target gene in the animal model and the target gene in a human.

In one embodiment, the administration of the multimeric oligonucleotide compound is parenteral, e.g. intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The composition can be provided in measured doses or in a dispenser which delivers a metered dose. Selected modes of delivery are discussed in more detail below.

H. Kits

In certain aspects of the invention, kits are provided, comprising a container housing a composition comprising a multimeric oligonucleotide compound. In some embodiments, the composition is a pharmaceutical composition comprising a multimeric oligonucleotide compound and a pharmaceutically acceptable carrier. In some embodiments, the individual components of the pharmaceutical composition may be provided in one container. Alternatively, it may be desirable to provide the components of the pharmaceutical composition separately in two or more containers, e.g., one container for multimeric oligonucleotide compounds, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The Examples do not in any way limit the invention.

EXAMPLES

Example 1

Design of Antisense Oligonucleotides

Antisense oligonucleotides against ApoC3, ApoB, Hif-1alpha, survivin and B2M were either selected using a series of bioinformatics filters and computational design algorithms or were derived from the literature. They were selected to be 13, 14 or more nucleotides in length and tested using one or multiple chemical modification design patterns (for example, 3LNAs-8DNAs-3LNAs). The list of all targeting oligonucleotide sequences is given in Table 1 and specific chemical modification patterns are explicitly specified when data is presented. Factors taken into account during the design include species homology, alignment to multiple human transcripts, off-target matches, SNPs, exon-exon boundaries, coverage of the transcript, and statistical models of efficacy and polyA regions. For species homology human, rat, mouse and macaque sequences were considered. For off-target matches, putative sequences were searched against the human transcriptome and perfect matches were identified along with compounds that had only 1 or 2 mismatches. Preference was given to compounds with no perfect off-target matches, but compounds were selected with 1 or 2 mismatches if the compound met many of the other criteria. Statistical classification models were derived from existing in-house projects for other targeting oligonucleotide projects. These models were applied to the potential ASOs and preference given to those classified as active. Known SNPs, exon-exon boundaries and polyA regions were also avoided in the design when possible. Other ASO design features are also well known in the art, such as avoidance of immune stimulatory sequences such as CpG motifs, avoidance of poly G regions, and avoidance of toxic sequences such as certain poly-pyrimidine motifs.

FIGS. 1A and 1B show schematic representation of exemplary dimeric/multimeric constructs. Specifically, in FIG. 1A, two 14-mer gapmers (e.g., 3LNA-8DNA-3LNA) are connected via a cleavable linker, which can be cleaved by enzymes, such as nucleases, peptidases or by reduction or oxidation. It could also be a linker which is cleaved by a pH shift within the cells (e.g. acidic pH in endosomes). The two antisense gapmers can be identical (homo-dimer), which leads to suppression of a single target mRNA1. However, the two antisense gapmers can also have different sequences (hetero-dimer) which are complementary to two or more different targets and which will lead to inhibition of two targets (mRNA1 and mRNA2) or trimers or tetramers, etc., specific to 3, 4, or more different targets.

Example 2

Synthesis of Antisense Oligonucleotides (A) General Procedure for Oligomer Synthesis All oligonucleotides were synthesized using standard phosphoramidite protocols (Beaucage, S. L.; Caruthers, M. H. "Deoxynucleoside phosphoramidites—A new class of key intermediates for deoxypolynucleotide synthesis". Tetrahedron Lett., 1981, 22:1859) on a MerMade 192 oligonucleotide synthesizer (BioAutomation) or Oligopilot 10 synthesizer (GE) at 200 to 1000 nmole scales employing standard CPG supports (BioSearch) or Glen UnySupport (Glen Research). The DNA, 2'-OMe, 2'-F, and G-clamp monomers were obtained from ChemGenes Corporation or Glen Research, and the LNA monomers were obtained from other commercially available sources. All phosphoramidites other than DNA were coupled with extended coupling times (e.g. 8 to 15 min for RNA, LNA, 2'-O-Methyl, 2'-Fluoro, 5-Propynyl and G-Clamps). After the synthesis, the oligonucleotides were cleaved from the support and deprotected using AMA (a 50:50 mixture of ammonium hydroxide and aqueous methylamine) at 65° C. for one hour or using aqueous ammonium hydroxide at 55° C. for 8 hours. The crude DMTr-on oligonucleotides were purified via DMTr-selective cartridge purification techniques and if necessary further purified via RP HPLC and desalted via cartridge-based methods. Alternatively, they were purified using ion exchange chromatography. The final oligonucleotides were characterized using LC-MS.

A C Technologies Solo VP Slope (Bridgewater, N.J.) reader equipped with "Quick Slope" software was used to determine the concentration of oligonucleotides. Fifty μl of sample was required for the measurement in a micro quartz vessel. The instrument measured the change in absorbance at varying path lengths, utilizing Beer's Law to determine final concentrations. Extinction coefficients were calculated using the nearest neighbor model.

(B) Synthesis of Linear Dimers and Trimers

The synthesis of linear dimers and trimers was completed by linear addition of all monomers until the full length sequence was obtained on solid support. First, ASO 1 was completely synthesized followed by addition of the cleavable or noncleavable linker X (e.g., tri-thymidyl, tetra-thymidyl, tetra-uridyl, disulfide, etc.) and finally either ASO 1 ("homo"-dimer) or an ASO with another sequence ASO 2 ("hetero"-dimer) and optionally directed against another target mRNA was added. The ASO synthesized first is connected to the linker X via its 5'-end whereas the finally synthesized ASO is connected via 3'. This might lead to 3'- and 5'-modified metabolites after cleavage. Due to its linearity, a trimer, tetramer, or other multimer could be synthesized by adding a second, third, or more cleavable linker(s) followed by another ASO (1, 2 or 3).

Formula I

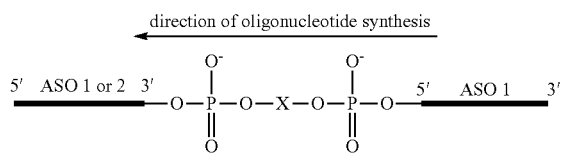

X is e.g. dT-dT-dT-dT or rU*rU*rU*rU or (CH$_2$)$_6$-S-S-(CH$_2$)$_6$

As illustrated above, for example, SED ID NO:2 (ApoC3-ApoC3 homodimer ASO) contains ASO1 (βA*βA*βG*dC*dA*dA*dC*dC*dT*dA*dC*βA*βG*βG (SEQ ID NO:1)), with X being dT-dT-dT (tri-thymidyl), wherein "-" is a phosphodiester linkage and "*" is a phosphorothioate linkage, dN is 2'-deoxynucleotide and, βN is an LNA nucleotide).

A general example for a linear trimer is given below:

(C) Synthesis of 3'3'-Branched Dimers (Doubler Dimers)

For symmetric dimers, synthesis was performed using a triethylene glycol (teg) derivatized solid support and a symmetric doubler (brancher) phosphoramidite from Glen Research (catalog number 10-1920) illustrated below Formula III

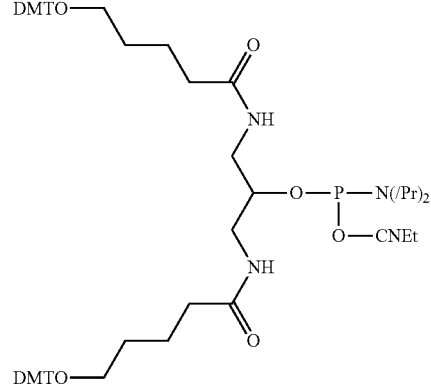

Figure 1C:
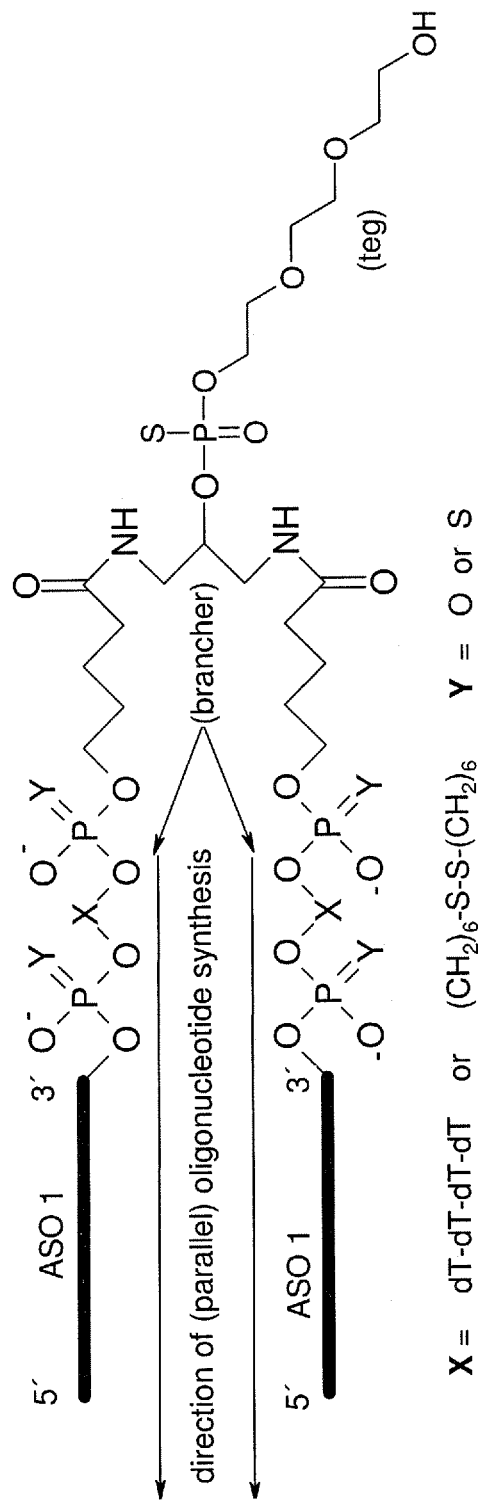
FIGS. 1C and 1D show details of the chemical structures of certain multimeric ASOs.
Figure 1D:
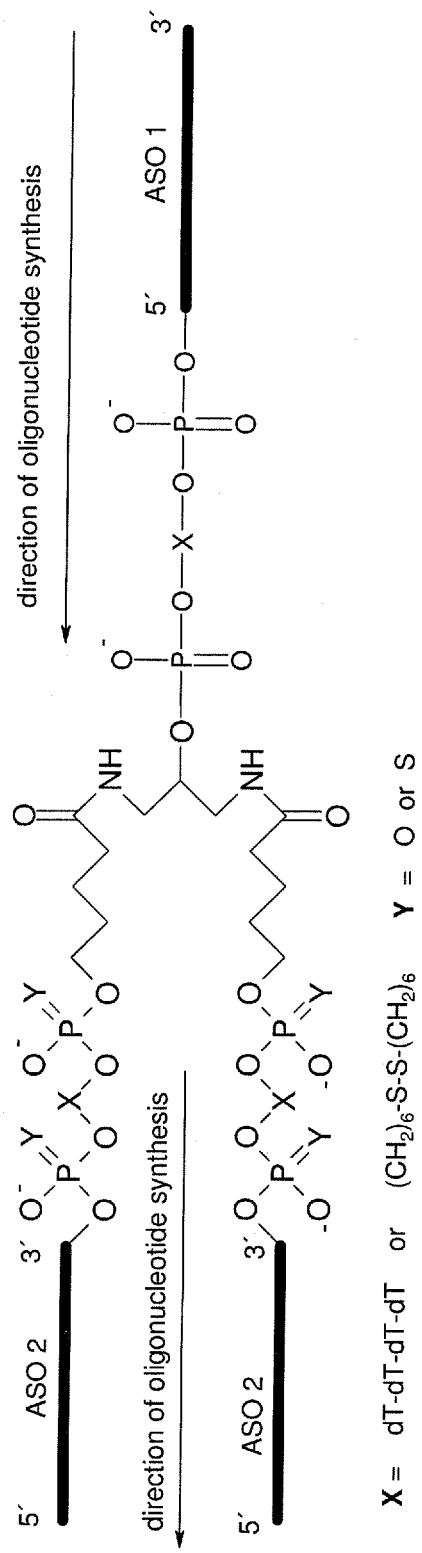

After coupling of the brancher phosphoramidite (catalog No. 10-1920) to the triethylene glycol bound to the solid phase, the DMT protecting groups were removed with acid and coupling of linker X and ASO 1 was performed in parallel as illustrated in FIG. 1C. For SEQ ID NO:4 (βA*βA*βG*dC*dA*dA*dC*dC*dT*dA*dC*βA*βG*βG-dT-dT-dT-dT-)2doub*teg, linker X is dT-dT-dT-dT, Y is Oxygen, * is phosphorothioate, - is phosphodiester, and "doub*teg" stands for the following substructure:

Formula IV

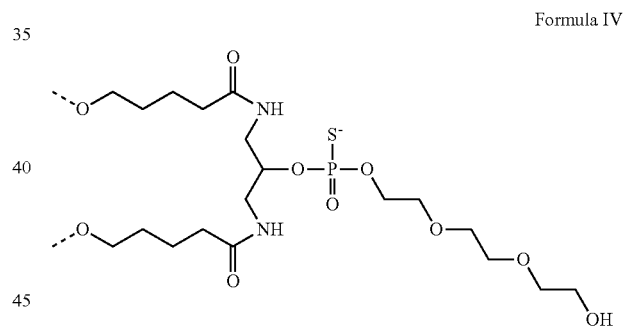

For the synthesis of two identical strands in parallel a double-coupling step was performed on the oligonucleotide synthesizer to yield maximum coupling efficiency on both strands.

With an asymmetric doubler phosphoramidite (Glen Research, catalog number 10-1921) the synthesis of "hetero"-dimers is possible. Thus, ASO 1 is connected first to the doubler and ASO 2 is connected second.

Formula II

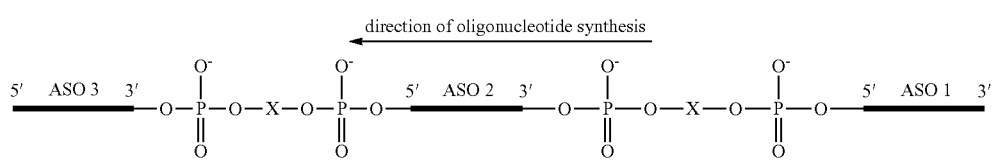

e.g X is dT-dT-dT-dTU or (CH$_2$)$_6$-S-S-(CH$_2$)$_6$

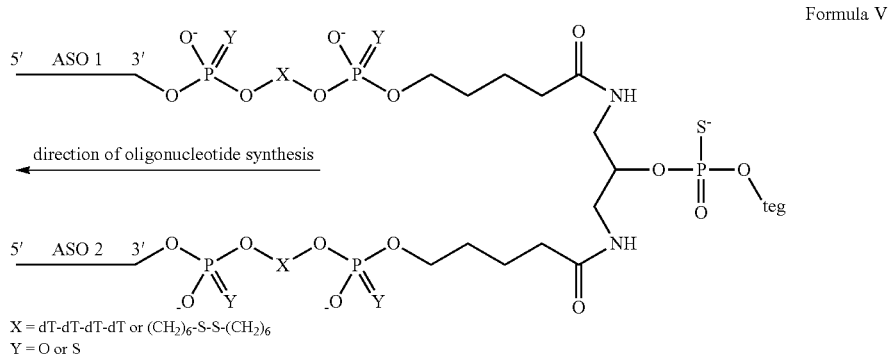

Formula V

X = dT-dT-dT-dT or (CH$_2$)$_6$-S-S-(CH$_2$)$_6$
Y = O or S

The symmetrical doubler or branching strategy was also performed with glycerol like CPG solid support from Chemgenes (N-5216-05 and N-7170-05). Symmetrical branching doubler N-5216-05 is shown in Formula VI.

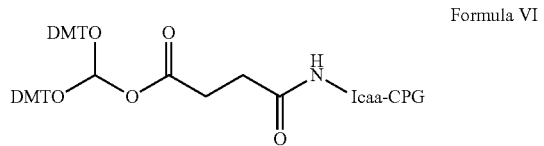

Formula VI

The asymmetrical branching doubler N-7170-05 is shown in Formula VII.

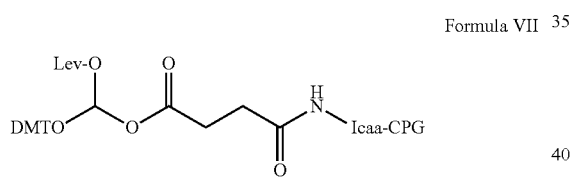

Formula VII

Oligonucleotide dimers synthesized with this doubler (brancher) have the following structure:

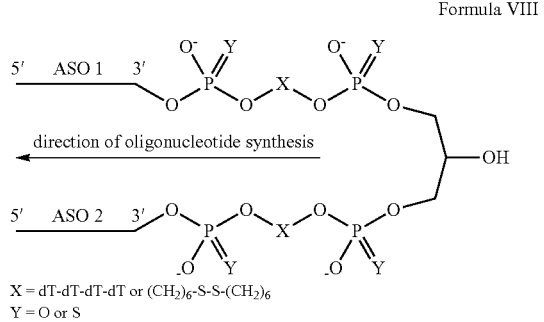

Formula VIII

X = dT-dT-dT-dT or (CH$_2$)$_6$-S-S-(CH$_2$)$_6$
Y = O or S (D) Synthesis of Branched Trimers For the synthesis of trimers with two different ASO molecules, the first ASO1 is synthesized by linear addition of all monomers until the full length sequence of ASO1 was obtained on solid support. Then, the cleavable (or noncleavable) linker X (tetrathymidyl, tetrauridyl, disulfide etc.) is synthesized followed by addition of the doubler using a symmetric doubler phosphoramidite (Glen Research, 10-1920) the solid phase synthesis of the linker X and ASO 1 was performed in parallel as indicated in the figure below.

After removal of the DMT protecting groups of the symmetric doubler, two ASO2 molecules are synthesized simultaneously from 3' to 5' direction using standard phosphoramidite chemistry. This results in a trimer consisting of two ASO2 molecules having two free 5'-ends and one ASO1 molecule having one free 3'-end of the structure shown in FIG. 1D.

For the synthesis of branched trimers consisting of three different ASO1, ASO2 and ASO3 molecules, the non-symmetric brancher phosphoramidite is coupled after first synthesis of ASO1, followed by sequential synthesis of ASO2 and ASO3. The non-symmetrical phosphoramidite structure is shown in Formula IX. The resulting trimer has the structure show in FIG. 1D.

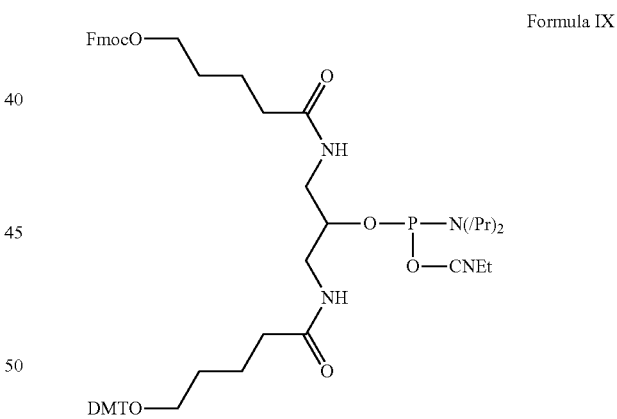

Formula IX

It is also possible to use a "trebler" phosphoramidite (Glen Research, 10-1922) shown in Formula X which results in symmetrical homo trimers.

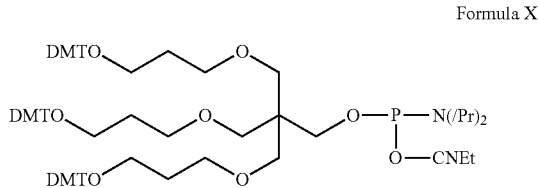

Formula X (E) Sequences of Synthesized Oligonucleotides and Characterization by Mass Spectrometry All compounds were purified by IEX HPLC or IP-RP HPLC and characterized using LC-MS methods. The following listing in Table 1 provides specific sequences and modification patterns with the corresponding SEQ ID NOs on the left followed by a detailed description.

TABLE 1

| SEQ ID NO: | Reference | Sequence Description |
|---|---|---|
| 1 | 103966 | βA*βA*βG*dC*dA*dA*dC*dC*dT*dA*dC*βA*βG*βG<br>3LNA-8DNA-3LNA gapmer (monomeric), fully phosphorothioated<br>ApoC3 |
| 2 | 105360 | βA*βA*βG*dC*dA*dA*dC*dC*dT*dA*dC*βA*βG*βG-dT-dT-dT-<br>βA*βA*βG*dC*dA*dA*dC*dC*dT*dA*dC*βA*βG*βG<br>linear homodimer from SEQ ID NO: 1 with 3 nt phosphodiester linker<br>ApoC3 |
| 3 | 105361 | βA*βA*βG*dC*dA*dA*dC*dC*dT*dA*dC*βA*βG*βG*teg*SS*teg*βA*βA*βG*dC*dA*dA*dC*dC*dT*dA*dC*βA*βG*βG<br>linear homodimer from SEQ ID NO: 1 with disulfide linker<br>ApoC3 |
| 4 | 105362 | (βA*βA*βG*dC*dA*dA*dC*dC*dT*dA*dC*βA*βG*βG-dT-dT-dT-dT-)₂doub*teg<br>3'3'-branched homodimer from SEQ ID NO: 1 with 2 x 4 nt phosphodiester linker<br>ApoC3 |
| 5 | 105363 | (βA*βA*βG*dC*dA*dA*dC*dC*dT*dA*dC*βA*βG*βG*teg*SS*)₂doub*teg<br>3'3'-branched homodimer from SEQ ID NO: 1 with disulfide linker<br>ApoC3 |
| 6 | 105395 | βA*βA*βG*dC*dA*dA*dC*dC*dT*dT*dC*βA*βG*βG-dT-dT-dT-<br>βA*βA*βG*dC*dA*dA*dC*dC*dT*dT*dC*βA*βG*βG<br>mouse ortholog of SEQ ID NO: 2<br>ApoC3 |
| 7 | 105513 | βA*βA*βG*dC*dA*dA*dC*dC*dT*dT*dC*βA*βG*βG-dT-dT-dT-<br>βG*βZ*dA*dT*dT*dG*dG*dT*dA*dT*βT*βZ*βA<br>linear heterodimer (from SEQ ID NOs: 13/14) with 3 nt phosphodiester-linker<br>ApoB/ApoC3 (mouse) |
| 8 | 105514 | βG*βZ*dA*dT*dT*dG*dG*dT*dA*dT*βT*βZ*βA-dT-dT-dT-<br>βT*βZ*βZ*dT*dC*dG*dG*dC*dC*dT*βZ*βT*βG<br>linear heterodimer (from SEQ ID NOs: 13/10) with 3 nt phosphodiester-linker<br>ApoB/ApoC3 |
| 9 | 104109 | βZ*βZ*βT*dC*dT*dT*dC*dG*dG*dC*dC*βZ*βT*βG<br>3LNA-8DNA-3LNA gapmer (monomeric), fully phosphorothioated<br>ApoB |
| 10 | 104111 | βT*βZ*βZ*dT*dC*dG*dG*dC*dC*dT*βZ*βT*βG<br>3LNA-7DNA-3LNA gapmer (monomeric), fully phosphorothioated<br>ApoC3 |
| 11 | 104112 | βT*βZ*βT*dT*dC*dG*dG*dC*dC*dC*βT*βG<br>3LNA-7DNA-2LNA gapmer (monomeric), fully phosphorothioated<br>ApoB |
| 12 | 105576 | βT*βZ*βT*dT*dZ*dG*dG*dC*dC*dC*βT*βG<br>5-methyl-dC (dZ) analog of SEQ ID NO: 11<br>ApoB |
| 13 | 102102 | βG*βZ*dA*dT*dT*dG*dG*dT*dA*dT*βT*βZ*βA<br>2LNA-8DNA-3LNA gapmer (monomeric), fully phosphorothioated<br>ApoB |

TABLE 1-continued

| SEQ ID NO: | Reference | Sequence Description |
|---|---|---|
| 14 | 105515 | βA*βA*βG*dC*dA*dA*dC*dC*dT*dT*dC*βA*βG*βG<br>mouse ortholog of SEQ ID NO: 1<br>ApoC3 |
| 15 | 106200 | βG*βZ*dA*dC*dT*dG*dA*dG*dA*dA*dT*dA*βZ*βT-dT-dT-dT-dT-<br>βG*βZ*dA*dC*dT*dG*dA*dG*dA*dA*dT*dA*βZ*βT<br>linear homodimer from SEQ ID NO: 30 with 4 nt phosphodiester DNA linker<br>ApoC3 |
| 16 | 106201 | βG*βZ*dA*dC*dT*dG*dA*dG*dA*dA*dT*dA*βZ*βT*dT*dT*dT*dT*βG*βZ*dA*dC<br>*dT*dG*dA*dG*dA*dA*dT*dA*βZ*βT<br>linear homodimer from SEQ ID NO: 30 with 4 nt phosphorothioate DNA linker<br>ApoC3 |
| 17 | 106202 | (βG*βZ*dA*dC*dT*dG*dA*dG*dA*dA*dT*dA*βZ*βT-dT-dT-dT-dT-)$_2$doub*teg<br>3'3'-branched homodimer from SEQ ID NO: 30, 2 × 4 nt phosphodiester DNA linker<br>ApoC3 |
| 18 | 106203 | βG*βZ*dA*dT*dT*dG*dG*dT*dA*dT*βT*βZ*βA-dT-dT-dT-dT-<br>βG*βZ*dA*dT*dT*dG*dG*dT*dA*dT*βT*βZ*βA<br>linear homodimer from SEQ ID NO: 13 with phosphodiester DNA linker<br>ApoB |
| 19 | 106204 | βG*βZ*dA*dT*dT*dG*dG*dT*dA*dT*βT*βZ*βA*dT*dT*dT*dT*βG*βZ*dA*dT*dT<br>*dG*dG*dT*dA*dT*βT*βZ*βA<br>linear homodimer from SEQ ID NO: 13 with phosphorothioate DNA linker<br>ApoB |
| 20 | 106205 | (βG*βZ*dA*dT*dT*dG*dG*dT*dA*dT*βT*βZ*βA-dT-dT-dT-dT-)$_2$doub*teg<br>3'3'-branched homodimer from SEQ ID NO: 13, phosphodiester DNA linker<br>ApoB |
| 21 | 106206 | βG*βZ*dA*dC*dT*dG*dA*dG*dA*dA*dT*dA*βZ*βT-dT-dT-dT-dT-<br>βG*βZ*dA*dT*dT*dG*dG*dT*dA*dT*βT*βZ*βA<br>linear heterodimer from SEQ ID NO: 30/13 with phosphodiester DNA linker<br>ApoC3/ApoB |
| 22 | 106207 | βG*βZ*dA*dT*dT*dG*dG*dT*dA*dT*βT*βZ*βA-dT-dT-dT-dT-<br>βG*βZ*dA*dC*dT*dG*dA*dG*dA*dA*dT*dA*βZ*βT<br>linear heterodimer from SEQ ID NO: 13/30 with phosphodiester DNA linker<br>ApoB/ApoC3 |
| 23 | 106413 | βG*βG*dC*dA*dA*dG*dC*dA*dT*dC*βZ*βT*βG-dT-dT-dT-dT-<br>βZ*βA*dA*dC*dC*dA*dT*dG*dG*βZ*βA*βG<br>linear heterodimer from SEQ ID NO: 27/28 with phosphodiester DNA linker<br>HIF-1alpha/survivin |
| 24 | 106414 | βG*βG*dC*dA*dA*dG*dC*dA*dT*dC*βZ*βT*βG-dT-dT-dT-dT-<br>βG*βZ*βG*dT*dG*dC*dA*dT*dA*dA*dA*βT*βT*βG<br>linear heterodimer from SEQ ID NO: 27/29 with phosphodiester DNA linker<br>HIF-1alpha/B2M |
| 25 | 106415 | βG*βG*dC*dA*dA*dG*dC*dA*dT*dC*βZ*βT*βG-dT-dT-dT-dT-<br>βG*βZ*dA*dT*dT*dG*dG*dT*dA*dT*βT*βZ*βA<br>linear heterodimer from SEQ ID NO: 27/13 with phosphodiester DNA linker<br>HIF-1alpha/ApoB |
| 26 | 106416 | βG*βZ*dA*dT*dT*dG*dG*dT*dA*dT*βT*βZ*βA-dT-dT-dT-dT-<br>βG*βZ*dA*dC*dT*dG*dA*dG*dA*dA*dT*dA*βZ*βT-dT-dT-dT-dT-<br>βG*βG*dC*dA*dA*dG*dC*dA*dT*dC*βZ*βT*βG<br>linear heterotrimer from SEQ ID NO: 13/30/27 with two phosphodiester DNA linkers<br>ApoB/ApoC3/HIF-1alpha |

TABLE 1-continued

| SEQ ID NO: | Reference | Sequence Description |
|---|---|---|

27  101443
βG*βG*dC*dA*dA*dG*dC*dA*dT*dC*βZ*βT*βG
2LNA-8DNA-3LNA gapmer (monomeric), fully phosphorothioated
HIF-1alpha 28  101441
βZ*βA*dA*dT*dC*dC*dA*dT*dG*dG*βZ*βA*βG
2LNA-8DNA-3LNA gapmer (monomeric), fully phosphorothioated
Survivin 29  105758
βG*βZ*βG*dT*dG*dC*dA*dT*dA*dA*dA*βT*βT*βG
3LNA-8DNA-3LNA gapmer (monomeric), fully phosphorothioated
B2M 30  104975
βG*βZ*dA*dC*dT*dG*dA*dG*dA*dA*dT*dA*βZ*βT
2LNA-10DNA-2LNA gapmer (monomeric), fully phosphorothioated
ApoC3

31  102103
βZ*βG*dT*dC*dT*dA*dT*dG*dT*dA*βT*βA*βG
2LNA-8DNA-3LNA gapmer (monomeric), fully phosphorothioated
ApoB negative control (mismatched)

32  104882
mU*mU*APC*dA*dG*dT*dG*dT*dG*dA*dT*mG*mA*APC
2me-9DNA-2me gapmer with 2 G-clamps (APC), fully phosphorothioated
(monomeric),
ApoC3

33  106417
βZ*βZ*mA*dG*dT*dA*dG*dT*dC*dT*dT*mU*βZ*βA-dT-dT-dT-dT-
βG*βZ*dA*dT*dT*dG*dG*dT*dA*dT*βT*βZ*βA
linear heterodimer from SEQ ID NO: 55/13 with phosphodiester DNA linker
ApoC3/ApoB 34  106418
βZ*βZ*mA*dG*dT*dA*dG*dT*dC*dT*dT*mU*mC*mA-dT-dT-dT-dT-
βG*βZ*dA*dT*dT*dG*dG*dT*dA*dT*βT*βZ*βA
linear heterodimer from SEQ ID NO: 56/13 with phosphodiester DNA linker
ApoC3/ApoB 35  106419
βZ*βZ*fA*dG*dT*dA*dG*dT*dC*dT*dT*fU*fC*fA-dT-dT-dT-dT-
βG*βZ*dA*dT*dT*dG*dG*dT*dA*dT*βT*βZ*βA
linear heterodimer from SEQ ID NO: 57/13 with phosphodiester DNA linker
ApoC3/ApoB 36  106420
βG*βG*βA*dA*dC*dT*dG*dA*dA*dG*dC*dC*dA*dT-dT-dT-dT-dT-
βG*βZ*dA*dT*dT*dG*dG*dT*dA*dT*βT*βZ*βA
linear heterodimer from SEQ ID NO: 58/13 with phosphodiester DNA linker,
(5' nucleotide can also be substitute with a G)
ApoC3/ApoB 37  106206
βG*βZ*dA*dC*dT*dG*dA*dG*dA*dA*dT*dA*βZ*βT-dT-dT-dT-dT-
βG*βZ*dA*dT*dT*dG*dG*dT*dA*dT*βT*βZ*βA
linear heterodimer from SEQ ID NO: 30/13 with phosphodiester DNA linker,
(5' nucleotide can also be substitute with a G)
ApoC3/ApoB 38  106421
mU*mU*APC*dA*dG*dT*dG*dT*dG*dA*dT*mG*mA*APC-dT-dT-dT-dT-
βG*βZ*dA*dC*dT*dG*dA*dG*dA*dA*dT*dA*βZ*βT
linear heterodimer from SEQ ID NO: 32/13 with phosphodiester DNA linker
ApoC3/ApoB 39  106422
βA*βA*βG*dC*dA*dA*dC*dC*dT*dA*dC*βA*βG*βG-dT-dT-dT-dT-
βG*βZ*dA*dT*dT*dG*dG*dT*dA*dT*βT*βZ*βA
linear heterodimer from SEQ ID NO: 1/13 with phosphodiester DNA linker
ApoC3/ApoB

TABLE 1-continued

| SEQ ID NO: | Reference | Sequence Description |
|---|---|---|
| 40 | 106423 | (βG*βG*βA*βA*dC*dT*dG*dA*dA*dG*dC*dC*dA*dT-dT-dT-dT-dT)₂doub*teg<br>3'3'-branched homodimer from SEQ ID NO: 58, phosphodiester DNA linker<br>ApoC3 |
| 41 | 106424 | βG*βZ*dA*PC*dT*dG*dA*dG*dA*dA*dT*dA*βZ*βT-dT-dT-dT-dT-<br>βG*βZ*dA*PC*dT*dG*dA*dG*dA*dA*dT*dA*βZ*βT<br>linear homodimer with 5-propynyl-dC with phosphodiester DNA linker<br>ApoC3 |
| 42 | 106425 | βG*βZ*dA*PC*PU*dG*dA*dG*dA*dA*dT*dA*βZ*βT-dT-dT-dT-dT-<br>βG*βZ*dA*PC*PU*dG*dA*dG*dA*dA*dT*dA*βZ*βT<br>linear homodimer with 5-propynyl-dC/dU and with phosphodiester DNA linker<br>ApoC3 |
| 43 | 106426 | βG*βZ*dA*PC*PU*dG*dA*dG*dA*dA*PU*dA*βZ*βT-dT-dT-dT-dT-<br>βG*βZ*dA*PC*PU*dG*dA*dG*dA*dA*PU*dA*βZ*βT<br>linear homodimer with 5-propynyl-dC/dU and with phosphodiester DNA linker<br>ApoC3 |
| 44 | 106234 | βG*βZ*dA*dT*dT*dG*dG*dT*dA*dT*βT*βZ*βA-dT-dT-<br>βG*βZ*dA*dT*dT*dG*dG*dT*dA*dT*βT*βZ*βA<br>linear homodimer of SEQ ID NO: 13 with 3 phosphodiester linkages in the 2 nt DNA linker<br>ApoB |
| 45 | 106235 | βG*βZ*dA*dT*dT*dG*dG*dT*dA*dT*βT*βZ*βA-dT-dT-dT-<br>βG*βZ*dA*dT*dT*dG*dG*dT*dA*dT*βT*βZ*βA<br>linear homodimer of SEQ ID NO: 13 with 4 phosphodiester linkages in the 3 nt DNA linker<br>ApoB |
| 46 | 106236 | βG*βZ*dA*dT*dT*dG*dG*dT*dA*dT*βT*βZ*βA-dT-dT-dT-dT-<br>βG*βZ*dA*dT*dT*dG*dG*dT*dA*dT*βT*βZ*βA<br>linear homodimer of SEQ ID NO: 13 with 5 phosphodiester linkages in the 4 nt DNA linker<br>ApoB |
| 47 | 106237 | βG*βZ*dA*dT*dT*dG*dG*dT*dA*dT*βT*βZ*βA-dT-dT-dT-dT-dT-<br>βG*βZ*dA*dT*dT*dG*dG*dT*dA*dT*βT*βZ*βA<br>linear homodimer of SEQ ID NO: 13 with 6 phosphodiester linkages in the 5 nt DNA linker<br>ApoB |
| 48 | 106238 | βG*βZ*dA*dT*dT*dG*dG*dT*dA*dT*βT*βZ*βA-dT-dT-dT-dT-dT-dT-<br>βG*βZ*dA*dT*dT*dG*dG*dT*dA*dT*βT*βZ*βA<br>linear homodimer of SEQ ID NO: 13 with 7 phosphodiester linkages in the 6 nt DNA linker<br>ApoB |
| 49 | 106239 | βG*βZ*dA*dT*dT*dG*dG*dT*dA*dT*βT*βZ*βA-dT-dT-dT-dT-dT-dT-dT-<br>βG*βZ*dA*dT*dT*dG*dG*dT*dA*dT*βT*βZ*βA<br>linear homodimer of SEQ ID NO: 13 with 8 phosphodiester linkages in the 7 nt DNA linker<br>ApoB |
| 50 | 106241 | βG*βZ*dA*dT*dT*dG*dG*dT*dA*dT*βT*βZ*βA*dT*dT-dT-dT-dT-<br>dT*dT*βG*βZ*dA*dT*dT*dG*dG*dT*dA*dT*βT*βZ*βA<br>linear homodimer of SEQ ID NO: 13 with 4 phosphodiester/4 phosphorothioate linkages in the 7 nt DNA linker<br>ApoB |

TABLE 1-continued

| SEQ ID NO: | Reference | Sequence Description |
|---|---|---|
| 51 | 106242 | βG*βZ*dA*dT*dT*dG*dG*dT*dA*dT*βT*βZ*βA*rU*βG*βZ*dA*dT*dT*dG*dG*dT*dA*dT*βT*βZ*βA<br>linear homodimer of SEQ ID NO: 13 with 2 phosphorothioate linkages in the 1 nt RNA linker<br>ApoB |
| 52 | 106243 | βG*βZ*dA*dT*dT*dG*dG*dT*dA*dT*βT*βZ*βA*rU*rU*βG*βZ*dA*dT*dT*dG*dG*dT*dA*dT*βT*βZ*βA<br>linear homodimer of SEQ ID NO: 13 with 3 phosphorothioate linkages in the 2 nt RNA linker<br>ApoB |
| 53 | 106244 | βG*βZ*dA*dT*dT*dG*dG*dT*dA*dT*βT*βZ*βA*rU*rU*rU*βG*βZ*dA*dT*dT*dG*dG*dT*dA*dT*βT*βZ*βA<br>linear homodimer of SEQ ID NO: 13 with 4 phosphorothioate linkages in the 3 nt RNA linker<br>ApoB |
| 54 | 106245 | βG*βZ*dA*dT*dT*dG*dG*dT*dA*dT*βT*βZ*βA*rU*rU*rU*rU*βG*βZ*dA*Dt*dT*dG*dG*dT*dA*dT*βT*βZ*βA<br>linear homodimer of SEQ ID NO: 13 with 5 phosphorothioate linkages in the 4 nt RNA linker<br>ApoB |
| 55 | 105448 | βZ*βZ*mA*dG*dT*dA*dG*dT*dC*dT*dT*mU*βZ*βA<br>2LNA-1me-8DNA-1me-2LNA gapmer (monomeric), fully phosphorothioated<br>ApoC3 |
| 56 | 105382 | βZ*βZ*mA*dG*dT*dA*dG*dT*dC*dT*dT*mU*mC*mA<br>2LNA-1me-8DNA-3me gapmer (monomeric), fully phosphorothioated<br>ApoC3 |
| 57 | 105390 | βZ*βZ*fA*dG*dT*dA*dG*dT*dC*dT*dT*fU*fC*fA<br>2LNA-1fluoro-8DNA-3fluoro gapmer (monomeric), fully phosphorothioated<br>ApoC3 |
| 58 | 105704 | βG*βG*βA*βA*dC*dT*dG*dA*dA*dG*dC*dC*dA*dT<br>4LNA-10DNA antisense (monomeric), fully phosphorothioated<br>ApoC3 |

Table 2 provides a descriptive legend for chemical structure designations used throughout the specification, including in Table 1.

TABLE 2

| Designation | Description | Chemical Structure |
|---|---|---|
| - (in some contexts) | phosphodiester | O=P(OH)(OH)—OH |
| * | phosphorothioate | O=P(OH)(SH)—OH |

TABLE 2-continued

| Designation | Description | Chemical Structure |
|---|---|---|
| dA | 2'-deoxyadenosine | (structure) |
| rA | (ribo)adenosine | (structure) |
| mA | 2'-O-methyl-adenosine | (structure) |
| βA | LNA [2',4']-locked adenosine | (structure) |
| fA | 2'-fluoro-ribo-adenosine | (structure) |
| dC | 2'-deoxycytidine | (structure) |

TABLE 2-continued

| Designation | Description | Chemical Structure |
|---|---|---|
| rC | (ribo)cytidine | 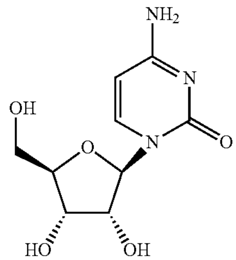 [SMILES: Nc1ccn([C@@H]2O[C@H](CO)[C@@H](O)[C@H]2O)c(=O)n1] |
| βC | LNA [2',4']-locked-cytidine | 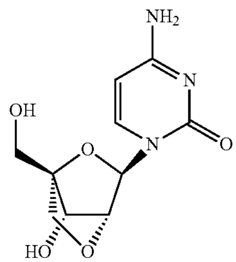 [SMILES: Nc1ccn([C@@H]2O[C@@]3(CO)CO[C@@H]2[C@@H]3O)c(=O)n1] |
| fC | 2'-fluoro-ribo-cytidine | 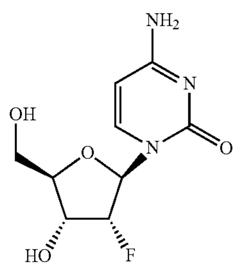 [SMILES: Nc1ccn([C@@H]2O[C@H](CO)[C@@H](O)[C@H]2F)c(=O)n1] |
| dG | 2'-deoxyguanosine | 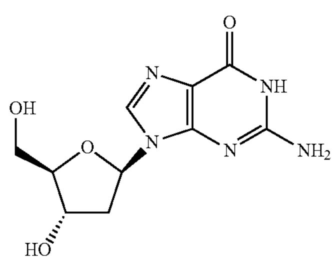 [SMILES: Nc1nc2c(ncn2[C@H]2C[C@H](O)[C@@H](CO)O2)c(=O)[nH]1] |
| rG | guanosine | 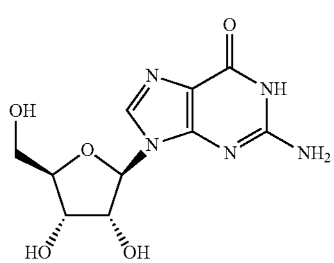 [SMILES: Nc1nc2c(ncn2[C@@H]2O[C@H](CO)[C@@H](O)[C@H]2O)c(=O)[nH]1] |
| mG | 2'-O-methyl-guanosine | 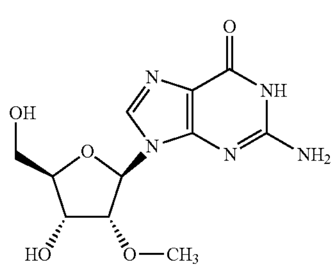 [SMILES: CO[C@@H]1[C@H](O)[C@@H](CO)O[C@H]1n1cnc2c(=O)[nH]c(N)nc21] |

TABLE 2-continued
| Designation | Description | Chemical Structure |
| --- | --- | --- |
| βG | LNA [2',3']-locked guanosine | 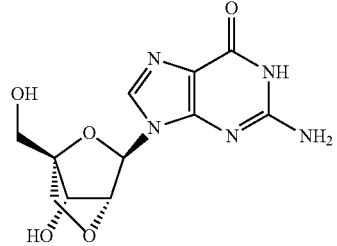 [SMILES: CC[C@]1(CO)O[C@@H](n2cnc3c(=O)[nH]c(N)nc32)[C@H](O)[C@@H]1O] |
| fG | 2'-fluoro-ribo-guanosine | 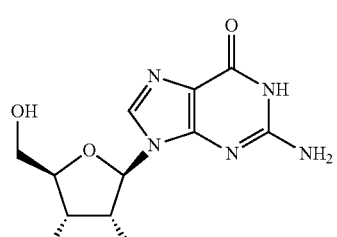 |
| dT | 2'-deoxythmidine | 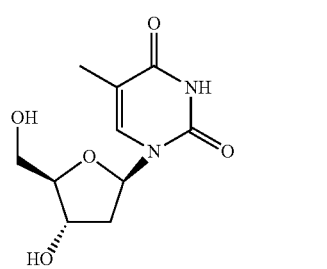 [SMILES: Cc1cn([C@H]2C[C@H](O)[C@@H](CO)O2)c(=O)[nH]c1=O] |
| mT | 2'-O-methyl-"ribo"-thymidine (3'-5') | 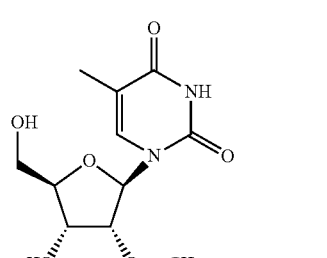 |
| βT | LNA [2',4']-locked "ribo"-thymidine | 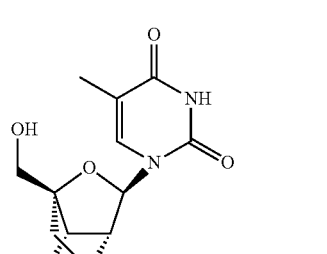 |
| dU | 2'-deoxyuridine | 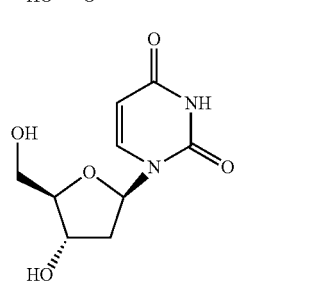 |

TABLE 2-continued
| Designation | Description | Chemical Structure |
|---|---|---|
| rU | uridine | 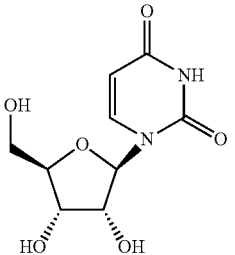 [SMILES: O=c1ccn([C@@H]2O[C@H](CO)[C@@H](O)[C@H]2O)c(=O)[nH]1] |
| mU | 2'-O-methyl-uridine | 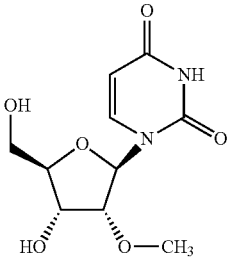 [SMILES: CO[C@@H]1[C@H](O)[C@@H](CO)O[C@H]1n1ccc(=O)[nH]c1=O] |
| fU | 2'-fluoro-ribo-uridine | 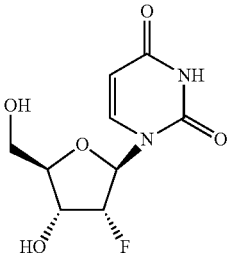 [SMILES: O=c1ccn([C@@H]2O[C@H](CO)[C@@H](O)[C@H]2F)c(=O)[nH]1] |
| βU | LNA [2',4']-locked uridine | 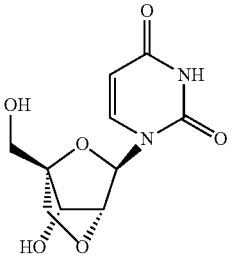 [SMILES: CC[C@]1(CO)O[C@@H](n2ccc(=O)[nH]c2=O)[C@H](O)[C@@H]1O] |
| Z | 5-methyl-2'-deoxy-cytidine | 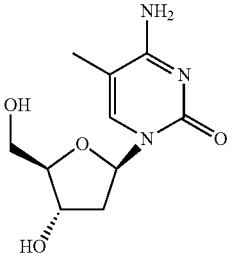 [SMILES: Cc1cn([C@H]2C[C@H](O)[C@@H](CO)O2)c(=O)nc1N] |
| βZ | LNA [2',4']-locked 5-methyl-cytidine | 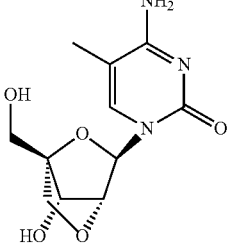 |

TABLE 2-continued
| Designation | Description | Chemical Structure |
|---|---|---|
| APC | G-Clamp deoxyphenoxazine | 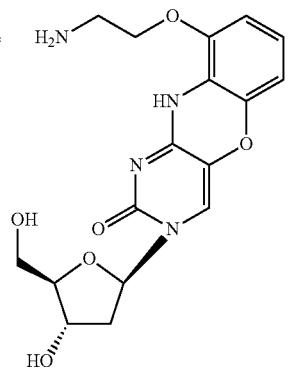 |
| PC | 5-propynyl-2'-deoxycytidine | 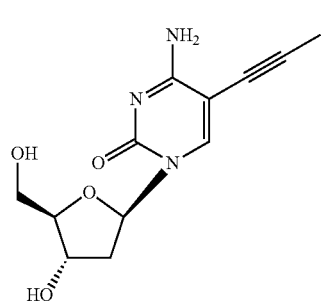 [SMILES: CC#Cc1cn([C@H]2C[C@H](O)[C@@H](CO)O2)c(=O)nc1N] |
| PU | 5-propynyl-2'-deoxythymidine | 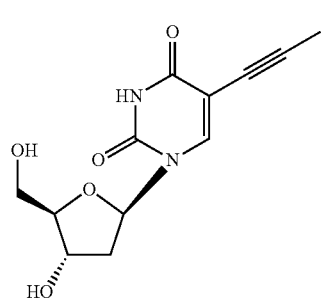 [SMILES: CC#Cc1cn([C@H]2C[C@H](O)[C@@H](CO)O2)c(=O)[nH]c1=O] |
| teg | triethylenglycol | 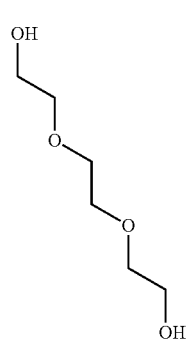 |

TABLE 2-continued

| Designation | Description | Chemical Structure |
|---|---|---|
| doub | doubler | (structure shown) |
| (NH2-C12-amino) | (NH2-C12-amino) | (structure shown) |
| Spacer 18 | Spacer 18 | (structure shown) |
| dT-Biotin | dT-Bitotin | (structure shown) |
| Bioten TEG | Biotin TEG | (structure shown) |
| HEG | HEG | ----O(CH2)2-O[(CH2)2-O]4-(CH2)2-O---- |

The measured molecular weights of the oligonucleotides were tested and found to be in agreement with the calculated values (see Table 3).

TABLE 3

| SEQ ID NO: | Ref. Number | Calculated MW | MW by LC-MS |
|---|---|---|---|
| 1 | 103966 | 4642.7 | 4642.4 |
| 2 | 105360 | 10260.1 | 10259.9 |
| 3 | 105361 | 10164.0 | 10164.2 |
| 4 | 105362 | 12362.7 | 12361.7 |
| 5 | 105363 | 11105.6 | 11105.3 |
| 6 | 105395 | 10242.1 | 10241.9 |
| 7 | 105513 | 9933.9 | 9933.7 |
| 8 | 105514 | 9580.6 | 9580.3 |
| 9 | 104109 | 4585.7 | 4585.5 |

TABLE 3-continued

| SEQ ID NO: | Ref. Number | Calculated MW | MW by LC-MS |
|---|---|---|---|
| 10 | 104111 | 4280.5 | 4280.1 |
| 11 | 104112 | 3913.2 | 3918 |
| 12 | 105576 | 4655.9 | 4655.6 |
| 13 | 102102 | 4325.5 | 4325.4 |
| 14 | 105515 | 4633.8 | 4633.5 |
| 15 | 10620 | 10520.3 | 10520.4 |
| 16 | 106201 | 10600.6 | 10600.4 |
| 17 | 106202 | 12317.7 | 12318.5 |
| 18 | 106203 | 9929.7 | 9929.8 |
| 19 | 106204 | 10010.1 | 10010.1 |
| 20 | 106205 | 11727.2 | 11727.0 |
| 21 | 106206 | 10225.0 | 10225.2 |
| 22 | 106207 | 10225.0 | 10225.1 |
| 23 | 106413 | 9889.7 | 9889.7 |
| 24 | 106414 | 10279.0 | 10279.2 |
| 25 | 106415 | 9910.7 | 9910.8 |
| 26 | 106416 | 15810.2 | 15810.6 |
| 27 | 101443 | 4306.5 | 4307.3 |
| 28 | 101441 | 4306.5 | 4304.5 |
| 29 | 105758 | 4693.8 | 4692.7 |
| 30 | 104975 | 4620.8 | 4620.0 |
| 31 | 102103 | 4311.5 | 4310.4 |
| 32 | 104882 | 4893.1 | 4893 |
| 33 | 106417 | 10227.0 | 10227.4 |
| 34 | 106418 | 10217.0 | 10217.2 |
| 35 | 106419 | 10168.9 | 10168.8 |
| 36 | 106420 | 10222.0 | 10222.3 |
| 37 | 106206 | 10225.0 | 10225.2 |
| 38 | 106421 | 10792.6 | n.d. |
| 39 | 106422 | 10247.0 | 10247.1 |
| 40 | 106423 | 12311.6 | 12311.5 |
| 41 | 106424 | 10596.4 | 10596.5 |
| 42 | 106425 | 10644.4 | 10644.6 |
| 43 | 106426 | 10692.57 | n.d. |
| 44 | 106234 | 9017.1 | 9017.1 |
| 45 | 106235 | 9321.3 | 9321.1 |
| 46 | 106236 | 9625.5 | 9626.1 |
| 47 | 106237 | 10233.9 | 10234.2 |
| 48 | 106238 | 10538.1 | 10538.6 |
| 49 | 106239 | 10842.3 | 10842.5 |
| 50 | 106241 | 10906.6 | 10906.8 |
| 51 | 106242 | 9051.2 | 9051.1 |
| 52 | 106243 | 9373.5 | 9373.2 |
| 53 | 106244 | 9695.7 | 9695.5 |
| 54 | 106245 | 10017.9 | 10017.5 |
| 55 | 105448 | 4622.8 | 4622.6 |
| 56 | 105382 | 4612.8 | 4612.6 |
| 57 | 105390 | 4564.7 | 4564.4 |
| 58 | 105704 | 4617.8 | 4617.5 |

Sequence correlation for the unmodified versions of the sequences (except the linker/bridge) and the respective fully modified sequences is shown in Table 4.

TABLE 4

| SEQ ID NO:* | Sequence | SEQ ID NO:** |
|---|---|---|
| 118 | AAGCAACCTACAGG | 1 |
| 61 | AAGCAACCTACAGG-T-T-T-AAGCAACCTACAGG | 2 |
| 62 | AAGCAACCTACAGGtegSStegAAGCAACCTACAGG | 3 |
| 63 | (AAGCAACCTACAGG-T-T-T-T-)₂doubteg | 4 |
| 64 | (AAGCAACCTACAGG-tegSS)₂doubteg | 5 |
| 65 | AAGCAACCTTCAGG-T-T-T-AAGCAACCTTCAGG | 6 |
| 66 | AAGCAACCTTCAGG-T-T-T-GZATTGGTATTZA | 7 |
| 67 | GZATTGGTATTZA-T-T-T-TZZTCGGCCTZTG | 8 |
| 68 | ZZTCTTCGGCCZTG | 9 |
| 69 | TZZTCGGCCTZTG | 10 |
| 70 | TZTTCGGCCCTG | 11 |
| 71 | TZTTZGGCCCTG | 12 |
| 72 | GZATTGGTATTZA | 13 |
| 73 | AAGCAACCTTCAGG | 14 |
| 74 | GZACTGAGAATAZT-T-T-T-GZACTGAGAATAZT | 15 |
| 75 | GZACTGAGAATAZTTTTTGZACTGAGAATAZT | 16 |
| 76 | (GZACTGAGAATAZT-T-T-T-T-)₂doubteg | 17 |
| 77 | GZATTGGTATTZA-T-T-T-T-GZATTGGTATTZA | 18 |
| 78 | GZATTGGTATTZATTTTGZATTGGTATTZA | 19 |
| 79 | (GZATTGGTATTZA-T-T-T-T-)₂doubteg | 20 |
| 80 | GZACTGAGAATAZT-T-T-T-T-GZATTGGTATTZA | 21 |
| 81 | GZATTGGTATTZA-T-T-T-T-GZACTGAGAATAZT | 22 |
| 82 | GGCAAGCATCZTG-T-T-T-T-ZAATCCATGGZAG | 23 |
| 83 | GGCAAGCATCZTG-T-T-T-T-GZGTGCATAAATTG | 24 |
| 84 | GGCAAGCATCZTG-T-T-T-T-GZATTGGTATTZA | 25 |
| 85 | GZATTGGTATTZA-T-T-T-T-GZACTGAGAATAZT-T-T-T-T-GGCAAGCATCZTG | 26 |
| 86 | GGCAAGCATCZTG | 27 |
| 87 | ZAATCCATGGZAG | 28 |
| 88 | GZGTGCATAAATTG | 29 |
| 89 | GZACTGAGAATAZT | 30 |
| 90 | ZGTCTATGTATAG | 31 |
| 91 | UU(APC)AGTGTGATGA(APC) | 32 |
| 92 | ZZAGTAGTCTTUZA-T-T-T-T-GZATTGGTATTZA | 33 |
| 93 | ZZAGTAGTCTTUCA-T-T-T-T-GZATTGGTATTZA | 34 |
| 94 | ZZAGTAGTCTTUCA-T-T-T-T-GZATTGGTATTZA | 35 |
| 95 | GGAACTGAAGCCAT-T-T-T-T-GZATTGGTATTZA | 36 |
| 96 | GZACTGAGAATAZT-T-T-T-T-GZATTGGTATTZA | 37 |
| 97 | UU(APC)AGTGTGATGA(APC)-T-T-T-T-GZACTGAGAATAZT | 38 |
| 98 | AAGCAACCTACAGG-T-T-T-T-GZATTGGTATTZA | 39 |
| 99 | (GGAACTGAAGCCAT-T-T-T-T-)₂doubteg | 40 |
| 100 | GZA(PC)TGAGAATAZT-T-T-T-GZA(PC)TGAGAATAZT | 41 |
| 101 | GZA(PC)(PU)GAGAATAZT-T-T-T-T-GZA(PC)(PU)GAGAATAZT | 42 |
| 102 | GZA(PC)(PU)GAGAA(PU)AZT-T-T-T-T-GZA(PC)(PU)GAGAA(PU)AZT | 43 |
| 103 | GZATTGGTATTZA-T-T-GZATTGGTATTZA | 44 |
| 104 | GZATTGGTATTZA-T-T-T-GZATTGGTATTZA | 45 |
| 105 | GZATTGGTATTZA-T-T-T-T-GZATTGGTATTZA | 46 |
| 106 | GZATTGGTATTZA-T-T-T-T-T-GZATTGGTATTZA | 47 |
| 107 | GZATTGGTATTZA-T-T-T-T-T-T-GZATTGGTATTZA | 48 |
| 108 | GZATTGGTATTZA-T-T-T-T-T-T-T-GZATTGGTATTZA | 49 |
| 109 | GZATTGGTATTZATT-T-T-T-TTGZATTGGTATTZA | 50 |
| 110 | GZATTGGTATTZAUGZATTGGTATTZA | 51 |
| 111 | GZATTGGTATTZAUUGZATTGGTATTZA | 52 |
| 112 | GZATTGGTATTZAUUUGZATTGGTATTZA | 53 |
| 113 | GZATTGGTATTZAUUUUGZATTGGTATTZA | 54 |
| 114 | ZZAGTAGTCTTUZA | 55 |
| 115 | ZZAGTAGTCTTUCA | 56 |
| 116 | ZZAGTAGTCTTUCA | 57 |
| 117 | GGAACTGAAGCCAT | 58 |

In Table 4,
A is adenosine
C is cytidine
G is guanosine
T is thymidine
U is uridine
Z is 5-methyl-cytosine
APC is a G-clamp
PU is 5-propynyl-uridine
PC is 5-propynyl-cytidine and
doubteg is

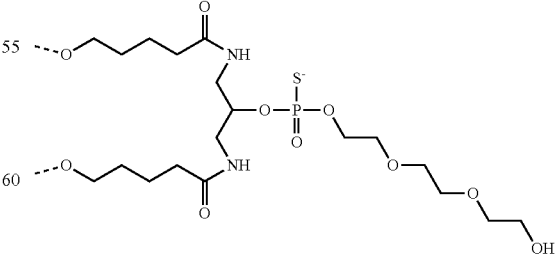

(Formula XI)

*Sequence without chemical modifications (except bridge/linker)
**The sequence of the fully chemically modified sequence corresponding to SEQ ID NO:*

Example 3

Dimer Stability in Plasma and Cleavage in Liver Homogenates

Stability measurements were performed using 4 different oligonucleotides (including dimers and the monomer, SEQ ID NOs:1, 2, 3, 4).

Briefly, oligos were incubated in 95% plasma of mouse or monkey and in 5% liver homogenate at a concentration of 30 µM and at 37° C. Samples for measurement were taken after 0, 7, 24 and 48 h of incubation. Samples were subjected to a phenol/chloroform extraction and analyzed using LC-MS.

In detail, stock solutions with a final concentration of 600 µM and a final volume of 100 µl have been prepared of all oligonucleotides. Twelve pieces of approximately 50 mg of liver from CD 1 mouse (female, Charles River) were added to individual Lysing matrix tubes. A calculated volume of 1×PBS to give a final concentration of 5% liver (W/W) was added to each of the twelve tubes. All samples were homogenized using a BioRad Fast prep System. The resulting homogenate solutions were combined to give about 12 ml of 5% liver homogenate in 1×PBS which was subsequently used for incubation.

Plasmas used were a Na-Citrate plasma from female NMRI mice (Charles River) and K-EDTA plasma from male Cynomolgous monkeys (Seralab International).

Four samples of each oligo were prepared representing each individual incubation time point (0, 7, 24 and 48 h) in mouse and monkey plasma and in mouse liver homogenate, respectively. In addition, a blank sample and a recovery sample were prepared of each oligo and incubation matrix. Generally, plasma samples were prepared by adding 5 µl of the 600 µM oligo stock solution to 95 µl of mouse or monkey plasma, respectively, with a final oligo concentration of 30 µM. Recovery samples were prepared by adding 5 µl of water to 95 µl of plasma. Blank samples are oligo in water with a final concentration of 100 µM. Liver samples and recoveries were prepared in the same way except that liver homogenate in PBS was used instead of plasma.

All samples and recoveries were incubated at 37° C. Samples were cooled to room temperature after 0, 7, 24 and 48 h and was subjected to phenol/chloroform purification. To that end, 370 µl of ammonium hydroxide (15%), 10 µl dithiothreitol (DTT, 1 M, Sigma Cat. No. 43816) and 800 µl premixed phenol/chloroform/isoamyl alcohol (Sigma P2069) was added to each sample. Samples were then vortexed for 10 min at a maximum vortex speed and incubated at 4° C. for 20 min. The samples were then centrifuged at 3500 RFC for 20 min at 4° C. and 400 µl of the aqueous layer were removed and dried in a lyophilizer.

The dried samples were dissolved in water (100 µl). The recovery samples were dissolved in water (95 µl) and spiked with 5 µl of the respective oligo stock solution (600 µM).

Samples were analyzed by LC-MS (Agilent 1200, Bruker Esquire 3000) using a Waters Acquity UPLC OST C18 column (1.7 µm, 2.1×50) with HFIP/TEA/water (385 min 1,1,1,3,3,3-hexafluoroisopropanol, 14.4 min triethylamine in water) as buffer A and methanol as buffer B at a flow rate of 0.3 ml/min and a column temperature of 60° C. The following gradient was used: 3 min at 5% B, 5-15% B in 2.5 min (10%/min), 15-23% B in 5.5 min, 23-30% B in 3 min, 30-100% B in 0.5 min, 5 min at 100% B, 100-5% B in 0.5 min, 5 min at 5% B.

Samples were analyzed in 96-well plate format. A standard curve with 8 standards (5, 10, 15, 20, 50, 75, 90, 100 µg/ml; 25 µg/ml IS), standard 0 (0 µg/ml; 25 µg/ml IS) and three recovery samples (20, 50, 100 µg/ml; 25 µg/ml IS) were prepared for each oligo. Samples related to one oligo were analyzed together on the same plate.

Standards were prepared as follows. A piece of approximately 50 mg of tissue was cut from the respective organ tissue, weighted and placed into the respective well of a 2.2 ml 96-deepwell plate (VWR 732-0585). Two steel balls (5 mm diameter, KGM Kugelfabrik GmbH, part No. 1.3541) were placed into each well and 500 µl homogenization buffer (vide infra), 20 µl DTT (1 M, Sigma 43816), 50 µl of proteinase K solution (Qiagen, 19133) was added. Furthermore, 10 µl working solution analyte and 10 µl working solution internal standard was added into each well of the standards to give the corresponding final concentrations of (5, 10, 15, 20, 50, 75, 90, 100 µg/ml; 25 µg/ml IS (Internal Standard)). Standard 0 and recovered material were spiked with 10 µl of working solution internal standards only; recoveries were spiked with 10 µl of working solution analyte after the entire extraction process and prior to analysis.

Samples were processed as follows. A piece of approximately 50 mg of tissue was cut from the respective organ tissue, weighed and placed into the respective well of a 96-deepwell plate. Two steel balls were placed into each well and 500 µl homogenization buffer 20 µl DTT (1 M), 50 µl of proteinase K solution was added. The plate was sealed with STAR lab foils (StarLab E 2796 3070) and samples were homogenized using a Qiagen Tissue Lyzer 3×30 s at 17 Hz. Subsequently, the plate was incubated in a water bath for 2 hours at 55° C. followed by transfer of the samples to a new 96-deepwell plate using an automated liquid-handling system (TomTec Quadra 3). After the addition of 200 µl ammonium hydroxide (25%) and 500 µl phenol/chloroform/isoamyl alcohol (25:24:1) the plate was vortexed using a Multitubevortex for 5 min. Subsequently, the plate was incubated for 10 min at 4° C. and centrifuged at 4° C. for another 10 min at 3500 RCF. The plate was then passed to the TomTec system which was used to remove the aqueous layer. The remaining organic layer was washed by adding 500 µl water. The aqueous phase was again removed using the TomTec system. The aqueous phases were combined, 50 µl HCl (1 N), 500 µl SAX Load High buffer (see below) and 300 µl acetonitrile were added, and the resulting solution was mixed thoroughly by up-and-down pipetting using the TomTec system. The program "SPE extraction of tissue samples 100416" was used for the subsequent solid-phase extraction procedure.

VARIAN Bond Elut 96 square-well SAX 100 mg (Cat. No.: A396081C) were equilibrated with acetonitrile, water and SAX load buffer (see below), samples were loaded and washed with SAX load buffer. The samples were eluted with SAX elute buffer (vide infra) and subsequently diluted with SAX/RP dilution buffer (vide infra). WATERS Oasis HLB LP 96-well Plate 60 µm 60 mg (Part No. 186000679) were equilibrated with acetonitrile, water and SAX dilution buffer (see below). The samples were loaded and the cartridge washed with water. The samples were eluted with RP elute buffer (vide infra). Freeze the elution plate for 1 hour at −80° C. and lyophilize to dryness. The dried samples were reconstituted in 50 µl water and dialyzed for 60 min against water using Thermo Slide-A-Lyzer. The samples were then subjected to CGE analysis on a Beckman Coulter PACE/MDQ system. The conditions were: (i) Capillary: eCAP DNA, neutral, 21 cm, 100 µm I.D. (Beckman #477477); (ii) Capillary temperature: 20° C.; (iii) Sample storage temperature: 10° C., (iv) Gel: ssDNA 100 R (Beckman #477621) (v) Buffer: Tris/boric acid/EDTA buffer containing 7 M Urea (Beckman #338481) (vi) Detection wavelength: 260 nm; (vii) Separation voltage: 30 kV; (viii) Injection time: 60 s; (ix) Injection voltage: 10 kV; (x) Run time: 20 minutes; (xi) Data acquisition rate: 4 pt/sec. Analysis was done using the Karat 7.0 software (Beckman).

Figure 2A:
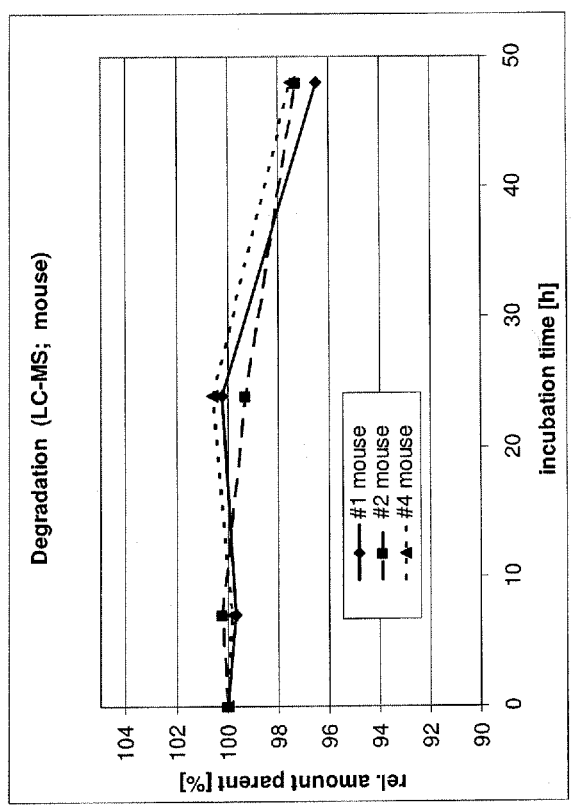
FIGS. 2A and 2B demonstrate slow degradation of both ApoC3 ASO monomer (SEQ ID NO:1, designated as per Example 2(E)) and cleavable ApoC3-ApoC3 ASO dimers (SEQ ID NO:2 and SEQ ID NO:4) in murine and monkey plasmas respectively.
Figure 2B:
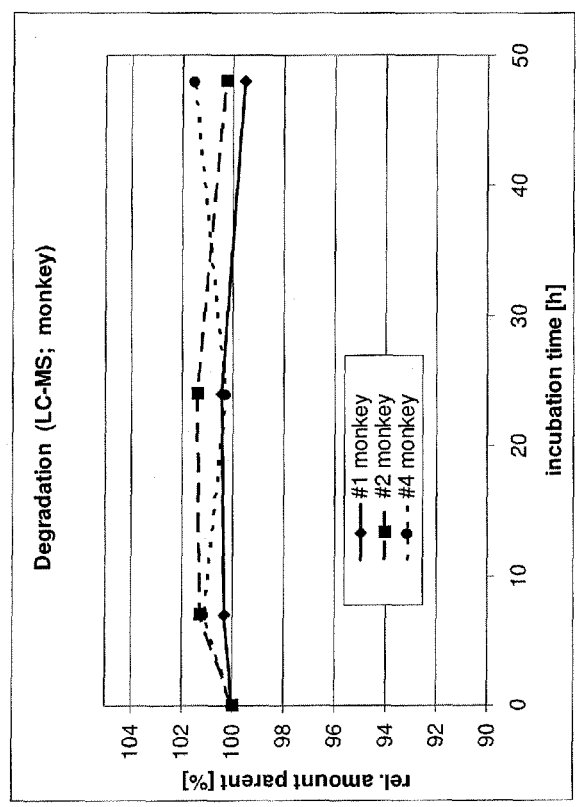
Figure 2C:
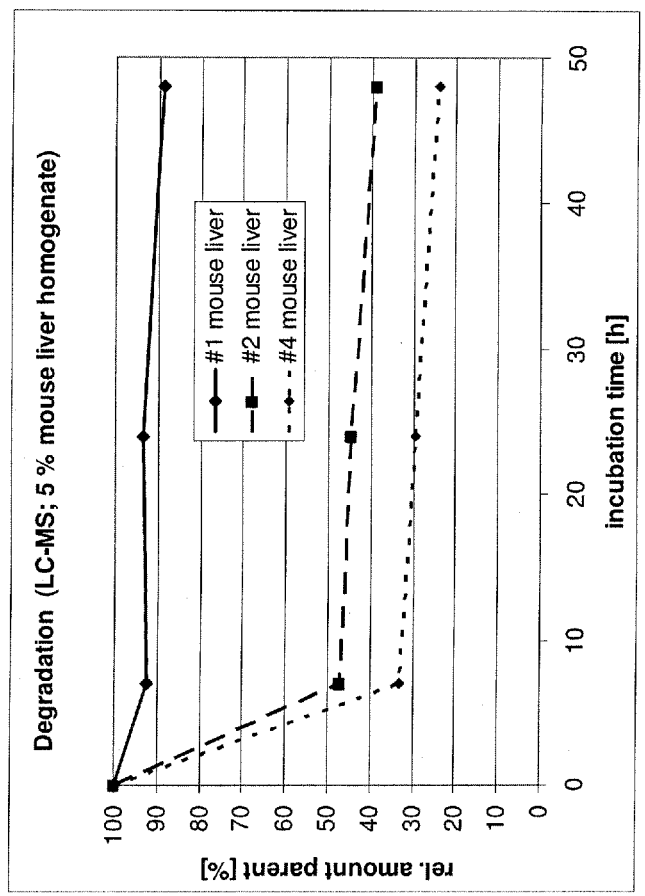
FIG. 2C demonstrates efficient cleavage into monomers of the cleavable ApoC3-ApoC3 ASO dimers (SEQ ID NO:2 and SEQ ID NO:4) and the relative stability ApoC3 ASO monomer (SEQ ID NO:1) in mouse liver homogenate.
Figure 2D:
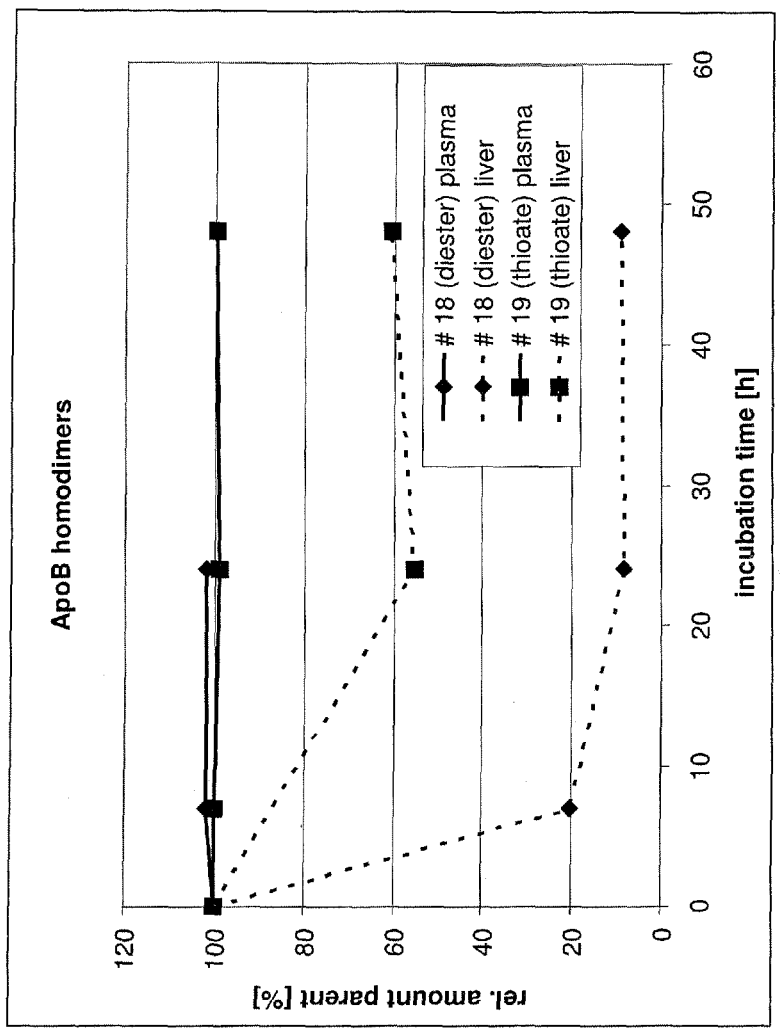
FIG. 2D shows cleavable SEQ ID NO:18) and noncleavable SEQ ID NO:19) ApoB-ApoB ASO homodimers incubated in murine plasma or liver homogenate, demonstrating stability of both types of molecules in plasma, and a more efficient cleavage into monomers of the cleavable version in the liver homogenate.

In vitro dimer stability in murine and monkey plasmas and liver homogenates was assessed using the assay described above. Subsequently to the incubation, samples were extracted with the phenol/chloroform extraction method and analyzed by LC-MS, as described above. FIG. 2 illustrates in vitro dimer stability in murine or monkey plasmas and degradation of dimer in liver homogenates as determined by LC-MS. FIGS. 2A and 2B demonstrate slow degradation of both ApoC3 ASO monomer (SEQ ID NO:1, designated as per Example 2(E)) and cleavable ApoC3-ApoC3 ASO dimers (SEQ ID NO:2 and SEQ ID NO:4) in murine and monkey plasmas respectively. FIG. 2C demonstrates efficient degradation of the cleavable ApoC3-ApoC3 ASO dimers (SEQ ID NO:2 and SEQ ID NO:4) and the relative stability ApoC3 ASO monomer (SEQ ID NO:1) in mouse liver homogenate. FIG. 2D shows cleavable SEQ ID NO:18) and noncleavable SEQ ID NO:19) ApoB-ApoB ASO homodimers incubated in murine plasma or liver homogenate, demonstrating stability of both types of molecules in plasma, and a more efficient degradation of the cleavable version in the liver homogenate.

Example 4

Figure 3A:
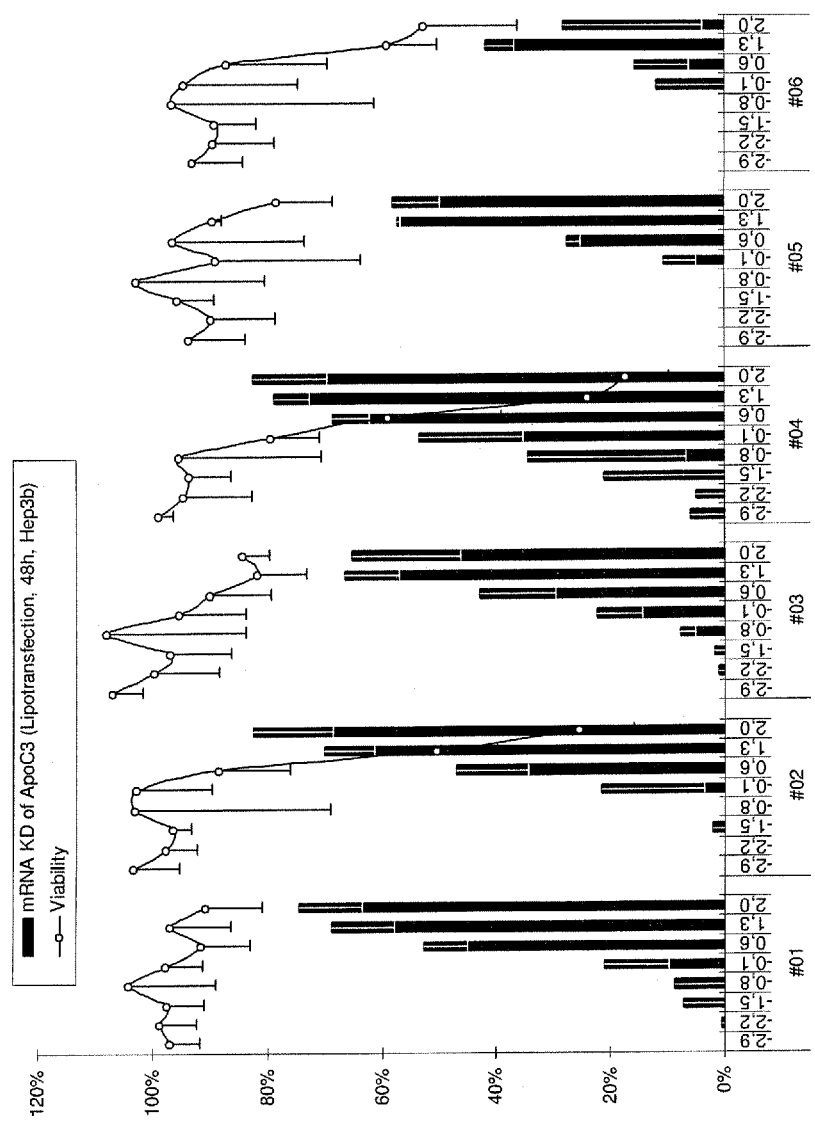
FIG. 3 addresses various aspects of linker designs in homodimers. For the results shown in FIGS. 3A, 3B and 3D, Hep3B cells were treated at various concentrations (0.001, 0.006, 0.03, 0.2, 0.8, 4.0, 20 and 100 nM) of the indicated oligonucleotides formulated with a lipotransfection agent. mRNA content and cell viability was determined 48 hours after treatment. For the results shown in FIGS. 3C and 3E-3K, Hep3B cells were treated at eight concentrations (0.1, 0.6, 3.0, 20, 80, 400, 2000 and 10,000 nM) of the indicated oligonucleotides without any transfection agent ("gymnotic delivery"). mRNA content and cell viability were determined after 8 days of treatment. In all cases, the graphs depict percentage effect relative to a non-specific oligonucleotide (negative control).

In Vitro Tests of Various Linker Designs with ApoC3 ASO Homodimers (FIG. 3A)

Cell Culture Protocol

Human hepatocarcinoma cells (Hep3B) were acquired from the "Deutsche Sammlung von Mirkoorganismen and Zellkulturen GmbH" (DSMZ). For the KD studies, 3.000-10.000 cells/well were seeded (1-3 days prior to treatment) into 96 multi-titer plates yielding 70-80% confluence on the day of treatment. For assays using lipotransfection delivery techniques, cells were incubated with indicated concentrations of ASO formulated with 0.3 µl Lipofectamine 2000 (L2k) for 48 hr in Earle's Balanced Salt Solution (Lonza, Verviers, Belgium) with L-glutamine (2 min).

Knock-Down Analysis Protocol

Following the treatment period mRNA levels of target and reference (a housekeeping gene) mRNA was determined by the Quanti Gene Assay (Affymetrix, Santa Clara, Calif., USA) according to the manufactures standard protocol. Prior to lysis, cell viability was analyzed by Cell Titer Blue Assay (Promega, Madison, Wis., USA). Inactive, scrambled, ASO was used as negative control and reference (SEQ ID NO:31). The QuantiGene 2.0 assay (Affymetrix, Santa Clara, Calif.) was utilized to measure the expression level of target genes in Hep3B cells before and after the incubation with the ASOs. Human ApoB/ApoC3 probes and housekeeping gene PPIB probes were purchased from Affymetrix. Standard assay procedures were carried out according to the manufacturer's recommendations. On the day of harvesting, 200 µl/well of lysis buffer (with 1:100 protease K) was added to the cells. A total of 60 µl of lysate was used for human ApoC3 probes, while 20 µl lysate was used for human ApoB and PPIB probes respectively. Assay plates were read on the GloRunner Microplate Luminometer (Promega Corp, Sunnyvale, Calif.). The data were normalized against housekeeping gene PPIB.

Transfection Protocol

Hep3B cells were treated with 8 consecutive concentrations (0.001, 0.006, 0.03, 0.2, 0.8, 4.0, 20 and 100 nM) of oligonucleotide were formulated with the Lipotransfection agent. mRNA content and cell viability were determined after 48 hr of treatment.

The results of the above experiments are presented in FIG. 3A. All homodimers derived from the human sequence show knockdown. Homodimers with thiol (S—S) bridges (SEQ ID NOs:2 and 4) showed increased cytotoxicity. At the same time, the homodimer made from the murine ApoC3 ortholog (SEQ ID NO:6) was ineffective Example 5

In Vitro Comparisons of Cleavable Vs. Noncleavable Linker Designs with ApoC3 Homodimers (FIGS. 3B, 3C, 3J, 3K)

Cell were treated and analyzed as described in Example 4. For "gymnotic delivery," the cells were not transfected with the ASO, but instead were incubated with indicated concentrations of unformulated ASO in MEM with high glucose (6 g/l; Invitrogen, Carlsbad, Calif., USA) without L-glutamine for 8 days. The results are presented in FIGS. 3B, 3C, 3J and 3K.

Figure 3B:
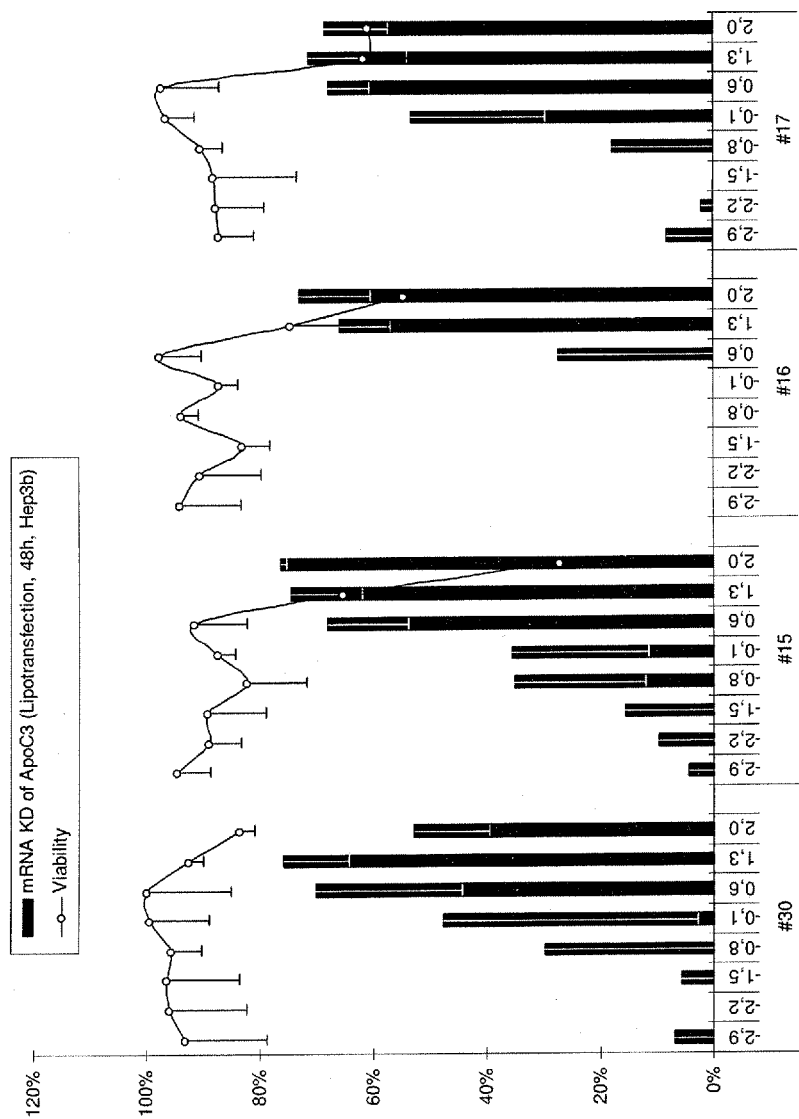
Figure 3C:
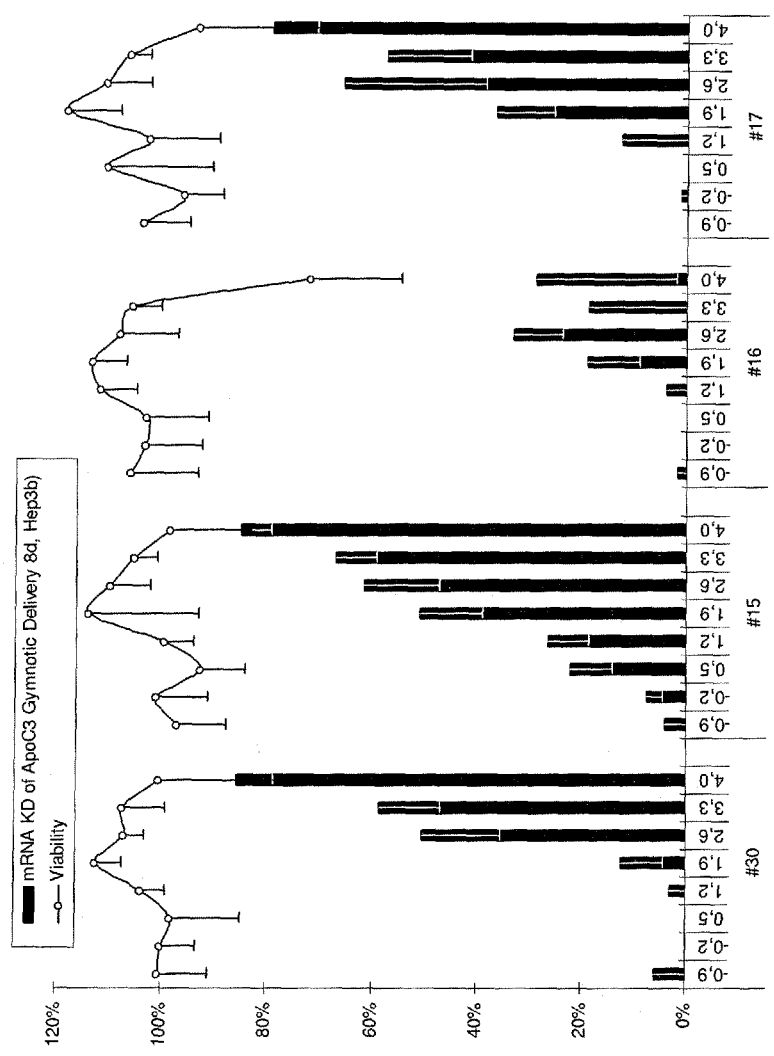
Figure 3D:
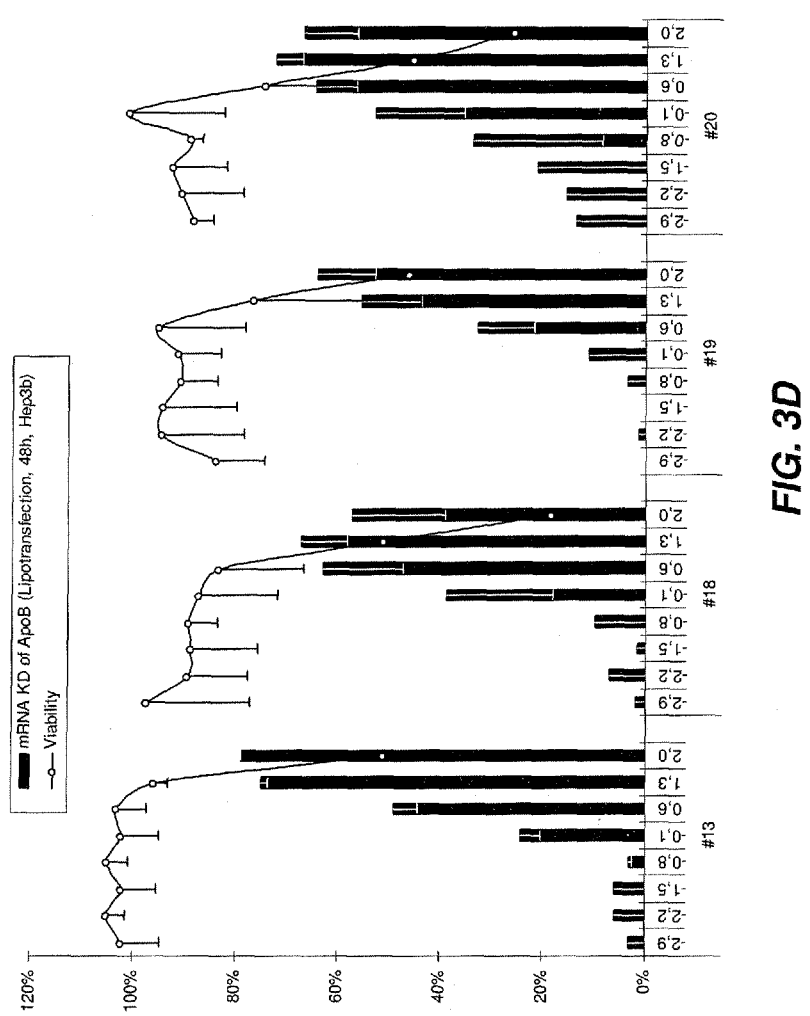
Figure 3E:
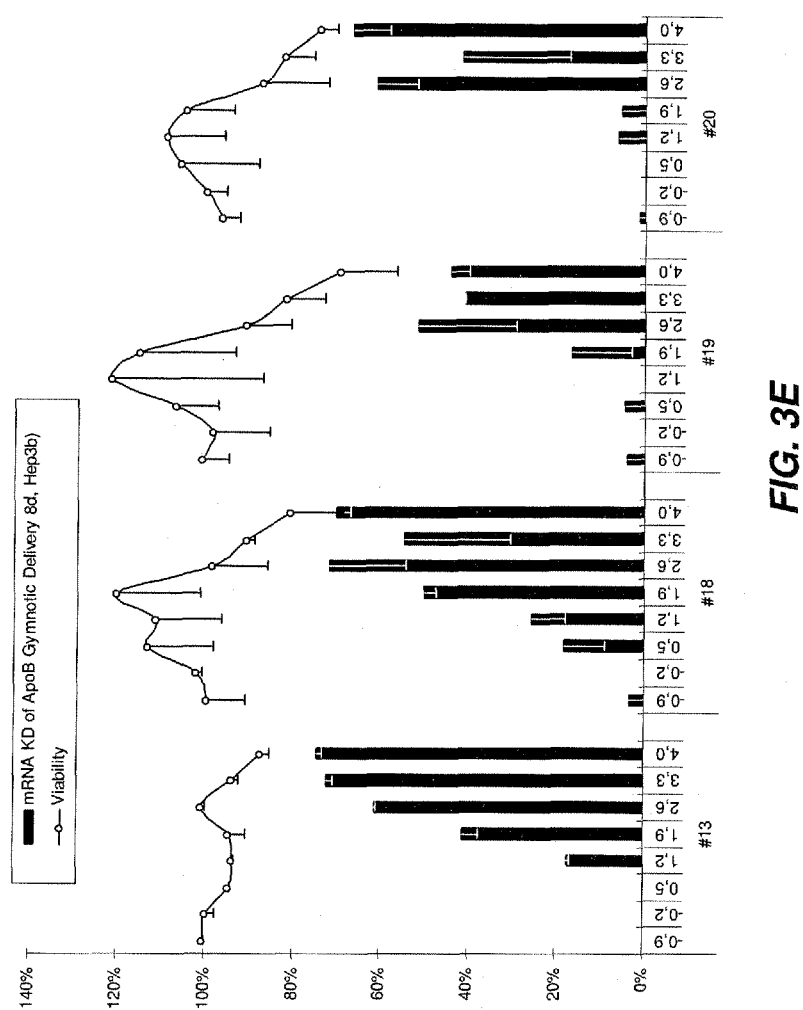

When using lipotransfection techniques, the ApoC3 homodimers with more easily cleavable linkers (FIG. 3B, SEQ ID NOs:15 and 17) showed a higher knock-down activity than their less cleavable counterpart (FIG. 3B, SEQ ID NO:16). The same effect was seen with gymnotic delivery (FIG. 3C). FIG. 3J shows that the knock-down activity from the ApoC3 homodimer (SEQ ID NO:15) is better compared to the same sequence used as monomer (SEQ ID NO:30). FIG. 3K shows that the ApoC3 homodimer, if connected via a metabolically unstable linker (SEQ ID NO:15), is much more effective than its counterpart connected by a stable linker (SEQ ID NO:16).

Example 6

In Vitro Tests of Cleavable Vs. Noncleavable Linker Designs with ApoB Homodimers (FIGS. 3D, 3E, 3H, 3I)

Cell culture, knock-down analysis and transfection procedures were performed as described in Example 5. The results are presented in FIGS. 3D, 3E, 3H and 3I. In lipotransfection assays, the ApoB homodimers with easily cleavable linkers (FIG. 3D, SEQ ID NOs:18, 20) showed a higher knock-down activity than their metabolic more stable analog (FIG. 3D, SEQ ID NO:19). The same effect was seen with gymnotic delivery (FIG. 3E). FIG. 3H shows that the knock-down activity from the ApoB homodimer (SEQ ID NO:18) is better compared to the same sequence used as a monomer (SEQ ID NO:13). FIG. 3I shows that the ApoB homodimer, if connected via a metabolically unstable linker (SEQ ID NO:18), is much more effective than its counterpart connected by a stable linker (SEQ ID NO:19).

Example 7

Figure 3F:
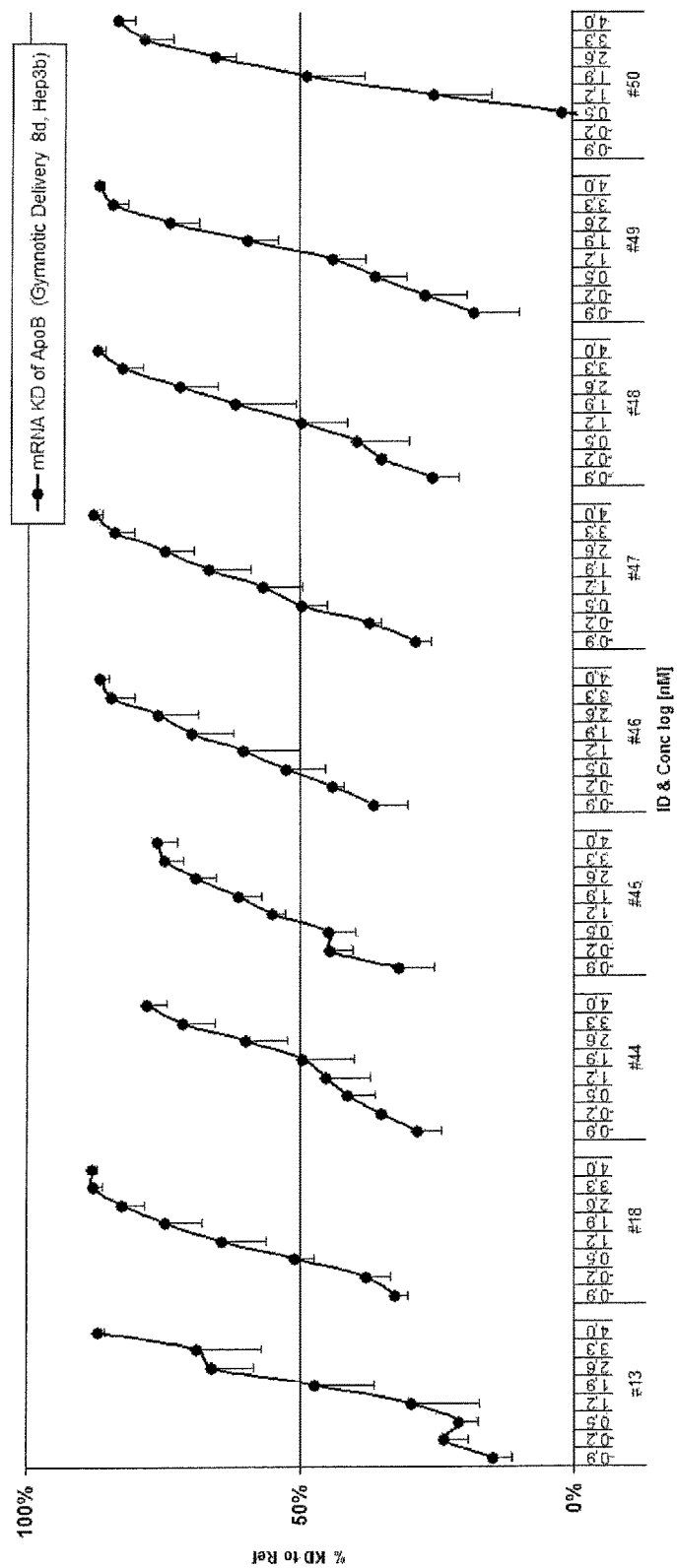
Figure 3G:
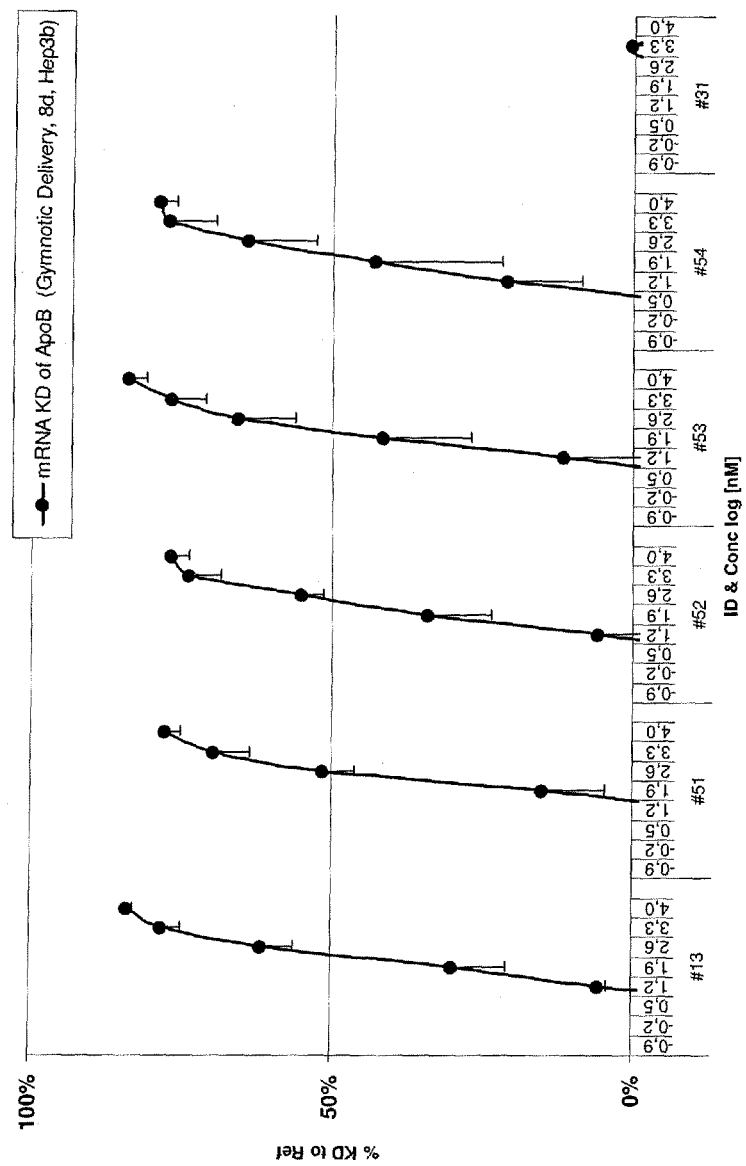
Figure 3H:
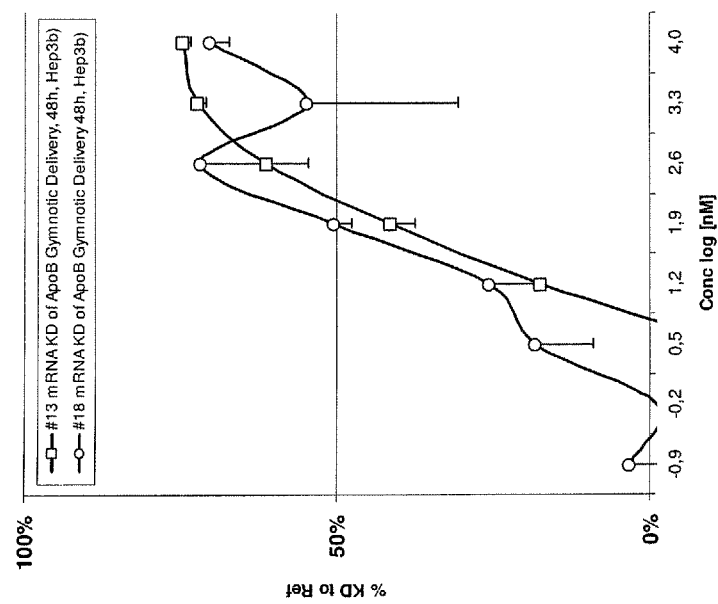
Figure 3I:
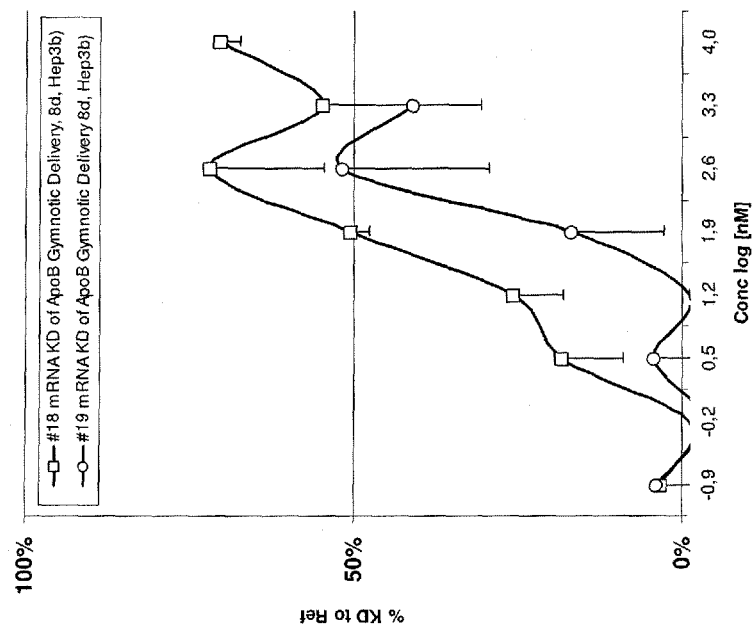
Figure 3J:
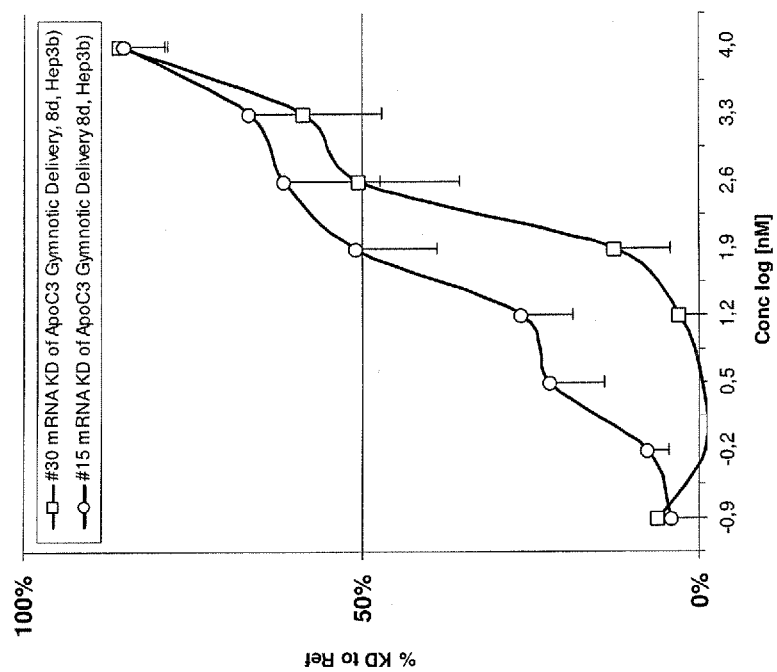
Figure 3K:
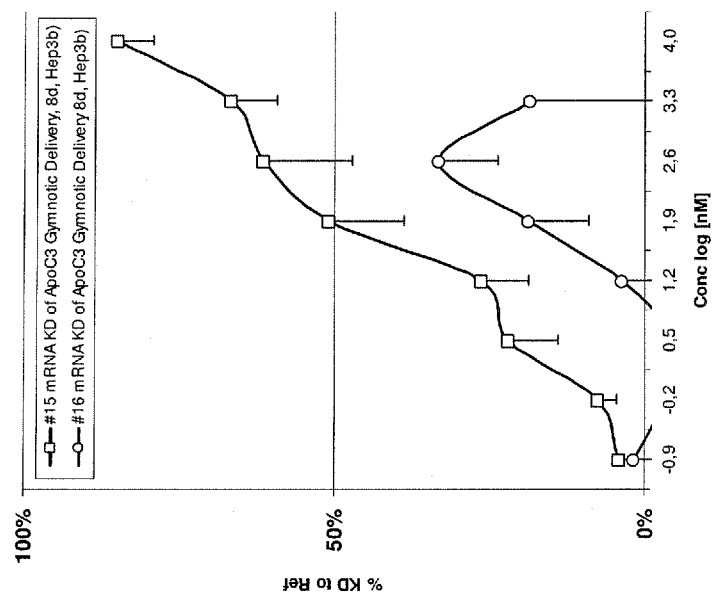

In Vitro Tests of Cleavable Linkers of Different Lengths with ApoB Homodimers (FIG. 3F, 3G)

Cell culture, knock-down analysis and transfection procedures were performed as described in Example 5. The results are presented in FIGS. 3F and 3G. For FIG. 3F, increasing numbers of DNA-phosphodiester linkages (ranging from one (SEQ ID NO:44) to eight (SEQ ID NO:49)) were used to link the ApoB ASO sequences. The increasing the length of the linker did not have a significant effect on the knockdown activity of the homodimer. FIG. 3G demonstrates that using RNA-phosphorothioate linkers of different lengths (from one (SEQ ID NO:51) to four (SEQ ID NO:54)) also did not produce a significant impact on the knockdown activity of the homodimer.

Example 8

Figure 4A:
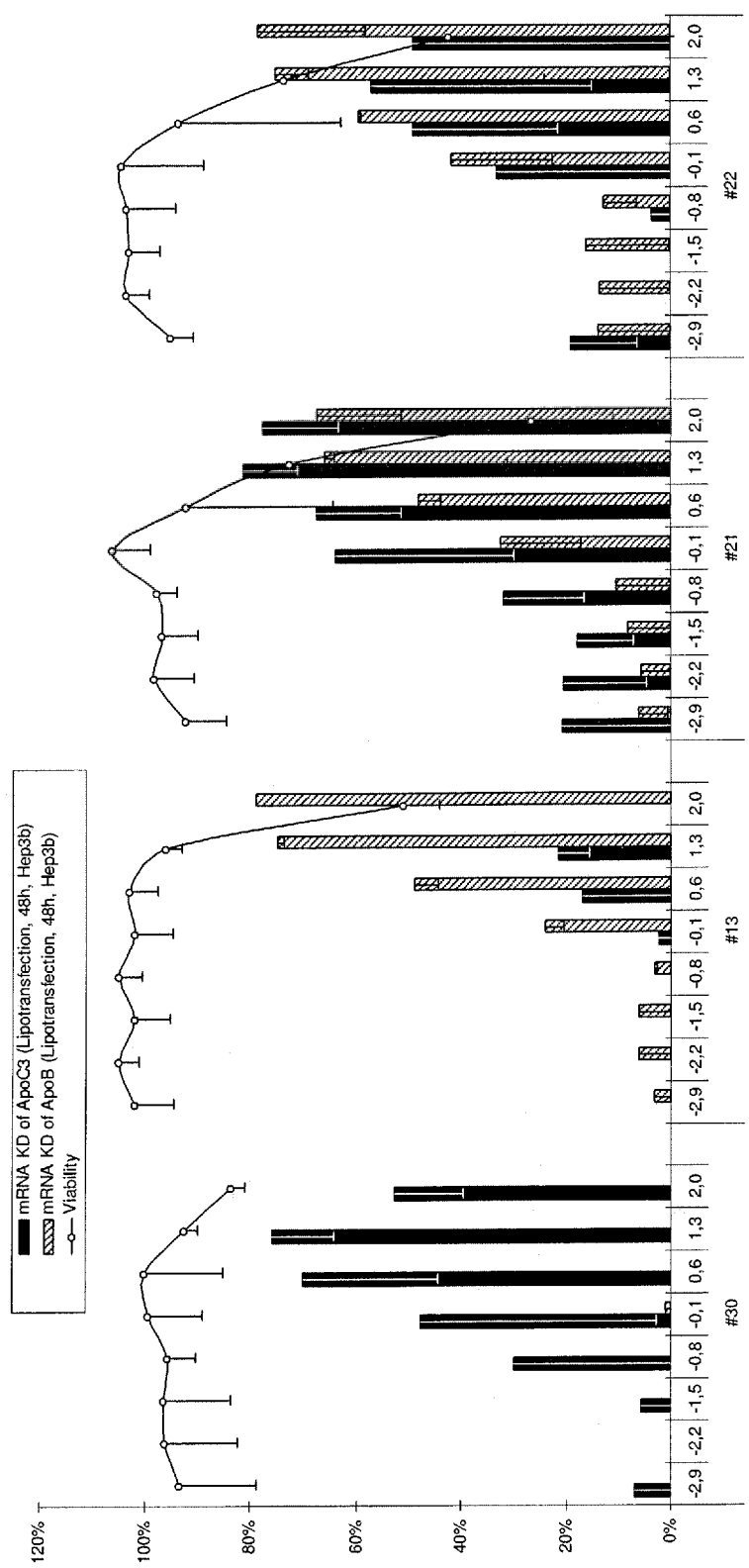
FIG. 4 addresses various aspects of the design of various heterodimers (di- and trimers). For the results shown in FIG. 4A, Hep3B cells were treated at various concentrations (0.001, 0.006, 0.03, 0.2, 0.8, 4.0, 20 and 100 nM) of the indicated oligonucleotides formulated with a lipotransfection agent. mRNA content and cell viability were determined 48 hours after treatment. For the results shown in FIGS. 4B-4M, Hep3B cells were treated at eight concentrations (0.1, 0.6, 3.0, 20, 80, 400, 2000 and 10,000 nM) of the indicated oligonucleotides without any transfection agent ("gymnotic delivery"). mRNA content and cell viability were determined after 8 days of treatment. In all cases, the graphs depict percentage effect relative to a non-specific oligonucleotide (negative control).
Figure 4B:
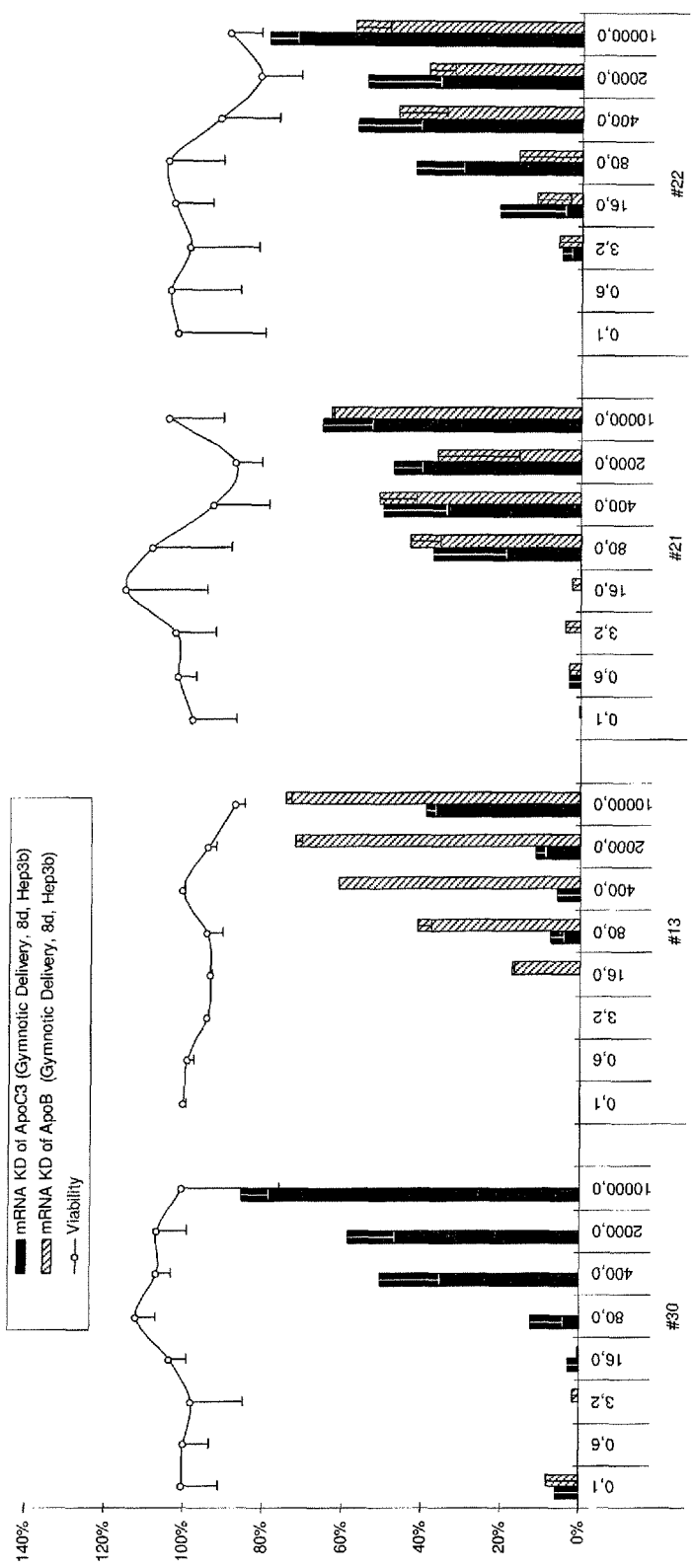

In Vitro Activity Assessment of Knock-Down Activity Of Cleavable ApoB/ApoC3 ASO Heterodimers Using Lipotransfection and Gymnotic delivery (FIGS. 4A and 4B)

Cell culture, knock-down analysis and transfection procedures were performed as described in Example 5. The results are presented in FIGS. 4A and 4B, wherein the monomers for ApoC3 (SEQ ID NO:30) and ApoB (SEQ ID NO:13) show specific knock-down of the target mRNA, the ApoC3/ApoB heterodimers (SEQ ID NOs:21 and 22) show an intrinsic knock-down potential for both targets, independent of the transfection method used (FIG. 4A—lipotransfection; FIG. 4B—gymnotic delivery).

Example 9

In Vitro Activity Assessment by Gymnotic Delivery for Knock-Down Activity of Cleavable ApoB/ApoC3 Heterodimers with Various Chemical Modifications (FIGS. 4C, 4D, 4E, 4F, 4G, 4H, 4I, and 4J)

Figure 4C:
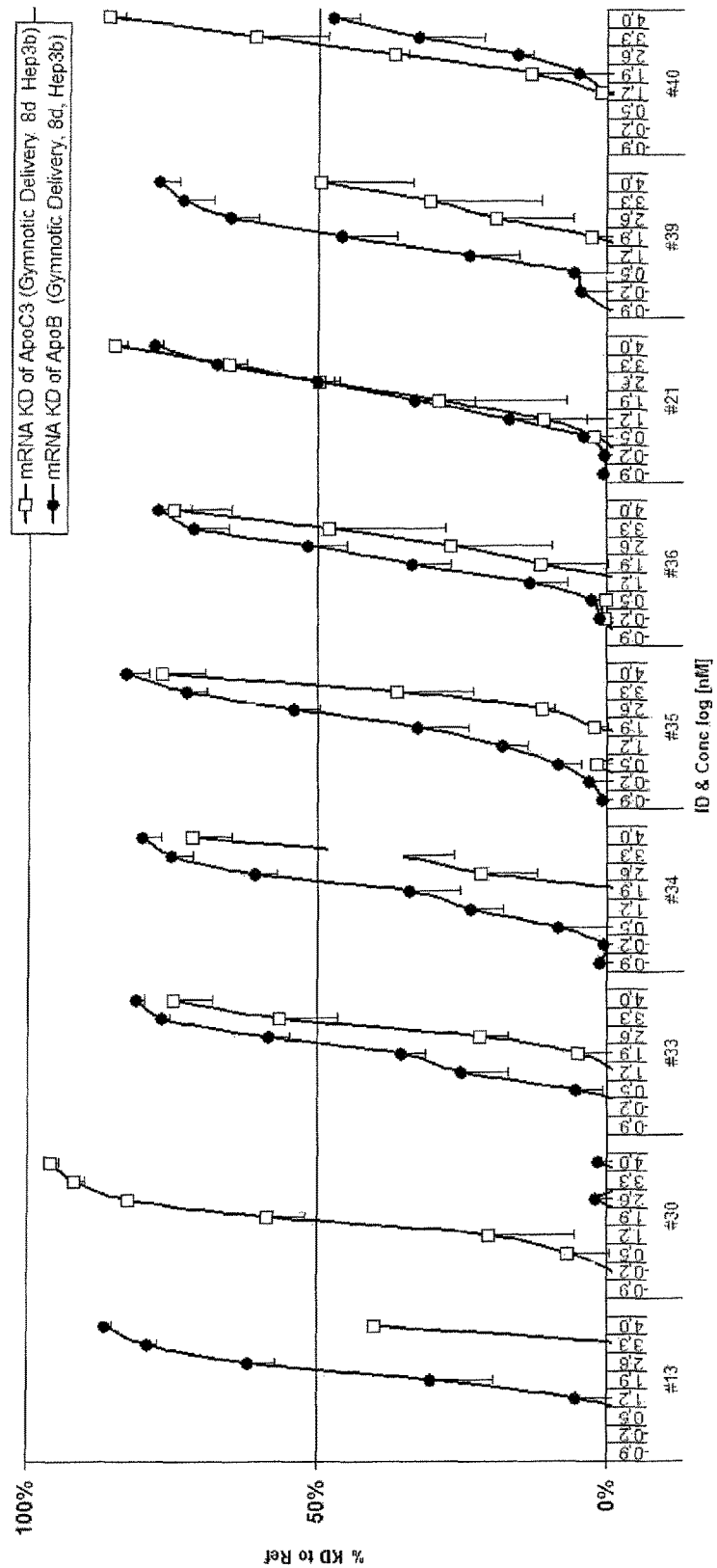
Figure 4D:
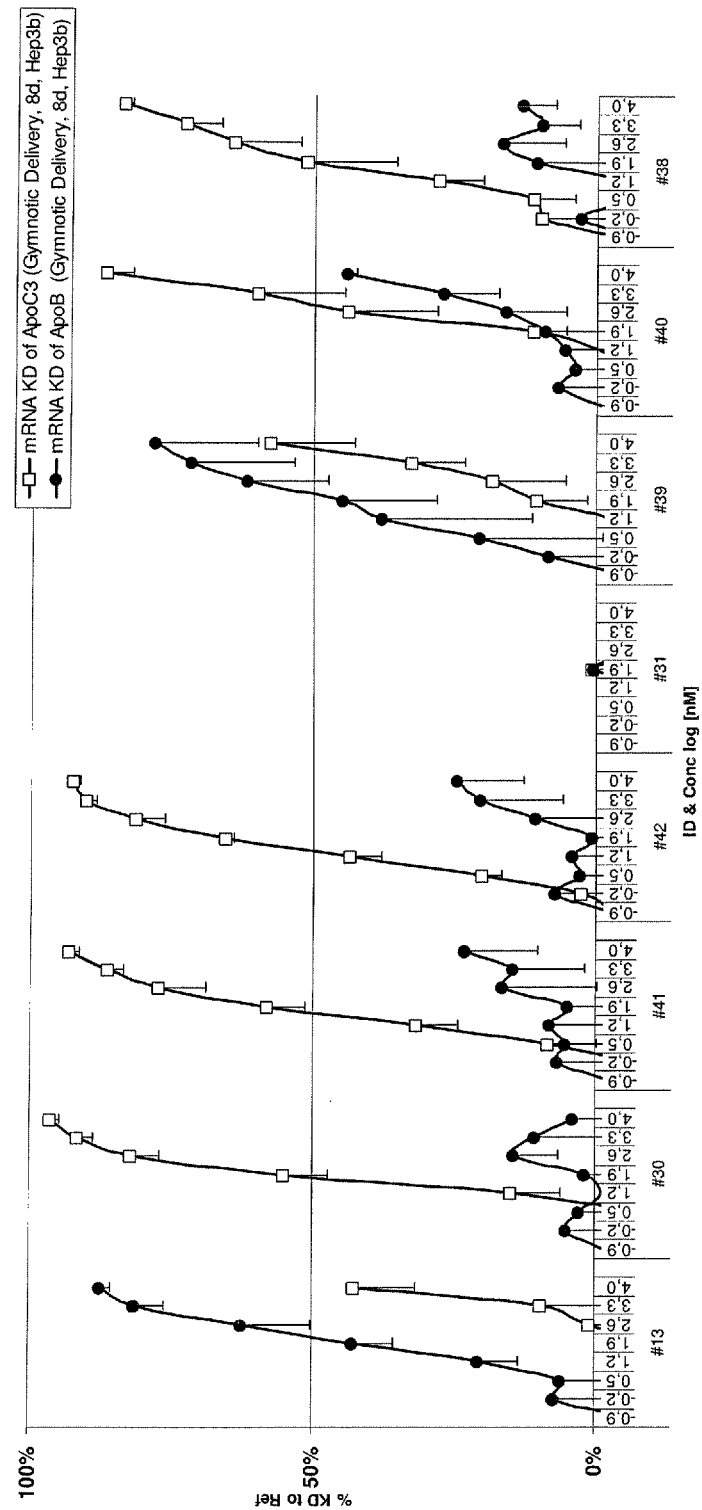
Figure 4E:
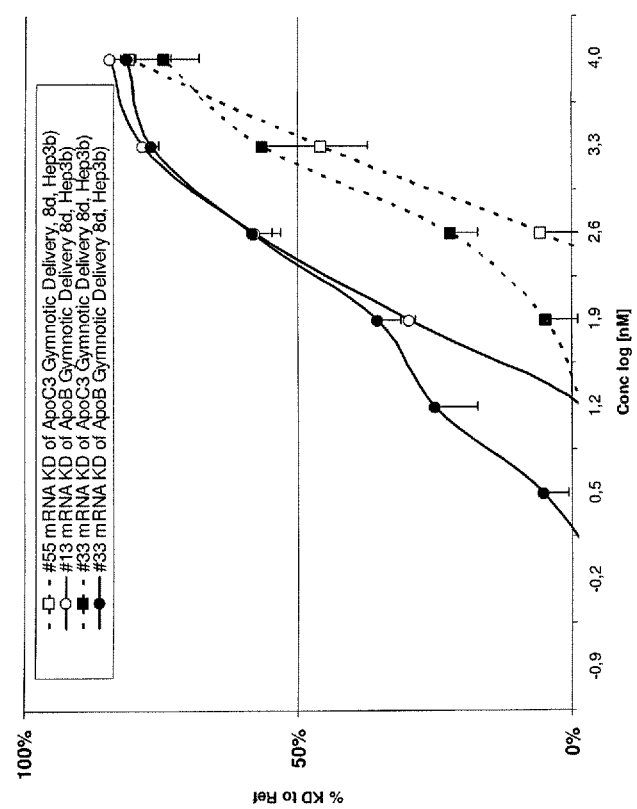
Figure 4F:
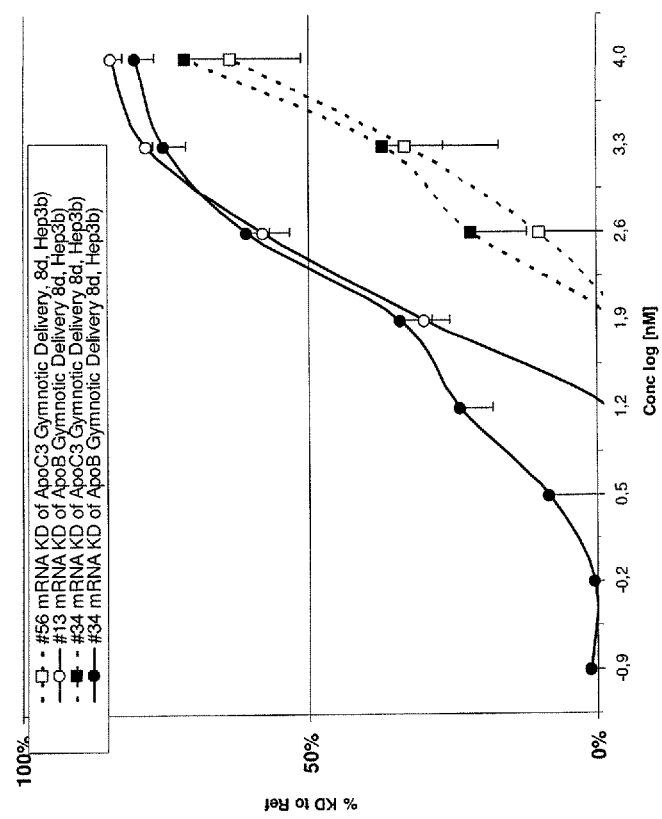
Figure 4G:
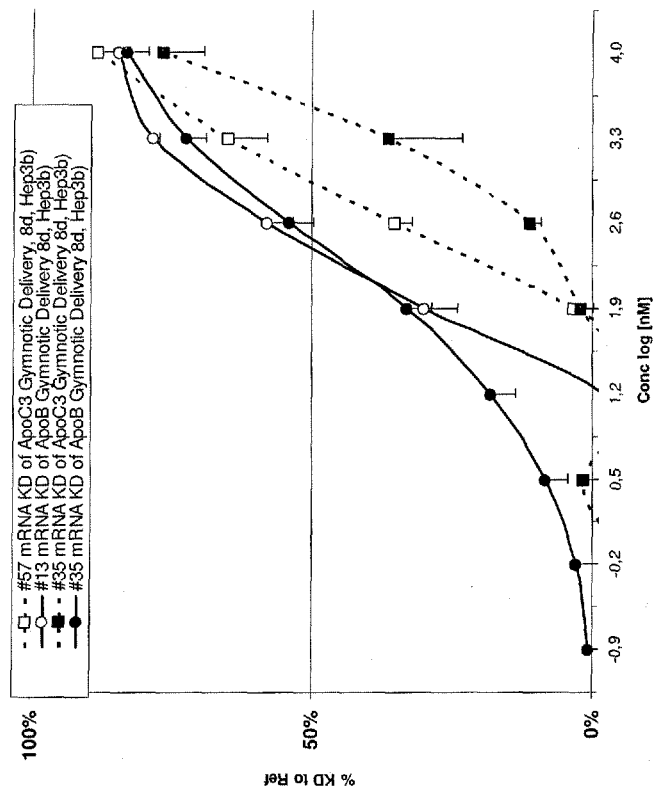
Figure 4H:
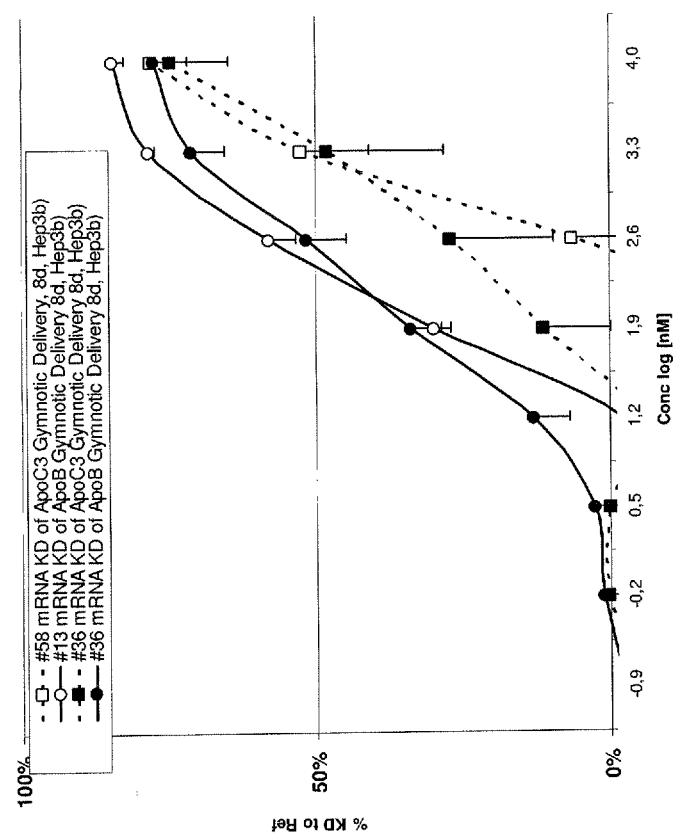
Figure 4I:
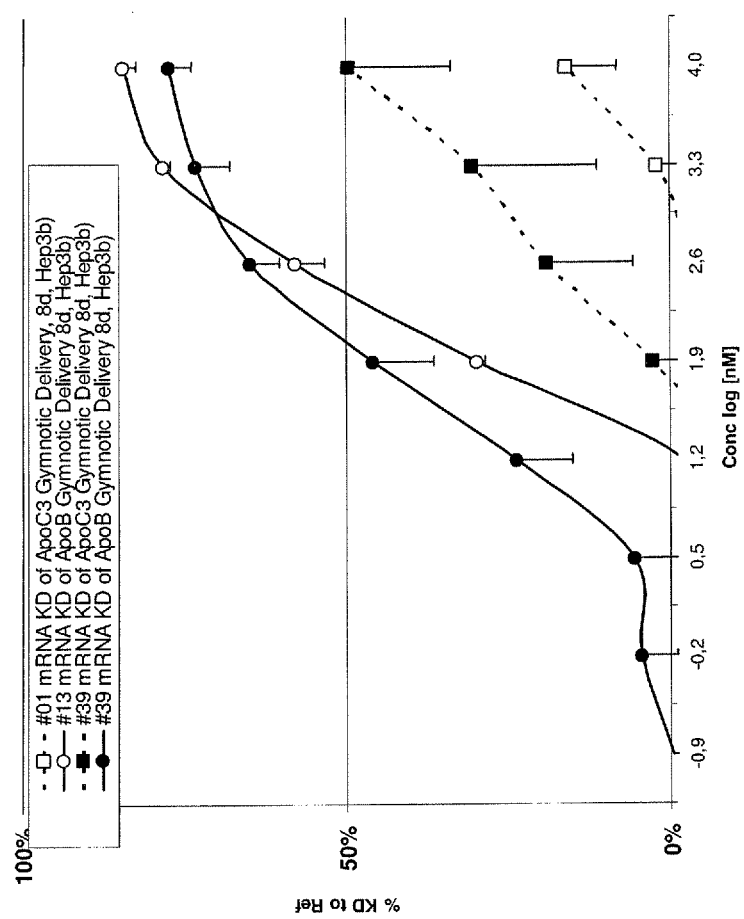
Figure 4J:
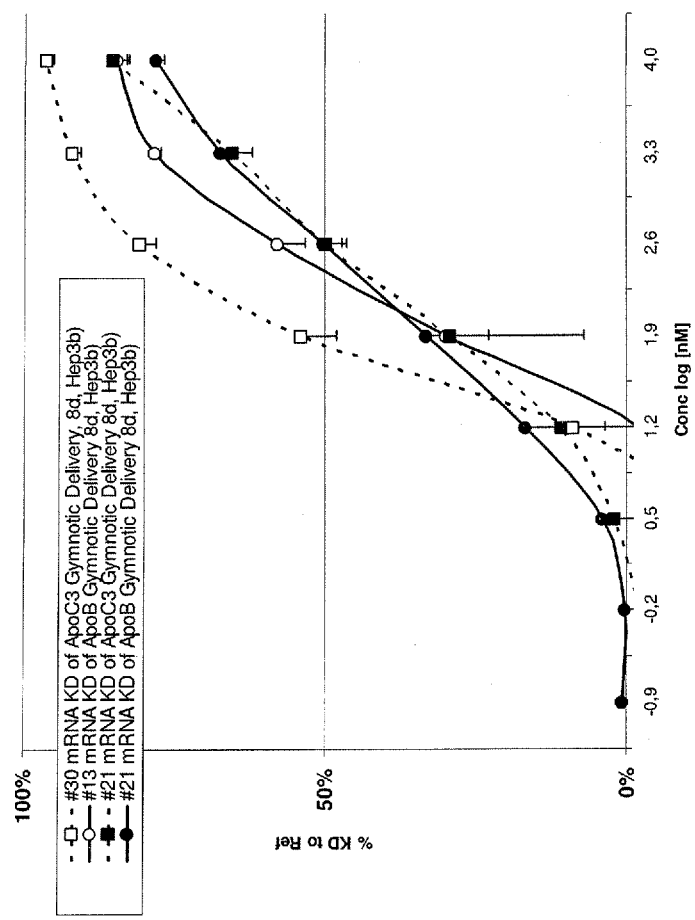

Cell culture, knock-down analysis and transfection procedures were performed as described in Example 5. The results are presented in FIGS. 4C and 4D. In FIG. 4C, all ApoC3/ApoB heterodimers with different modifications (e.g., 2'-OMe, 2'F, 5-Prop.) showed a comparable knock-down activity toward both targets. FIG. 4D shows that also 5-propynyl modifications (SEQ ID NOs:41 and 42) and different amounts of LNA motifs (SEQ ID NO:40) do not change the overall knock-down activity. However, using a G-clamp modification for the ApoB ASO sequence (SEQ ID NO:38) decreases the knock-down potential for ApoB mRNA. FIGS. 4F-J depict the individual heterodimers versus the monomers used for the design. In FIG. 4E, the heterodimer (SEQ ID NO:33) assembled from SEQ ID NO:13 and SEQ ID NO:55 increases in knock-down activity toward both targets. In FIG. 4F, the heterodimer (SEQ ID NO:34) assembled from SEQ ID NO:13 and SEQ ID NO:56 increased in potency in lower concentration only for the ApoB target. In FIG. 4G, the heterodimer (SEQ ID NO:35) assembled from SEQ ID NO:13 and SEQ ID NO:57 increased in potency in lower concentrations for ApoB, while losing activity for ApoC3. In FIG. 4H, the heterodimer (SEQ ID NO:36) assembled from SEQ ID NO:13 and SEQ ID NO:58 increased in knock-down potency in lower concentrations for ApoB, while losing activity for ApoC3. In FIG. 4I, the heterodimer (SEQ ID NO:39) assembled from SEQ ID NO:13 and SEQ ID NO:1 increased in potency in lower concentrations for ApoB, while showing a strong increase in knock-down activity for ApoC3. In FIG. 4J, the heterodimer SEQ ID NO:21 assembled from SEQ ID NO:13 and SEQ ID NO:30 showed no modification of knock-down for ApoB, while ApoC3 knock-down activity decreased.

Example 10

Figure 4K:
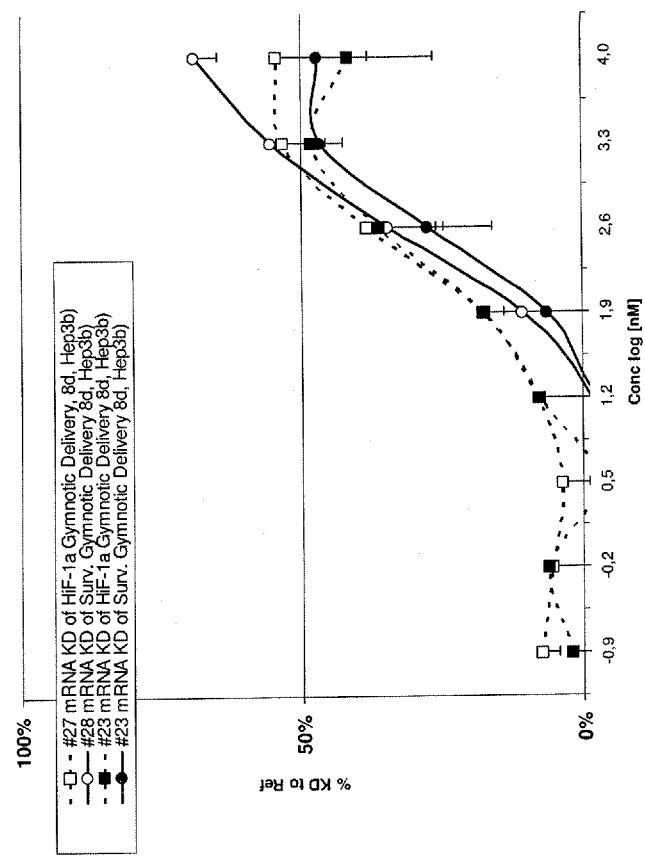

Direct Comparison of Knock-Down Activity of a Cleavable Hif-1Alpha/Survivin Heterodimer Versus its Parent Monomers Using Gymnotic Delivery (FIG. 4K)

Cell culture, knock-down analysis and transfection procedures were performed as described in Example 5. The diagram in FIG. 4K depicts that the assembled HiF-1a/Survivin heterodimer (SEQ ID NO:23) inherits the individual knock-down potentials of both parent sequences (SEQ ID NOs:27 and 28).

Example 11

Figure 4L:
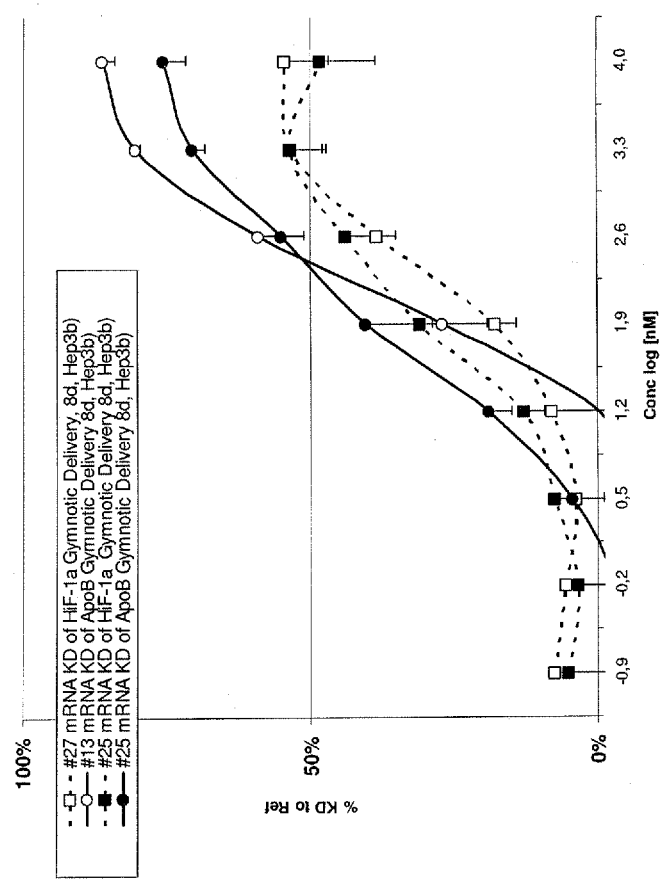

Direct Comparison of Knock-Down Activity of a Cleavable HIF-1alpha/ApoB Heterodimer Versus its Parent Monomers Using Gymnotic Delivery (FIG. 4L)

Cell culture, knock-down analysis and transfection procedures were performed as described in Example 5. The diagram in FIG. 4L depicts that the assembled HIF-1alpha/ApoB heterodimer (SEQ ID NO:25) inherits the individual knock-down potentials of both parent sequences (SEQ ID NOs:13 and 27).

Example 12

Figure 4M:
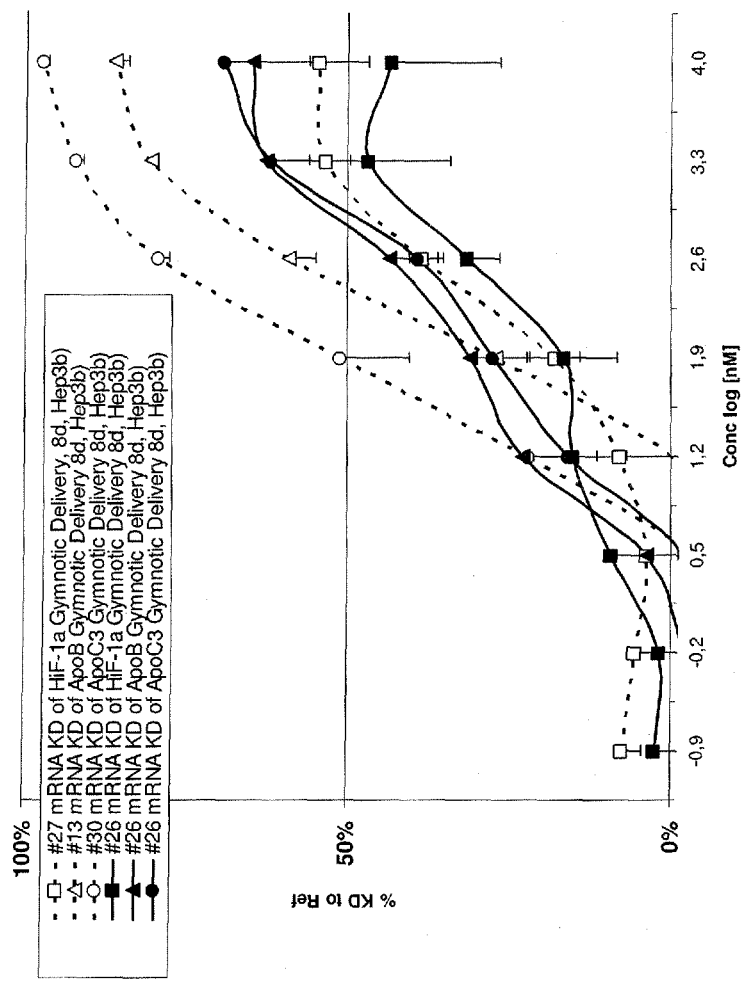

Direct Comparison Knock-Down Activity of a Cleavable HIF-1alpha/ApoB/ApoC3 Heterotrimers Versus its Parent Monomers by Using Gymnotic Delivery (FIG. 4M)

Cell culture, knock-down analysis and transfection procedures were performed as described in Example 5. The diagram in FIG. 4M depicts that the assembled HIF-1alpha/ApoB/ApoC3 heterotrimer (SEQ ID NO:26) inherits the individual knock-down potentials of all parent sequences (SEQ ID NO:13, SEQ ID NO:27, SEQ ID NO:30). A decrease in activity was observed for ApoC3 and ApoB.

Example 13

Comparison of Dimer and Monomer Activity In Vivo

Acute in vivo activity assessments were performed in male and female human ApoC3 transgenic mice (Jackson Labs Stock 905918, B6; CBA Tg (APOC3) 3707Bres/J), which are on a C57BL/6 background and express the human apoC3 gene including the human promoter. Male (22-30 g) and female mice (20-25 g) employed in this study were 10 weeks old and fed regular chow diet.

ApoC3 ASO homodimers (SEQ ID NOs:4, 5, 2, or 3) or ApoC3 ASO monomer SEQ ID NO:1 were formulated in sterile PBS pH7.0 (Gibco) for each dose immediately before subcutaneous (sc) injection. Animals were administered equal volumes (100 µl) of the homodimers or monomer via sc route between the shoulder blades. A control group was treated using equal volumes of PBS in parallel. Each treatment group consisted of 3 male and 4 female transgenic mice.

Mouse blood was collected at Day 0 and Day 7 via submandibular puncture (50-75 µl), as well as at study termination (Day 14) by cardiac puncture, post-euthanasia. Blood was collected in serum separator tubes at room temperature and allowed to clot for 30 minutes. Tubes were spun at 1000 rpm for 5 min at room temperature and serum above separator layer was collected and immediately aliquoted and frozen at −80° C. for future analysis. ApoC3 protein was determined using an ELISA (Wang et al., J. Lipid Res., 2011, 52(6):1265-71).

Effects on ApoC3 expression in the liver were also assessed at study termination (Day 14) and baseline ApoC3 mRNA levels were determined from a group of mice euthanized on Day 0 of the study. Liver lobes were excised immediately after euthanasia and snap frozen in liquid nitrogen. RNA was subsequently isolated and ApoC3 mRNA expression was determined using the Affymetrix bDNA kit (QuantiGene, Affymetrix). The ApoC3 mRNA expression was normalized to mouse GAPDH, a housekeeper gene, and reported as percent ApoC3 knockdown (KD) when compared to a PBS-treated control group.

Figure 5A:
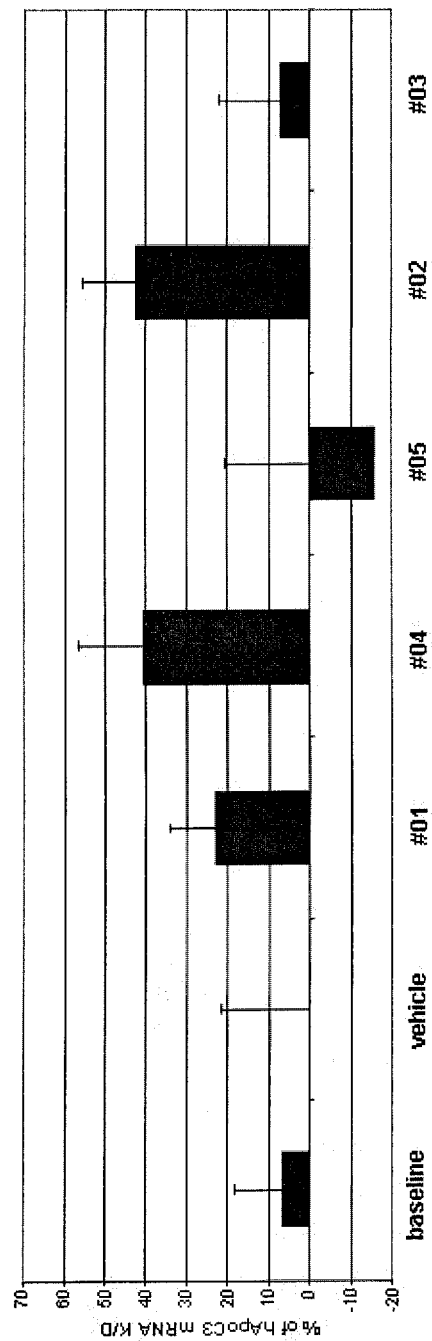
FIGS. 5A-5C demonstrate that under the conditions tested, the time course of knock-down depended on the type of linker used to connect the two antisense moieties in the dimeric ASOs. Human ApoC3 transgenic mice were administered a single subcutaneous dose of homodimers SEQ ID NO:5 or 3 (which are disulphide-linked homodimers of the same monomer) at 10 mg/kg, or vehicle.
Figure 5C:
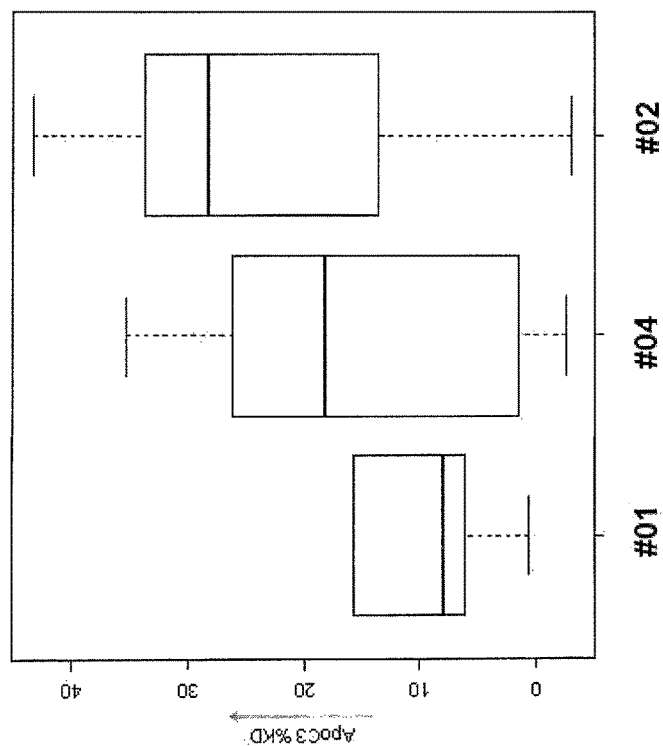
Figure 5B:
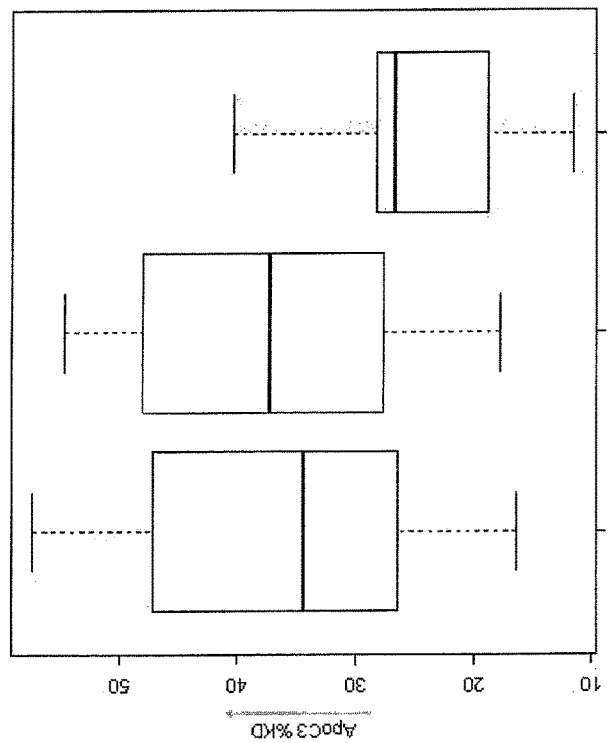

The results of the in vivo studies are shown in FIGS. 5A-C, which demonstrate that under the conditions tested, the time course of knock-down depended on the type of linker used to connect the two antisense moieties in the dimeric antisense ODN. FIG. 5A demonstrates an associated increased reduction of liver ApoC3 mRNA levels in human ApoC3 transgenic mice following treatment with the endonuclease-sensitive phosphodiester-linked homodimers (SEQ ID NO:4 and SEQ ID NO:2). Human ApoC3 transgenic mice were administered a single subcutaneous dose of homodimers SEQ ID NO:5 or 3, which are disulphide-linked homodimers of the same monomer (each at 10 mg/kg), or vehicle. SEQ ID NO:4 and 2 exhibited an increased reduction of liver ApoC3 mRNA levels compared to the monomer (SEQ ID NO:1) after 14 days. FIGS. 5B and 5C show ApoC3 protein knock-down 7 days (FIG. 5B) and 14 days (FIG. 5C) after a single 10 mg/kg dose of the monomer and dimeric LNA gapmers (SEQ ID NO:4 and 3) in human ApoC3 transgenic mice. The 3'3'-phosphodiester-linked dimer with a total of eight phosphodiester linkages (SEQ ID NO:4) shows the fastest onset of knockdown after a single 10 mg/kg dose. This demonstrates that the pharmacokinetic/pharmacodynamic properties can be modulated by selecting a desirable linker.

Example 14

Biodistribution of Dimers

In a separate in vivo experiment, the bio-distribution of three dimers SEQ ID NOs:4, 2 and 3 was investigated in mice. The cleavage products were analyzed by capillary gel electrophoresis (CGE) which was performed on a PACE/MDQ system (Beckman Coulter) equipped with the Karat 7.0 software (Beckman Coulter). Further parts were: eCAP DNA capillary, neutral, 21 cm, 100 µm I.D. (Beckman #477477); ssDNA 100 R gel (Beckman #477621); buffer: Tris/boric acid/EDTA buffer containing 7 M urea (Beckman #338481). The cleavage products were further characterized using LC-ESI-TOF experiments which were performed on a Bruker Esquire 6000 and an Agilent 1200 HPLC system, together with Waters ACQUITY UPLC OST C18 1.7 µm (part #186003949) column. Tissue homogenization was done with a Multi-Tube Vortexer (VWR) and Lysing Matrix D (MP Biomedicals). Plate shaking was done using a VarioMag monoshaker. Deep-well plates were from VWR (2.2 ml, cat. No. 732-0585) and were sealed with Clear seal diamond foil (Thermo, cat. No. 732-4890) prior to tissue homogenization and were resealed for phenol/chloroform-extraction using Re-Seal (3M Empore 98-0604-0472-4 adhesive). Acetonitrile was purchased from Merck.

Phenol/chloroform/isoamyl alcohol (25:24:1, P2069-100ML) and dithiothreitol (DTT, cat. No. 43816) were from Sigma, Proteinase K was from Qiagen (cat. No. 19133), Slide-A-lyzer (200 µl, 10 kDa cut-off) were purchased from Fisher Scientific. High-grade 18 MOhm$^{-1}$ water (Millipore Milli-Q system) was used for reagent and sample preparations. A TomTec Quadra3 system was used for all liquid handling steps.

Plasma and Liver Homogenate Stability Experiments

Stock solutions with a final concentration of 600 µM and a final volume of 100 µL have been prepared of all oligonucleotides.

Twelve pieces of approximately 50 mg of liver from CD1 mouse (female, Charles River) were added to individual Lysing matrix tubes. A calculated volume of 1×PBS to give a final concentration of 5% liver (W/W) was added to each of the twelve tubes. All samples were homogenized using a Biorad Fast prep System. The resulting homogenate solutions were combined to give about 12 ml of 5% liver homogenate in 1×PBS which was subsequently used for incubation.

Plasma was Na-Citrate plasma from female NMRI mouse (Charles River) K-EDTA plasma from male Cynomolgous monkey (Seralab International).

Four samples of each oligo were prepared representing each individual incubation time point (0, 7, 24 and 48 h) in mouse and monkey plasma and in mouse liver homogenate, respectively. In addition, a blank sample and a recovery sample were prepared of each oligo and incubation matrix. Generally, plasma samples were prepared by adding 5 µl of the 600 µM oligo stock solution to 95 µl of mouse or monkey plasma, respectively, with a final oligo concentration of 30 µM. Recovery samples were prepared by adding 5 µl of water to 95 µl of plasma. Blank samples are oligo in water with a final concentration of 100 µM. Liver samples and recoveries were prepared equally; apart from the fact that liver homogenate in PBS was used instead of plasma.

Analysis of the Study Samples

Samples were analyzed in 96-well plate format. A standard curve with 8 standards (5, 10, 15, 20, 50, 75, 90, 100 µg/ml; 25 µg/ml IS), a standard 0 (0 µg/ml; 25 µg/ml IS) and three recovery samples (20, 50, 100 µg/ml; 25 µg/ml IS) has been prepared for each oligo. Samples and standards of one particular oligo were analyzed together on the same plate.

Standards were prepared as follows. A piece of approximately 50 mg of tissue was cut from the respective organ tissue, weighted and placed into the respective well of a 2.2 ml 96-deepwell plate (VWR 732-0585). Two steel balls (5 mm diameter, KGM Kugelfabrik GmbH, part #1.3541) were placed into each well and 500 µl homogenization buffer (vide infra), 20 µl DTT (1 M, Sigma 43816), 50 µl of proteinase K solution (Qiagen, 19133) was added. Furthermore, 10 µl working solution analyte and 10 µl working solution internal standard was added into each well of the standards to give the corresponding final concentrations of (5, 10, 15, 20, 50, 75, 90, 100 µg/ml; 25 µg/ml IS). Standard 0 and recoveries were spiked with 10 µl working solution internal standards only; recoveries were spiked with 10 µl working solution analyte after the entire extraction process and prior to analysis.

A piece of approximately 50 mg of tissue was cut from the respective organ tissue, weighted and placed into the respective well of a 96-deepwell plate. Two steel balls were placed into each well and 500 μl homogenization buffer 20 μl DTT (1 M), 50 μl of proteinase K solution was added. The plate was sealed with STAR lab foils (StarLab E 2796 3070) and samples are homogenized using a Qiagen Tissue Lyzer for 3×30 s at 17 Hz. Subsequently the plate was incubated in a water bath for 2 h at 55° C. followed by transfer of the samples to a new 96-deepwell plate using an automated liquid-handling system (TomTec Quadra 3). After the addition of 200 μl ammonium hydroxide (25%) and 500 μl Phenol/Chloroform/Isoamyl alcohol (25:24:1) the plate was vortexed using a Multitubevortex for 5 min. Subsequently, the plate was incubated for 10 min at 4° C. and centrifuged at 4° C. for another 10 min at 3500 RCF. The plate was then handled to the TomTec System which was used to remove the aqueous layer. The remaining organic layer was washed by adding 500 μl water. The aqueous phase was again removed using the TomTec system. The aqueous phases were combined, 50 μl HCl (1 N), 500 μl SAX Load High buffer (vide infra) and 300 μl acetonitrile was added and the resulting solution was mixed thoroughly by up and down pipetting using the TomTec system. ('The program "SPE extraction of tissue samples 100416" was used for the subsequent solid-phase extraction procedure).

Briefly: VARIAN Bond Elute 96 square-well SAX 100 mg (Cat. No. A396081C) were equilibrated with acetonitrile, water and SAX load buffer (see below), samples were load and washed with SAX load buffer. The samples were eluted with SAX elute buffer (vide infra) and subsequently diluted with SAX/RP dilution buffer (vide infra). WATERS Oasis HLB LP 96-well Plate 60 μm 60 mg (Part No.: 186000679) were equilibrated with acetonitrile, water and SAX dilution buffer (vide infra). The samples were load and the cartridge washed with water. The samples were eluted with RP elute buffer (vide infra).

Freeze the elution plate for 1 h at −80° C. and lyophilize to dryness. The dried samples are reconstituted in 50 μl water and dialyzed for 60 min against water using Thermo Slide-A-Lyzer. The samples were then subjected to CGE analysis on a Beckman Coulter PACE/MDQ system. The conditions were: (i) Capillary: eCAP DNA, neutral, 21 cm, 100 μm I.D. (Beckman #477477); (ii) Capillary temperature: 20° C.; (iii) Sample storage temperature: 10° C., (iv) Gel: ssDNA 100 R (Beckman #477621) (v) Buffer: Tris/boric acid/EDTA buffer containing 7 M Urea (Beckman #338481) (vi) Detection wavelength: 260 nm; (vii) Separation voltage: 30 kV; (viii) Injection time: 60 s; (ix) Injection voltage: 10 kV; (x) Run time: 20 minutes; (xi) Data acquisition rate: 4 pt/sec. Analysis was done using the Karat 7.0 software (Beckman).

All samples and recoveries were incubated at 37° C. A sample of each oligo and type of matrix was cooled to room temperature after 0, 7, 24 and 48 h and was subjected to Phenol/Chloroform purification. To this end, 370 μl of ammonium hydroxide (15%), 10 μl dithiothreitole (DTT, 1 M, Sigma 43816) and 800 μl premixed Phenol/Chloroform/Isoamyl alcohol (Sigma P2069) was added to each sample. The sample was vortexed for 10 min at maximum vortex speed and then incubated at 4° C. for 20 min. Subsequently, the sample was centrifuged at 3500 RFC for 20 min at 4° C. and 400 μl of the aqueous layer were removed and dried in a lyophilizer. The dried samples were dissolved in water (100 μl). The recovery samples were dissolved in water (95 μl) and spiked with 5 μl of the respective oligo stock solution (600 μM). Samples were analyzed by LC-MS (Agilent 1200, Bruker Esquire 3000) using a Waters Acquity UPLC OST C18 column (1.7 μm, 2.1×50) with HFIP/TEA/water (385 min 1,1,1,3,3,3-hexafluoroisopropanol, 14.4 min triethylamine in water) as buffer A and methanol as buffer B and a flow rate of 0.3 ml/min at a column temperature of 60° C. The following gradient was used: 3 min at 5% B, 5-15% B in 2.5 min (10%/min), 15-23% B in 5.5 min, 23-30% B in 3 min, 30-100% B in 0.5 min, 5 min at 100% B, 100-5% B in 0.5 min, 5 min at 5% B.

Surprisingly, the levels of dimers in the liver (organ target for ApoB and ApoC3) and kidney were dramatically increased after a single i.v. bolus injection. It was found that about 10 to 16% monomeric metabolite of the total dose in liver 24 hours after injection of the dimers (Table 5), while previously it was known that only 2 to 5% of the total dose of the monomeric 14-mer (SEQ ID NO:1)) in mice or monkeys (Table 6) was detected in a separate study. Accordingly, dimers exhibited significantly higher biodistribution to liver and kidney as compared to the monomers. Table 5 shows organ-distribution of antisense dimers SEQ ID NO:2, 3 and 4 as percent of total administered dose 24 hrs after a single i.v. bolus injection into mice. (Peak 1 refers to the degradation product, whereas Peak 2 is remaining dimer starting material. The sum of both components represents the percentage of total dose in the corresponding organ.) Organ-distribution of monomeric SEQ ID NO:1 as percent of total administered in mice and monkeys in previous studies as compared to the dimers (last row) is shown Table 6. Percent total dose calculation based on: 5 kg monkey, 135 g liver, 30 g kidney (Davies et al., Pharm. Res., 1993, 10 (7):1093).

TABLE 5

| Linker | Oligo | Animal | Peak 1 | Peak 2 | % totaldose* |
|---|---|---|---|---|---|
| Liver | | | | | |
| Diester | SEQ ID NO: 2 | 1-3 | 8.1 μg/g | 9.1 μg/g | 14% |
| SS | SEQ ID NO: 3 | 4 & 6 | 20.8 μg/g | — | 16% |
| Diester doubler | SEQ ID NO: 4 | 7-9 | 12.2 μg/g | — | 10% |
| Kidney | | | | | |
| Diester | SEQ ID NO: 2 | 1-3 | 16.7 μg/g | 58.1 μg/g | 15% |
| SS | SEQ ID NO: 3 | 4-6 | 29.9 μg/g | 47.4 μg/g | 15% |
| Diester doubler | SEQ ID NO: 4 | 7 & 9 | 54.9 μg/g | 6.4 μg/g | 12% |

*based on 25 g mouse, 2 g liver, 0.5 g kidney

TABLE 6

| Study | Liver | Kidney |
|---|---|---|
| SEQ ID NO: 1 Monkey tox 2, 10, 60 mpk Necrop @ day 25 4 doses @ day 1, 8, 15, 22 | 2.5-5% 13 μg/g (2 mpk) 50 μg/g/10 mpk) 300 μg/g (60 mpk) | 1.2-3% 60 μg/g (2 mpk) 300 μg/g (10 mpk) 800 μg/g (60 mpk) |
| SEQ ID NO: 1 Mouse tox Twice/week 25 mpk Necrop @ day 15 (100 mpk) | 0.3% total dose 3.7 μg/g | 0.4% total dose 21 μg/g |
| SEQ ID NO: 1 Monkey PK Single bolus iv 3, 30 mpk Necrop @ 24 h | 4.1% (30 mpk) 3.6% (3 mpk) 45 μg/g (30 mpk) 4 μg/g (3 mpk) | 6% (30 mpk) 16% (3 mpk) 300 μg/g (30 mpk) 80 μg/g (3 mpk) |

TABLE 6-continued

| Study | Liver | Kidney |
|---|---|---|
| SEQ ID NO: 2, 3 or 4 (dimers) Mouse Single bolus iv 10 mpk Necrop @t 48 h | 10-16% 16 µg/g (10 mpk)* *mean over 3 | 12-15% 70 µg/g (10 mpk)* *mean over 3 |

Figure 6C:
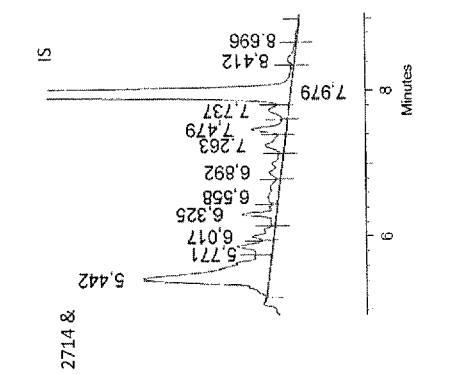
FIGS. 6A-6C show illustrative LC-MS results for samples extracted from liver for the following ASOs respectively SEQ ID NO:2 (FIG. 6A), SEQ ID NO:3 (FIG. 6B), and SEQ ID NO:4 (FIG. 6C). "IS" designates an internal standard.
Figure 6B:
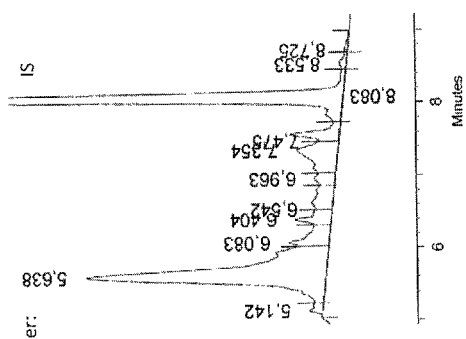
Figure 6A:
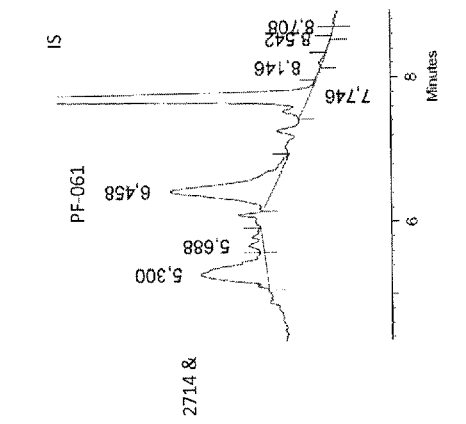

The high levels of the monomeric equivalent (peak 1) were very surprising, since most of the injected dimer was already processed to a monomeric form (left peak 1 with shortest retention time, as shown in FIG. 6). In the case of dimer of SEQ ID NO:2, the intact dimer was detected at 6.458 min), as well as the monomer and the monomer with an additional dT (SEQ ID NO:1 plus dT) from the incomplete cleavage of the linker. The internal standard (IS) is poly-(dT)$_{30}$ phosphorothioate. The dimers SEQ ID NOs:4 and 2 were already completely converted to the monomeric forms comprising the monomer (SEQ ID NO:1) and the monomer plus dT. In case of dimer SEQ ID NO:3 with a disulfide linker, the monomeric cleavage product was slightly larger than monomer resulting from reductive disulfide cleavage and is indicated as "#1 plus X" in the figure, where X is a yet unidentified organic radical with the molecular weight of less 100 Da. It could be hypothesized that that "#1 plus X" results from oxidative cleavage rather than reductive cleavage of the disulfide bond. If the dimers had been already cleaved in the serum, the bio-distribution to liver and kidneys should not have increased so dramatically as compared to monomers. Thus, the stability of the dimers in plasma and in liver homogenates was investigated. It was demonstrated in Example 3 that plasma stability of the dimers is relatively high over 48 hours, while the dimers are rapidly cleaved in liver homogenates. Further cleavage product analysis of samples extracted from the liver homogenate treatment showed that the dimer is completely converted to the monomeric form. This observation is compatible with a bio-distribution mechanism, in which dimers are relatively stable after injection into animal. The dimers distributed more efficiently to the organs like liver and kidney as opposed to the corresponding monomer. In the organs (e.g., liver and kidney), the dimer is cleaved to the monomer and can act as a normal antisense oligonucleotide. Since the dimers are stable in serum (plasma), the linkers can be designed to undergo an organ-specific cleavage by using appropriate linker chemistry.

Example 15

In Vivo Activity Assessment of a Cleavable ApoC3/ApoB ASO Heterodimer

In vivo activity of a heterodimer of a human ApoC3 ASO linked to an ApoB ASO with a cleavable linker was assessed in male and female human ApoC3 transgenic mice which were 14-18 weeks old at termination.

The ApoC3/ApoB ASO heterodimer (SEQ ID NO: 21) or a non-targeting ASO (SEQ ID NO: 119) were formulated in sterile saline (pH7.0) immediately before intravenous (iv) injection via the tail vein. Animals were administered heterodimer (0.3, 1, 3, or 10 mg/kg) or negative control ASO (10 mg/kg) or saline (0 mg/kg) as a vehicle control in a volume of 5 ml/kg.

Groups of mice consisted of 2 male and 2 female transgenic mice which were terminated on days 1, 3, 7, 14 and 29 after treatment administration. After euthanasia by $CO_2$ inhalation, blood was obtained by cardiac puncture (0.5-1 ml). Livers were dissected, weighed, and a fragment saved in a labeled histology cassette snap frozen by immersion in liquid nitrogen. Liver samples were maintained at −80° C. for subsequent analyses.

Each blood sample was divided in half. Serum was prepared in serum separator tubes which were allowed to clot for 4 hours on ice. Plasma was prepared in EDTA-containing tubes which were maintained on ice until processed. Tubes were spun at 10,000 rpm for 5 min at 4° C. and supernatants collected and frozen at −80° C. for future analyses.

Quantification of Target mRNAs

Total liver RNA was isolated in TRIzol reagent (Ambion) from snap frozen tissue homogenized in Fastprep24 Lysing Matirx D tubes (MP Biomedicals). Trizol-chloroform extraction was followed by further purification using a column-based method (Qiagen, RNeasy) as per manufacturer's instruction. Purification included treatment with DNase I for 15 minutes at room temperature (Qiagen, Rnase-Free Dnase). RNA quantity and purity were evaluated spectophotometrically by readings at 260 nm and 280 nm (Nanodrop). Liver fragments were lysed with RLT buffer and QIAshredder columns (Qiagen), and then purified by RNeasy columns as indicated above.

Samples were amplified as per manufacturer's instructions (Qiagen, Quantitect Probe RT-PCR kit). Quantitative real-time PCR (qRT-PCR) was performed in a 7900HT Fast Real-Time PCR System (Applied Biosystems). All samples were analyzed in triplicate in Microamp Optical 384well reaction plates (Applied Biosystems) and normalized with Gapdh signal as the internal control. Primers were Apolipoprotein C-III (Applied Biosystems, Mm00445670_m1 and Hs00163644_m1), Apolipoprotein B (Applied Biosystems, Mm01545156_m1 and Hs01071209_m1), and Mouse GAPDH (Applied Biosystems, 4352932E). Results are expressed as fold induction relative to vehicle-treated samples.

Data for each of the target mRNAs were analyzed by two-way ANOVA using "time" and "treatment" as the variables in GraphPad Prism software. Bonferroni post-hoc tests were conducted when significant main effects ($p<0.05$) were observed.

Figures 7A, 7B:
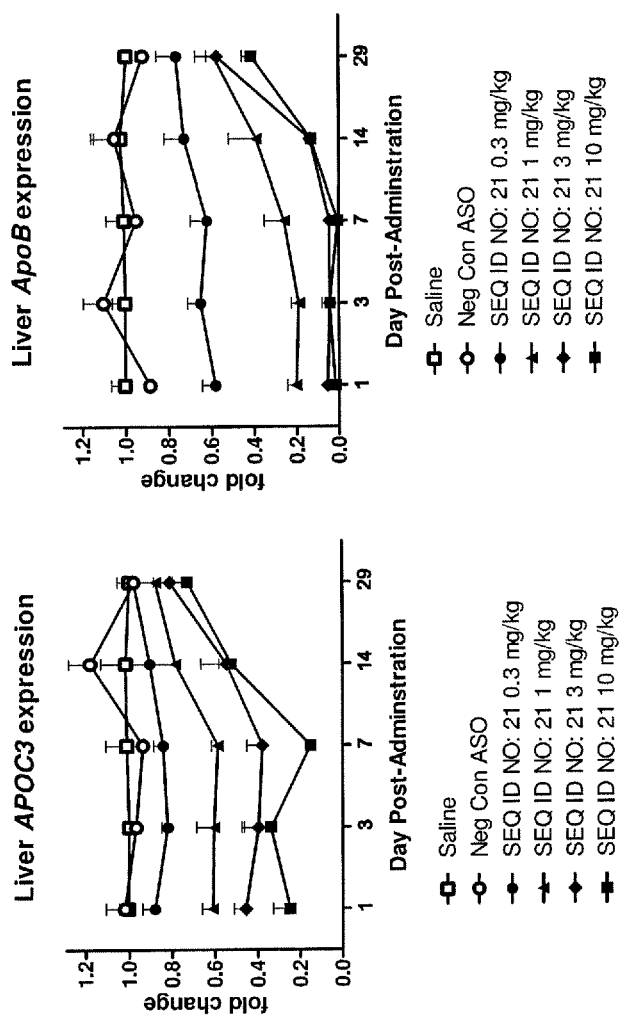
FIGS. 7A and 7B illustrate that SEQ ID NO: 21, an ApoC3/ApoB heterodimer ASO with an endonuclease sensitive phosphodiester linker, significantly down-regulated liver expression of both target mRNAs [i.e., human APOC3 (FIG. 7A) and mouse ApoB (FIG. 7B)].

The results of this in vivo experiment are shown in FIGS. 7A and 7B. The data demonstrate that SEQ ID NO: 21, an ApoC3/ApoB heterodimer ASO with an endonuclease sensitive phosphodiester linker, significantly down-regulated liver expression of both target mRNAs [i.e., human APOC3 (FIG. 7A) and mouse ApoB (FIG. 7B)]. Target mRNA knockdown was dependent on both administered dose and time. That is, in animals which received more ASO construct, a greater target knockdown was observed. The greatest degree of knockdown for any dose level was observed during the first week post-administration, with significant effects persisting until 29 days post-administration, the longest time point at which samples were obtained.

Example 16

In Vivo Comparison of Heterodimer ASOs and Monomers: Effects on Target mRNAs

In vivo activity of three heterodimers of a human ApoC3 ASO linked to an ApoB ASO, the ApoC3 ASO monomer, the ApoB ASO monomer and the physical combination of the two monomers was assessed in male human ApoC3 transgenic mice which were 9-18 weeks old at termination.

An ApoC3/ApoB ASO heterodimer linked with four diester bases (cleavable; SEQ ID NO: 21), or an ApoC3/ApoB ASO heterodimer linked with four phosphothioate bases (stable; SEQ ID NO: 59), or an ApoC3/ApoB ASO heterodimer linked with PEG-6 (stable; SEQ ID NO: 60), or the ApoC3 monomer ASO (SEQ ID NO: 30), or the ApoB monomer ASO (SEQ ID NO: 13), or the physical combination of the ApoC3 and ApoB monomers (SEQ ID NO: 30 plus SEQ ID NO: 13), or a non-targeting ASO (SEQ ID NO: 119) were formulated in sterile SALINE (pH7.0) immediately before intravenous (iv) injection via the tail vein. Animals were administered equal molar amounts of heterodimer (0.3 µMol/kg~3 mg/kg), monomer (0.3 µMol/kg~1.3 mg/kg), co-formulated monomers (0.3 µMol/kg each) or negative control ASO (0.3 µMol/kg~1.4 mg/kg) or SALINE (0 mg/kg) as a vehicle control at a volume of 5 ml/kg.

Groups consisted of 6-7 male transgenic mice which were terminated 3 or 14 days after treatment administration. After euthanasia by $CO_2$ inhalation, blood was obtained by cardiac puncture (0.5-1 ml). Livers were dissected, weighed, and a fragment put in a labeled histology cassette snap frozen by immersion in liquid nitrogen. Whole kidneys were also stored in labeled histology cassettes and snap frozen in liquid nitrogen. Liver and kidney samples were maintained at −80° C. for subsequent analyses.

Each blood sample was divided in half. Serum was prepared in serum separator tubes which were allowed to clot for 4 hours on ice. Plasma was prepared in EDTA-containing tubes which were maintained on ice until processed. Tubes were spun at 10,000 rpm for 5 min at 4° C. and supernatants collected and frozen at −80° C. for future analyses.

Data for each of the target mRNAs on either Day 3 or Day 14 were analyzed by one-way ANOVA followed by Dunnett's post-hoc test to determine differences between treatments using GraphPad Prism software.

Figures 8A, 8B:
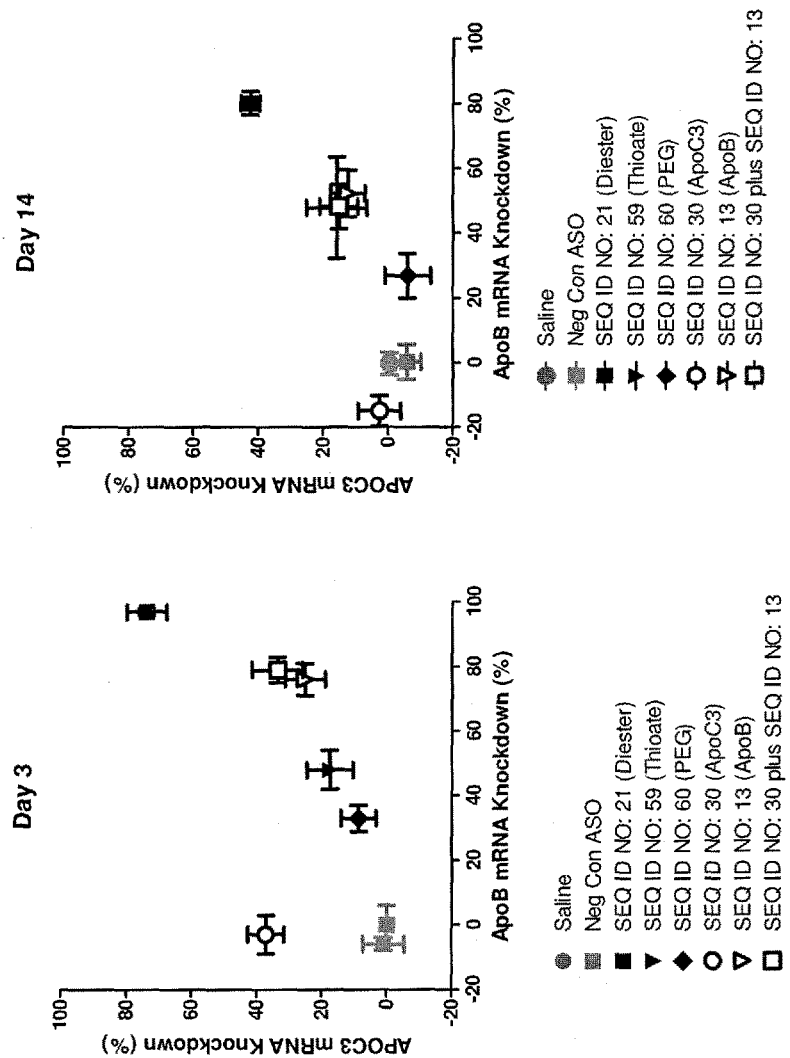
FIGS. 8A and 8B illustrate the effects of these treatments on in vivo target mRNAs in the liver. Data in these figures are plotted as % knockdown of the target mRNAs with knockdown of mouse apoB mRNA plotted on the x axis and knockdown of human ApoC3 (i.e., the transgene) plotted on the y axis.

The effects of these treatments on in vivo target mRNAs in the liver are shown in FIGS. 8A and 8B. Data in these figures are plotted as % knockdown of the target mRNAs with knockdown of mouse apoB mRNA plotted on the x axis and knockdown of human ApoC3 (i.e., the transgene) plotted on the y axis. The data demonstrate that SEQ ID NO: 21, an ApoC3/ApoB heterodimer ASO with an endonuclease sensitive phosphodiester linker, was superior to all other treatments on both day 3 (FIG. 8A) and day 14 (FIG. 8B) in the extent to which it down-regulated liver expression of both target mRNAs.

On day 3 (FIG. 8A), ApoB mRNA in the liver was significantly decreased by all treatments, except the ApoC3-targeted ASO monomer (SEQ ID NO: 30) and the negative control ASO (SEQ ID NO: 119). In general, the effectiveness of constructs given on day 0 to suppress target mRNAs was weaker 14 days after treatment administration than observed 3 days post-treatment. Nevertheless, ApoB mRNA in the liver (FIG. 8B) was suppressed by all treatments except the ApoC3-targeted ASO monomer (SEQ ID NO: 30), the ApoC3/ApoB ASO heterodimer linked with PEG-6 (stable; SEQ ID NO: 60, and the negative control ASO (SEQ ID NO: 119). Importantly, treatment with SEQ ID NO: 21, an ApoC3/ApoB heterodimer ASO with an endonuclease sensitive phosphodiester linker resulted in significantly greater knockdown of liver ApoB mRNA than any other treatment at each of the times at which samples were taken (FIGS. 8A and 8B).

Qualitatively similar results were observed for knockdown of human ApoC3 mRNA in these human ApoC3 transgenic mice. On Day 3 (FIG. 8A), the ApoC3 monomer (SEQ ID NO: 30), the physical combination of the ApoC3 and Apo B monomers (SEQ ID NO: 30 plus SEQ ID NO: 13), the ApoB monomer (SEQ ID NO: 13), and the ApoC3/ApoB ASO heterodimer linked with four diester bases (cleavable; SEQ ID NO: 21) significantly decreased expression of human ApoC3 mRNA. On Day 14 (FIG. 8B), only the ApoC3/ApoB ASO heterodimer linked with four diester bases (cleavable; SEQ ID NO: 21) significantly suppressed expression of human ApoC3. Similar to its effectiveness in suppressing ApoB, administration of SEQ ID NO: 21 resulted in significantly greater knockdown of liver human ApoC3 mRNA expression than any other treatment (FIGS. 8A and 8B).

Example 17

Tissue Stability of Heterodimer ASOs

Hybridization assays were developed (see below) to measure the tissue concentrations of the ApoC3/ApoB ASO heterodimer linked with four diester bases (cleavable; SEQ ID NO: 21), the ApoC3/ApoB ASO heterodimer linked with four phosphothioate bases (stable; SEQ ID NO: 59), and the ApoB monomer ASO (SEQ ID NO: 13) in plasma and homogenates of liver and kidney. Samples from the experiment described in Example 16 were measured.

Capture and Detection Probes:

Complementary hybridization probes to the hetero-dimeric ASOs were designed and custom synthesized with LNA-modified phosphodiester backbones (BioSpring GmbH). The capture probes contained an amino linker (C12-amino) and Spacer-18s (hexaethyleneglycole phosphate, PEG-282) at the 5'-end. The detection probes contain Spacer-18s at the 3'-end of the specific probe sequence and were biotin labeled at the 3'-end (Elfer et al., 2005). The specific sequences of capture and detection probes used in the assays are showed in table below.

TABLE 7

Capture and Detection Probes used in Hybridization Assays

| Probe | | SEQ ID NO | Sequences |
|---|---|---|---|
| Dimer Probes | Capture | 120 | 5'-(C12-amino)(Spacer-18)(Spacer-18)-βG-βC-βA-βA-βA-βA-βA-βG-3' |
| | Detection | 122 | 5'-βT-βC-βA-βG-βT-βG-βC-(Spacer-18)(Spacer-18)(dT-biotin)(biotin TEG)-3' |
| apoB Probes | Capture | 124 | 5'-(C12-amino)(Spacer-18)(Spacer-18)-βT-βG-βA-βA-βT-βA-βC-3' |

TABLE 7-continued

Capture and Detection Probes used in Hybridization Assays

| Probe | SEQ ID NO | Sequences |
|---|---|---|
| Detection | | 5'-βC-βA-βA-βT-βG-βC-(Spacer-18)(Spacer-18)(dT-biotin)(biotin TEG)-3' |

Chemistry:
Synthesis of Oligonucleotide,: The procedure below covers the synthesis of two oligonucleotides [SEQ ID NO: 59 (5-βG*βZ*dA*dC*dT*dG*dA*dG*dA*dA*dT*dA*βZ*βT*dT*dT*dT*dT*βG*βZ*dA*dT*dT*dG*dG*dT*dA*dT*βT*βZ*βA-3') and SEQ ID NO: 60 (5'-βG*βZ*dA*dC*dT*dG*dA*dG*dA*dA*dT*dA*βZ*βT-HEG-βG*βZ*dA*dT*dT*dG*dG*dT*dA*dT*βT*βZ*βA-3')]. The synthesis was performed using a standard synthesis protocol on an AKTA oligopilot 10 Plus synthesizer using the conditions summarized in Table 8.

TABLE 8

Oligonucleotide Synthesis Conditions

| Column size/scale | 3.5 ml/63 μmol |
| Solid support; loading | Nittophase Universal Support; 100 μmol/g |
| Amidite concentration | 0.1M |
| Amidite equivalents | 4 |

The oligonucleotide was cleaved from solid support using a solution of ammonium hydroxide and ethanol (3:1) at 55° C. for 17 hours. The crude oligonucleotides were purified in a two-step IEX-purification procedure using a Source 30Q column and buffer system containing sodium hydroxide. The mass spectrometer analysis was done using ESI-MS and the purity was established using HPLC and generic method. The endotoxin levels were measured using LAL-test procedure.
Synthesis of Capture and Detection Probes: This procedure covers the synthesis of both capture and detection probes [SEQ ID NO: 120 (5'-(C12-amino)(Spacer-18)(Spacer-18)-βG-βC-βA-βA-βA-βA-βA-βG3'); SEQ ID NO: 122 (5'-βT-βC-βA-βG-βT-βG-βC-(Spacer-18)(Spacer-18)(dT-biotin)(biotin TEG)-3'); SEQ ID NO: 123 (5'-(C12-amino)(Spacer-18)(Spacer-18)-βT-βG-βA-βA-βT-βA-βC-3') and SEQ ID NO: 121 (5'-βC-βA-βA-βT-βG-βC-(Spacer-18)(Spacer-18)(dT-biotin)(biotin TEG)-3')]. The synthesis was performed using a standard synthesis protocol on an AKTA oligopilot 10 Plus synthesizer using the conditions summarized in Table 9.

TABLE 9

Conditions Used to Synthesize Capture and Detection Probes

| Column size/scale | 1.2 ml/22 μmol or 17 μmol |
| Solid support; loading | Nittophase Universal Support; 100 μmol/g |
| Amidite concentration | 0.1M |
| Amidite equivalents for LNA | 5 |
| Amidite equivalents for Spacer-18 and NH2-C12-amino | 3 |

The oligonucleotide was cleaved from solid support using a solution of ammonium hydroxide and ethanol (3:1) at 55° C. for 17 hours. The crude oligonucleotides were purified in a two-step RP—/IEX—purification procedure. The RP-purification was by applying a TEAA-containing buffer system, the IEX purification was carried out at physiological conditions. The mass spectrometer analysis was done using ESI-MS and the purity was established using HPLC and generic method.

Tissue Sample Preparation:
Liver and kidney homogenate was prepared from animals treated with heterodimeric or monomeric ASOs. Tissue samples collected at specified time points were minced and weighed in ready-to-use Lysing Matrix D tubes containing 1.4 mm ceramic spheres beads (Catalogue#6913-100, MP Biomedicals). DNase/RNAse free water (Catalogue #SH30538.02, Thermo) was added to the tube with ratio of 5 or 10 mL per g of tissue. Each tissue sample was mixed and homogenized using a MP Biomedicals Fast Prep-24 at 4° C. for 20 seconds twice. The tissue homogenate was stored in freezer or kept on ice before analyzed with the hybridization assay.

Preparation of Standards and Controls:
Standards and assay quality controls (QCs) were prepared in K2 EDTA plasma or control tissue matrix and diluted serially in 2-fold steps from 100 ng/mL to 0.098 ng/mL. The QCs were set at 50 ng/mL, 40 ng/mL, 10 ng/mL, 1 ng/mL and 0.4 ng/mL. The standards and QCs were analyzed by the hybridization assay with the samples.

Hybridization Methods with Colorimetric Detection:
DNA-Bind plates (96-well) (Catalogue #2505, Costar) were coated overnight at 4° C. with 100 μL of 50 nM capture probes in HEPES/1 min $Na_2$ EDTA buffer. The plates were then washed three times with wash buffer (Tris Buffer/0.1% Tween 20) and incubated in blocking buffer (PBS/3% BSA) for 1-2 hrs. 30 μL of Samples, Standards, and QCs were mixed with 270 μL of 50 nM detection probe in hybridization buffer (4×SSC/0.5% Sarkosyl) in Costar cluster tubes and two 100 μL aliquots from the mixture were transferred into 96-well PCR plate and denatured on the thermocycler for 12.5 minutes at 95° C. After the samples were cooled to 40° C., they were transferred to DNA-Bind plate already coated with capture probe. The plate was sealed and incubated at 40° C. for two hours. Following the hybridization, Poly-HRP Streptavidin conjugate (Catalogue #N200, Thermo) at 1:10,000 dilution in Poly-HRP dilution buffer (Catalogue #N500, Thermo) was added. Color development was initiated by adding SureBlue TMB substrate (Catalogue #52-00-00, KPL) and stopped with stop reagent for TMB substrate (Catalogue #S5814, Sigma).

Results:
The ApoC3/ApoB ASO heterodimer linked with four diester bases (cleavable; SEQ ID NO: 21) or the ApoC3/ApoB ASO heterodimer linked with four phosphothioate bases (stable; SEQ ID NO: 59) were spiked into liver or kidney (n=2 each) and homogenized as described above. The homogenate was divided into two aliquots. One of the aliquots was stored at −80° C., the other aliquot was placed at 37° C. for 15 hours before storage at −80° C. The two aliquots were thawed and analyzed together for the concentration of heterodimeric ASOs and apoB monomer with the hybridization assay.

Figures 9A, 9B:
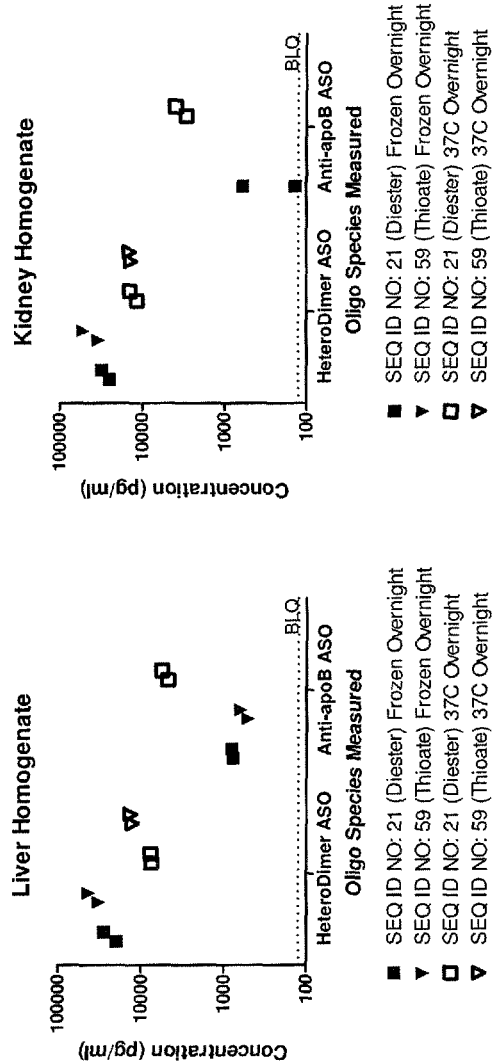
FIGS. 9A and 9B illustrate differences in concentrations of ApoB monomer after overnight incubation at 37° C. or under frozen conditions of heterodimers and ApoB monomer ASOs in liver and kidney homogenates. BLQ is "Beneath Limit of Quantification."

As shown in FIGS. 9A and 9B, concentrations of both heterodimers were lower after overnight incubation at 37° C., suggesting degradation in tissue at physiological temperature. The ApoB monomer ASO was detectable as a metabolite in both liver and kidney samples spiked with the ApoC3/ApoB ASO heterodimer linked with four diester bases (cleavable; SEQ ID NO: 21) and the levels were more than 5 fold higher in samples incubated at 37° C. After spiking with the ApoC3/ApoB ASO heterodimer linked with four phosphothioate bases (stable; SEQ ID NO: 59), the ApoB monomer ASO was only detectable in liver homogenates which had been frozen. Taken together, the data suggest that SEQ ID NO: 21 is degraded to active ApoB monomer (SEQ ID NO: 13) metabolite more readily from the ApoC3/ApoB ASO heterodimer linked with four diester bases (SEQ ID NO: 21) than from the ApoC3/ApoB ASO heterodimer linked with four phosphothioate bases (stable; SEQ ID NO: 59).

Example 18

In Vivo Distribution of Heterodimer ASOs and ApoB Monomer ASO

Figure 10:
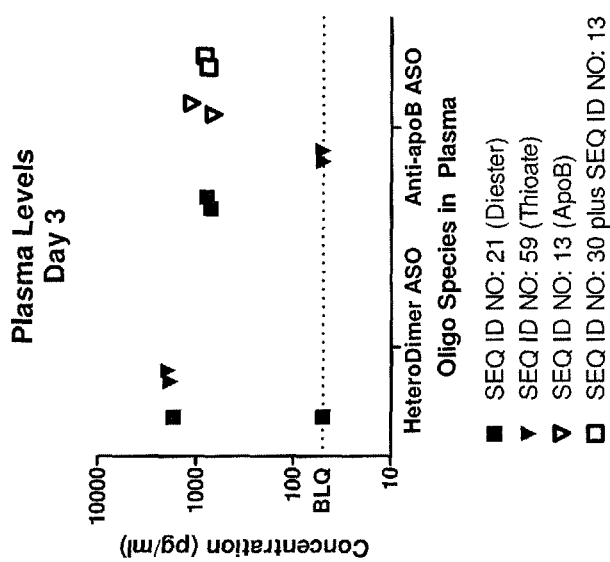
FIG. 10 illustrate differences in concentrations of ApoB monomer detected in plasma 3 days post-treatment with heterodimers and ApoB monomer ASOs.

In plasma, heterodimer ASOs and the ApoB monomer were measured using the methods above in 2 pools of 3 individuals each after treatment with the ApoC3/ApoB ASO heterodimer linked with four diester bases (cleavable; SEQ ID NO: 21), the ApoC3/ApoB ASO heterodimer linked with four phosphothioate bases (stable; SEQ ID NO: 59), the ApoB monomer ASO (SEQ ID NO: 13) or the physical combination of the ApoC3 and ApoB monomer ASOs (SEQ ID NO: 30 plus SEQ ID NO: 13). As shown in FIG. 10, both heterodimer ASOs were detected in plasma 3 days post-treatment. ApoB monomer was also detected 3 days after treatment with the ApoB monomer ASO alone or in physical combination with the ApoC3 monomer. However, ApoB monomer ASO was detected as a metabolite of the ApoC3/ApoB ASO heterodimer linked with four diester bases (cleavable; SEQ ID NO: 21) 3 days after treatment, but not after administration of the ApoC3/ApoB ASO heterodimer linked with four phosphothioate bases (stable; SEQ ID NO: 59), demonstrating that the endonuclease sensitive linker resulted in enhanced metabolism to active ASO monomers. None of the analytes were detected in plasma pools taken 14 days after treatment.

Differences between heterodimer or monomer concentrations in tissues were determined statistically by unpaired t-test (heterodimers) or one-way ANOVA followed by Bonferroni post-hoc comparisons (monomers) using GraphPad Prism.

Figures 11A, 11B:
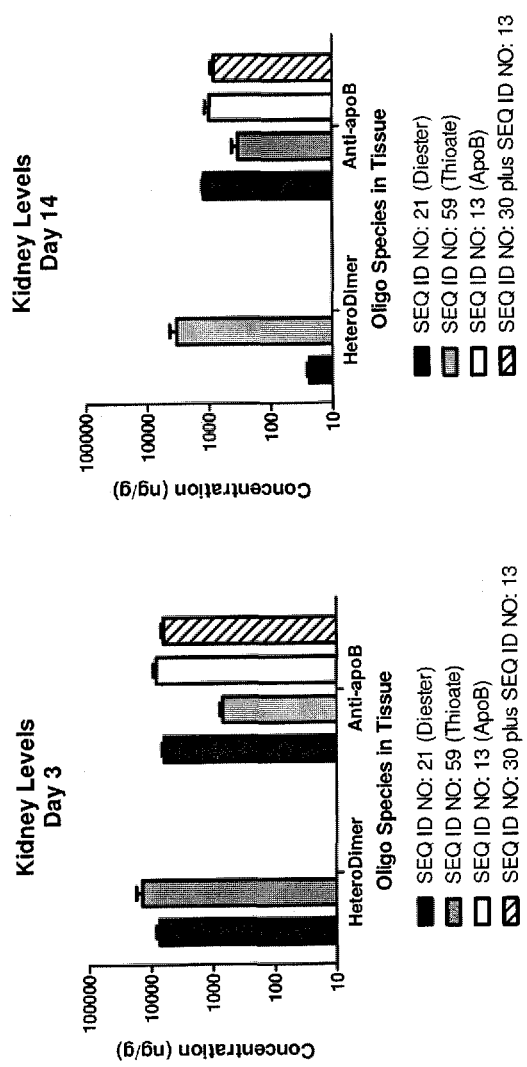
FIGS. 11A and 11B illustrate measured concentrations of ApoB monomer metabolite in kidneys at Day 3 and Day 14 following administration of heterodimers and ApoB monomer ASOs.

In the kidney, measured concentrations of all administered constructs and the ApoB monomer metabolite decrease significantly between 3 and 14 days after administration. The decline in the concentrations of the ApoC3/ApoB ASO heterodimer linked with four diester bases (cleavable; SEQ ID NO: 21) is the most rapid/marked, which is compatible with the hypothesis that the construct is most vulnerable to metabolism via cleavage of the linker (see FIGS. 11A and 11B). On both day 3 and day 14, levels of the ApoB monomer are lowest after administration of the ApoC3/ApoB ASO heterodimer linked with four phosphothioate bases (stable; SEQ ID NO: 59) while the levels of intact SEQ ID NO: 59 are the highest of the constructs measured. Taken together, these observations demonstrate slower metabolism of the relatively stable phosphothioate linker.

Figures 12A, 12B:
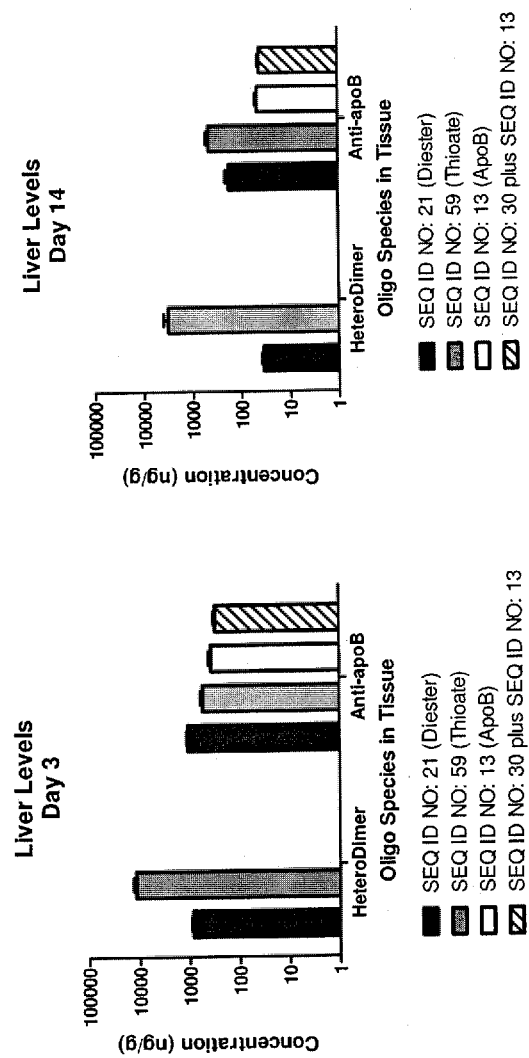
FIGS. 12A and 12B illustrate measured concentrations of ApoB monomer metabolite in liver at Day 3 and Day 14 following administration of heterodimers and ApoB monomer ASOs.

In liver, the ApoC3/ApoB ASO heterodimer linked with four diester bases (cleavable; SEQ ID NO: 21) was present at lower concentrations than the ApoC3/ApoB ASO heterodimer linked with four phosphothioate bases (stable; SEQ ID NO: 59) after treatment with the respective constructs (see FIGS. 12A and 12B), demonstrating that SEQ ID NO: 21 is metabolized more quickly in liver. Monomer levels that were measured on day 3 and 14 were significantly lower after administration of the ApoB monomer (SEQ ID NO: 13) either alone or in physical combination with the ApoC3 monomer than after administration of with either of the measured heterodimer of ApoC3/ApoB ASOs. On day 3, the concentration of ApoB monomer present in the liver as a metabolite after heterodimer administration was significantly higher after administration of the ApoC3/ApoB ASO heterodimer linked with four diester bases (cleavable; SEQ ID NO: 21) than the ApoC3/ApoB ASO heterodimer linked with four phosphothioate bases (stable; SEQ ID NO: 59), substantiating that the linker designed for cleavage by endonucleases resulted in higher concentration of active monomeric ASO metabolite within a few days of administration (see FIG. 12A). On day 14, the reverse was observed (see FIG. 12B). The concentration of ApoB monomer present in the liver as a metabolite after heterodimer administration was significantly higher after administration of the ApoC3/ApoB ASO heterodimer linked with four phosphothioate bases (stable; SEQ ID NO: 59) than the ApoC3/ApoB ASO heterodimer linked with four diester bases (cleavable; SEQ ID NO: 21). Since the phosphothioate linked heterodimer also degrades in tissue, albeit at a slower rate, relatively more monomer is present at this time point. The levels of ApoB monomer, after its administration or as a metabolite of administered ASO heterodimers is related to target mRNA knockdown, e.g., the highest levels of ApoB monomer are present after administration of the ApoC3/ApoB ASO heterodimer linked with four diester bases (cleavable; SEQ ID NO: 21) and the highest level of target mRNA knockdown is also observed in this treatment group (compare FIGS. 12A and 12B to FIGS. 8A and 8B)

Example 19

Oligo Sequences 15-mer gapmer oligos were designed as single monomers or as homodimers (30-mers) linked by an oligo-dT linker (4 bases) via cleavable phosphodiester bonds. The oligos were designed to target either miR-122 or MALAT-1 and consisted of three LNA-modified bases at each end of the monomer with 9 unmodified DNA bases in the center or gap region. The gapmer design facilitated cleavage of the bound target mRNA by RNAseH resulting in a decrease in target mRNA (either miR-122 or MALAT-1). The sequences of the following table correspond, from top to bottom, to SEQ ID NOS: 128 to 135.

| Oligo ID | Oligo Sequence |
|---|---|
| 122gap-mono | bCsbAsbTsTsGsTsCsAsCsAsCsTsbCsbCsbA |
| 122gap-dimer | bCsbAsbTsTsGsTsCsAsCsAsCsTsbCsbCsbAoToToToTobCsbAsbTs<br>TsGsTsCsAsCsAsCsTsbCsbCsbA |
| 122gap-control-mono | bTsbGsbAsAsGsGsTsTsCsCsTsCsbCsbTsbT |
| 122gap-control-dimer | bTsbGsbAsAsGsGsTsTsCsCsTsCsbCsbTsbToToToToTobTsbGsbAs<br>AsGsGsTsTsCsCsTsCsbCsbTsbT |
| Malat1-gap-mono | bCsbTsbAsGsTsTsCsAsCsTsGsAsbAsbTsbG |
| Malat1-gap-dimer | bCsbTsbAsGsTsTsCsAsCsTsGsAsbAsbTsbGoToToToTobCsbTsbAs<br>GsTsTsCsAsCsTsGsAsbAsbTsbG |
| Malat1-gap-control-mono | bTsbTsbCsCsCsTsGsAsAsGsGsTsbTsbCsbC |
| Malat1-gap-control-dimer | bTsbTsbCsCsCsTsGsAsAsGsGsTsbTsbCsbCoToToToTobTsbTsbCs<br>CsCsTsGsAsAsGsGsTsbTsbCsbC | all bases are DNA
b = LNA
s = Phosphorothioate linkage
o = Phosphodiester linkage Animal Care and Treatments:

Animal experiments were conducted in an Association for the Assessment and Accreditation of Laboratory Animal Care (AAALAC) facility under a constant light-dark cycle, maintained on a standard mouse diet, and allowed ad libitum access to food and water. Mice were euthanized by $CO_2$ inhalation. All mouse experiments were approved and conducted in compliance with the guidelines of the Institutional Animal Care and Use Committee at Vivisource Laboratories, Inc. Female C57BL6/J mice were obtained from the Jackson Laboratories (Bar Harbor, Me.) and female Balb/C mice obtained from the Charles River Laboratories. Oligonucleotides were dissolved in phosphate buffered saline (PBS) and administered to mice based on body weight by subcutaneous injection. Mice were injected once per week (MALAT-1) at 50 mg/kg or twice per week (MIR-122) at 10 mg/kg or 50 mg/kg. Mice were sacrificed after one week and at study termination (four weeks) and liver, kidney and plasma harvested for further analysis.

Triglycerides, HDL and Total Cholesterol Measurements.

Blood was collected by cardiac puncture and total plasma harvested by centrifugation in Minicollect tubes (Thermo Fisher). Plasma concentrations of Triglycerides, total cholesterol and LDL cholesterol were determined by enzymatic assay (Bioo Scientific) on a Molecular Devices SpectraMax M5 plate reader according to manufacturer's recommendations.

RNA Extraction, Reverse Transcription and mRNA qPCR.

Tissue was disrupted using a FastPrep-24 tissue homogenizer (MPBio) and total RNA isolated using Trizol (Invitrogen) and miRNEasy columns (Qiagen). RNA concentration was assessed using RlboGreen plates (Molecular Probes) and a Molecular Dynamics M5 multimodal plate reader. 250 ng of total RNA was reverse transcribed with random hexamers in a 50 ml reaction using High Capacity Multiscribe Reverse Transcriptase. qPCR was carried out using the equivalent of 12.5 ng cDNA in 20 µl reaction volumes using MIR122 or MALAT-1 specific TaqMan primers and probes on a Step-One Plus thermocycler. Relative qPCR expression of individual genes was normalized to the expression of reference genes GusB (accession# NM_010368), GAPDH (accession# NM_008084.2) or SNO-135 (accession# AF357323) RNA using the ΔΔCt method.

miR-122 Study Results

Two separate cohorts of C57B16/J mice (short and long dosing arm) were analyzed. The mice were females and, both cohorts were maintained on regular chow. Both cohorts were dosed at 10 mg/kg and 50 mg/kg by subcutaneous injection twice a week (day 1 and 4). Targeting oligonucleotides used were 15 base gapmers with LNA at the ends (3-9-3) and full phosphorothioate linkage. Animals were euthanized at day 7 (short arm) and day 28 (long arm). Dose Groups were n=5. The following parameters were analyzed in an ex vivo analysis: ALT, total cholesterol, triglycerides by ELISA.

Figure 13A:
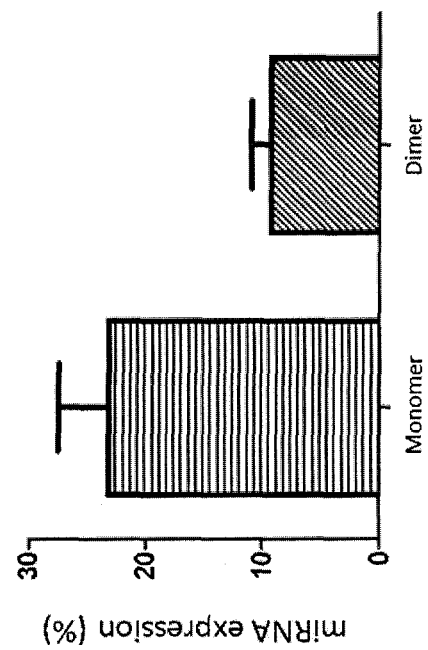
FIGS. 13A and 13B illustrate that dimer oligonucleotides significantly decreased miR-122 (10 mg/kg dose, mouse liver).
Figure 13B:
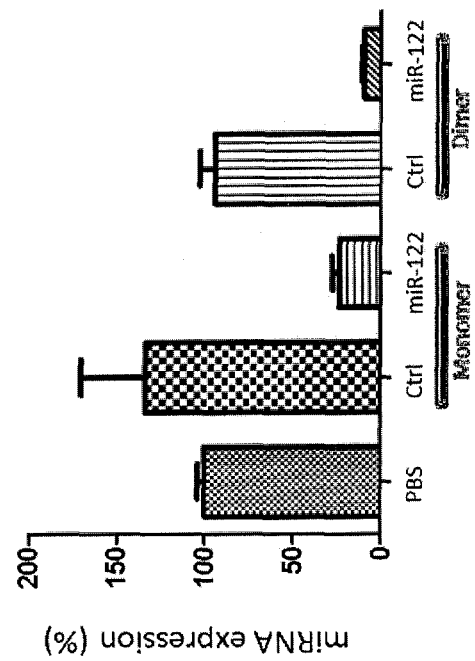

As depicted in FIGS. 13A and 13B, oligonucleotides targeting miR-122 decreased target miRNA in vivo by 75-90% compared to PBS treated controls. Monomers exhibited 75% knockdown of miR-122; whereas dimers caused 90% knockdown of miR-122.

Figure 14B:
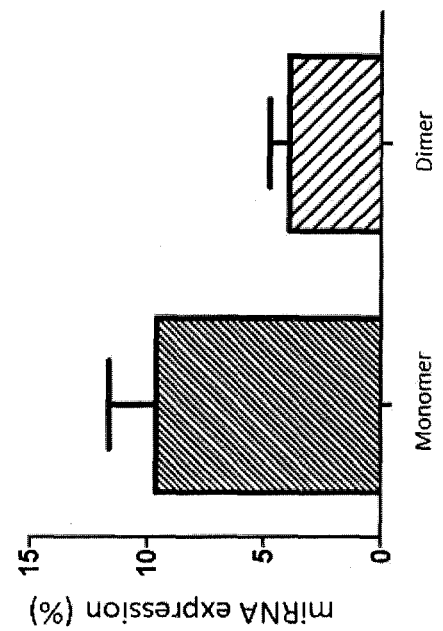
FIGS. 14A and 14B illustrate that dimer oligonucleotides significantly decreased miR-122 (50 mg/kg dose, mouse liver).
Figure 14A:
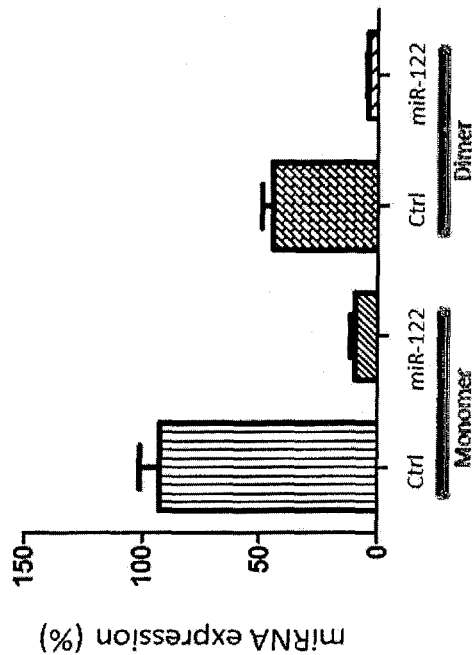

As depicted in FIGS. 14A and 14B, 50 mg/kg dose of oligonucleotides targeting miR-122 decreased target miRNA in vivo by 90-95% compared to PBS treated controls. Monomers exhibited 90% knockdown of miR-122; whereas dimers caused 95% knockdown of miR-122. It was noted that monomer at 50 mg/kg is equivalent to dimer at 10 mg/kg for % miR-122 knockdown.

Figure 15:
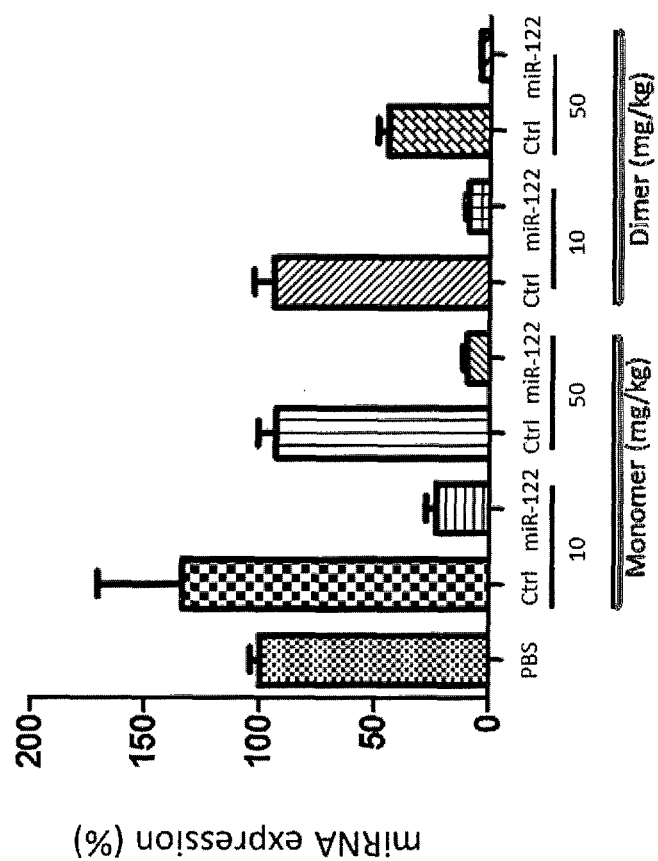
FIG. 15 illustrates that dimer oligonucleotides are ~5× more active than monomer (in vivo 7 d study).

As illustrated in FIG. 15, in vivo results show that dimers at 10 mg/kg exhibits similar knockdown as monomer at 50 mg/kg. Thus, dimer oligonucleotides are ~5× more active than monomer (in vivo 7 d study).

MALAT-1 Study Results

Figure 16A:
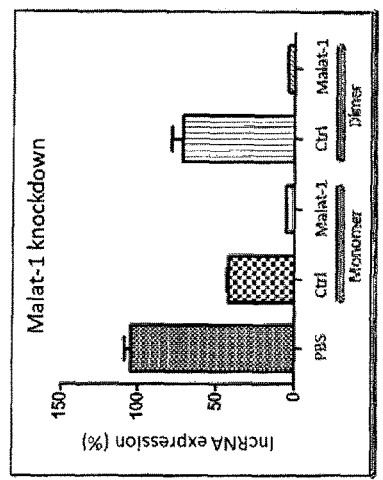
FIGS. 16A, 16B, and 16C illustrate that dimer oligonucleotides robustly decreased Malat-1 lncRNA expression.
Figure 16C:
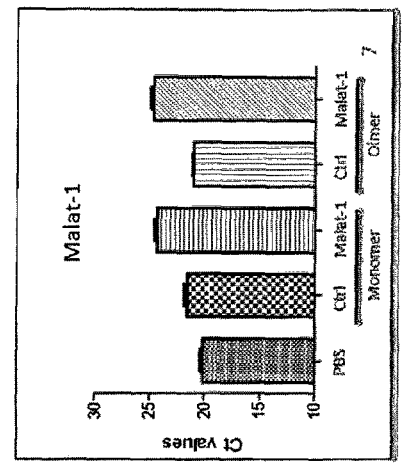
Figure 16B:
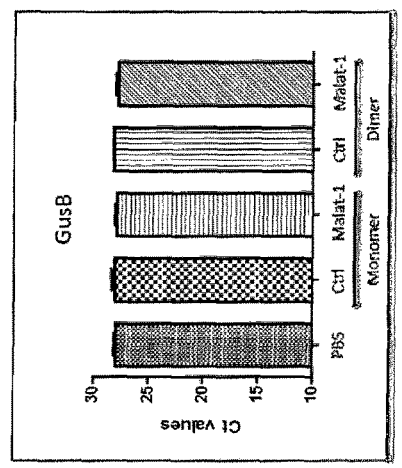

Female Balb/c mice which were 7 weeks at shipment were evaluated (N=5). The mice were dosed at 50 mg/kg on Thursday, and takedown was at 5 days post-dose. Sample obtained from the mice included tserum, kidney, brain, and liver. Organs with high levels of MALAT-1 are heart, kidney, brain and minimally found in spleen and skeletal muscle. qRT-PCR was performed to evaluate Malat-1 knockdown. As depicted in FIGS. 16A-16C, dimer oligonucleotides robustly decreased Malat-1 lncRNA expression; where the control GusB gene was unaffected.

\* \* \*

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. Those skilled in the art will recognize, or be able to ascertain using no more than routine experimentation, many equivalents to the specific embodiments of the invention described herein. Such equivalents are intended to be encompassed by the following claims.

What is claimed is:

1. A single-stranded nucleic acid compound comprising the general formula: 5'X3'-L-5'X3',
wherein each X is independently a single-stranded targeting oligonucleotide of 8 to 16 nucleotides in length having a region of complementarity comprising at least 7 contiguous nucleotides complementary to a different target nucleic acid than the other X, wherein adjacent nucleotides of the region of complementarity of each X comprise phosphorothioate linkages, and
wherein L is a linker consisting of 1 to 10 pyrimidine nucleotides linked through phosphodiester linkages that links the Xs and that is i) more susceptible to cleavage in a liver mammalian extract than each X and ii) more susceptible to cleavage in liver mammalian extract than in mammalian serum or plasma.

2. The single-stranded nucleic acid compound of claim 1, wherein the pyrimidine nucleotides are thymidines or uridines.

3. A composition comprising a single-stranded nucleic acid compound of claim 1 and a carrier.

4. A pharmaceutical composition comprising a single-stranded nucleic acid compound of claim 1 and a pharmaceutically acceptable carrier.

5. A kit comprising a container housing the composition of claim 3.

6. The single-stranded nucleic acid compound of claim 2, wherein the pyrimidine nucleotides are thymidines.

7. The single-stranded nucleic acid compound of claim 2, wherein the pyrimidine nucleotides are uridines.

8. The single-stranded nucleic acid compound of claim 1, wherein one of the different target nucleic acids is an mRNA.

9. The single-stranded nucleic acid compound of claim 1, wherein one of the different target nucleic acids is a long non-coding RNA (lncRNA).

10. The single-stranded nucleic acid compound of claim 1, wherein each targeting oligonucleotide comprises phosphorothioate internucleotide linkages between all nucleotides.

11. The single-stranded nucleic acid compound of claim 1, wherein each targeting oligonucleotide comprises a locked nucleic acid (LNA) nucleotide, ethylene bridged nucleic acid (ENA) nucleotide, 2'-O-methyl nucleotide, or 2'-fluoro-deoxyribonucleotide.

12. A method of delivering multiple targeting oligonucleotides to a cell, the method comprising:
contacting a cell with a single-stranded nucleic acid compound of claim 1 under conditions in which the compound enters into the cell.

13. The method of claim 12, wherein the cell is in vitro.

14. The method of claim 12, wherein the cell is in vivo.

15. The method of claim 14, wherein the single-stranded nucleic acid compound is delivered systemically to a subject comprising the cell.

16. The single-stranded nucleic acid compound of claim 1, wherein the linker consists of 2 to 4 pyrimidine nucleotides linked through phosphodiester linkages.

17. A compound comprising the general formula: 5'X3'-L-5'X3',
- wherein each X is independently a single-stranded targeting oligonucleotide of 8 to 16 nucleotides in length having a region of complementarity comprising at least 7 contiguous nucleotides complementary to a different target nucleic acid than the other X, wherein adjacent nucleotides of the region of complementarity of each X comprise phosphorothioate linkages,
- wherein L is a linker consisting of 1 to 10 pyrimidine nucleotides linked through phosphodiester linkages that links the Xs and that is i) more susceptible to cleavage in a liver mammalian extract than each X and ii) more susceptible to cleavage in liver mammalian extract than in mammalian serum or plasma, and
- wherein the compound does not mediate degradation of the target nucleic acids by an RNAi pathway.

18. The compound of claim 17, wherein the pyrimidine nucleotides are thymidines or uridines.

19. The compound of claim 18, wherein the pyrimidine nucleotides are thymidines.

20. The compound of claim 18, wherein the pyrimidine nucleotides are uridines.

21. The compound of claim 17, wherein one of the different target nucleic acids is an mRNA.

22. The compound of claim 17, wherein one of the different target nucleic acids is a long non-coding RNA (lncRNA).

23. The compound of claim 17, wherein each targeting oligonucleotide comprises phosphorothioate internucleotide linkages between all nucleotides.

24. The compound of claim 17, wherein each targeting oligonucleotide comprises a locked nucleic acid (LNA) nucleotide, ethylene bridged nucleic acid (ENA) nucleotide, 2'-O-methyl nucleotide, or 2'-fluoro-deoxyribonucleotide.

25. The compound of claim 17, wherein the linker consists of 2 to 4 pyrimidine nucleotides linked through phosphodiester linkages.

* * * * *